(12) United States Patent
Lee et al.

(10) Patent No.: US 10,741,768 B2
(45) Date of Patent: Aug. 11, 2020

(54) ORGANIC LIGHT-EMITTING DIODE WITH HIGH EFFICIENCY

(71) Applicant: SFC CO., LTD., Cheongju-si (KR)

(72) Inventors: Chang-Hee Lee, Cheongju-si (KR); Hyun-Jong Seo, Cheongju-si (KR); Seo-Yeon Yoon, Seongnam-si (KR); So Young Shim, Daejeon (KR); Si-In Kim, Daejeon (KR)

(73) Assignee: SFC CO., LTD., Cheongju-si (KR)

( * ) Notice: Subject to any disclaimer, the term of this patent is extended or adjusted under 35 U.S.C. 154(b) by 310 days.

(21) Appl. No.: 15/746,233

(22) PCT Filed: Jul. 28, 2016

(86) PCT No.: PCT/KR2016/008308
§ 371 (c)(1),
(2) Date: Jan. 19, 2018

(87) PCT Pub. No.: WO2017/023021
PCT Pub. Date: Feb. 9, 2017

(65) Prior Publication Data
US 2018/0233669 A1   Aug. 16, 2018

(30) Foreign Application Priority Data
Aug. 6, 2015 (KR) .................. 10-2015-0111093

(51) Int. Cl.
H01L 51/50 (2006.01)
H01L 51/00 (2006.01)
(Continued)

(52) U.S. Cl.
CPC ........ H01L 51/0061 (2013.01); C07D 239/70 (2013.01); C07D 307/77 (2013.01);
(Continued)

(58) Field of Classification Search
None
See application file for complete search history.

(56) References Cited

U.S. PATENT DOCUMENTS

2014/0054561 A1   2/2014  Nam et al.
2016/0351816 A1*  12/2016 Kim ................... H01L 51/0074
2018/0166638 A1*  6/2018  Park ...................... C09K 11/06

FOREIGN PATENT DOCUMENTS

CN    107690719 A    2/2018
EP    3309235 A1     4/2018
(Continued)

OTHER PUBLICATIONS

Office Action from China Intellectual Property Administration of 201680044437.2, dated Aug. 2, 2019.
(Continued)

Primary Examiner — Gregory D Clark
(74) Attorney, Agent, or Firm — STIP Law Group, LLC

(57) ABSTRACT

The present disclosure relates to an organic light-emitting diode exhibiting high luminance efficiency, low-voltage operation, and long lifespan and, more particularly, to an organic light-emitting diode, comprising: a first electrode; a second electrode facing the first electrode; and a light-emitting layer and an electron density control layer sequentially arranged between the first electrode and the second electrode wherein the light-emitting layer includes at least one of the amine compounds represented by Chemical Formula A or B and the electron density control layer includes at least one of the compounds represented by Chemical Formulas F to H. The structures of Chemical Formulas A, B, and F to H are as described in the specification.

20 Claims, 1 Drawing Sheet

(51) Int. Cl.
| | |
|---|---|
| *C09K 11/06* | (2006.01) |
| *C09B 1/00* | (2006.01) |
| *C09B 57/00* | (2006.01) |
| *C07D 239/70* | (2006.01) |
| *C07D 307/77* | (2006.01) |
| *C07D 307/91* | (2006.01) |
| *C07D 405/10* | (2006.01) |
| *C07D 491/048* | (2006.01) |
| *C07D 493/10* | (2006.01) |
| *C07F 7/08* | (2006.01) |
| *H01L 51/52* | (2006.01) |

(52) U.S. Cl.
CPC ......... *C07D 307/91* (2013.01); *C07D 405/10* (2013.01); *C07D 491/048* (2013.01); *C07D 493/10* (2013.01); *C07F 7/0812* (2013.01); *C09B 1/00* (2013.01); *C09B 57/008* (2013.01); *C09K 11/06* (2013.01); *H01L 51/0052* (2013.01); *H01L 51/0054* (2013.01); *H01L 51/0058* (2013.01); *H01L 51/0067* (2013.01); *H01L 51/0071* (2013.01); *H01L 51/0072* (2013.01); *H01L 51/0073* (2013.01); *H01L 51/0094* (2013.01); *C09K 2211/1018* (2013.01); *H01L 51/0002* (2013.01); *H01L 51/0003* (2013.01); *H01L 51/5012* (2013.01); *H01L 51/5016* (2013.01); *H01L 51/5068* (2013.01); *H01L 51/5084* (2013.01); *H01L 51/5088* (2013.01); *H01L 51/5092* (2013.01); *H01L 51/5206* (2013.01); *H01L 51/5221* (2013.01)

(56) References Cited

FOREIGN PATENT DOCUMENTS

| | | |
|---|---|---|
| JP | 2010034548 A | 2/2010 |
| KR | 1020060022676 A | 3/2006 |
| KR | 1020080015865 A | 2/2008 |
| KR | 1020120047706 A | 5/2012 |
| KR | 1020120092550 A | 8/2012 |
| KR | 1020120092555 A | 8/2012 |
| KR | 1020140128653 A | 11/2014 |
| KR | 1020160141359 A | 12/2016 |
| KR | 1020160146272 A | 12/2016 |
| WO | WO2015002208 A1 | 1/2015 |
| WO | WO2015022051 A1 | 2/2015 |

OTHER PUBLICATIONS

Office action from Korea Intellectual Property Office of 10-2016-0096092, dated Jul. 9, 2019.
International Search Report of PCT/KR2016/008308, dated Oct. 26, 2016, English Translation.
The extended European search report of 16833257, dated Mar. 22, 2019.
Office Action from Korean Intellectual Property Office of 10-2016-0096092, dated Oct. 4, 2018.

* cited by examiner

ORGANIC LIGHT-EMITTING DIODE WITH HIGH EFFICIENCY

CROSS-REFERENCE TO RELATED APPLICATIONS

This application is the U.S. National Phase under 35 U.S.C. § 371 of International Application No. PCT/KR2016/008308 filed on Jul. 28, 2016, which in turn claims the benefit of Korean Application No. 10-2015-0111093, filed on Aug. 6, 2015, the disclosures of which are incorporated by reference into the present application.

TECHNICAL FIELD

The present disclosure relates to an organic light-emitting diode and, more particularly, to an organic light-emitting diode exhibiting high luminance efficiency and low-voltage operation, wherein a compound of specific structure is used in a light-emitting layer and an electron density control layer having a specific structure is introduced between the light-emitting layer and an electron injection layer.

BACKGROUND ART

Organic light-emitting diodes, based on self-luminescence, exhibit the advantages of having a wide viewing angle, excellent contrast, fast response time, high brightness, excellent driving voltage, and response rate characteristics, and of allowing for a polychromic display.

A typical organic light-emitting diode includes a positive electrode (anode) and a negative electrode (cathode), facing each other, with an organic emission layer disposed therebetween.

As to a general structure of the organic light-emitting diode, a hole transport layer, a light-emitting layer, an electron transport layer, and a cathode are formed in that order on an anode. Here, all of the hole transport layer, the light-emitting layer, and the electron transport layer are organic films comprising organic compounds.

An organic light-emitting diode having such a structure operates as follows: when a voltage is applied between the anode and the cathode, the anode injects holes which are then transferred to the light-emitting layer via the hole transport layer while electrons injected from the cathode move to the light-emitting layer via the electron transport layer. In the luminescent zone, the carriers such as holes and electrons recombine to produce an exciton. When the exciton returns to the ground state from the excited state, the molecule of the light-emitting layer emits light.

Materials used as the organic layers in organic light-emitting diodes may be divided according to functions into luminescent materials and charge carrier materials, for example, a hole injection material, a hole transport material, an electron injection material, and an electron transport material. The light-emitting mechanism forms the basis of classification of luminescent materials as fluorescent and phosphorescent materials, which use excitons in singlet and triplet states, respectively.

Meanwhile, when a single material is employed as the luminescent material, intermolecular actions cause the maximum luminescence wavelength to shift toward a longer wavelength, resulting in a reduction in color purity and light emission efficiency due to light attenuation. In this regard, a host-dopant system may be used as a luminescent material so as to increase the color purity and the light emission efficiency through energy transfer. This is based on the principle whereby, when a dopant which is smaller in energy band gap than a host forming a light-emitting layer is added in a small amount to the light-emitting layer, excitons are generated from the light-emitting layer and transported to the dopant, emitting light at high efficiency. Here, light with desired wavelengths can be obtained depending on the kind of the dopant because the wavelength of the host move to the wavelength range of the dopant.

With regard to related arts pertaining to dopant compounds in the light-emitting layer, reference may be made to Korean Patent No. 10-2008-0015865 A (Feb. 20, 2008), which describes an organic light-emitting diode using an arylamine-coupled indenofluorene derivative, and Korean Patent No. 10-2012-0047706 A (May 14, 2012), which describes an organic light-emitting device using a compound in which dibenzofuran or dibenzothiophene coexists with fluorene or carbazole.

With the aim of solving the disadvantages, Korean Patent No. 10-2012-0092555 A (Aug. 21, 2012) proposes the effective occurrence of a triplet-triplet fusion (TTF) phenomenon accounting for the generation of singlet excitons through the collision and fusion of two triplet excitons. For this, this document discloses an electroluminescence device in which a blocking layer is interposed between a light-emitting layer and an electron injection layer, with an affinity difference between the electron injection layer and the blocking layer. In this regard, the blocking layer is set to have a triplet energy larger than that of the host of the light-emitting layer so as to confine triplet excitons within the light-emitting layer, whereby the effective occurrence of the TTF phenomenon is induced.

As described above, the disclosure set forth in the reference document is designed to cause the effective occurrence of a TTF phenomenon in order to provide high emission efficiency for an organic electroluminescence device. To this end, the blocking layer should include a material that is higher in triplet energy than the host to prevent the annihilation of the triplet excitations generated in the host, and an aromatic heterocyclic compound of a specific fused ring should be employed in the blocking layer.

Another technique for improving luminance efficiency can be found in Korean Patent No. 10-2006-0022676 A (Mar. 10, 2006), which describes an organic electroluminescence device having a blocking layer, disposed between a light-emitting layer and an electron transport layer, for controlling electron density.

In spite of various efforts made to fabricate organic light-emitting diodes having effective luminescence characteristics, however, there is still a continued need to develop organic light-emitting diodes having higher properties including high luminance efficiency, low-voltage operation, and long lifespan.

DETAILED DESCRIPTION OF THE INVENTION

Technical Problem

Accordingly, the present disclosure has been made keeping in mind the above problems occurring in the related art, and a purpose of the present disclosure is to provide an organic light-emitting diode that exhibits excellent properties including high luminous efficiency, low-voltage operation, and long lifespan.

Technical Solution

The present disclosure provides an organic light-emitting diode, comprising: a first electrode; a second electrode facing the first electrode; and a light-emitting layer and an electron density control layer sequentially arranged between the first electrode and the second electrode wherein the light-emitting layer includes at least one of the amine compounds represented by the following Chemical Formulas A and B and the electron density control layer includes at least one of the compounds represented by the following Chemical Formulas F to H:

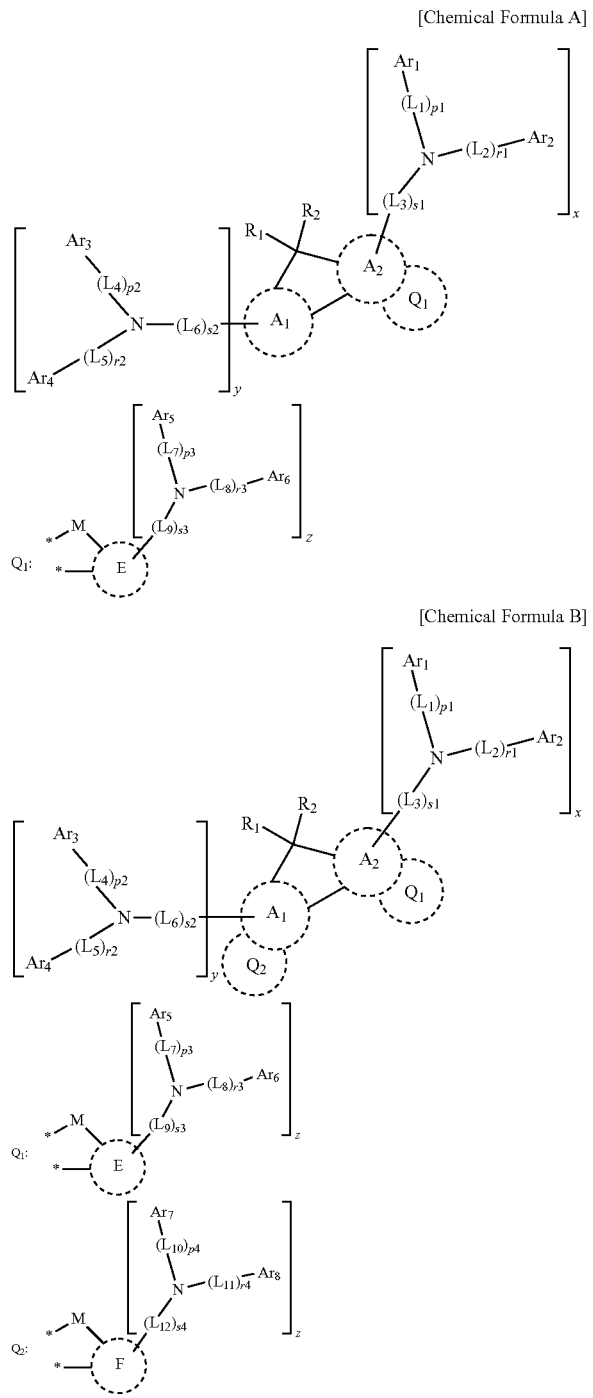

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms, wherein two adjacent carbon atoms of the aromatic ring $A_1$ and two adjacent carbon atoms of the aromatic ring $A_2$ form a 5-membered fused ring together with a carbon atom connected to both substituents $R_1$ and $R_2$;

linkers $L_1$ to $L_{12}$ may be the same or different and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se; $R_1$ to $R_9$ and $Ar_1$ to $Ar_8$ may be the same or different and are each independently any one selected from among a hydrogen atom, an deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 1 to 30 carbon atoms, a cyano, a nitro, and a halogen, with the proviso that $R_1$ and $R_2$ may be bonded to each other to form a mono- or polycyclic aliphatic or aromatic ring, which may be a heterocyclic ring bearing a heteroatom selected from among N, O, P, Si, S, Ge, Se, and Te as a ring member;

p1 to p4, r1 to r4, and s1 to s4 are each independently an integer of 1 to 3, with the proviso that when any of them is 2 or greater, the corresponding linkers may be the same or different;

x is an integer of 1 or 2, and y and z may be the same or different and are each independently an integer of 0 to 3; and $Ar_1$ may form a ring with $Ar_2$, $Ar_3$ may form a ring with $Ar_4$, $Ar_5$ may form a ring with $Ar_6$, and $Ar_7$ may form a ring with $Ar_8$;

two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring, and two adjacent carbon atoms of the $A_2$ ring moiety of Chemical Formula B may occupy respective positions * of Structural Formula $Q_1$ to form a fused ring;

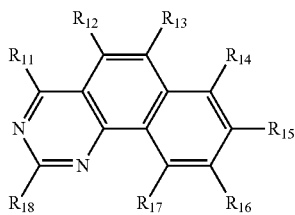

[Chemical Formula F]

wherein, substituents R11 to $R_{18}$ may be the same or different and are each independently selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted aryl of 6 to 50 carbon atoms, a substituted or unsubstituted heteroaryl of 3 to 50 carbon atoms, a substituted or unsubstituted alkoxy of 2 to 30 carbon atoms, a substituted or unsubstituted aryloxy of 6 to 50 carbon atoms, a substituted or unsubstituted alkylamine of 1 to 30 carbon atoms, a substituted or unsubstituted arylamine of 6 to 50 carbon atoms, a substituted or unsubstituted silyl, a halogen, and a cyano;

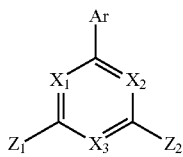

[Chemical Formula G]

wherein, $X_1$ to $X_3$ may be the same or different and are each independently a nitrogen atom or CR', with the proviso that at least one of $X_1$ to $X_3$ is a nitrogen atom, wherein R' is selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted aryl of 6 to 50 carbon atoms, a substituted or unsubstituted heteroaryl of 3 to 50 carbon atoms, a substituted or unsubstituted alkoxy of 2 to 30 carbon atoms, a substituted or unsubstituted aryloxy of 6 to 50 carbon atoms, a substituted or unsubstituted alkylamine of 1 to 30 carbon atoms, a substituted or unsubstituted arylamine of 6 to 50 carbon atoms, a substituted or unsubstituted silyl, a halogen, and a cyano;

Ar is selected from among a substituted or unsubstituted alkyl of 1 to 20 carbon atoms, a substituted or unsubstituted cycloalkyl of 3 to 30 carbon atoms, a substituted or unsubstituted aryl of 6 to 50 carbon atoms, and a substituted or unsubstituted heteroaryl of 3 to 50 carbon atoms;

$Z_1$ and $Z_2$ may be the same or different and are each independently a substituted or unsubstituted aryl of 6 to 30 carbon atoms, a substituted or unsubstituted heteroaryl of 3 to 30 carbon atoms, or a substituent represented by the following Structural Formula A:

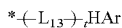 [Structural Formula A]

wherein, $L_{13}$ is selected from among a single bond, a substituted or unsubstituted alkylene of 1 to 30 carbon atoms, a substituted or unsubstituted cycloalkylene of 3 to 30 carbon atoms, a substituted or unsubstituted arylene of 6 to 50 carbon atoms, and a substituted or unsubstituted heteroarylene of 3 to 50 carbon atoms, HAr is a substituted or unsubstituted heteroaryl of 3 to 50 carbon atoms, and t is an integer of 0 to 3, with the proviso that when t is 2 or greater, the corresponding substituents $L_{13}$'s may be the same or different; and

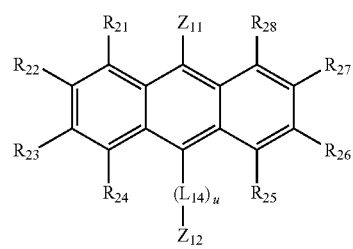

[Chemical Formula H]

wherein, substituents $Z_{11}$ and $Z_{12}$ may be the same or different and are each independently a substituted or unsubstituted aryl of 6 to 50 carbon atoms or a substituted or unsubstituted heteroaryl of 3 to 50 carbon atoms, linker $L_{14}$ is a single bond or a substituted or unsubstituted aryl of 6 to 50 carbon atoms, u is an integer of 0 to 2, with the proviso that when u is 2, the corresponding linkers $L_{14}$'s may be the same or different, and substituents $R_{21}$ to $R_{28}$ may be the same or different and are each independently selected from a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 2 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atom, a substituted or unsubstituted alkylgermanium of 1 to 30 carbon atoms, a substituted or unsubstituted arylgermanium of 1 to 30 carbon atoms, a cyano, a nitro, and a halogen.

Advantageous Effects

Employing a light-emitting layer and an electron density control layer in combination with specifically structured materials for respective layers, the organic light-emitting diode of the present disclosure exhibit better properties including high luminance efficiency, low-voltage operation and long lifespan, compared to conventional organic light-emitting diodes.

BRIEF DESCRIPTION OF THE DRAWINGS

FIG. 1 is a diagram of the structure of an organic light-emitting diode according to some embodiments of the present disclosure

MODE FOR CARRYING OUT THE INVENTION

Hereinafter, some embodiments which can be easily performed by those skilled in the art will be described with reference to the accompanying drawings. In the drawings of the disclosure, sizes and dimensions of structures are illustrated by enlarging or reducing as compared with the actual sizes and dimensions to clarify the disclosure, the known configurations are not illustrated to exhibit characteristic configurations, and the disclosure is not limited to the drawings.

In addition, the size and thickness of each configuration illustrated in the drawings are arbitrarily illustrated for the sake of convenience of explanation, and thus the present disclosure may not be necessarily limited to the illustration. Further, in the drawings, the thickness of layers and regions are illustrated in enlargement for clarity. For the sake of explanation, thicknesses of certain layers and regions are exaggerated.

Throughout the specification, when a portion may "include" a certain constituent element, unless explicitly described to the contrary, it may not be construed to exclude another constituent element but may be construed to further include other constituent elements. Further, throughout the specification, the word "on" means positioning on or below the object portion, but does not essentially mean positioning on the lower side of the object portion based on a gravity direction.

The present disclosure provides an organic light-emitting diode, comprising: a first electrode; a second electrode facing the first electrode; and a light-emitting layer and an electron density control layer sequentially arranged between the first electrode and the second electrode wherein the light-emitting layer includes at least one of the amine compounds represented by the following Chemical Formulas A and B and the electron density control layer includes at least one of the compounds represented by the following Chemical Formulas F to H:

[Chemical Formula A]

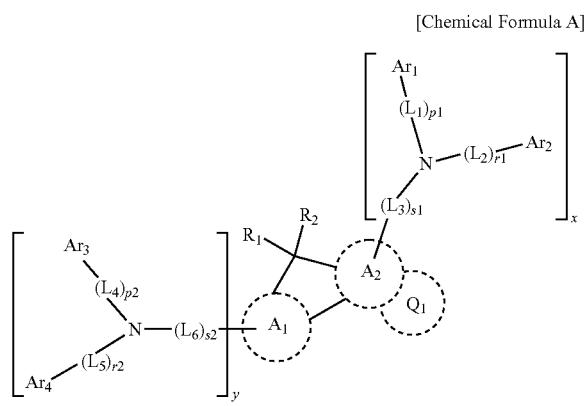

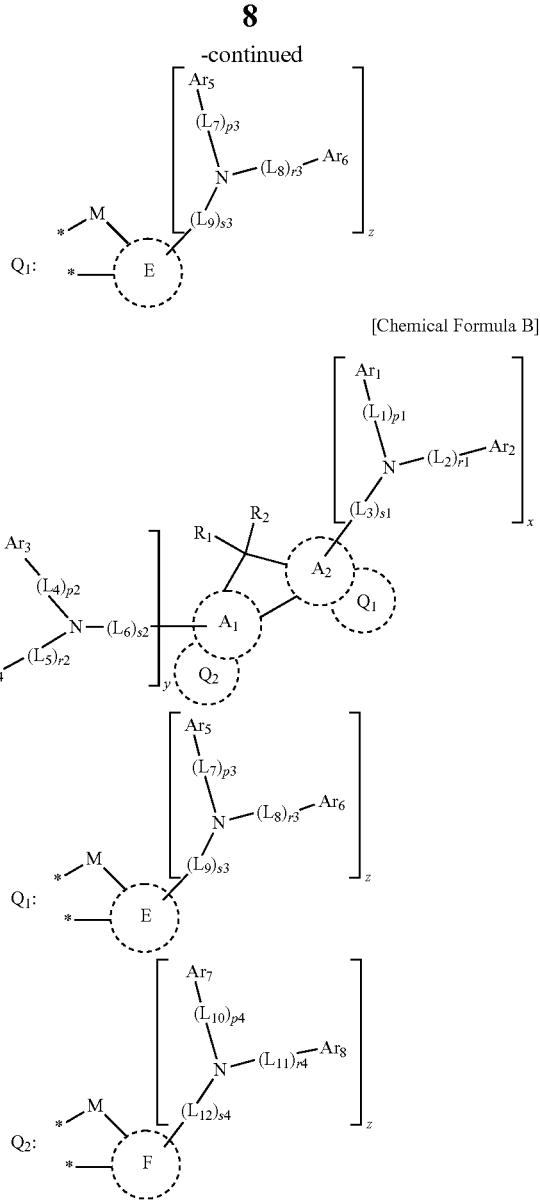

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms, wherein two adjacent carbon atoms of the aromatic ring $A_1$ and two adjacent carbon atoms of the aromatic ring $A_2$ form a 5-membered fused ring together with a carbon atom connected to both substituents $R_1$ and $R_2$; linkers $L_1$ to $L_{12}$ may be the same or different and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$ and $Ar_1$ to $Ar_8$ may be the same or different and are each independently any one selected from among a hydrogen atom, an deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 1 to 30 carbon atoms, a cyano, a nitro, and a halogen, with the proviso that $R_1$ and $R_2$ may be bonded to each other to form a mono- or polycyclic aliphatic or aromatic ring, which may be a heterocyclic ring bearing a heteroatom selected from among N, O, P, Si, S, Ge, Se, and Te as a ring member;

p1 to p4, r1 to r4, and s1 to s4 are each independently an integer of 1 to 3, with the proviso that when any of them is 2 or greater, the corresponding linkers may be the same or different;

x is an integer of 1 or 2, and y and z may be the same or different and are each independently an integer of 0 to 3; and $Ar_1$ may form a ring with $Ar_2$, $Ar_3$ may form a ring with $Ar_4$, $Ar_5$ may form a ring with $Ar_6$, and $Ar_7$ may form a ring with $Ar_8$;

two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring, and two adjacent carbon atoms of the $A_2$ ring moiety of Chemical Formula B may occupy respective positions * of Structural Formula $Q_1$ to form a fused ring;

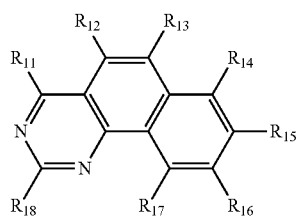

[Chemical Formula F]

wherein, substituents R11 to $R_{18}$ may be the same or different and are each independently selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted aryl of 6 to 50 carbon atoms, a substituted or unsubstituted heteroaryl of 3 to 50 carbon atoms, a substituted or unsubstituted alkoxy of 2 to 30 carbon atoms, a substituted or unsubstituted aryloxy of 6 to 50 carbon atoms, a substituted or unsubstituted alkylamine of 1 to 30 carbon atoms, a substituted or unsubstituted arylamine of 6 to 50 carbon atoms, a substituted or unsubstituted silyl, a halogen, and a cyano;

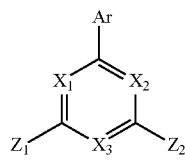

[Chemical Formula G]

wherein, $X_1$ to $X_3$ may be the same or different and are each independently a nitrogen atom or CR', with the proviso that at least one of $X_1$ to $X_3$ is a nitrogen atom, wherein R' is selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted aryl of 6 to 50 carbon atoms, a substituted or unsubstituted heteroaryl of 3 to 50 carbon atoms, a substituted or unsubstituted alkoxy of 2 to 30 carbon atoms, a substituted or unsubstituted aryloxy of 6 to 50 carbon atoms, a substituted or unsubstituted alkylamine of 1 to 30 carbon atoms, a substituted or unsubstituted arylamine of 6 to 50 carbon atoms, a substituted or unsubstituted silyl, a halogen, and a cyano;

Ar is selected from among a substituted or unsubstituted alkyl of 1 to 20 carbon atoms, a substituted or unsubstituted cycloalkyl of 3 to 30 carbon atoms, a substituted or unsubstituted aryl of 6 to 50 carbon atoms, and a substituted or unsubstituted heteroaryl of 3 to 50 carbon atoms;

$Z_1$ and $Z_2$ may be the same or different and are each independently a substituted or unsubstituted aryl of 6 to 30 carbon atoms, a substituted or unsubstituted heteroaryl of 3 to 30 carbon atoms, or a substituent represented by the following Structural Formula A:

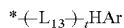 [Structural Formula A]

wherein, $L_{13}$ is selected from among a single bond, a substituted or unsubstituted alkylene of 1 to 30 carbon atoms, a substituted or unsubstituted cycloalkylene of 3 to 30 carbon atoms, a substituted or unsubstituted arylene of 6 to 50 carbon atoms, and a substituted or unsubstituted heteroarylene of 3 to 50 carbon atoms, HAr is a substituted or unsubstituted heteroaryl of 3 to 50 carbon atoms, and t is an integer of 0 to 3, with the proviso that when t is 2 or greater, the corresponding substituents $L_{13}$'s may be the same or different; and

[Chemical Formula H]

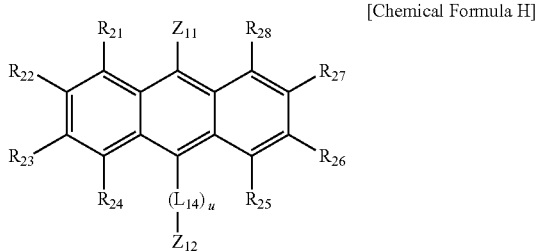

wherein, substituents $Z_{11}$ and $Z_{12}$ may be the same or different and are each independently a substituted or unsubstituted aryl of 6 to 50 carbon atoms or a substituted or unsubstituted heteroaryl of 3 to 50 carbon atoms, linker $L_{14}$ is a single bond or a substituted or unsubstituted aryl of 6 to 50 carbon atoms, u is an integer of 0 to 2, with the proviso that when u is 2, the corresponding linkers $L_{14}$'s may be the same or different, and substituents $R_{21}$ to $R_{28}$ may be the same or different and are each independently selected from a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 2 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atom, a substituted or unsubstituted alkylgermanium of 1 to 30 carbon atoms, a substituted or unsubstituted arylgermanium of 1 to 30 carbon atoms, a cyano, a nitro, and a halogen;

wherein the term 'substituted' in the expression 'substituted or unsubstituted' used in Chemical Formulas A, B, and F to H means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 2 to 24 carbon atoms, an alkylsilyl of 1 to 24 carbon atoms, an arylsilyl of 6 to 24 carbon atoms, and an aryloxy of 6 to 24 carbon atoms.

The expression indicating the number of carbon atoms, such as "a substituted or unsubstituted alkyl of 1 to 30 carbon atoms", "a substituted or unsubstituted aryl of 6 to 50 carbon atoms", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of 6 carbon atoms, even though it is substituted with a butyl radical of 4 carbon atoms.

As used herein, the term "aryl" means an organic radical derived from an aromatic hydrocarbon by removing one hydrogen that is bonded to the aromatic hydrocarbon. It may be a single or fused aromatic system including a 5- to 7-membered ring, and preferably a 5- to 6-membered ring. Further, the aromatic system may include a fused ring that is formed by adjacent substituents on the aryl radical.

Examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, but are not limited thereto.

At least one hydrogen atom of the aryl may be substituted by a deuterium atom, a halogen atom, a hydroxy, a nitro, a cyano, a silyl, an amino (—$NH_2$, —NH(R), —N(R') (R'') wherein R' and R'' are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms, or a heteroarylalkyl of 2 to 24 carbon atoms.

The heteroaryl substituent used in the compound of the present disclosure refers to a cyclic aromatic system of 2 to 24 carbon atoms bearing 1 to 3 heteroatoms selected from among N, O, P, Si, S, Ge, Se, and Te. In the aromatic system, two or more rings may be fused. One or more hydrogen atoms on the heteroaryl may be substituted by the same substituents as on the aryl.

In addition, the term "heteroaromatic ring", as used herein, refers to an aromatic ring bearing as a ring member at least one heteroatom selected from among N, O, P, Si, S, Ge, Se, and Te.

Examples of the alkyl substituent useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the alkoxy substituent useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atoms of the silyl may be substituted by the same substituent as in the aryl.

In the present disclosure, the phrase "(an organic layer) includes at least one organic compound" may be construed to mean "(an organic layer) may include a single organic compound species or two or more different species of organic compounds falling within the scope of the present disclosure".

The amine compound represented by Chemical Formula A or B in the present disclosure has the structural feature that if Structural Formula $Q_1$ is connected to the $A_2$ ring in Chemical Formula A, the amine moiety containing $Ar_1$ and $Ar_2$ must be bonded to the $A_2$ ring and that if Structural Formula $Q_2$ and $Q_1$ are connected respectively to $A_1$ and $A_2$ rings in Chemical Formula B, the amine moiety containing $Ar_1$ and $Ar_2$ must be bonded to the $A_2$ ring.

In this regard, $A_1$, $A_2$, E, and F in Chemical Formula A or B may be the same or different and may each be independently substituted or unsubstituted aromatic hydrocarbon rings of 6 to 50 carbon atoms.

As stated above, when $A_1$, $A_2$, E, and F in Chemical Formula A or B are each independently substituted or unsubstituted aromatic hydrocarbon rings of 6 to 50 carbon atoms, the substituted or unsubstituted aromatic hydrocarbon rings of 6 to 50 carbon atoms may be the same or different and are each independently selected from among compounds represented by Structural Formulas 10 to 21:

[Structural Formula 10]

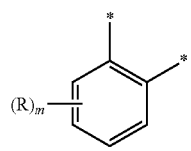

[Structural Formula 11]

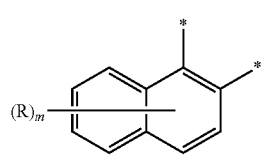

[Structural Formula 12]

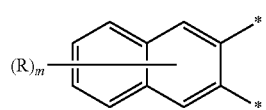

[Structural Formula 13]

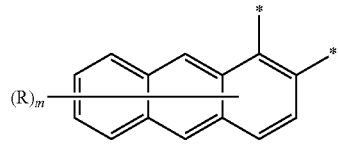

[Structural Formula 14]

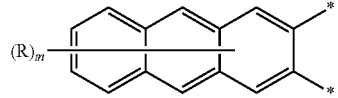

[Structural Formula 15]

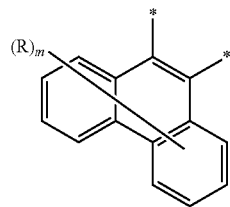

[Structural Formula 16]

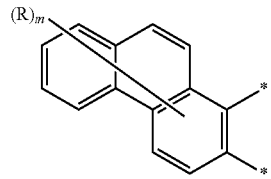

[Structural Formula 17]

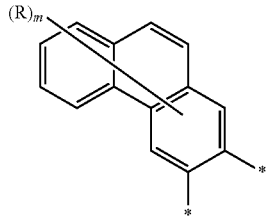

[Structural Formula 18]

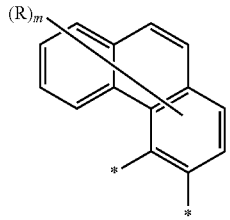

[Structural Formula 19]

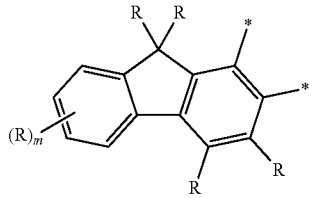

[Structural Formula 20]

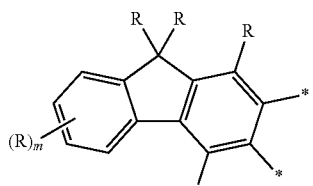

[Structural Formula 21]

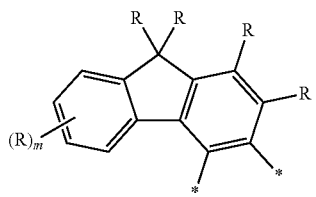

wherein

"-*" denotes a bonding site for forming a 5-membered ring bearing the carbon atom connected to the substituents $R_1$ and $R_2$ or a bonding site for forming a 5-membered ring bearing M of Structural Formula $Q_1$ and $Q_2$;

when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring;

R's are the same as defined above for $R_1$ and $R_2$, and m is an integer of 1 to 8, with the proviso that when m is 2 or greater or when two or more R's exist, the corresponding R's may be the same or different.

In addition, the linkers $L_1$ to $L_{12}$ in Chemical Formulas A and B may each be a single bond or any one selected from among the following Structural Formulas 22 to 30:

[Structural Formula 22]

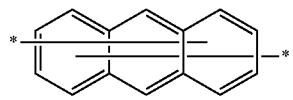

[Structural Formula 23]

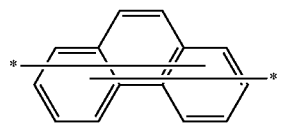

[Structural Formula 24]

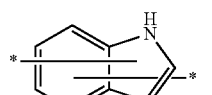

[Structural Formula 25]

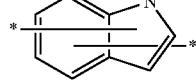

[Structural Formula 26]

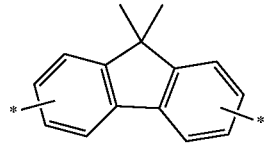

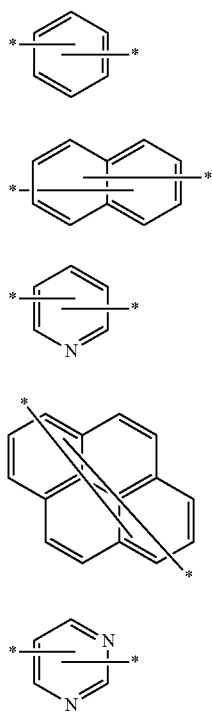

[Structural Formula 27]

[Structural Formula 28]

[Structural Formula 29]

[Structural Formula 30]

In the linkers, each of the unsubstituted carbon atoms of the aromatic ring moiety is bound with a hydrogen atom or a deuterium atom.

Concrete examples of the amine compounds represented by Chemical Formula A or B in the present disclosure include, but are not limited to, the compounds represented by the following Chemical Formulas 1 to 239:

<Chemical Formula 1>

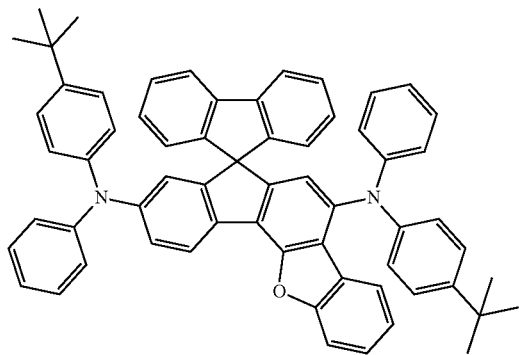

<Chemical Formula 2>

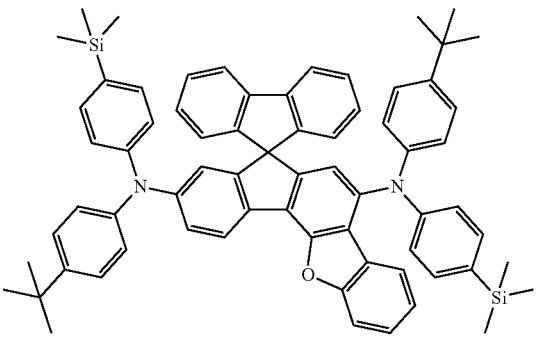

<Chemical Formula 3>

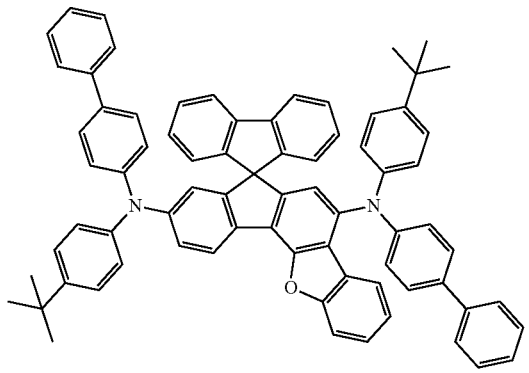

<Chemical Formula 4>

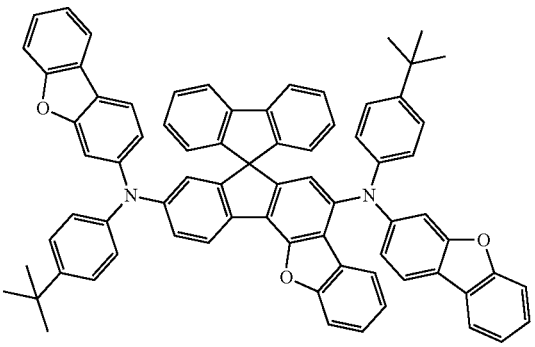

-continued
<Chemical Formula 5>
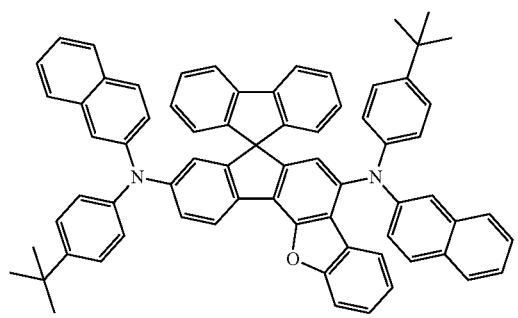
<Chemical Formula 6>
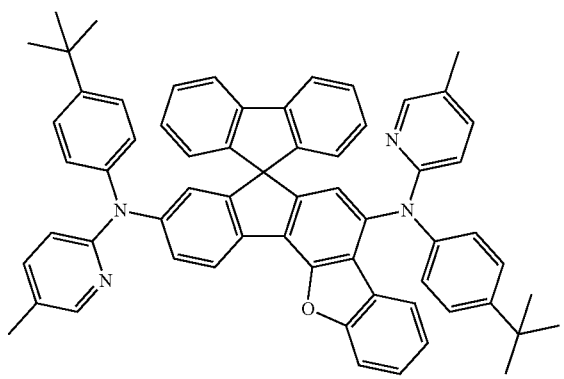
<Chemical Formula 7>
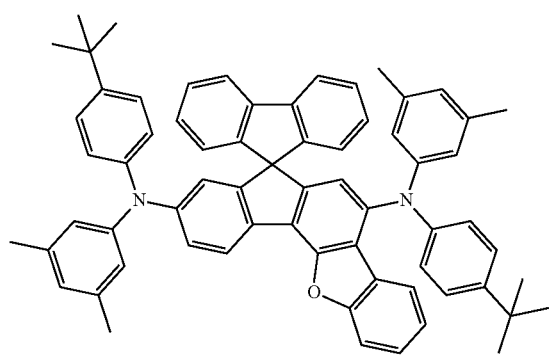
<Chemical Formula 8>
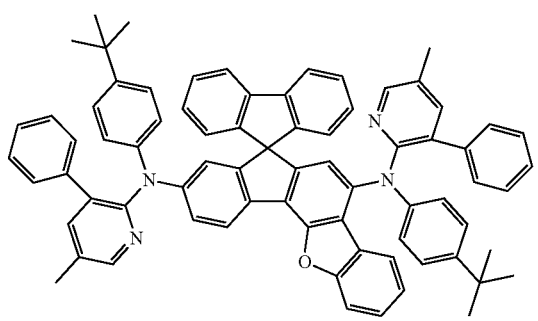
<Chemical Formula 9>
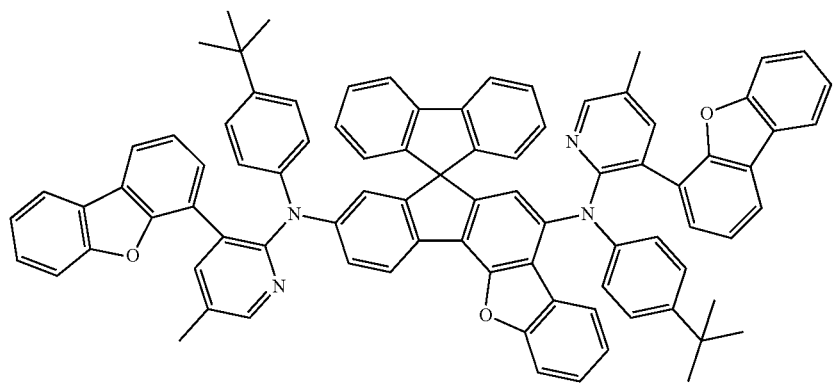
<Chemical Formula 10>
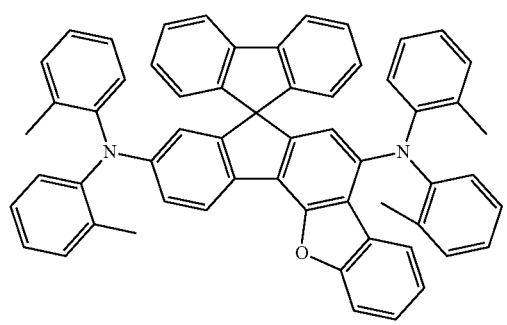
<Chemical Formula 11>
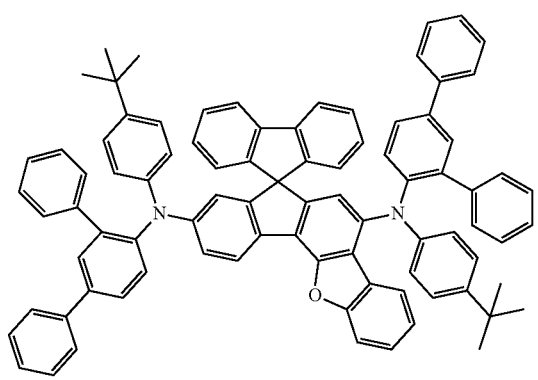

<Chemical Formula 12>
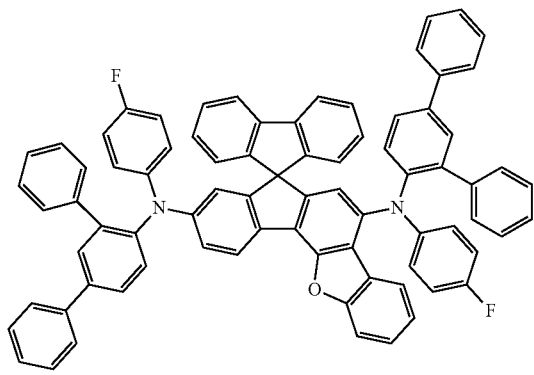
<Chemical Formula 13>
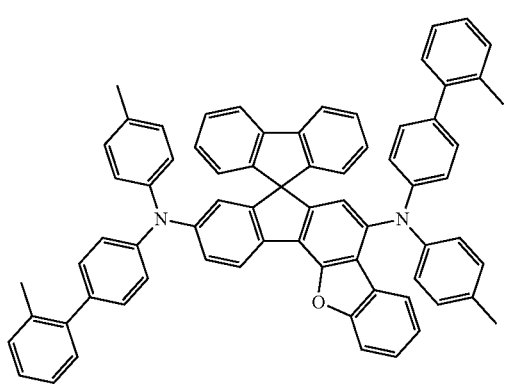
<Chemical Formula 14>
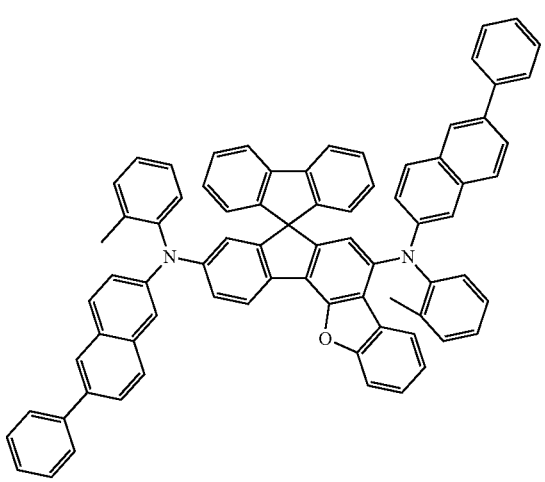
<Chemical Formula 15>
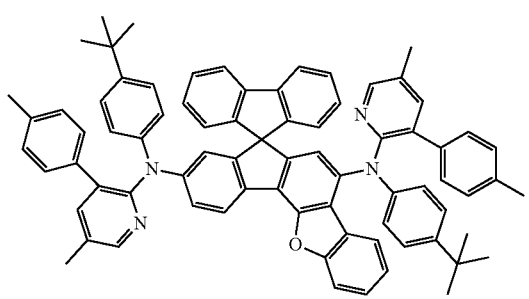
<Chemical Formula 16>
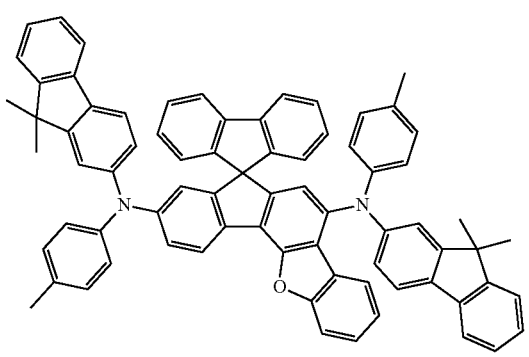
<Chemical Formula 17>
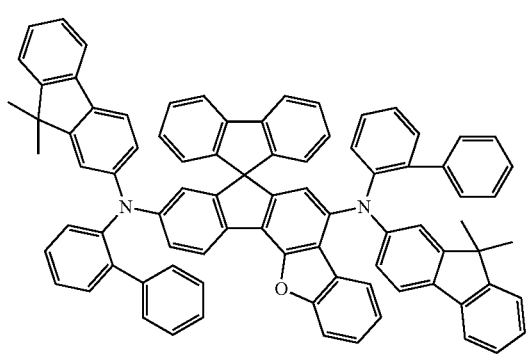
<Chemical Formula 18>
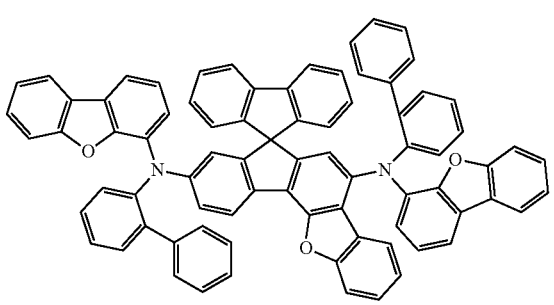

-continued
<Chemical Formula 19>
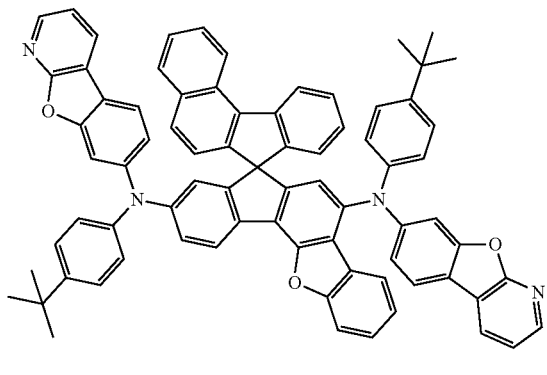
<Chemical Formula 20>
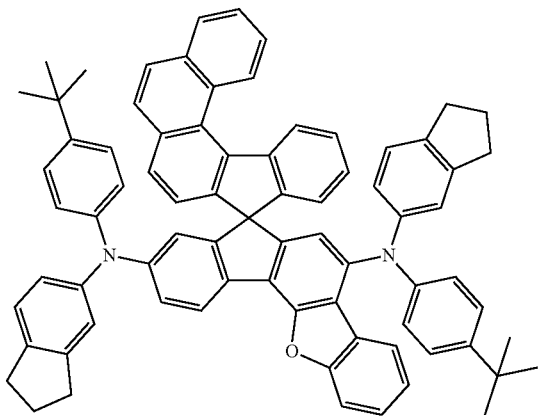
<Chemical Formula 21>
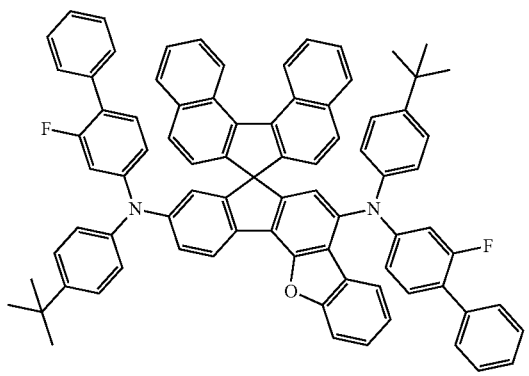
<Chemical Formula 22>
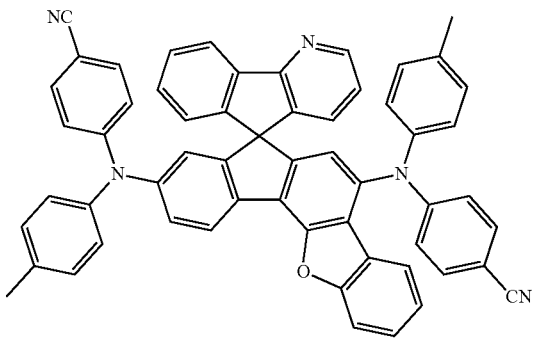
<Chemical Formula 23>
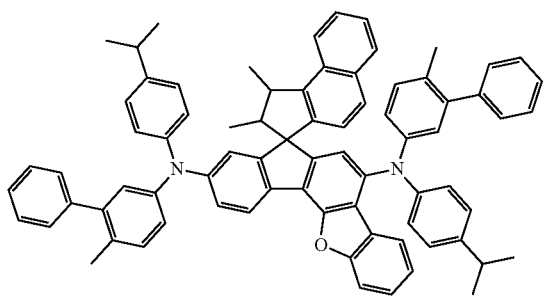
<Chemical Formula 24>
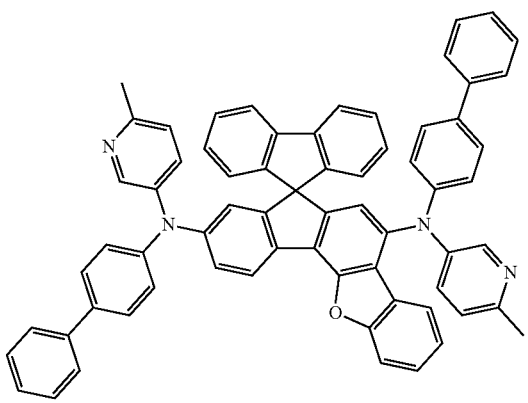

<Chemical Formula 25>
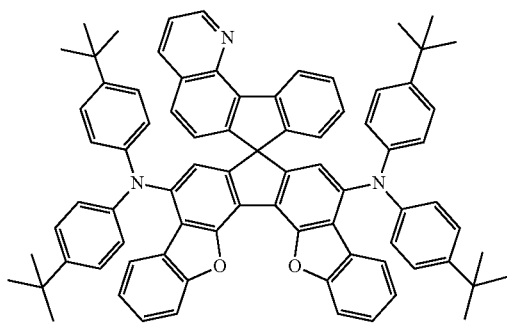
<Chemical Formula 26>
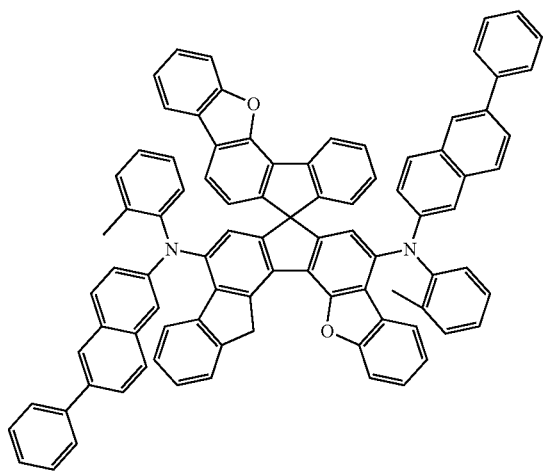
<Chemical Formula 27>
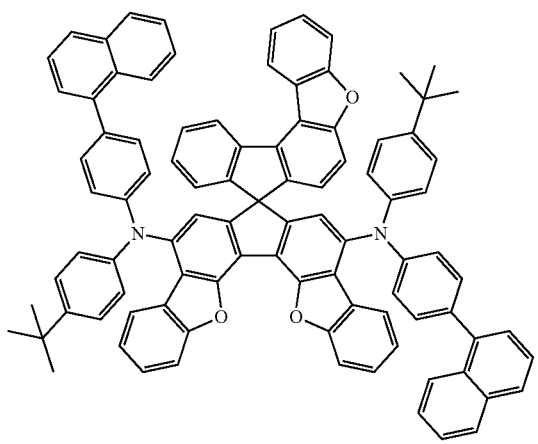
<Chemical Formula 28>
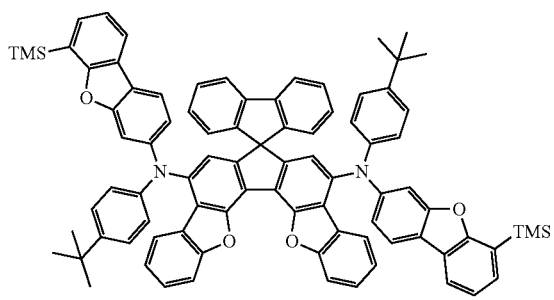
<Chemical Formula 29>
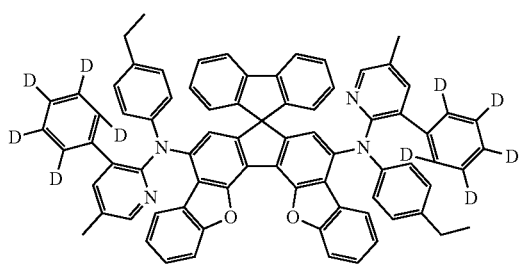
<Chemical Formula 30>
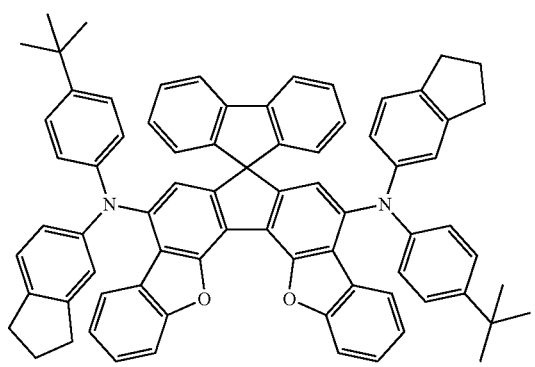

<Chemical Formula 31>
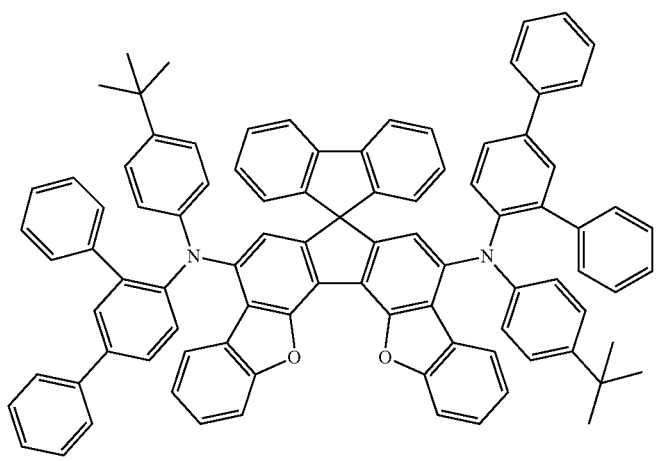
<Chemical Formula 32>
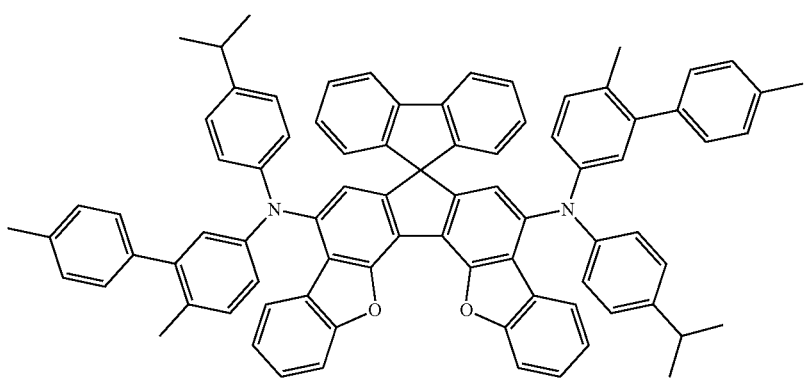
<Chemical Formula 33>
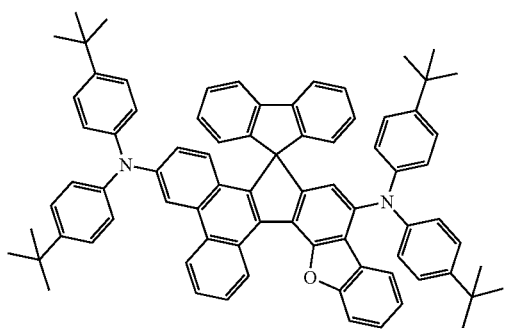
<Chemical Formula 34>
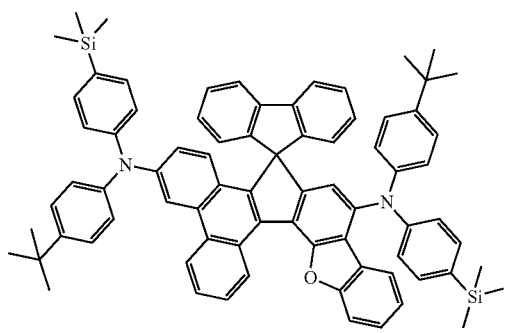

<Chemical Formula 35>
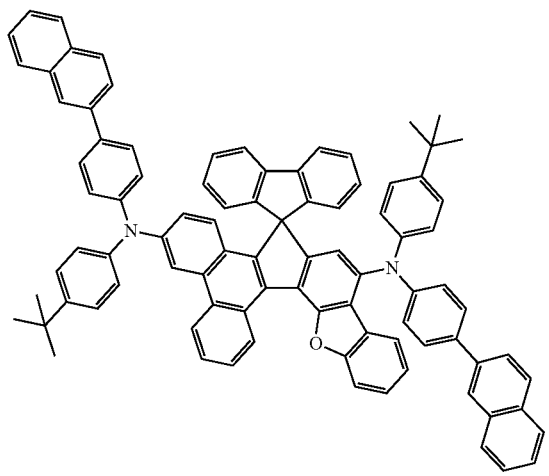
<Chemical Formula 36>
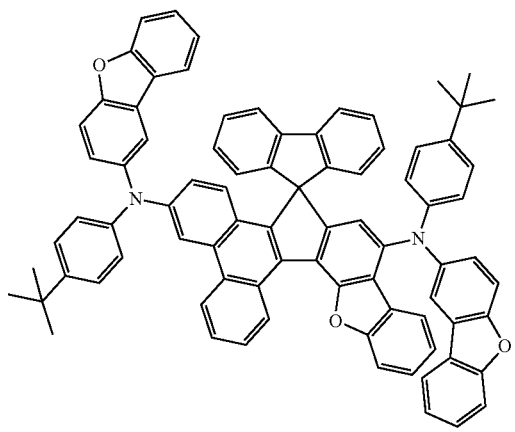
<Chemical Formula 37>
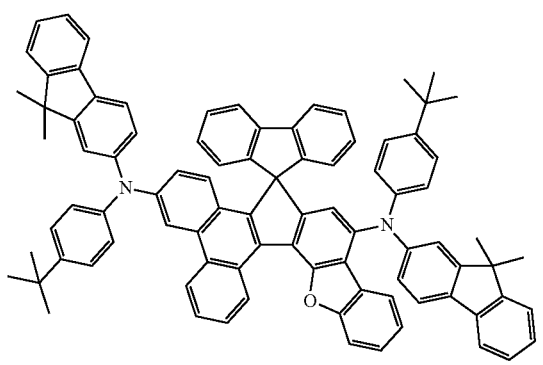
<Chemical Formula 38>
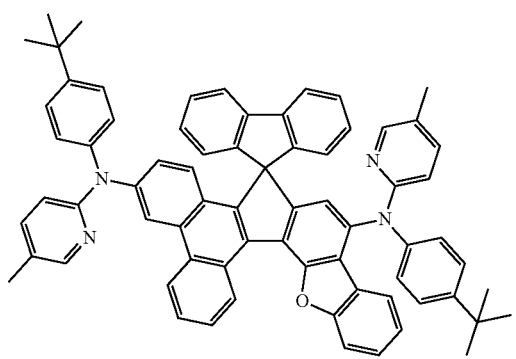
<Chemical Formula 39>
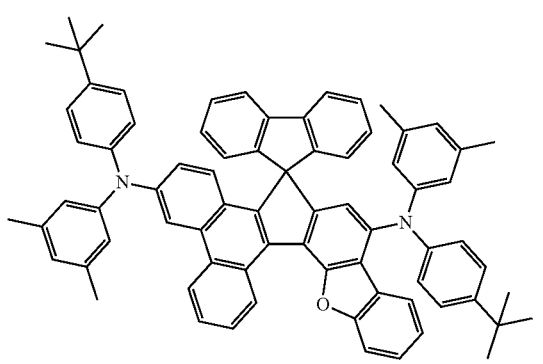
<Chemical Formula 40>
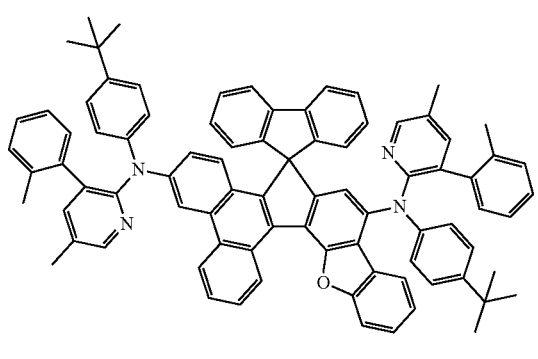
<Chemical Formula 41>
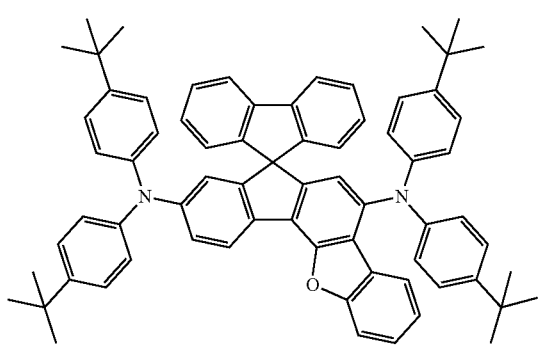
<Chemical Formula 42>
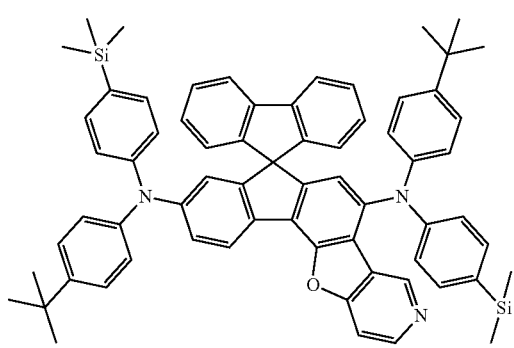

-continued
<Chemical Formula 43>
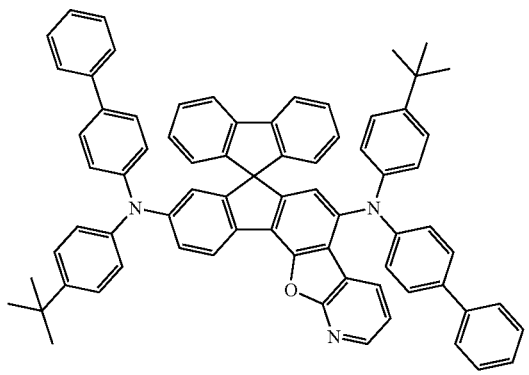
<Chemical Formula 44>
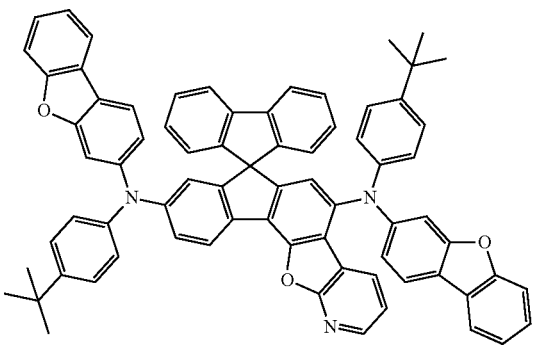
<Chemical Formula 45>
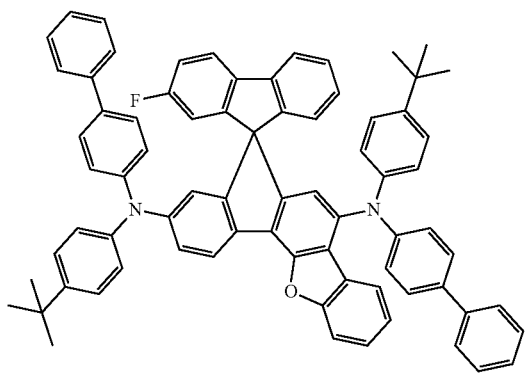
<Chemical Formula 46>
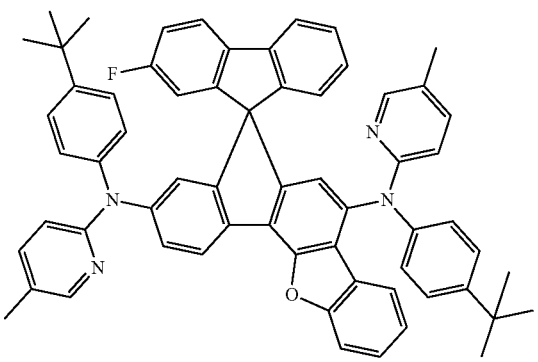
<Chemical Formula 47>
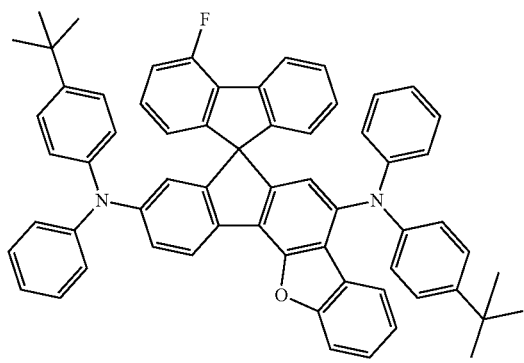
<Chemical Formula 48>
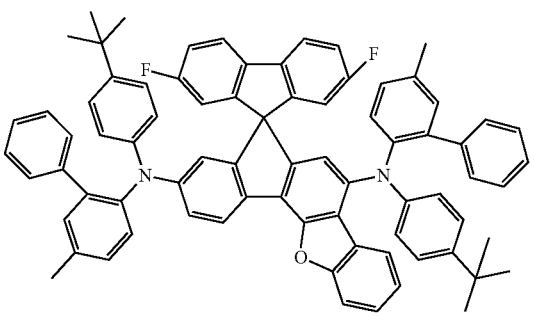
<Chemical Formula 49>
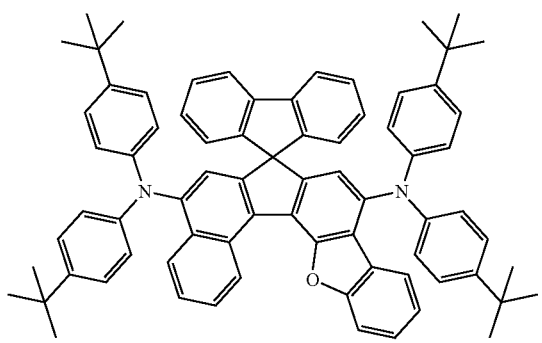
<Chemical Formula 50>
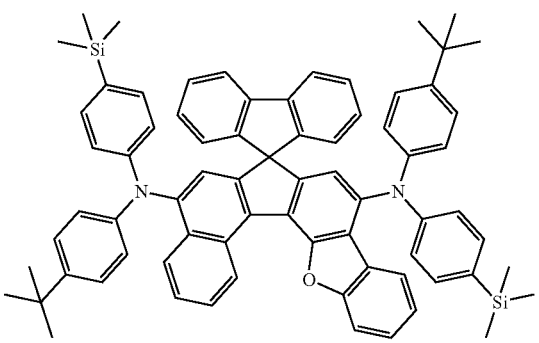

<Chemical Formula 51>
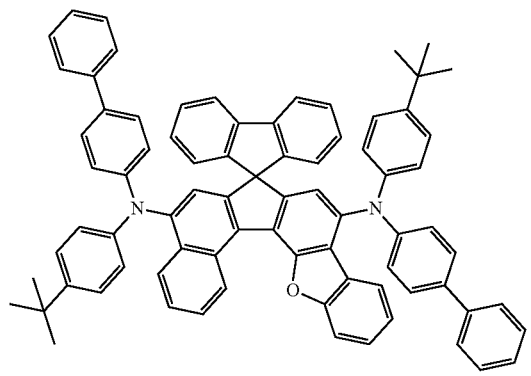
<Chemical Formula 52>
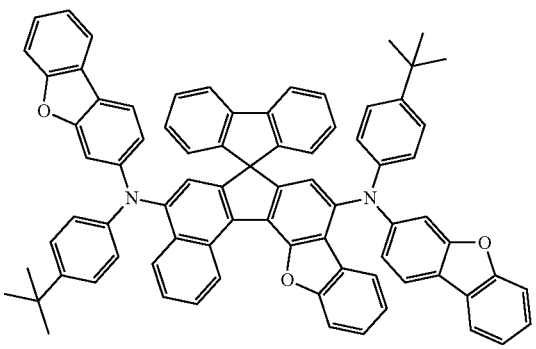
<Chemical Formula 53>
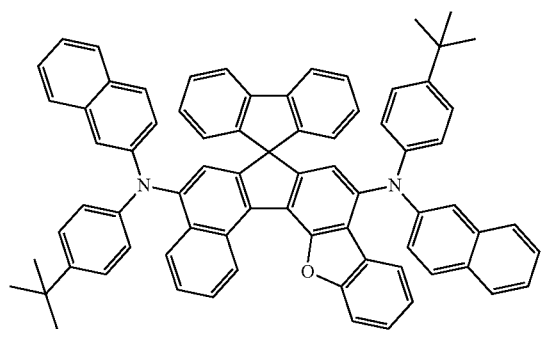
<Chemical Formula 54>
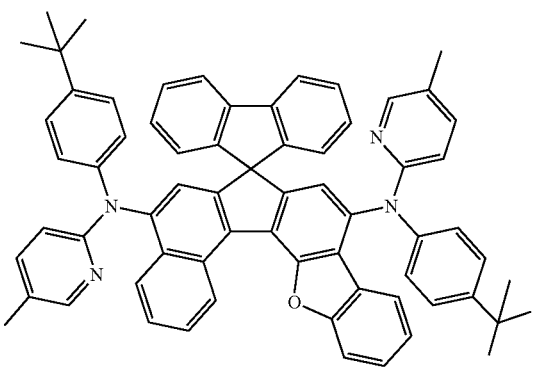
<Chemical Formula 55>
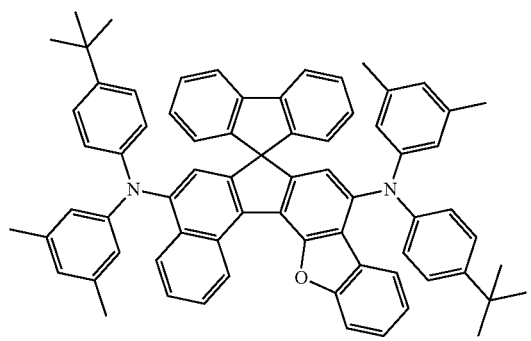
<Chemical Formula 56>
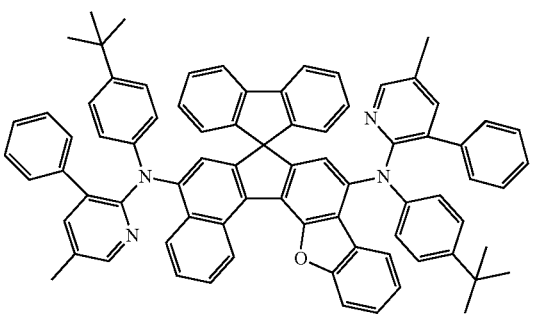
<Chemical Formula 57>
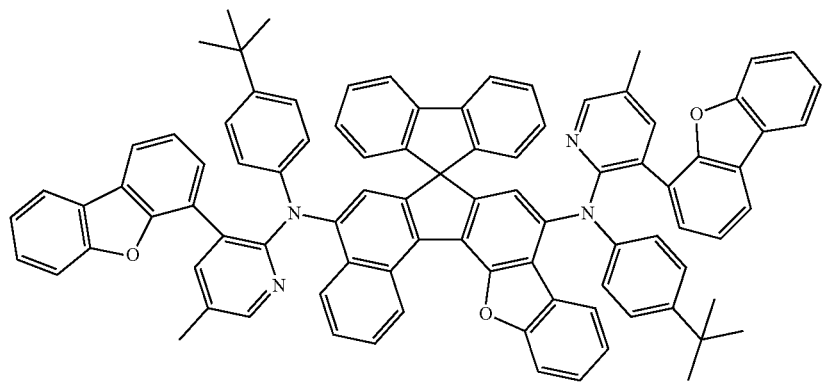

<Chemical Formula 58>
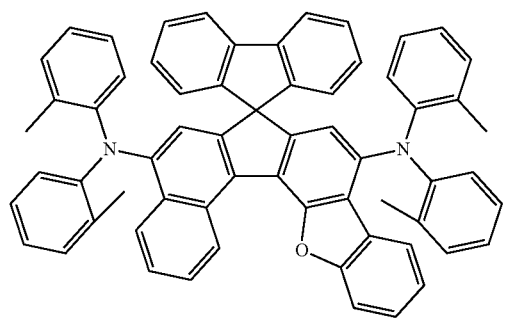
<Chemical Formula 59>
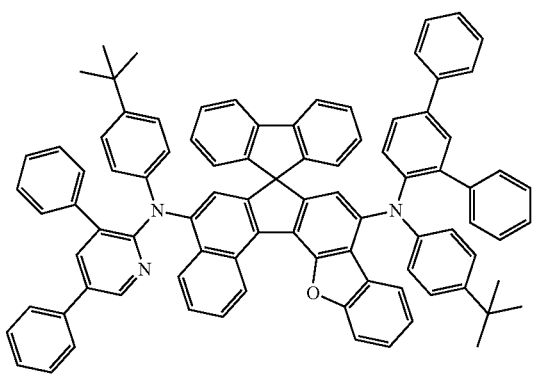
<Chemical Formula 60>
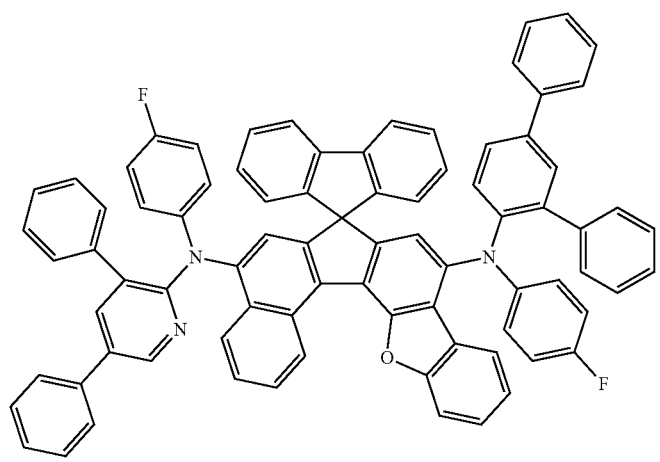
<Chemical Formula 61>
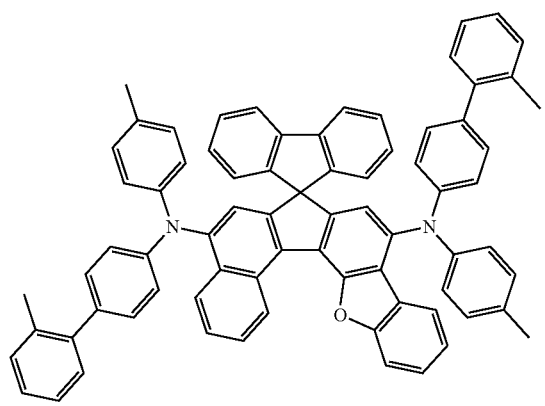
<Chemical Formula 62>
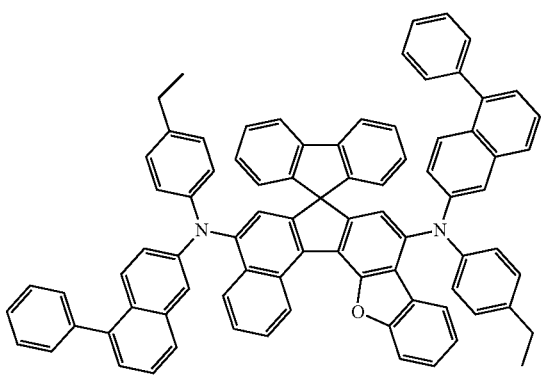
<Chemical Formula 63>
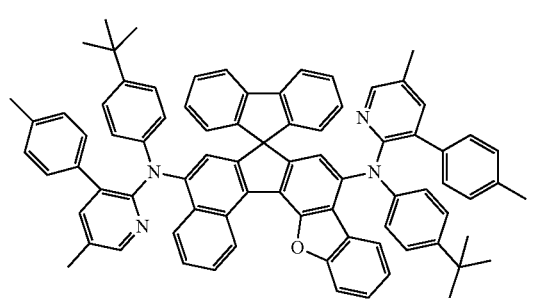
<Chemical Formula 64>
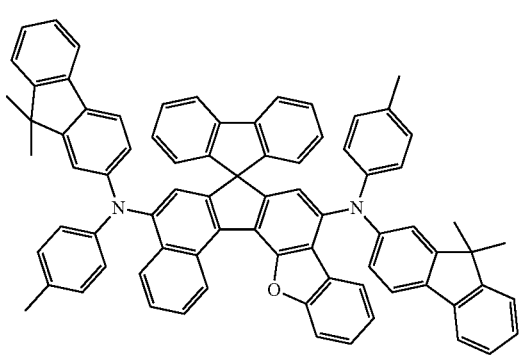

<Chemical Formula 65>
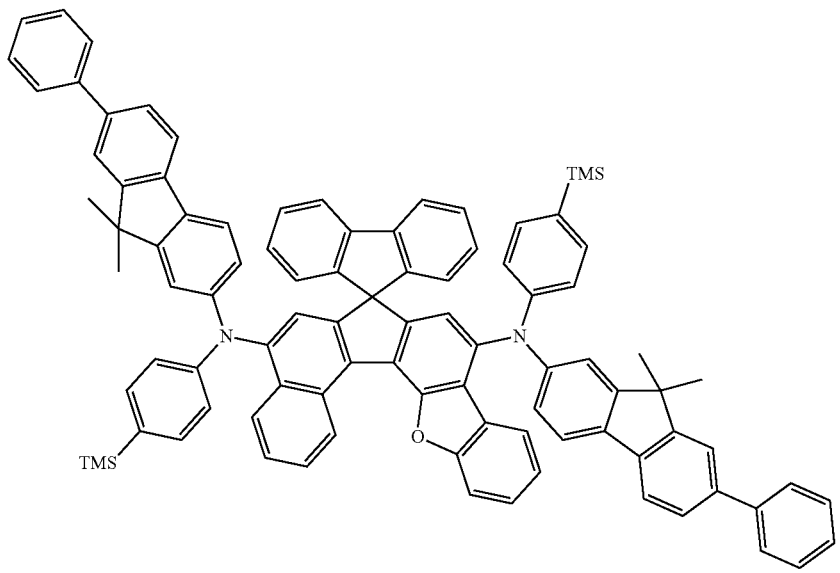
<Chemical Formula 66>
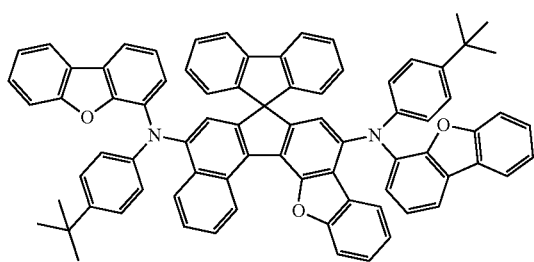
<Chemical Formula 67>
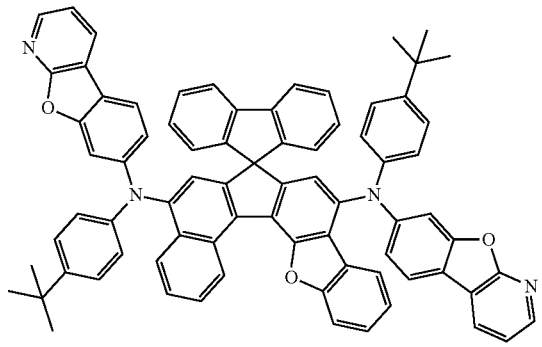
<Chemical Formula 68>
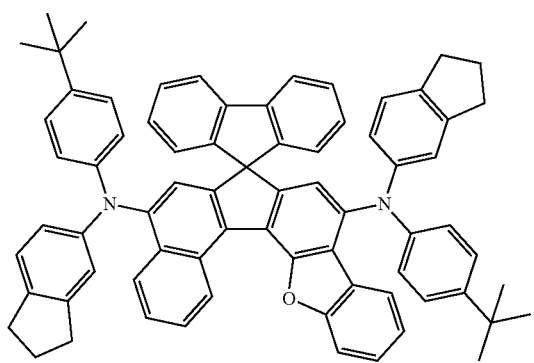
<Chemical Formula 69>
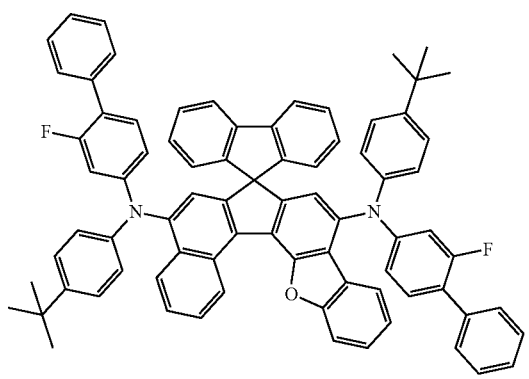

<Chemical Formula 70>
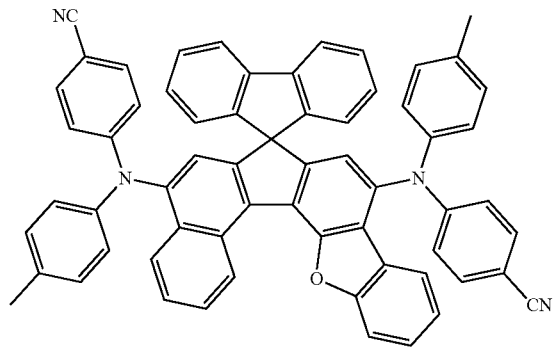
<Chemical Formula 71>
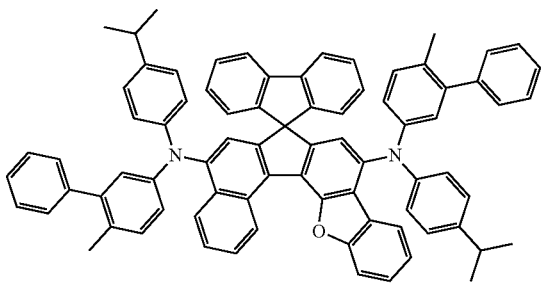
<Chemical Formula 72>
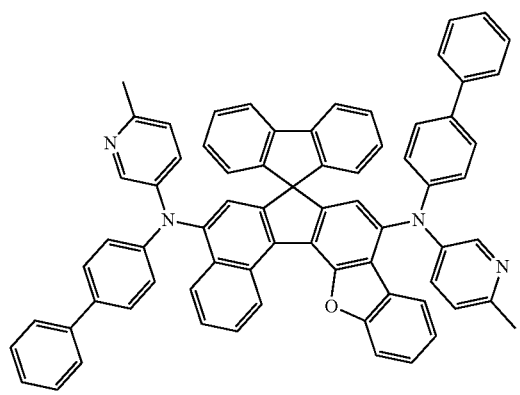
<Chemical Formula 73>
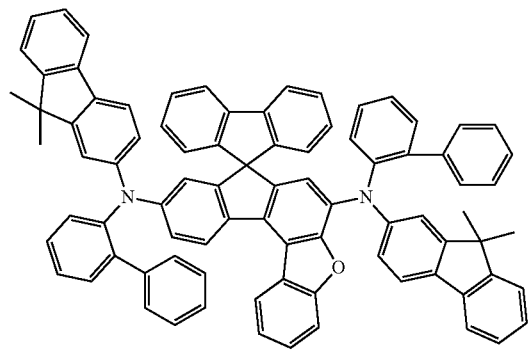
<Chemical Formula 74>
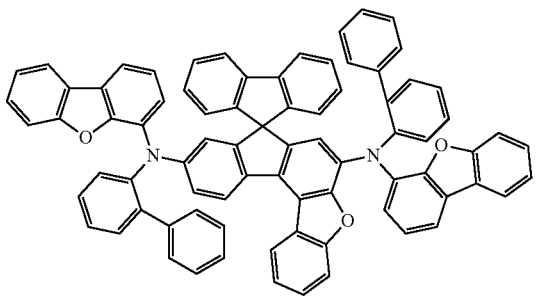
<Chemical Formula 75>
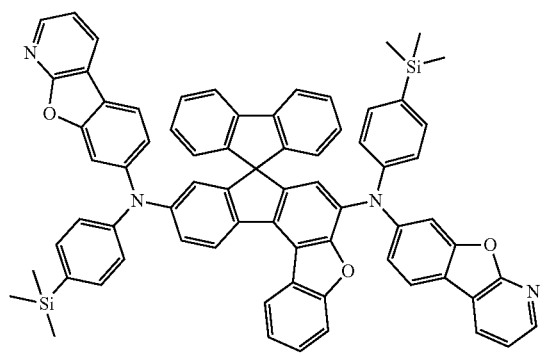
<Chemical Formula 76>
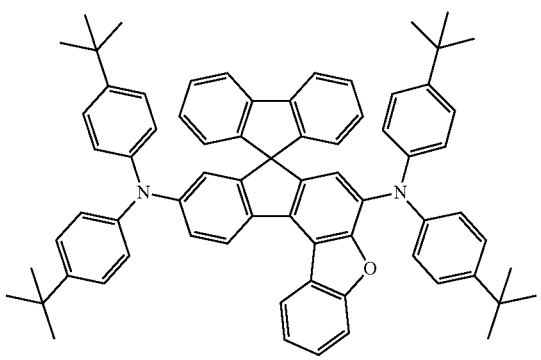

-continued
<Chemical Formula 77>
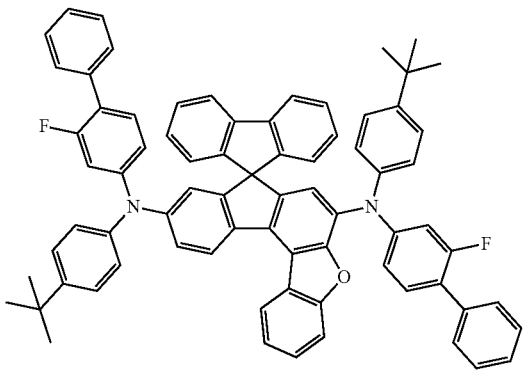
<Chemical Formula 78>
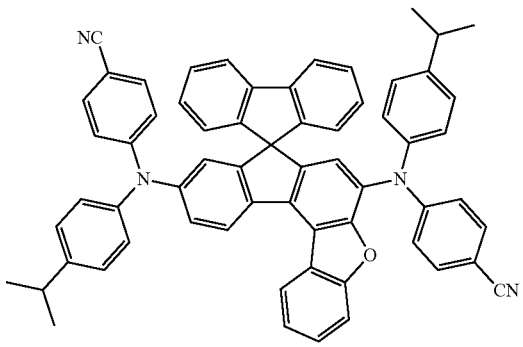
<Chemical Formula 79>
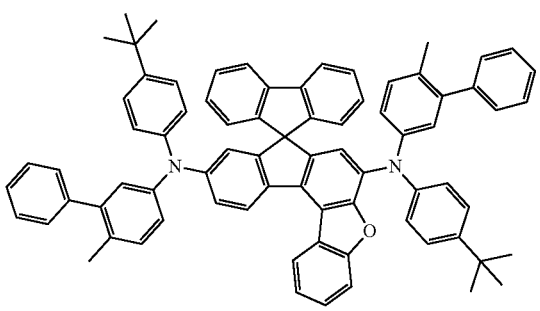
<Chemical Formula 80>
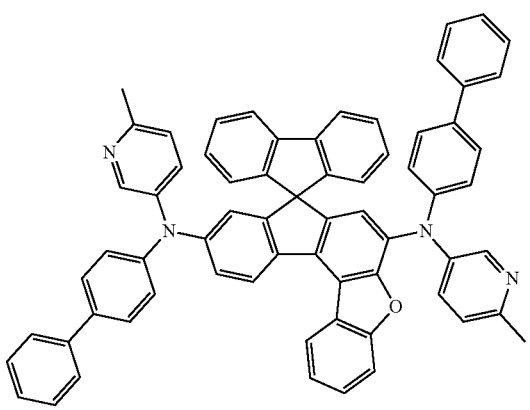
<Chemical Formula 81>
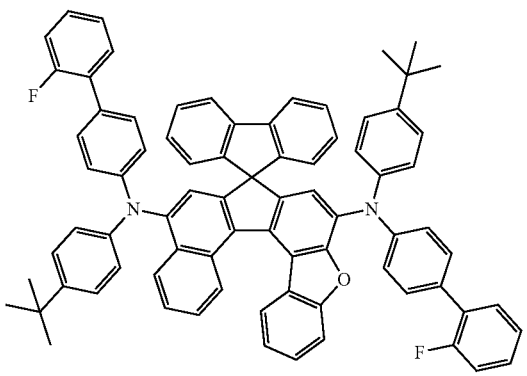
<Chemical Formula 82>
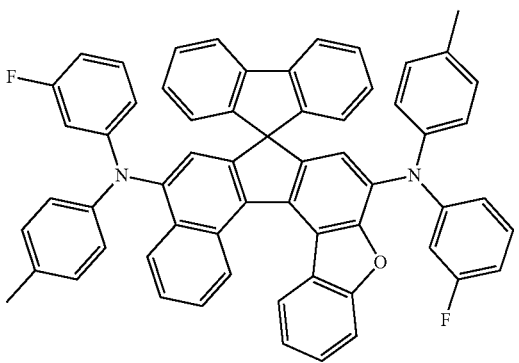
<Chemical Formula 83>
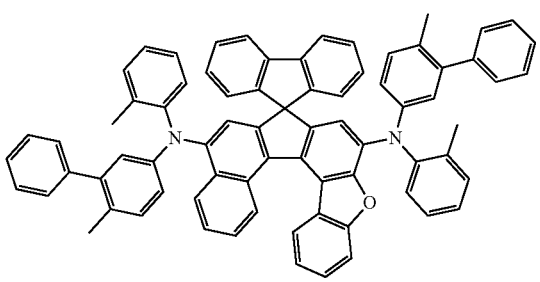
<Chemical Formula 84>
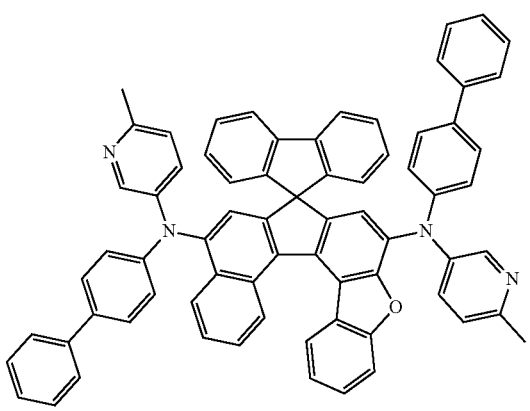

-continued
<Chemical Formula 85>
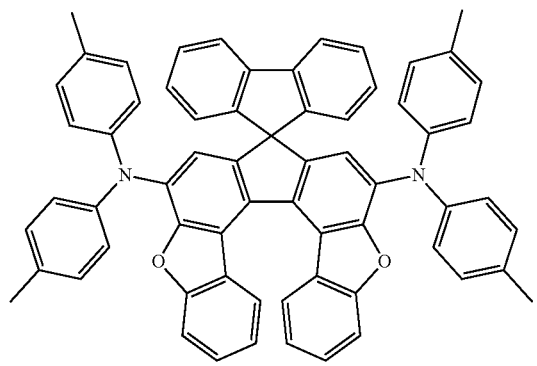
<Chemical Formula 86>
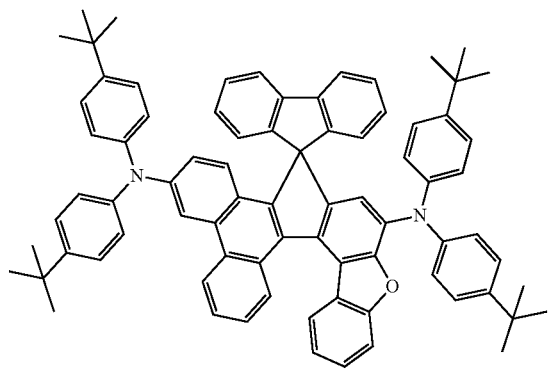
<Chemical Formula 87>
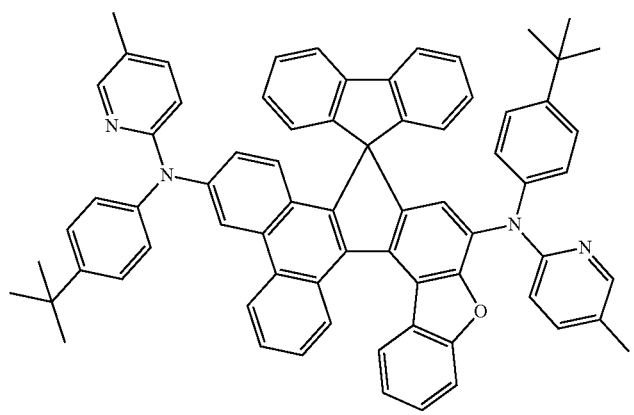
<Chemical Formula 88>
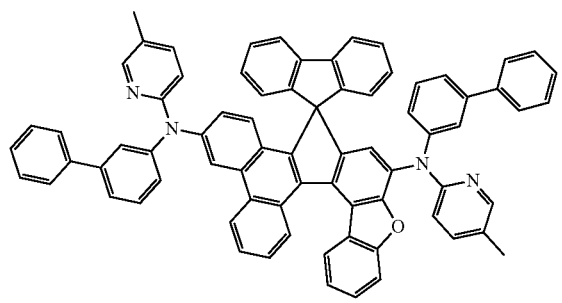
<Chemical Formula 89>
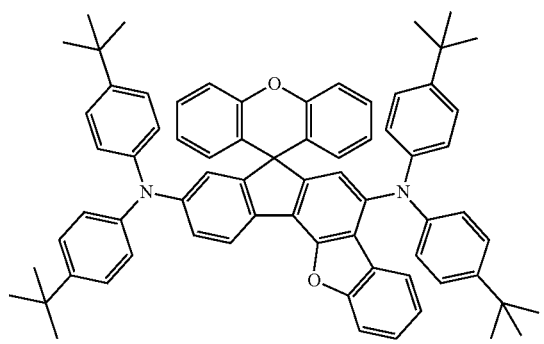
<Chemical Formula 90>
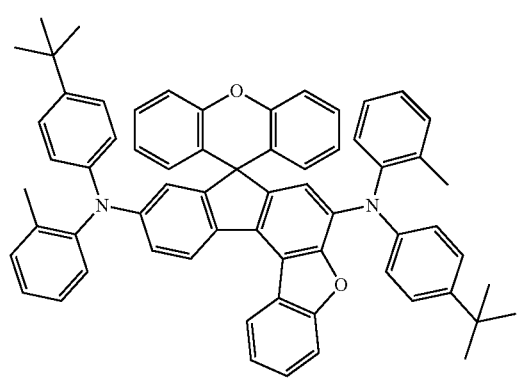
<Chemical Formula 91>
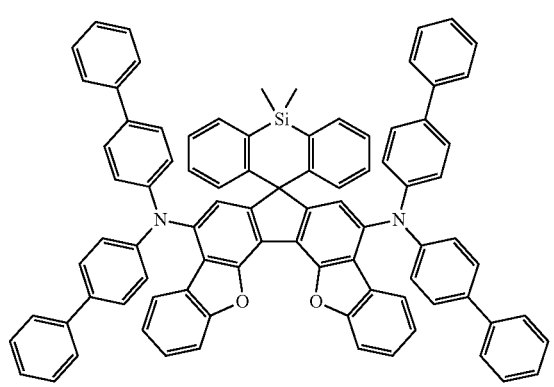

<Chemical Formula 92>
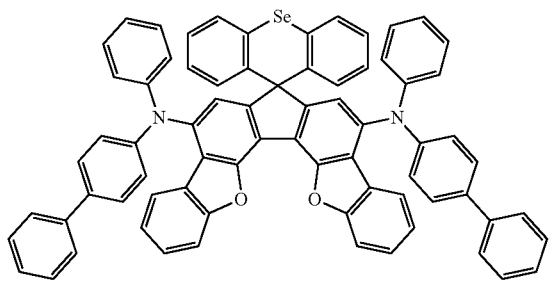
<Chemical Formula 93>
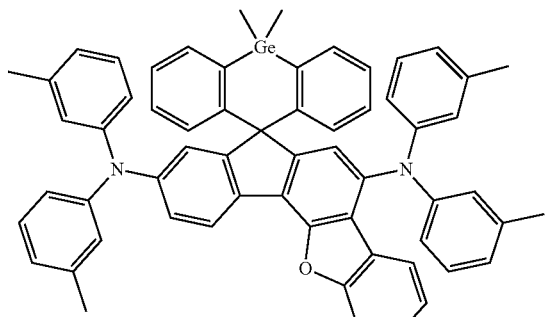
<Chemical Formula 94>
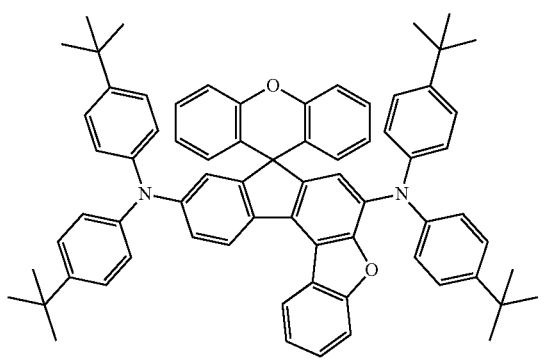
<Chemical Formula 95>
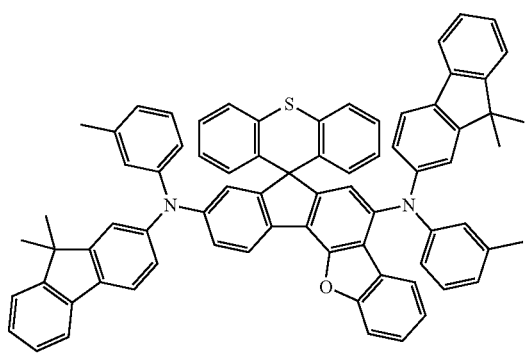
<Chemical Formula 96>
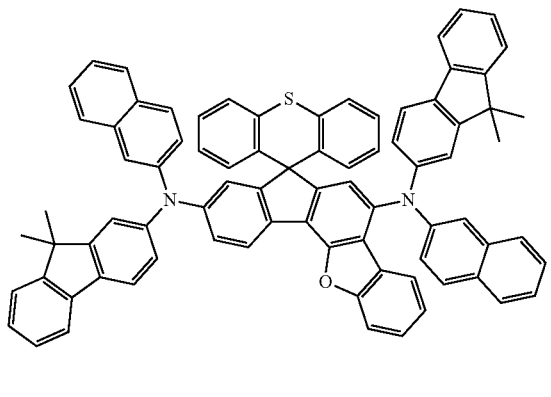
<Chemical Formula 97>
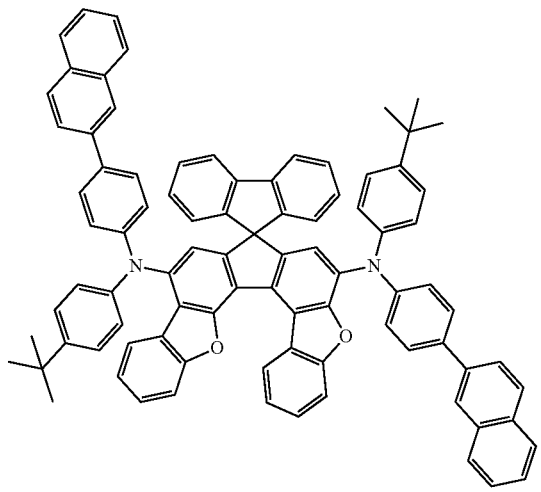
<Chemical Formula 98>
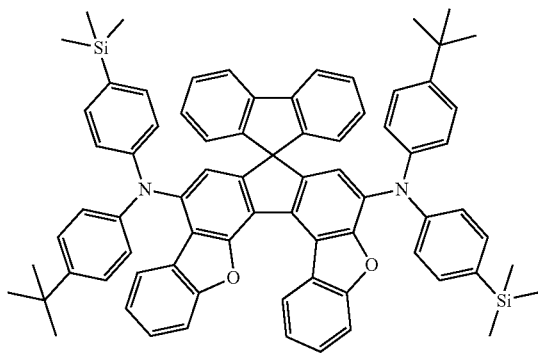
<Chemical Formula 99>
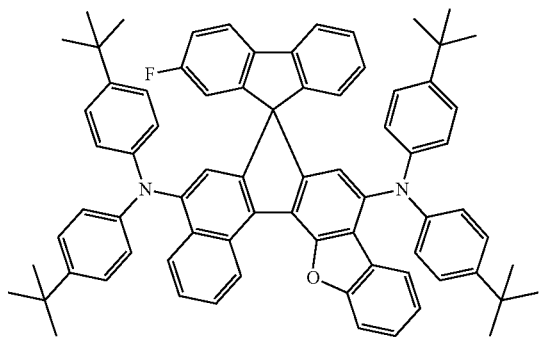

-continued
<Chemical Formula 100>
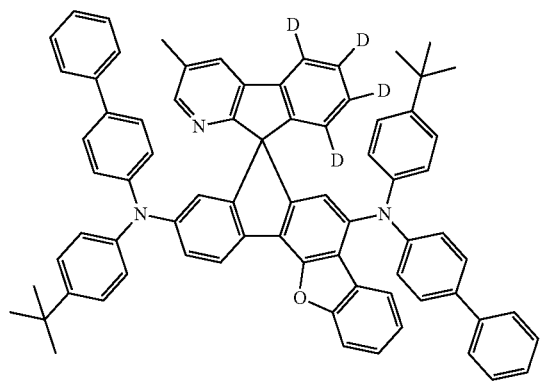
<Chemical Formula 101>
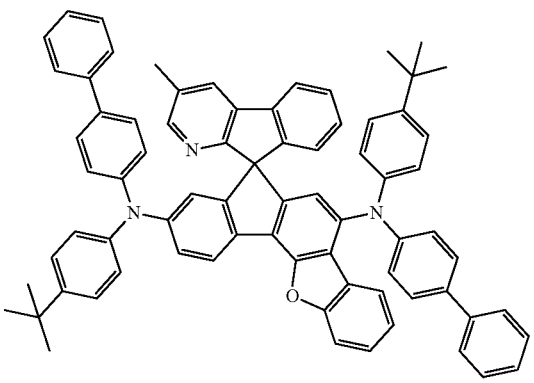
<Chemical Formula 102>
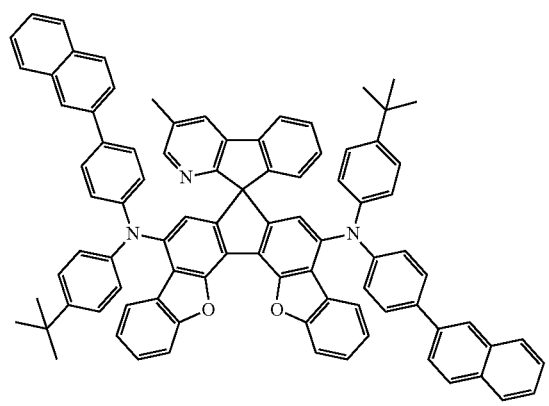
<Chemical Formula 103>
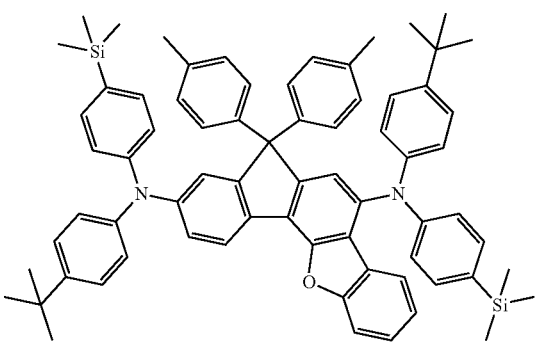
<Chemical Formula 104>
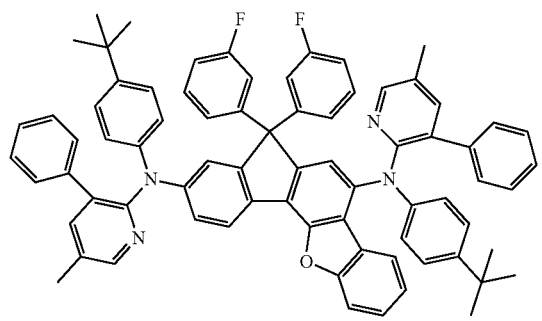
<Chemical Formula 105>
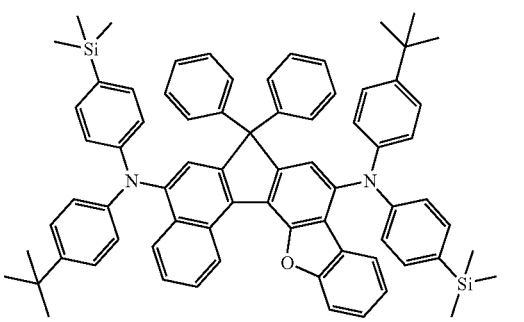
<Chemical Formula 106>
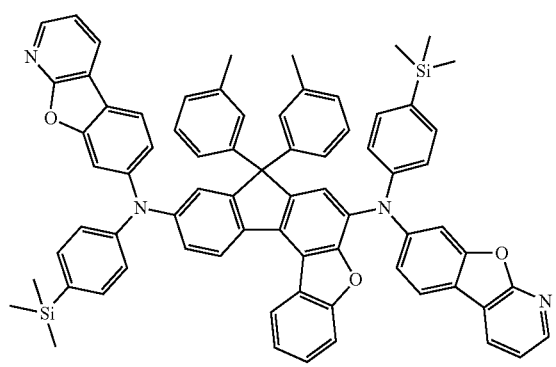
<Chemical Formula 107>
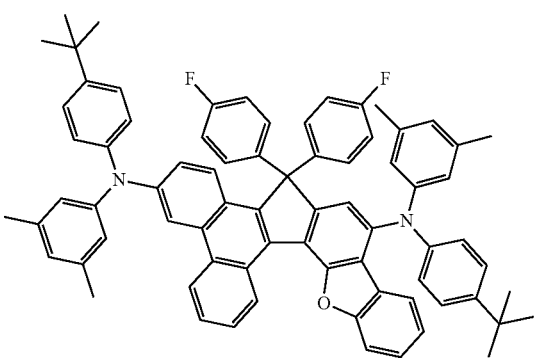

<Chemical Formula 108>
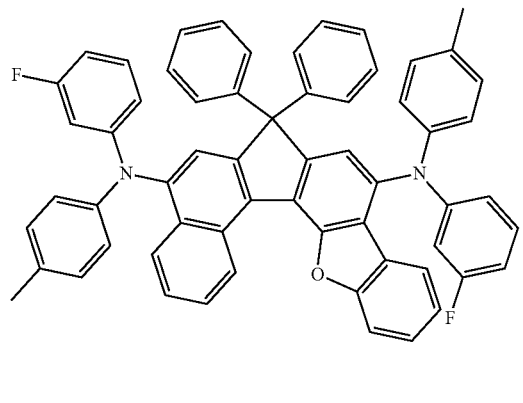
<Chemical Formula 109>
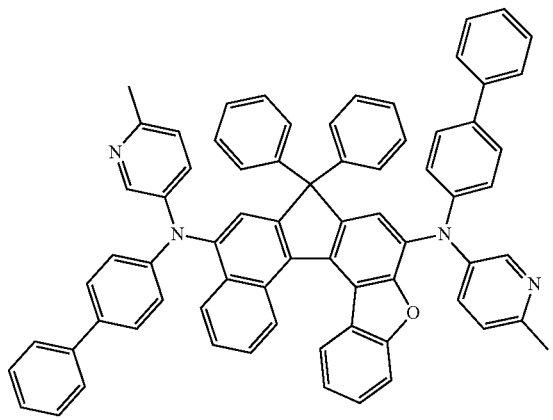
<Chemical Formula 110>
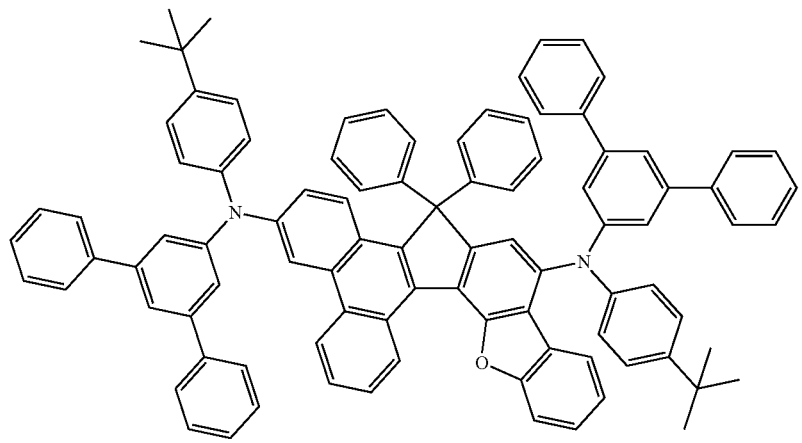
<Chemical Formula 111>
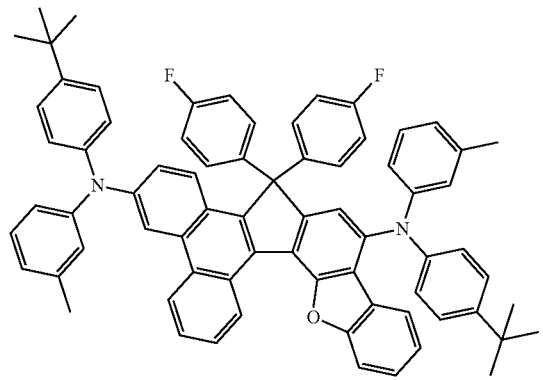
<Chemical Formula 112>
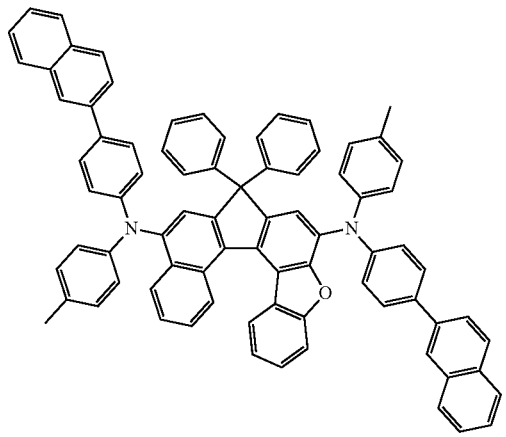

-continued
<Chemical Formula 113>
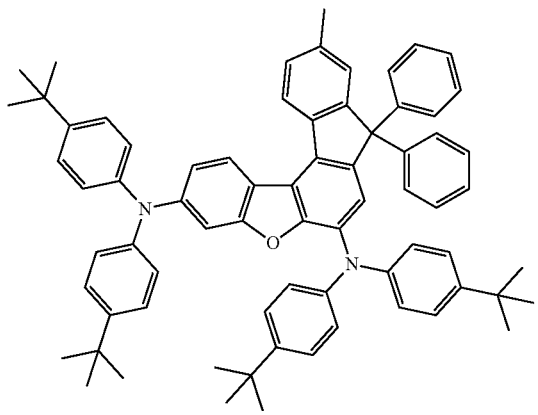
<Chemical Formula 114>
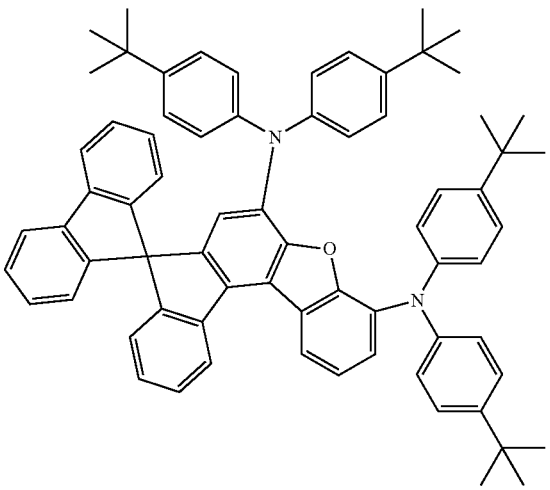
<Chemical Formula 115>
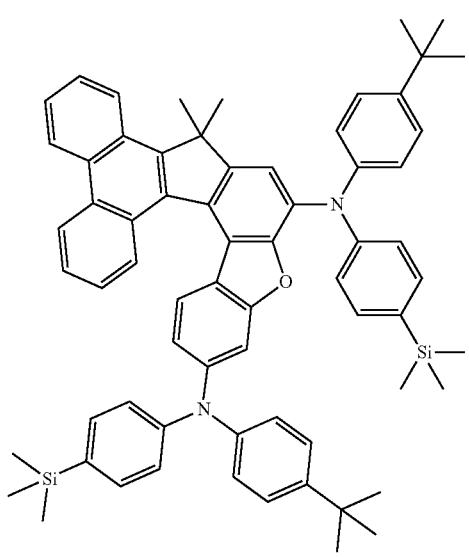
<Chemical Formula 116>
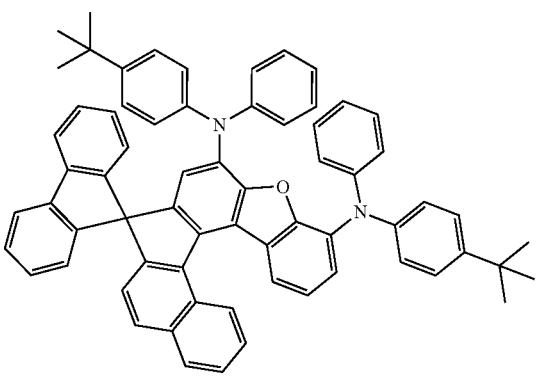
<Chemical Formula 117>
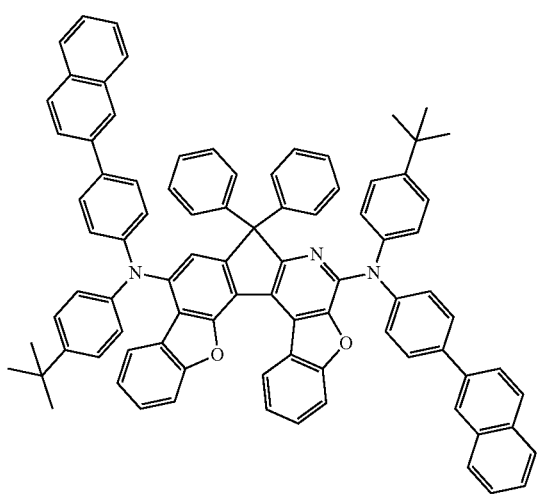
<Chemical Formula 118>
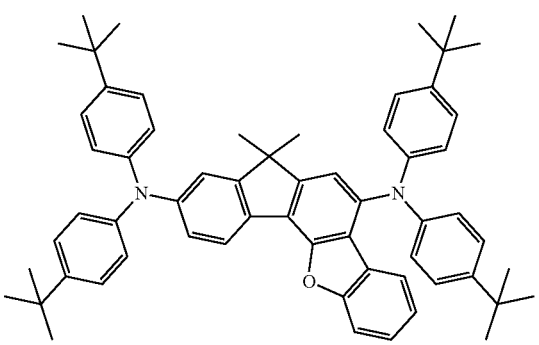

-continued
<Chemical Formula 119>
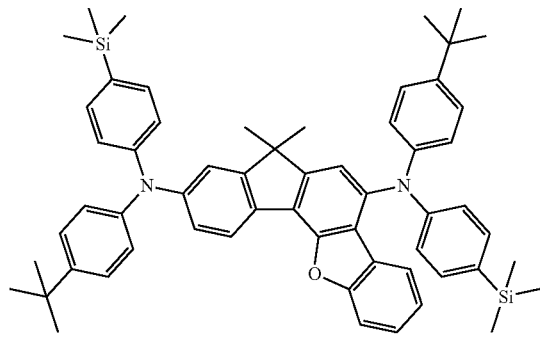
<Chemical Formula 120>
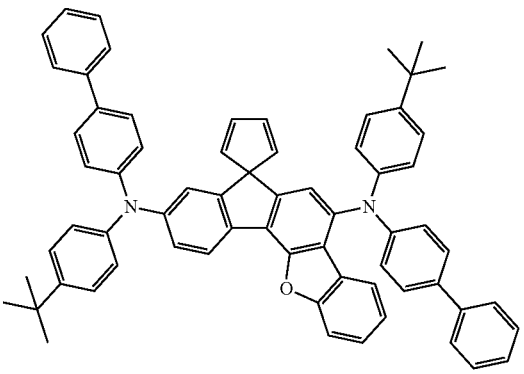
<Chemical Formula 121>
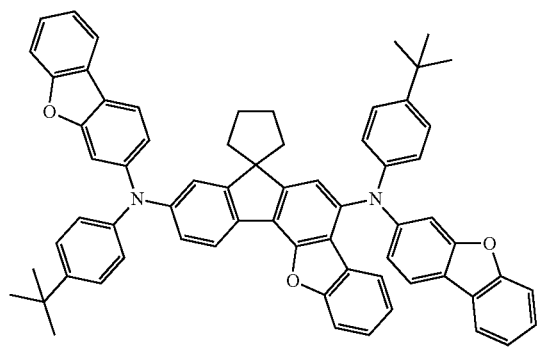
<Chemical Formula 122>
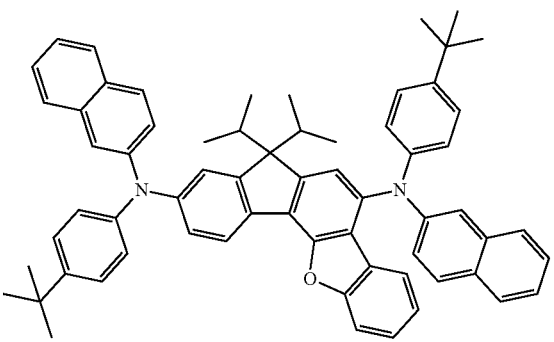
<Chemical Formula 123>
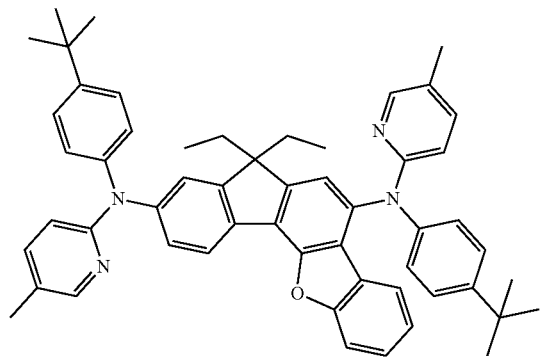
<Chemical Formula 124>
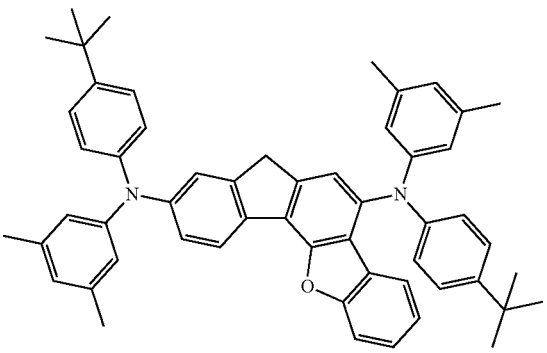
<Chemical Formula 125>
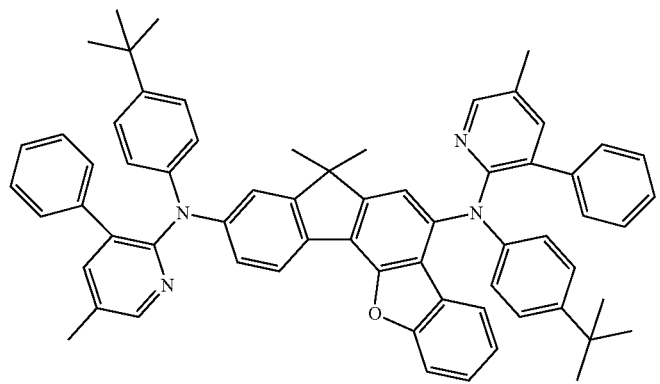

<Chemical Formula 126>
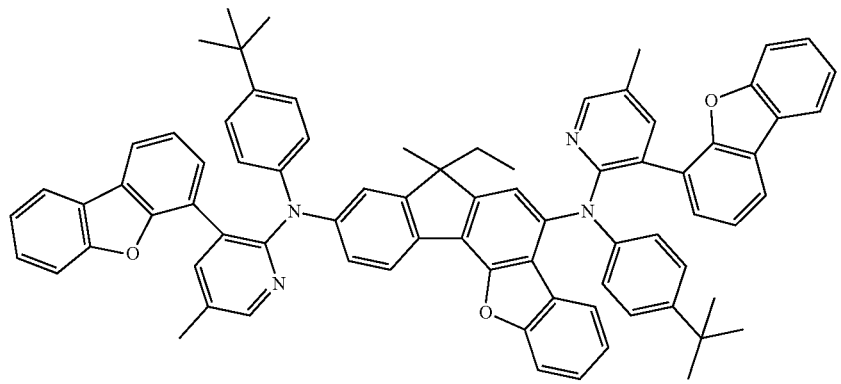
<Chemical Formula 127>
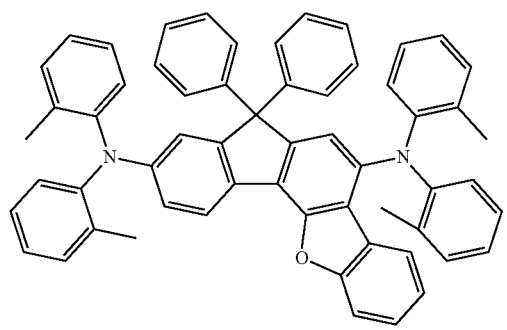
<Chemical Formula 128>
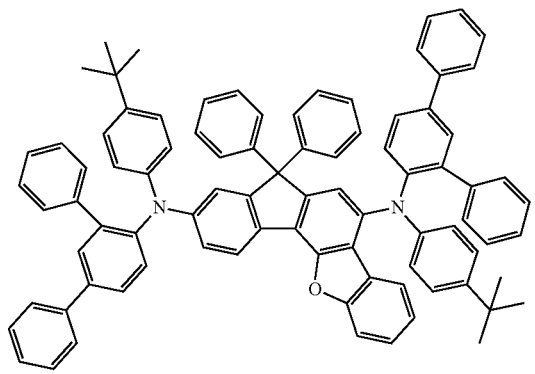
<Chemical Formula 129>
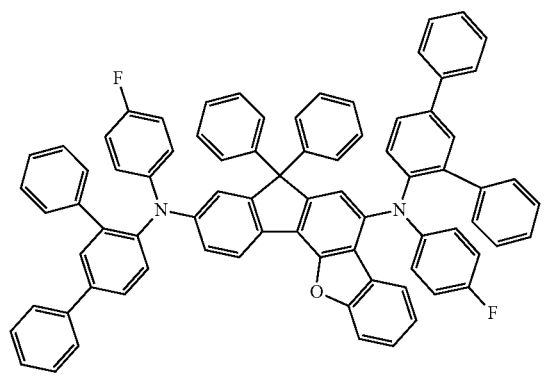
<Chemical Formula 130>
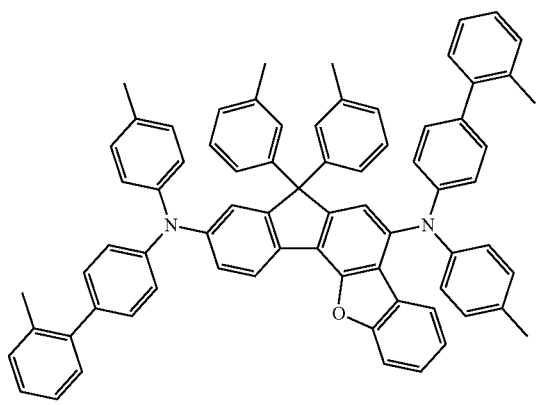

<Chemical Formula 131>
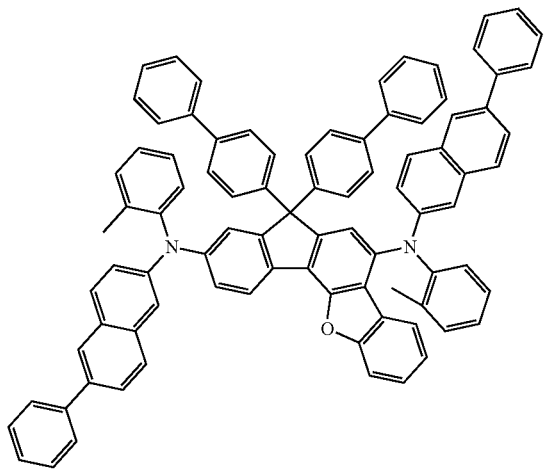
<Chemical Formula 132>
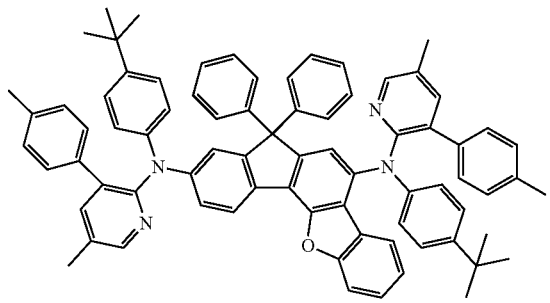
<Chemical Formula 133>
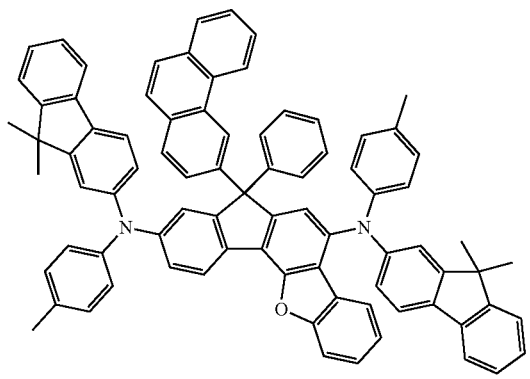
<Chemical Formula 134>
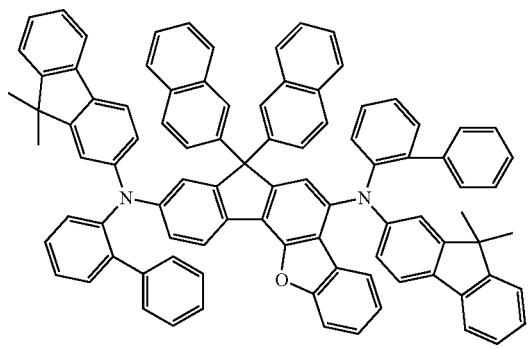
<Chemical Formula 135>
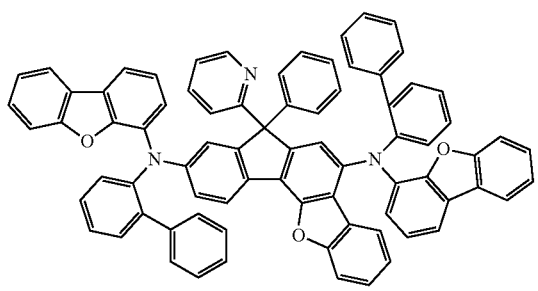
<Chemical Formula 136>
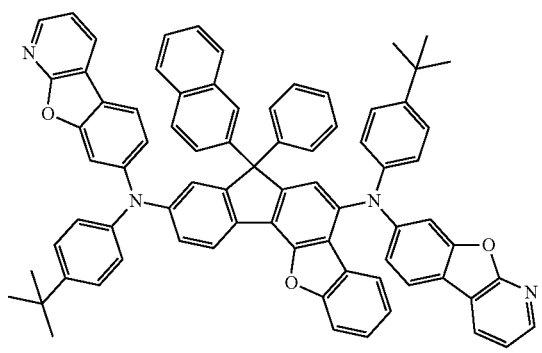
<Chemical Formula 137>
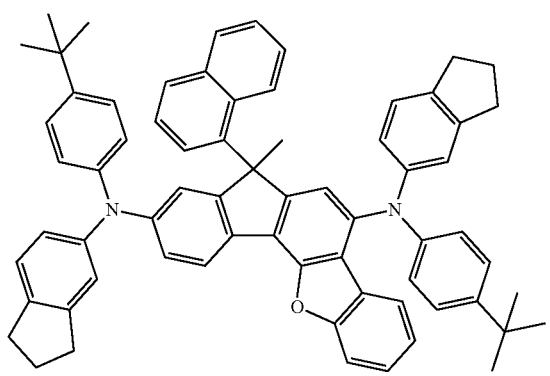
<Chemical Formula 138>
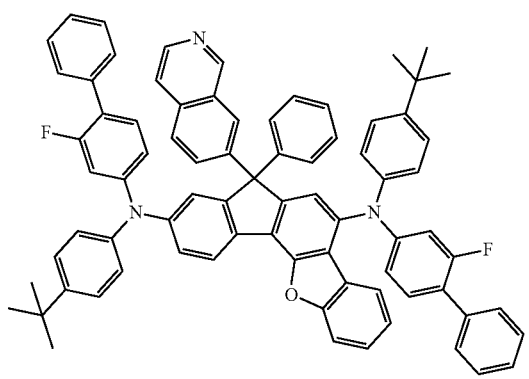

-continued
<Chemical Formula 139>
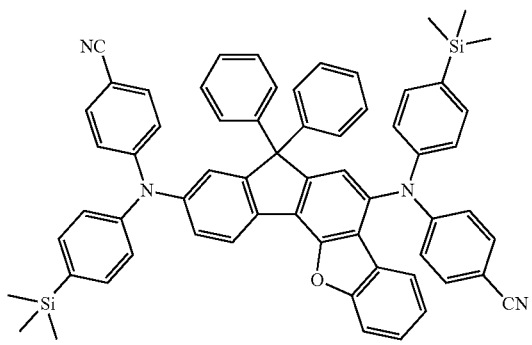
<Chemical Formula 140>
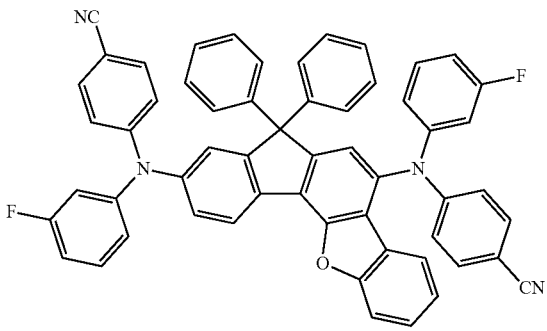
<Chemical Formula 141>
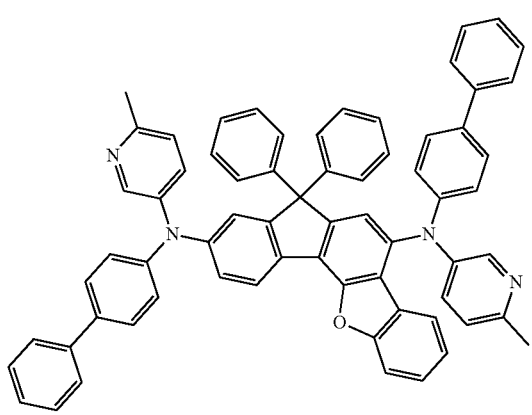
<Chemical Formula 142>
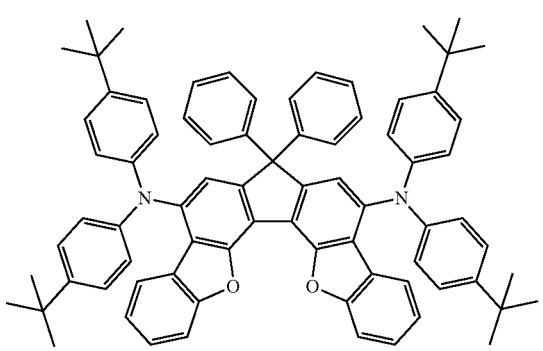
<Chemical Formula 143>
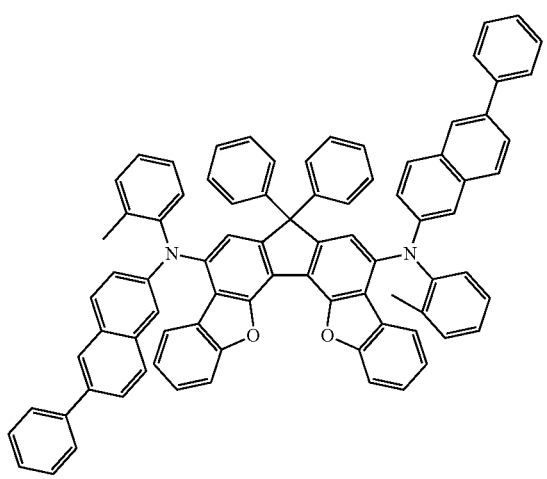
<Chemical Formula 144>
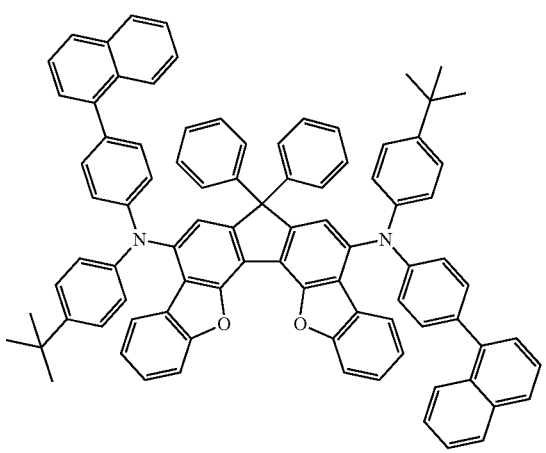
<Chemical Formula 145>
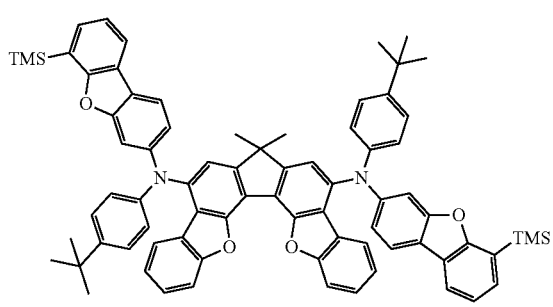
<Chemical Formula 146>
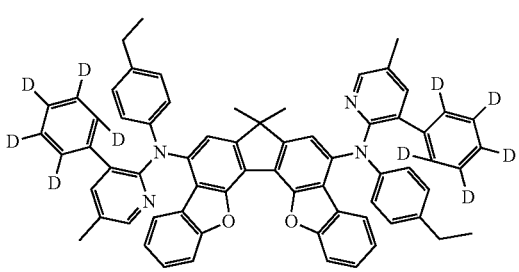

<Chemical Formula 147>
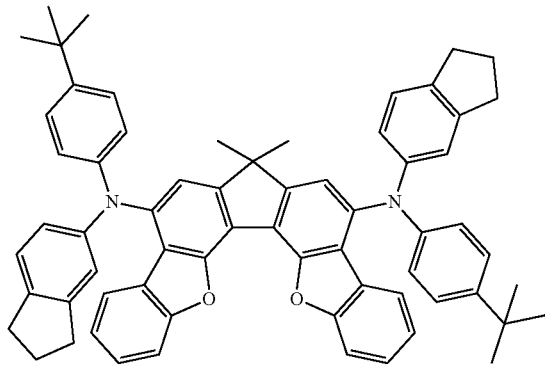
<Chemical Formula 148>
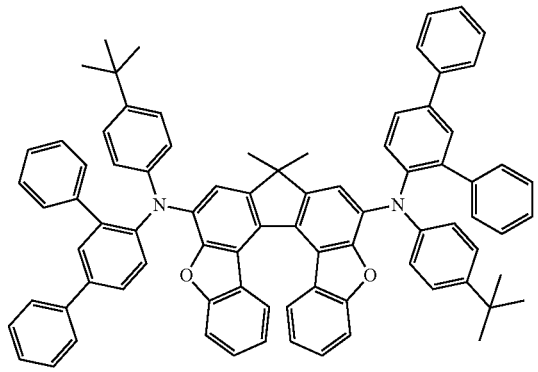
<Chemical Formula 149>
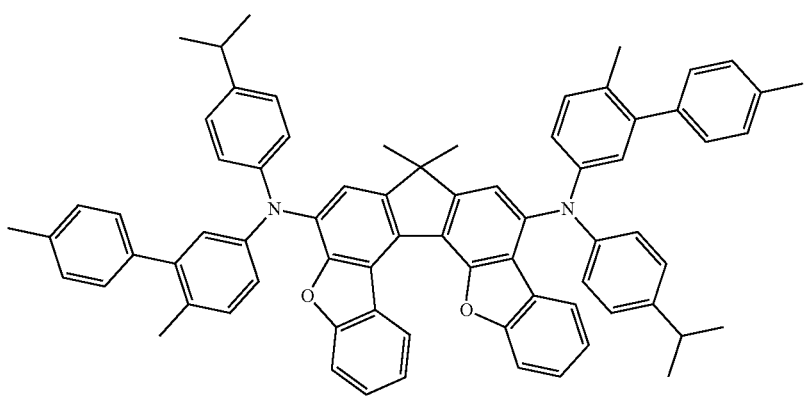
<Chemical Formula 150>
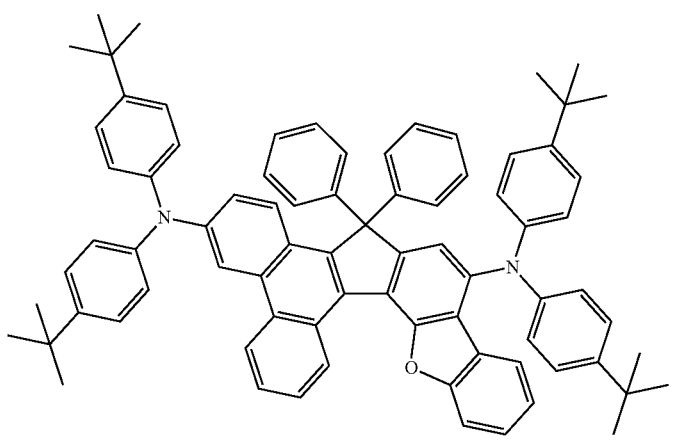

-continued
<Chemical Formula 151>
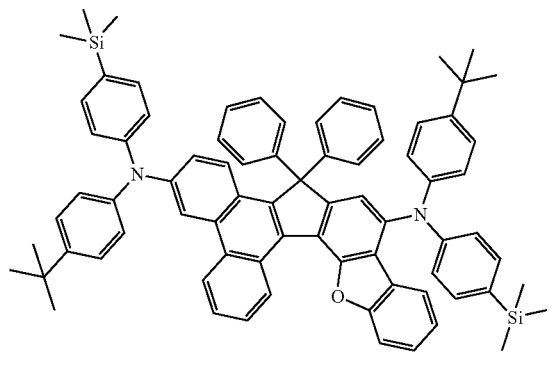
<Chemical Formula 152>
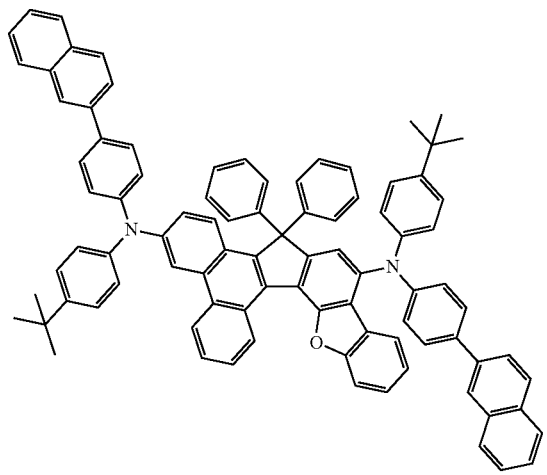
<Chemical Formula 153>
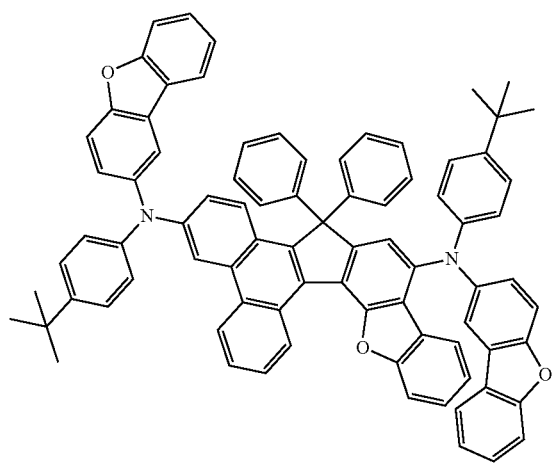
<Chemical Formula 154>
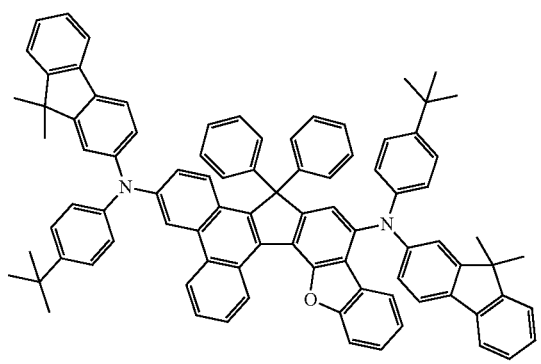
<Chemical Formula 155>
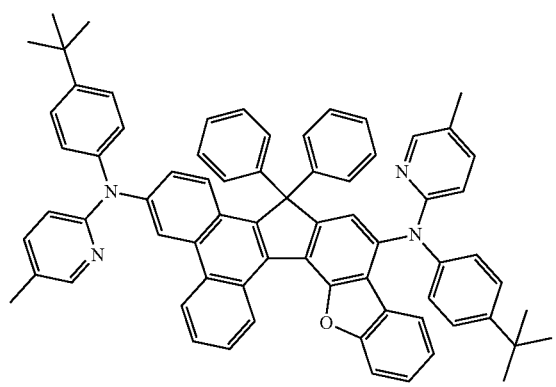
<Chemical Formula 156>
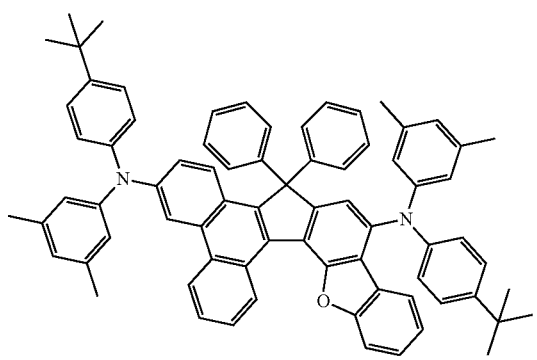

<Chemical Formula 157>
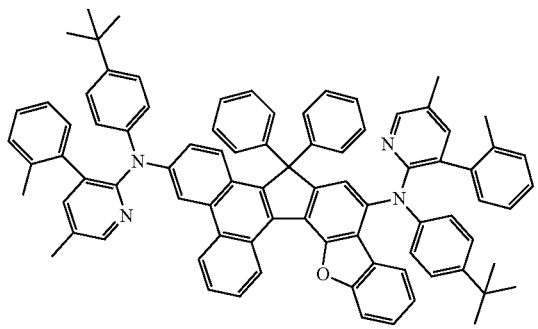
<Chemical Formula 158>
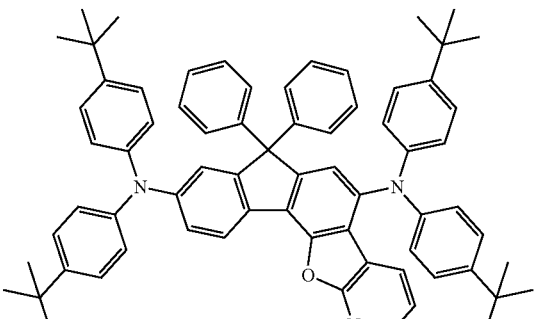
<Chemical Formula 159>
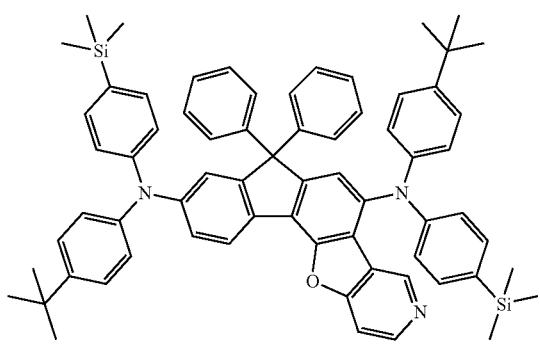
<Chemical Formula 160>
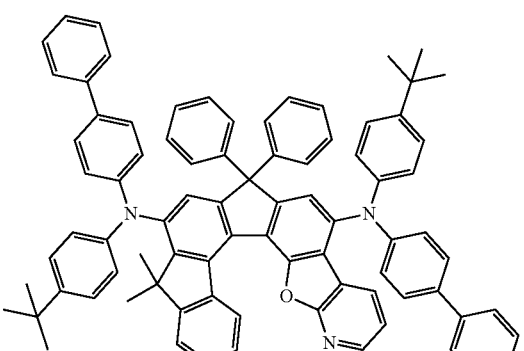
<Chemical Formula 161>
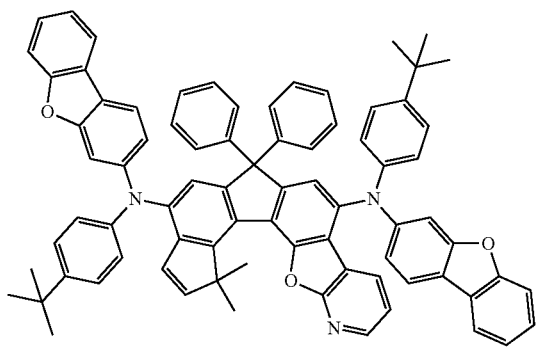
<Chemical Formula 162>
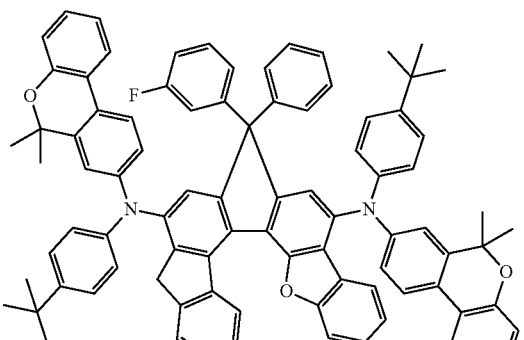
<Chemical Formula 163>
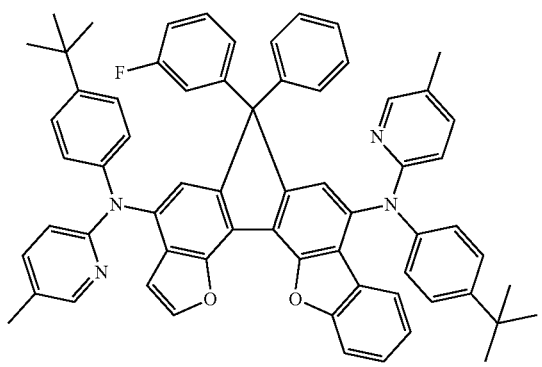
<Chemical Formula 164>
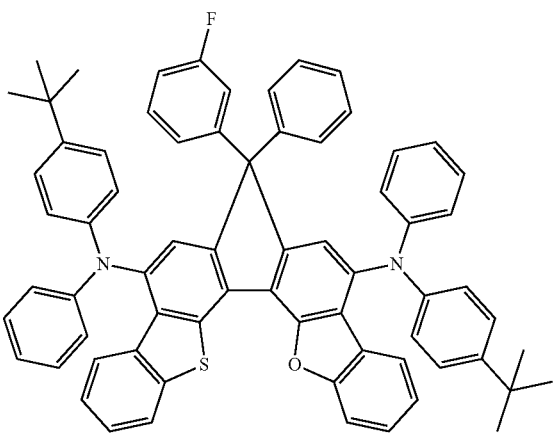

<Chemical Formula 165>
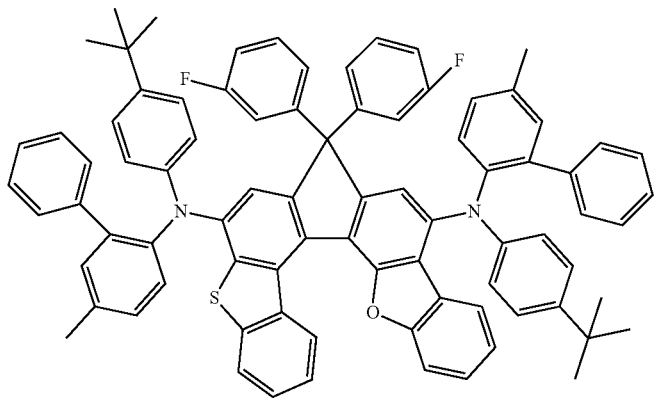
<Chemical Formula 166>
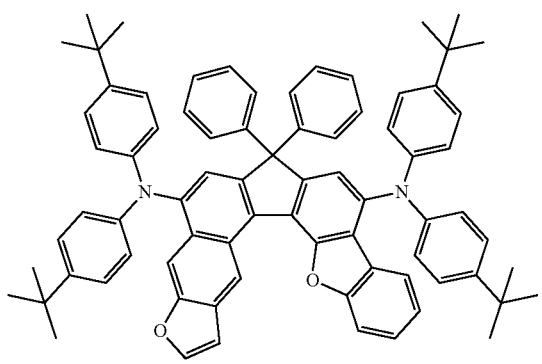
<Chemical Formula 167>
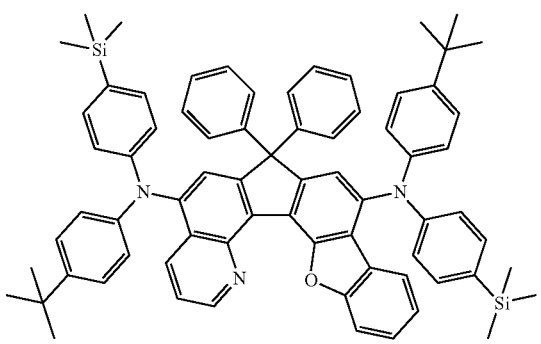
<Chemical Formula 168>
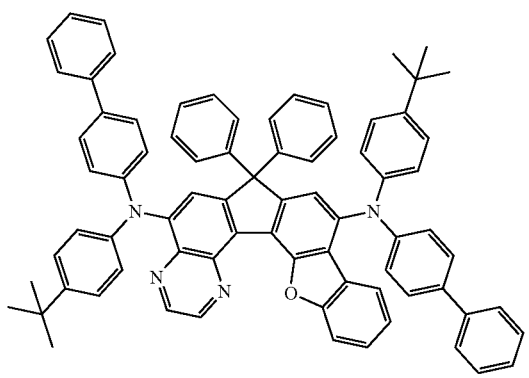
<Chemical Formula 169>
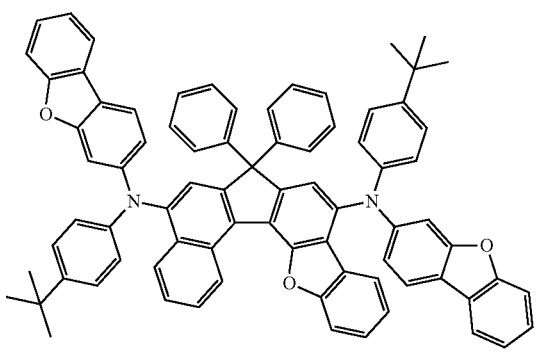
<Chemical Formula 170>
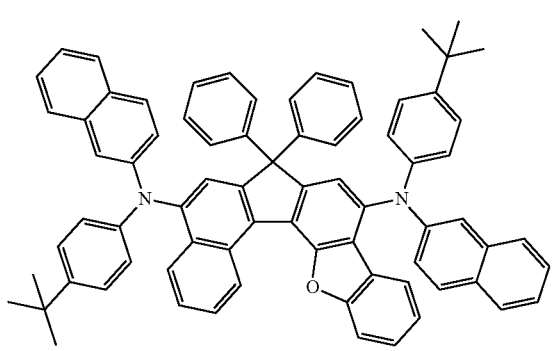
<Chemical Formula 171>
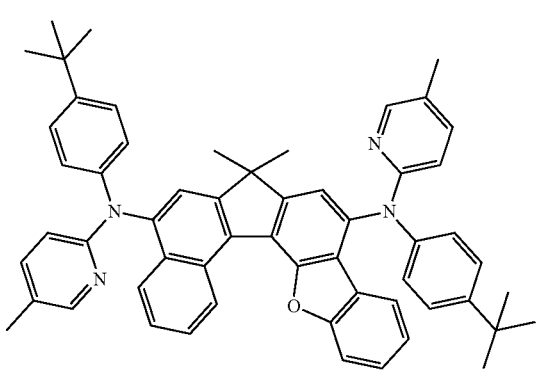

<Chemical Formula 172>
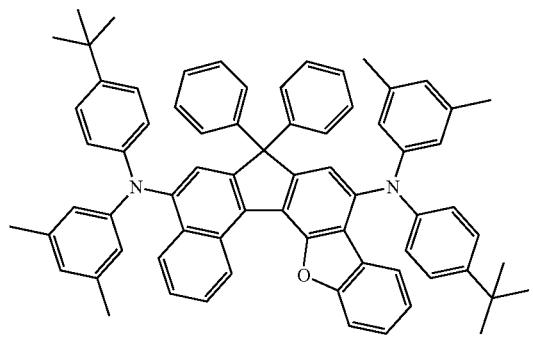
<Chemical Formula 173>
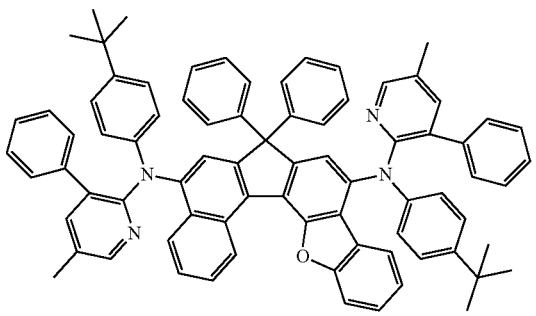
<Chemical Formula 174>
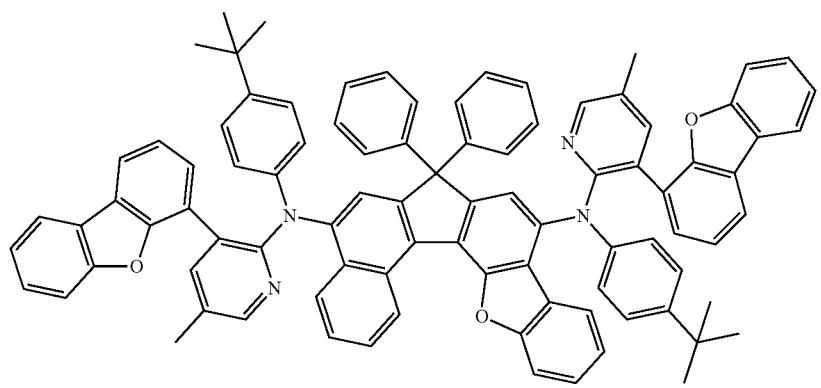
<Chemical Formula 175>
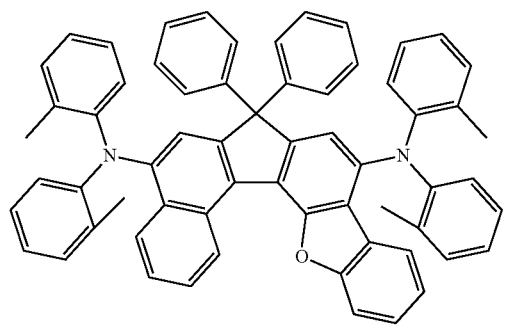
<Chemical Formula 176>
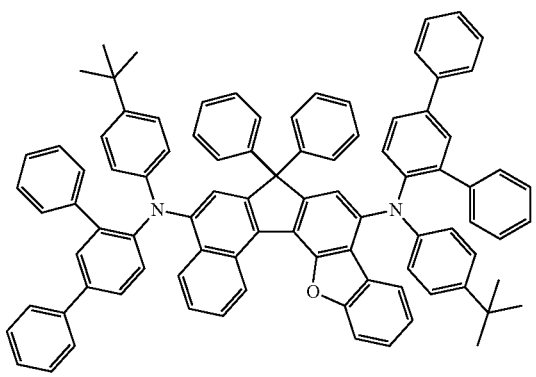
<Chemical Formula 177>
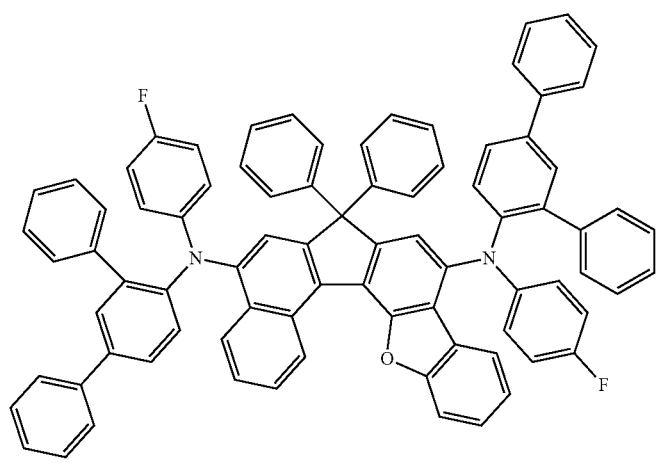

<Chemical Formula 178>
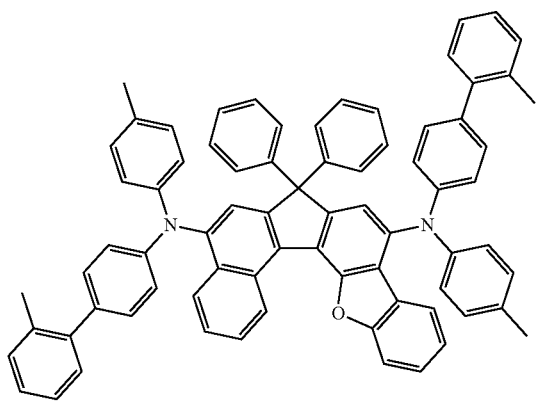
<Chemical Formula 179>
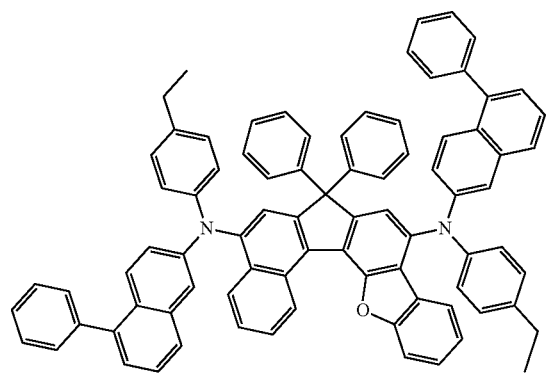
<Chemical Formula 180>
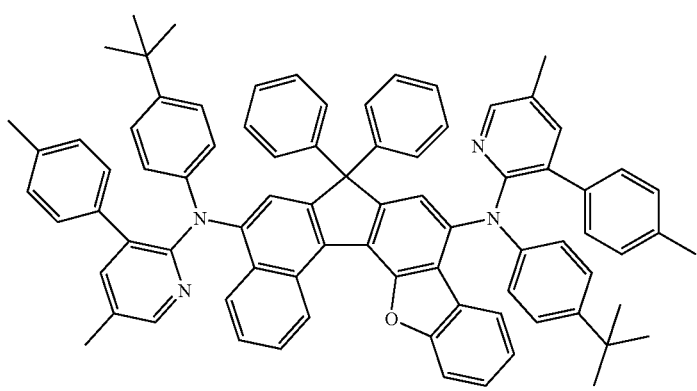
<Chemical Formula 181>
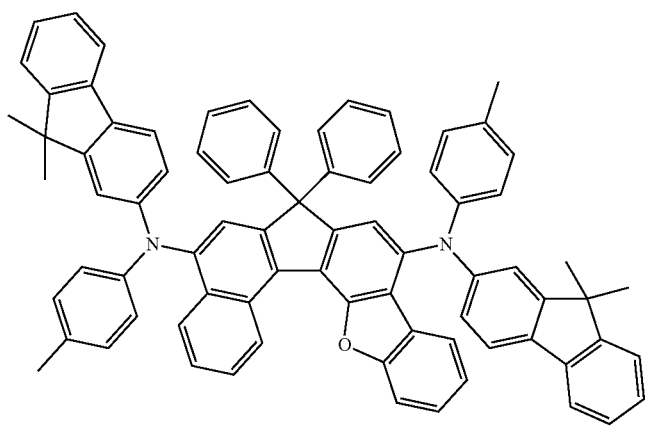

<Chemical Formula 182>
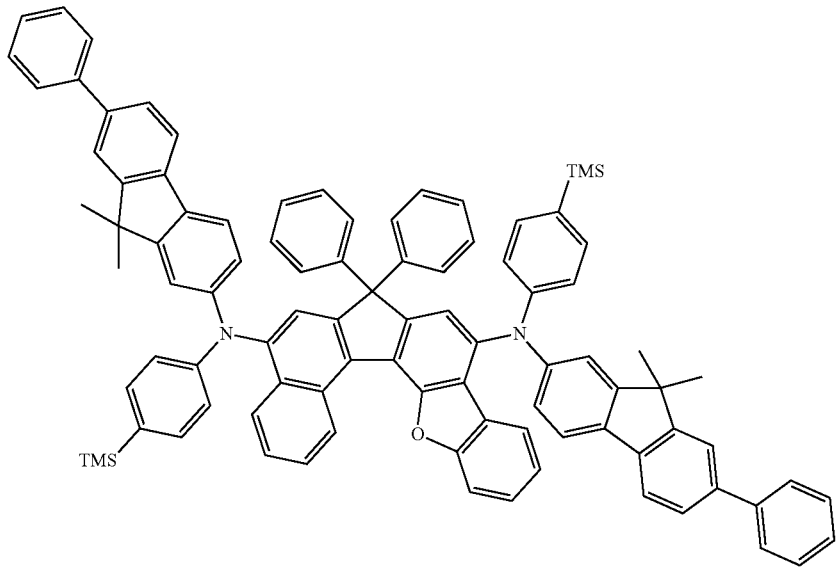
<Chemical Formula 183>
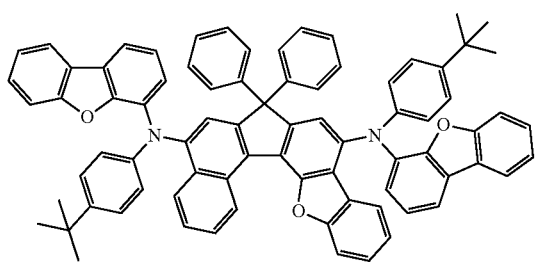
<Chemical Formula 184>
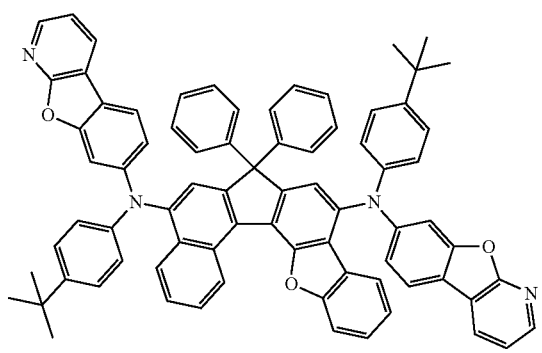
<Chemical Formula 185>
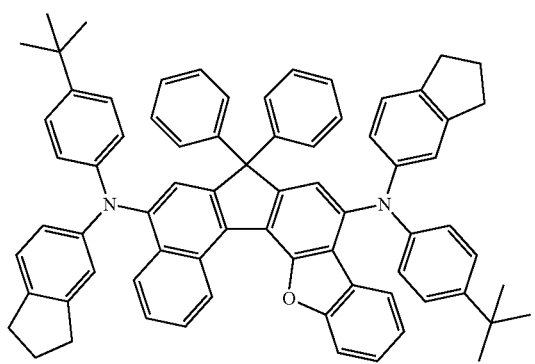
<Chemical Formula 186>
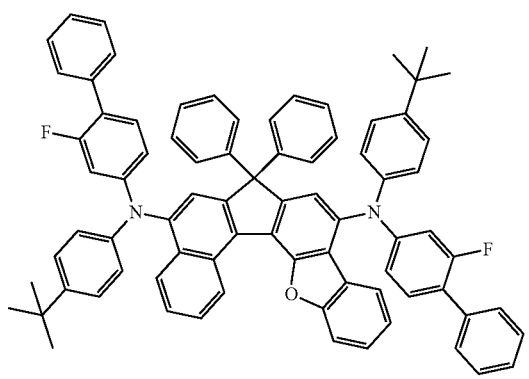

<Chemical Formula 187>
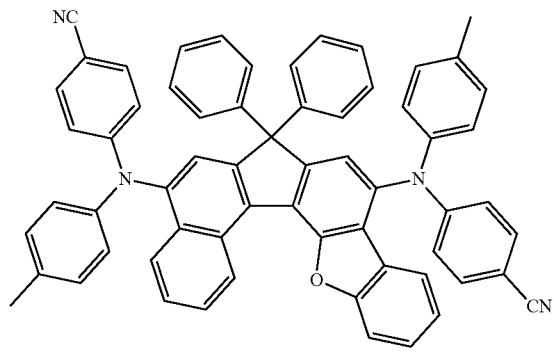
<Chemical Formula 188>
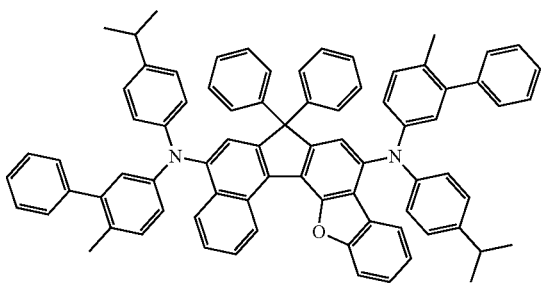
<Chemical Formula 189>
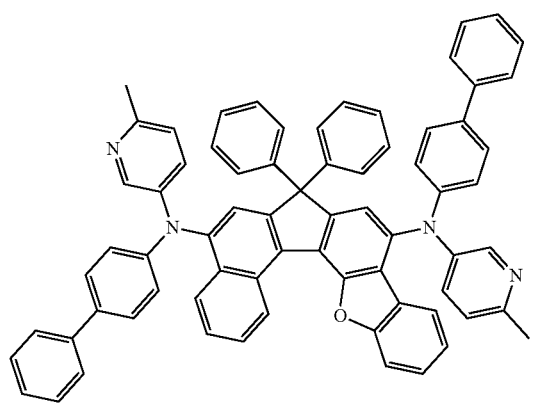
<Chemical Formula 190>
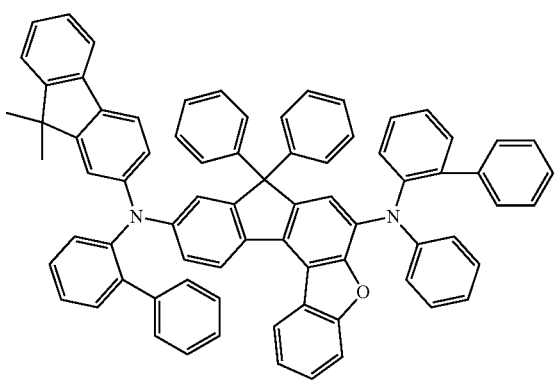
<Chemical Formula 191>
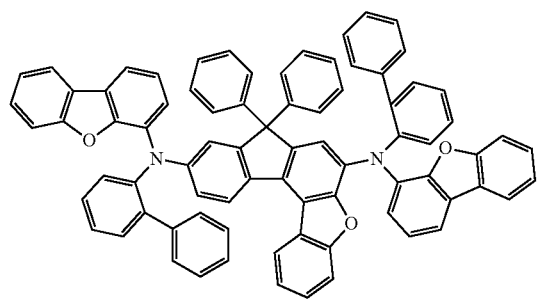
<Chemical Formula 192>
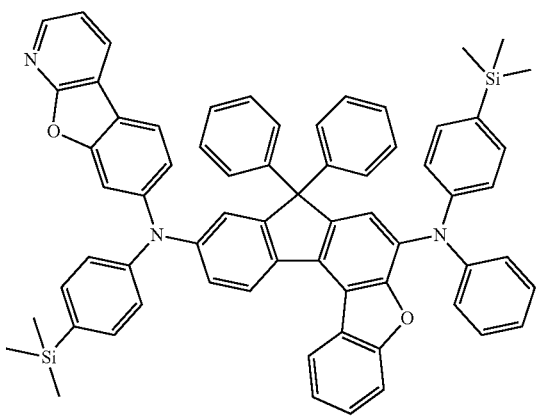

-continued
<Chemical Formula 193>
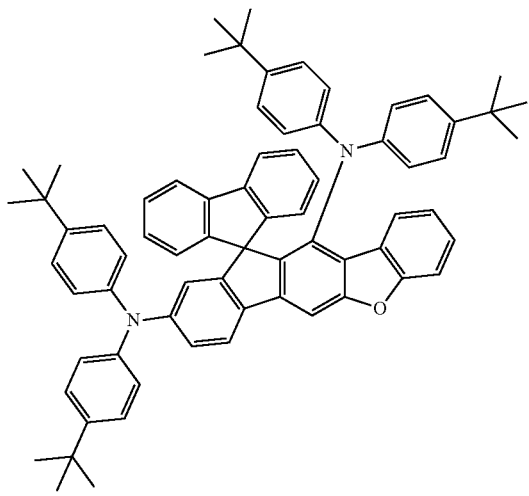
<Chemical Formula 194>
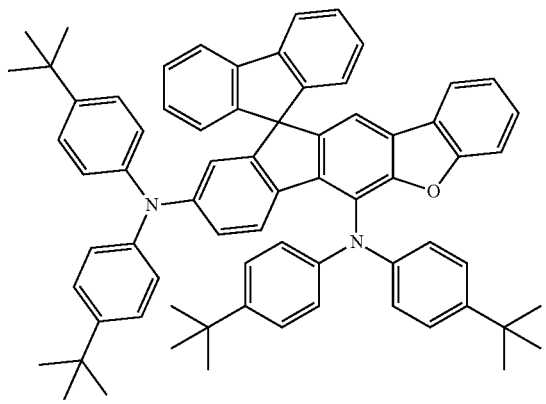
<Chemical Formula 195>
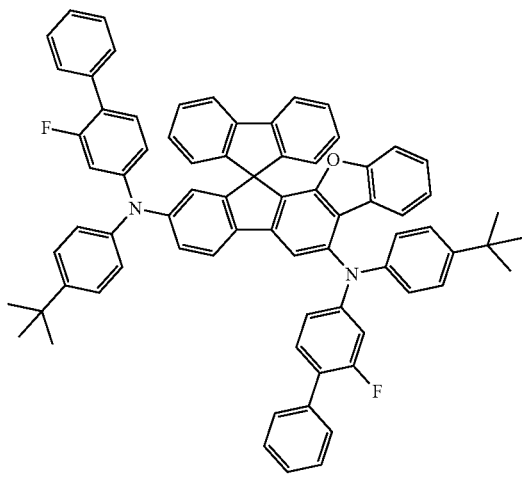
<Chemical Formula 196>
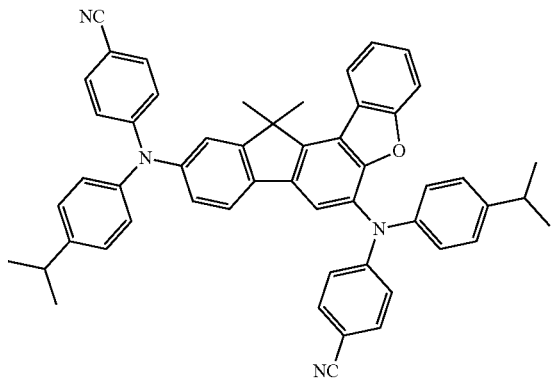
<Chemical Formula 197>
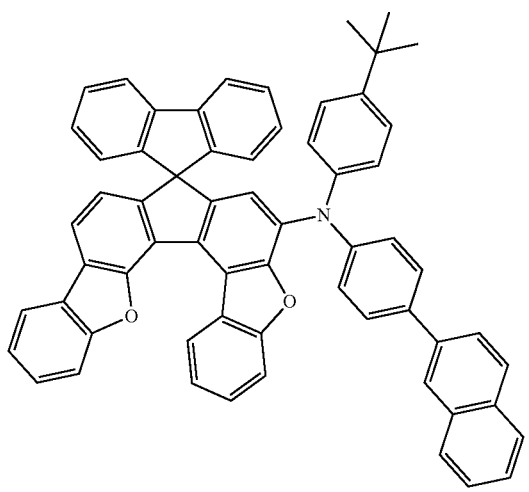
<Chemical Formula 198>
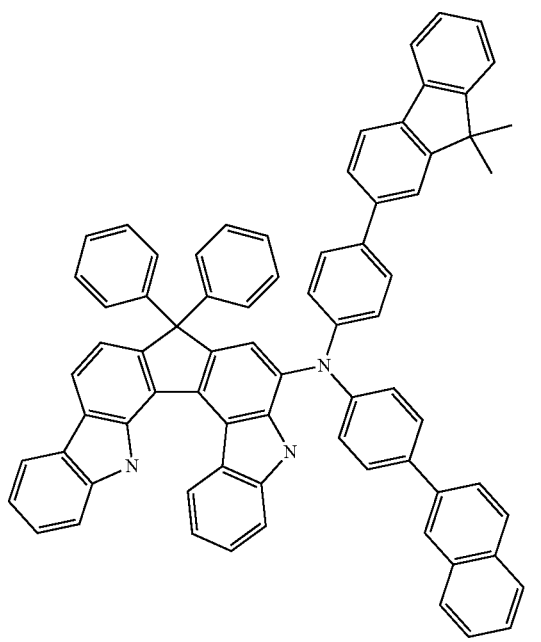

<Chemical Formula 199>
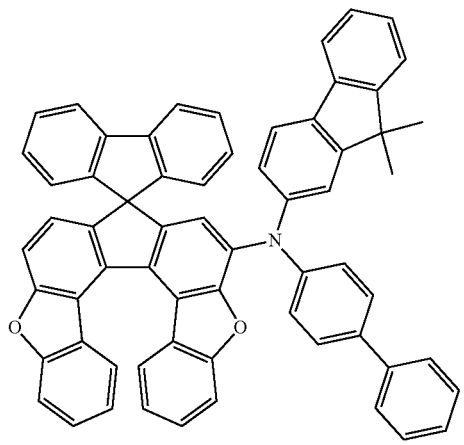
<Chemical Formula 200>
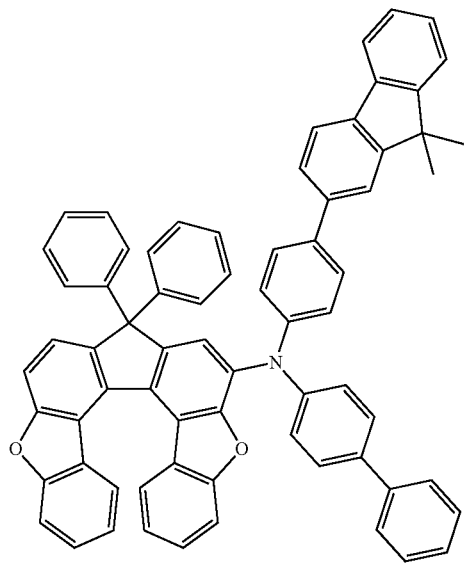
<Chemical Formula 201>
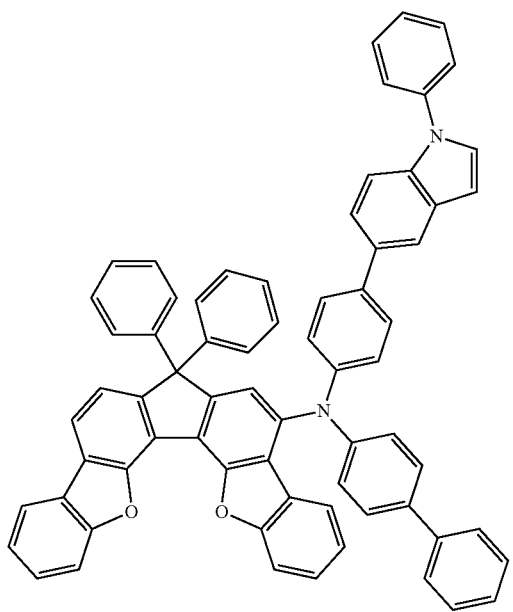
<Chemical Formula 202>
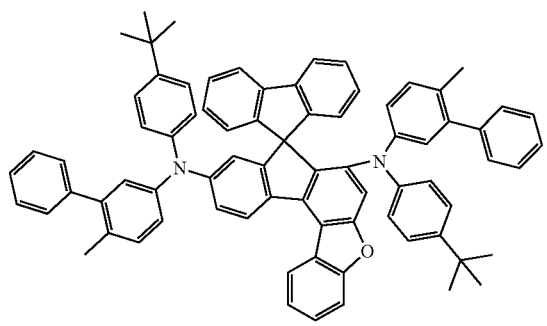

-continued
<Chemical Formula 203>
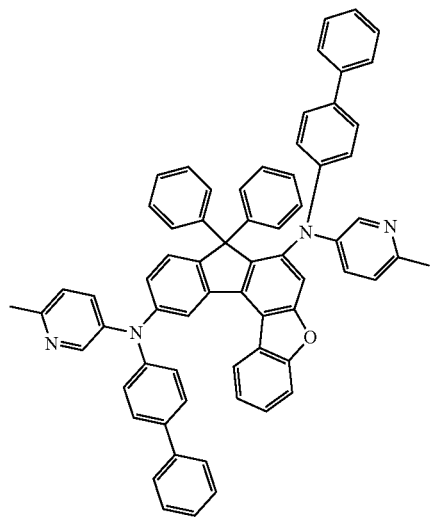
<Chemical Formula 204>
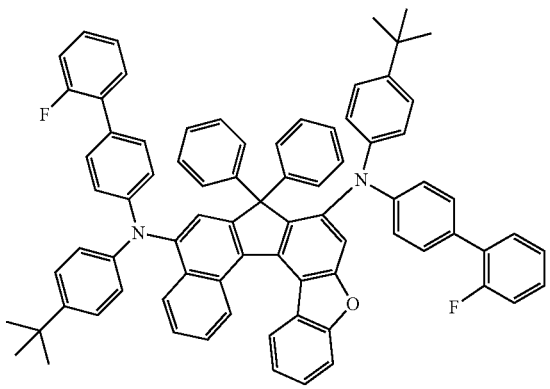
<Chemical Formula 205>
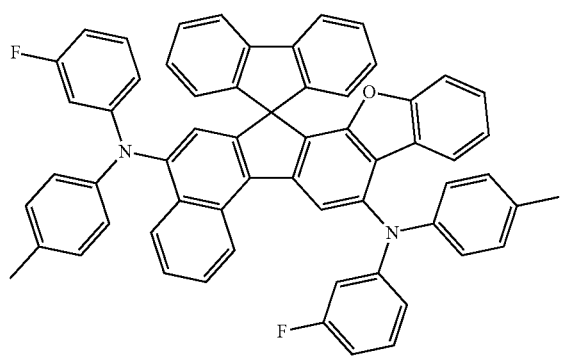
<Chemical Formula 206>
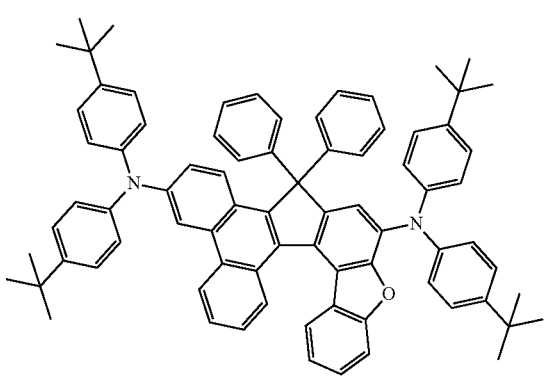
<Chemical Formula 207>
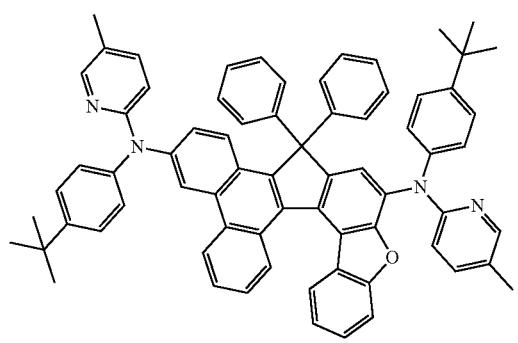
<Chemical Formula 208>
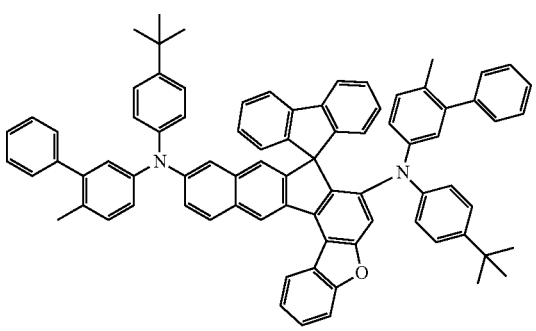

<Chemical Formula 209>
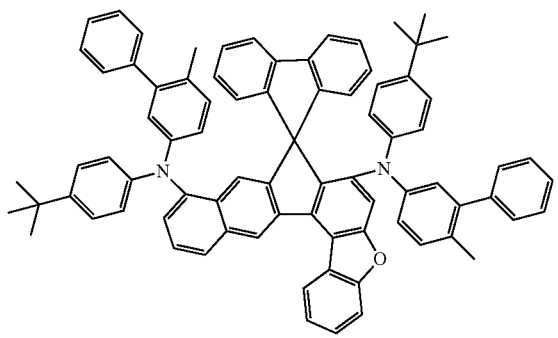
<Chemical Formula 210>
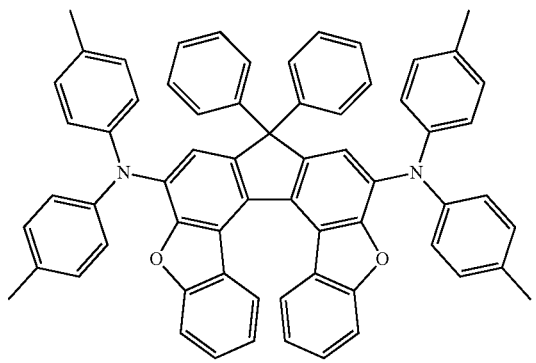
<Chemical Formula 211>
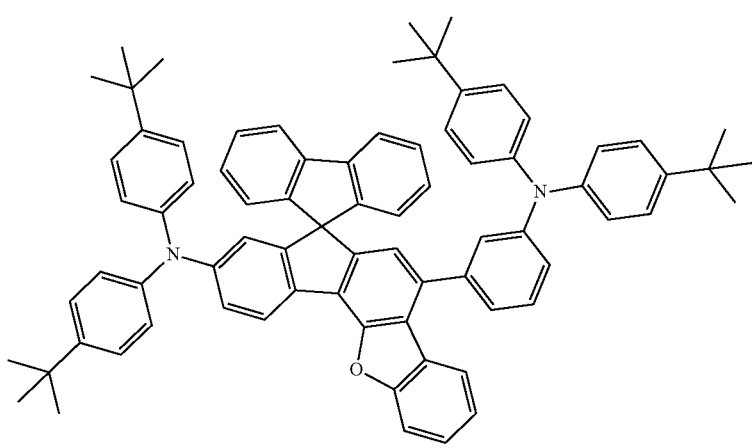
<Chemical Formula 212>
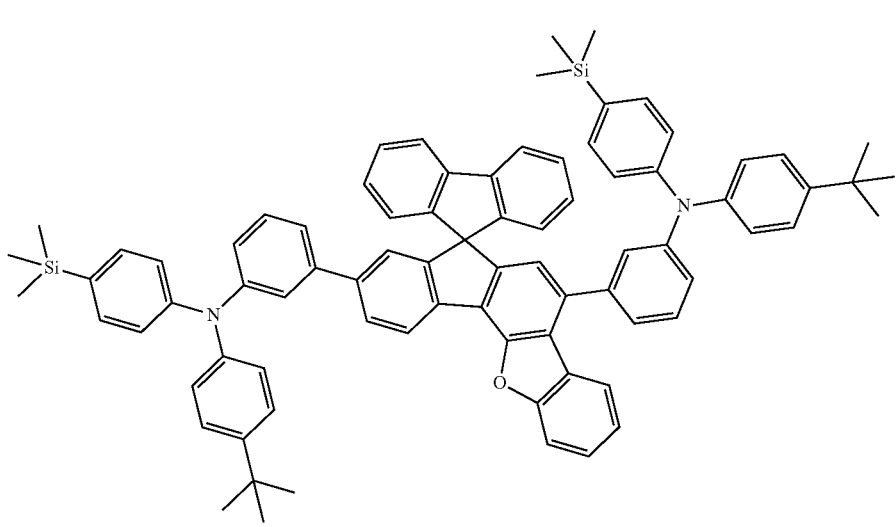

-continued
<Chemical Formula 213>
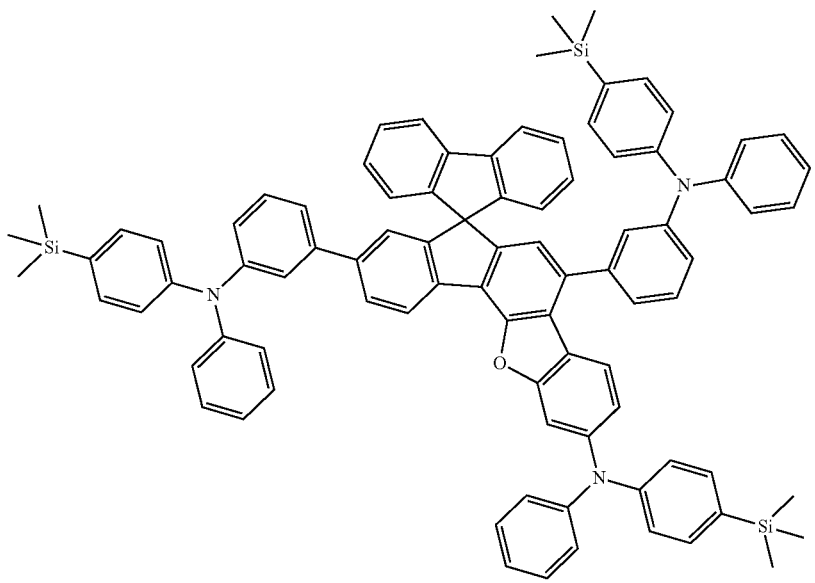
<Chemical Formula 214>
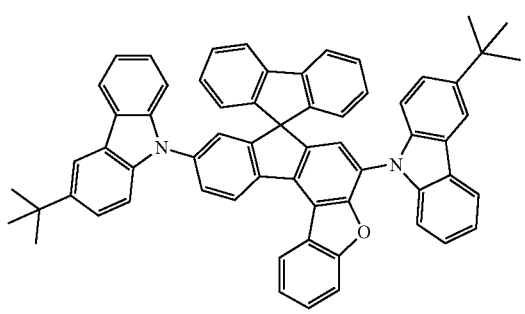
<Chemical Formula 215>
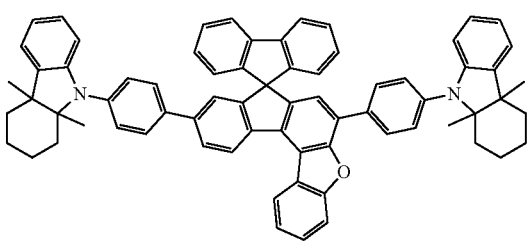
<Chemical Formula 216>
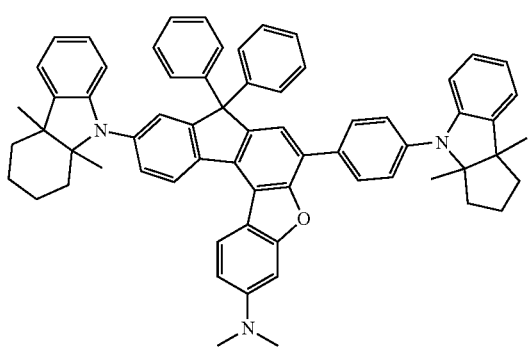
<Chemical Formula 217>
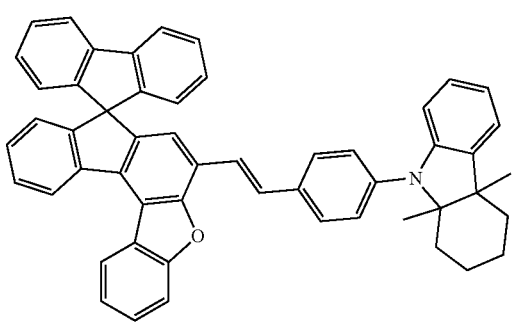
<Chemical Formula 218>
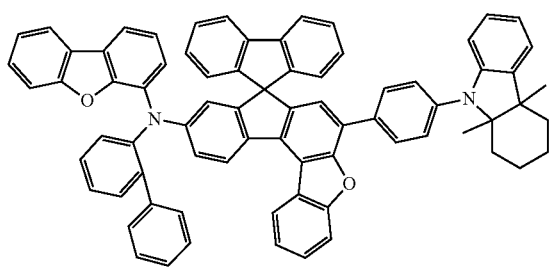
<Chemical Formula 219>
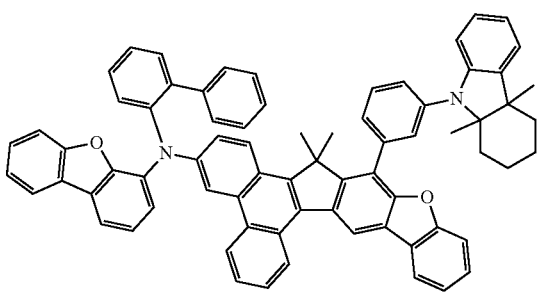

-continued
<Chemical Formula 220>
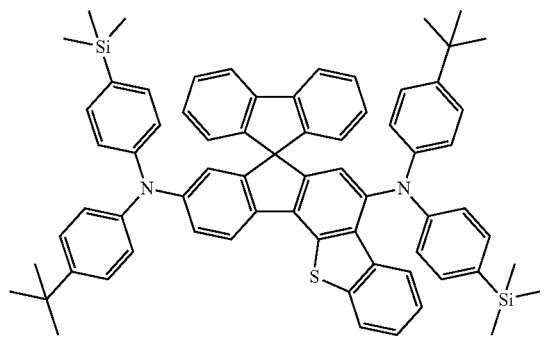
<Chemical Formula 221>
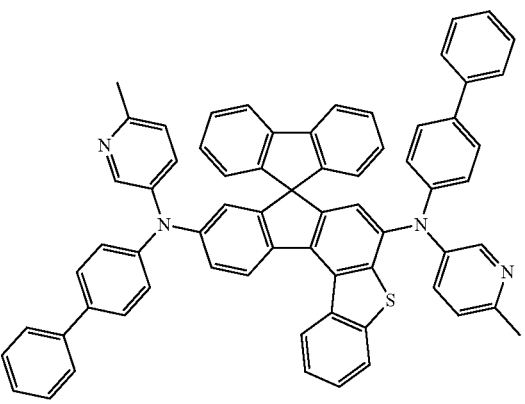
<Chemical Formula 222>
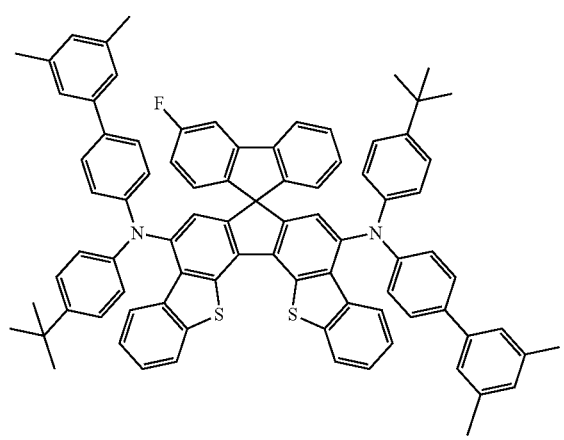
<Chemical Formula 223>
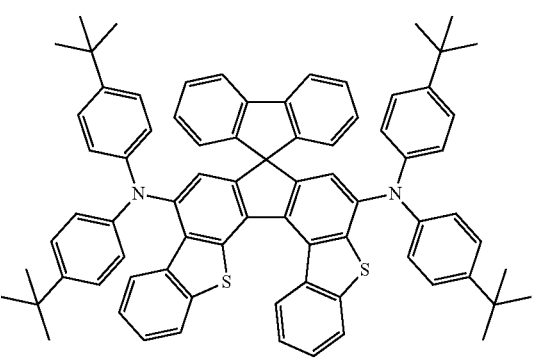
<Chemical Formula 224>
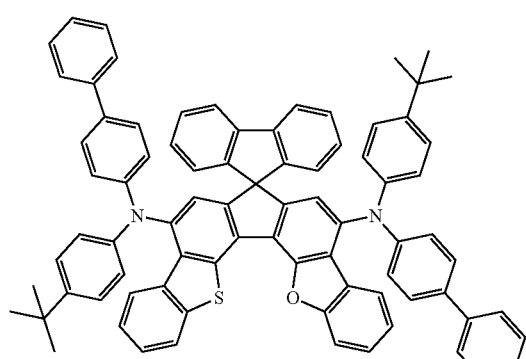
<Chemical Formula 225>
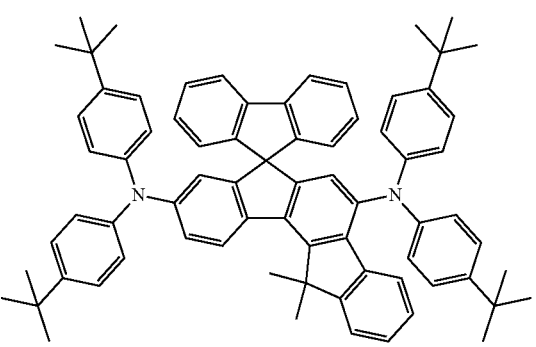
<Chemical Formula 226>
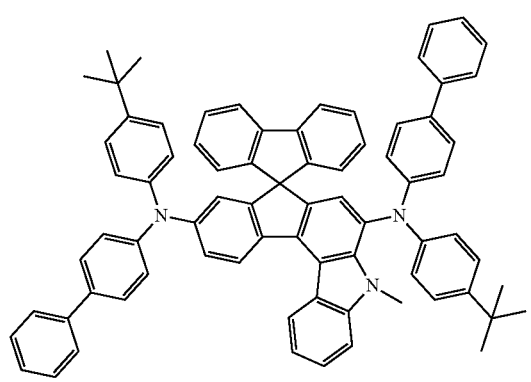
<Chemical Formula 227>
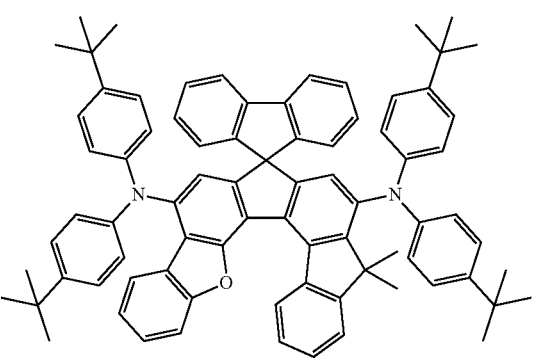

<Chemical Formula 228> <Chemical Formula 229>
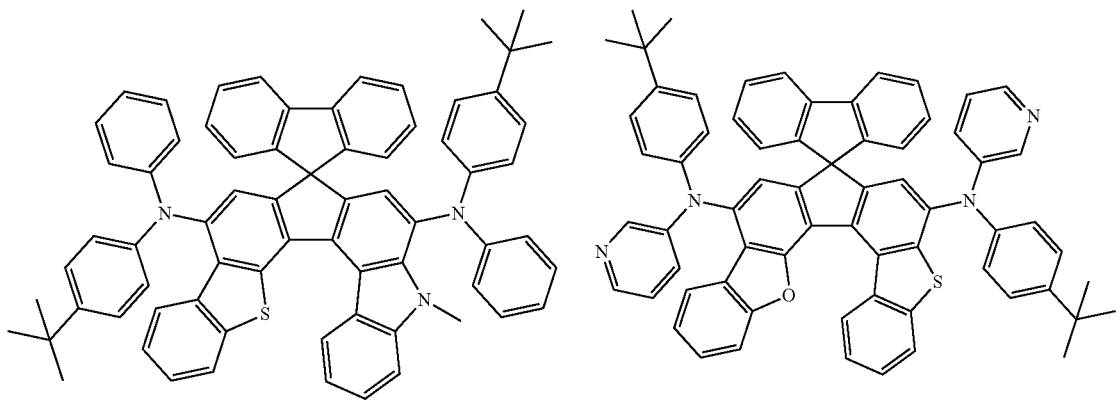
<Chemical Formula 230> <Chemical Formula 231>
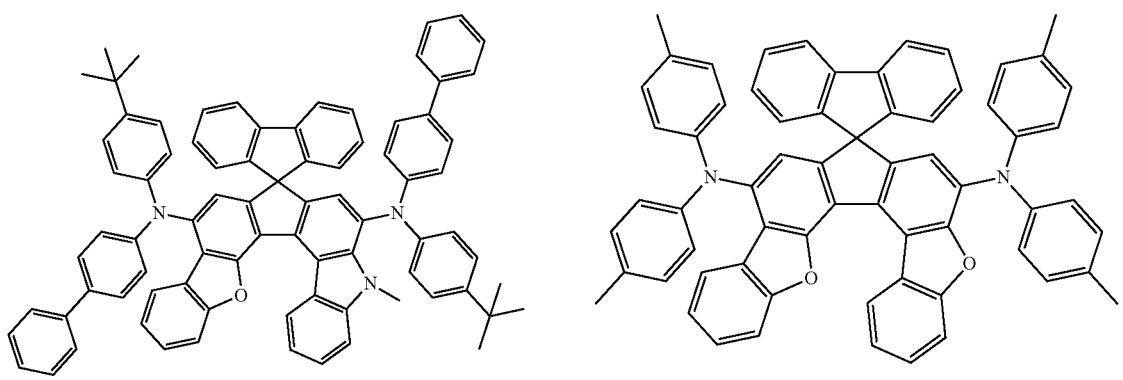
<Chemical Formula 232> <Chemical Formula 233>
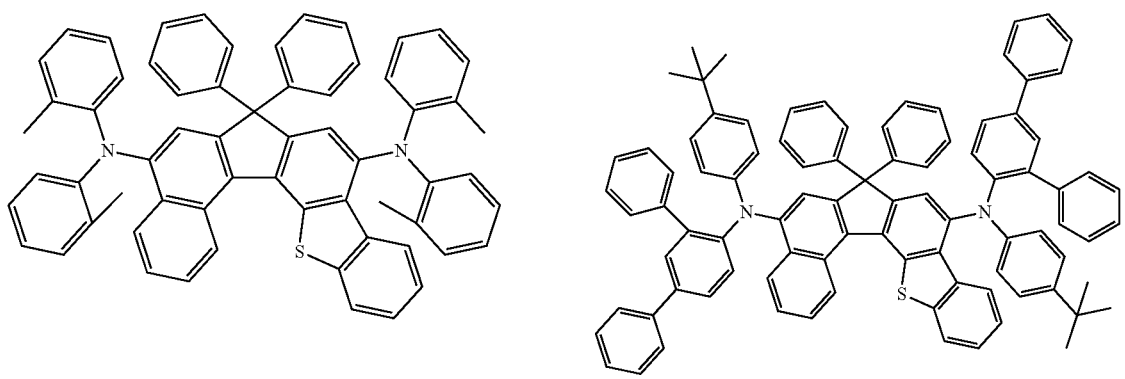
<Chemical Formula 234> <Chemical Formula 235>
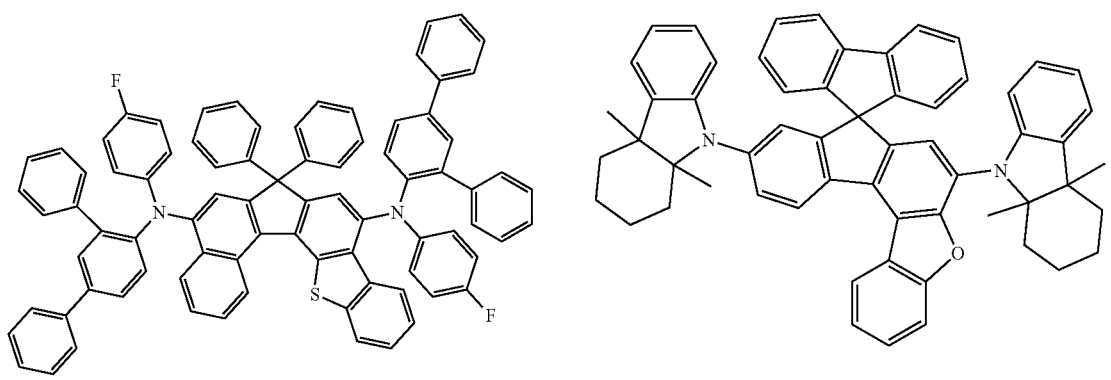

<Chemical Formula 236>

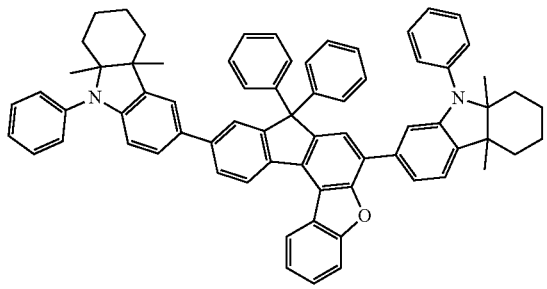

<Chemical Formula 237>

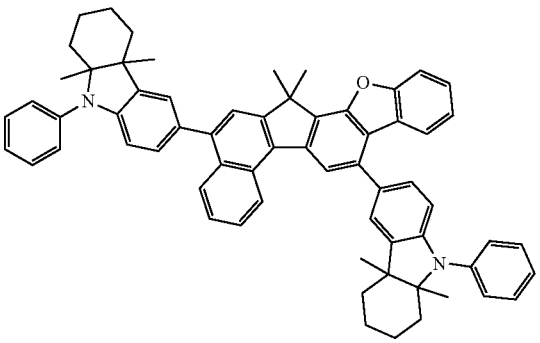

<Chemical Formula 238>

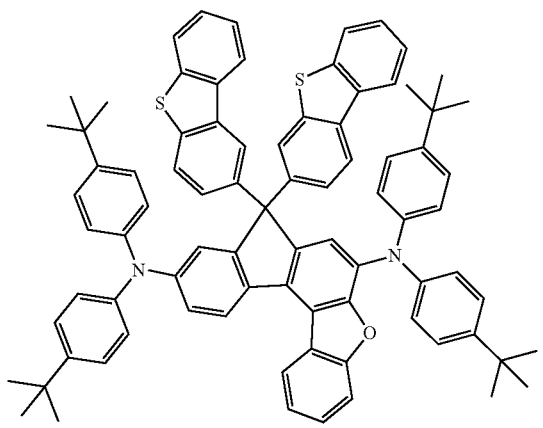

<Chemical Formula 239>

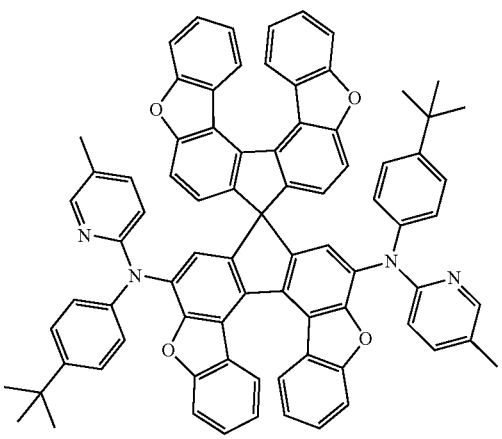

A light-emitting layer in the organic light-emitting layer according to the present disclosure may be composed of a host and a dopant wherein the amine compounds represented by Chemical Formulas A and B are used as the dopant while and an anthracene compound serves as the host, that is, the other component in the light-emitting layer, but the present invention is not limited thereby.

Used as a host in the present disclosure, the anthracene compound may be represented by the following Chemical Formula C:

[Chemical Formula C]

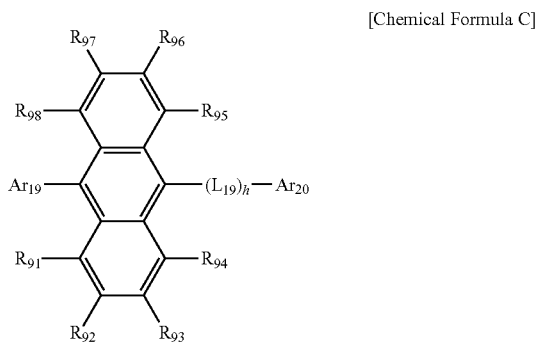

wherein $R_{91}$ to $R_{98}$ may be the same or different and are as defined for substituents $R_1$ to $R_9$ in Chemical Formulas A and B, $Ar_{19}$ and $Ar_{20}$ may be the same or different and are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 2 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, and a substituted or unsubstituted arylsilyl of 6 to 30 carbon atom;

$L_{19}$ is a single bond or any one selected from among a substituted or unsubstituted arylene of 6 to 20 carbon atoms and a substituted or unsubstituted heteroarylene of 2 to 20 carbon atoms, h is an integer of 1 to 3, with the proviso that when h is 2 or greater, the corresponding $L_{19}$'s are may be the same or different.

In greater detail, $Ar_{18}$ in the anthracene derivative represented by Chemical Formula C may be a substituent represented by the following Chemical Formula C-1:

[Chemical Formula C-1]

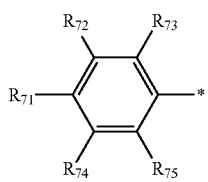

wherein $R_{71}$ to $R_{75}$ may be the same or different and are each as defined for the substituents $R_1$ to $R_9$ in Chemical Formulas A and B, with the proviso that adjacent substituents may form a saturated or unsaturated ring.

In this case, $L_{19}$ may be a single bond or a substituted or unsubstituted arylene of 6 to 20 carbon atoms, and h may be 1 or 2, with the proviso that when h is 2, corresponding $L_{19}$'s may be the same or different.

In addition to the above-mentioned dopants and hosts, the light-emitting layer may further include various host and dopant materials.

The organic light-emitting diode of the present disclosure in which a light-emitting layer and electron density control layer are arranged in that order with at least one amine compound represented by Chemical Formula A or B and at least one compound represented by Chemical Formulas F to H being respectively employed in the light-emitting layer and the electron density control layer is characterized by improved emission efficiency and low-voltage operation and exhibits the effect of long lifespan, compared to conventional organic light-emitting diodes.

In the compound represented by Chemical Formula F, which is available for the electron density control layer in the present disclosure, substituent $R_{18}$ on the benzoquinazoline ring moiety may be a substituted or unsubstituted aryl of 6 to 18 carbon atoms.

In detail, the compound represented by Chemical Formula F may be one selected from the group consisting of the following Compounds 1 to 30, but is not limited thereto:

[Compound 1]

[Compound 2]

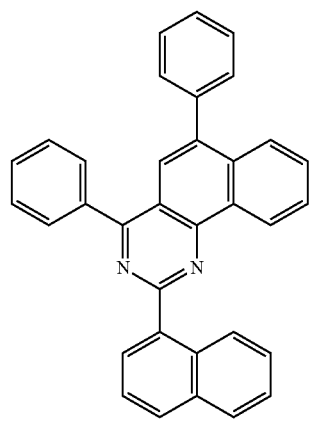

[Compound 3]

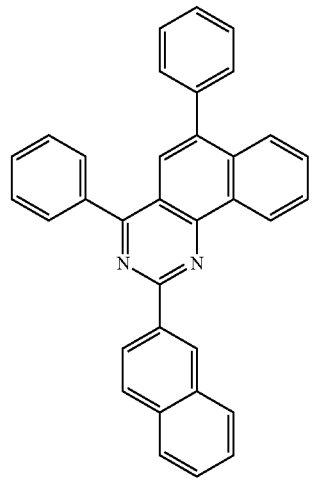

[Compound 4]

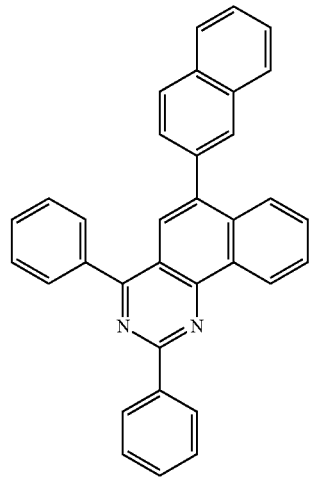

[Compound 5]
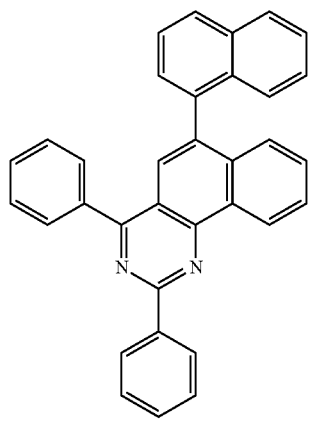
[Compound 6]
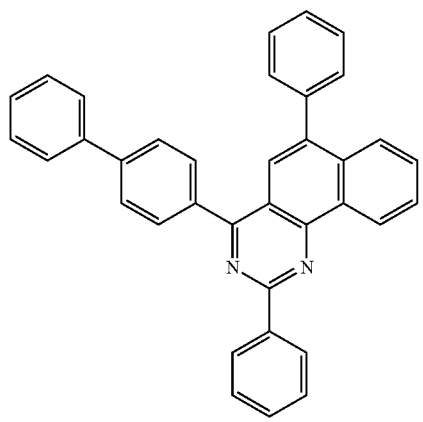
[Compound 7]
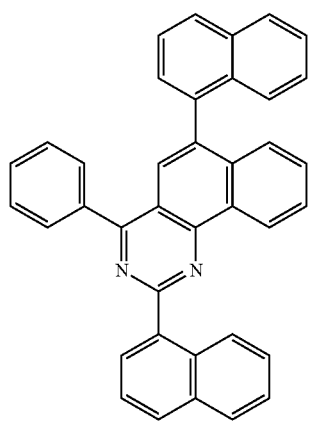
[Compound 8]
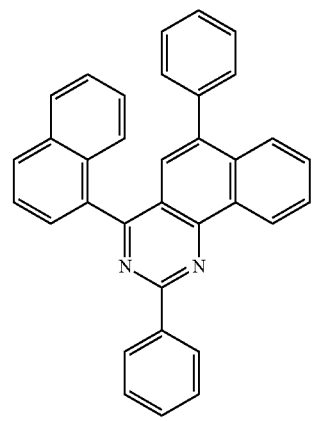
[Compound 9]
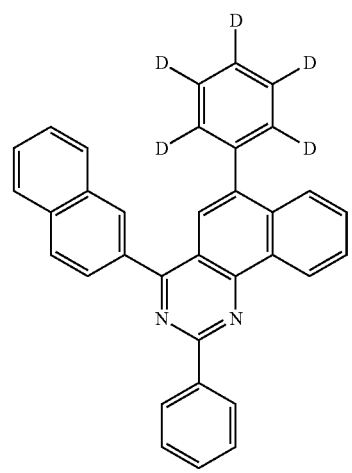
[Compound 10]
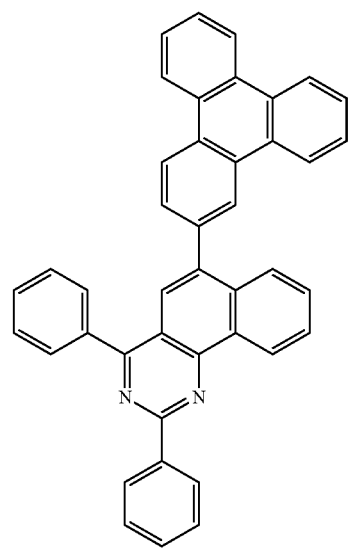

[Compound 11]
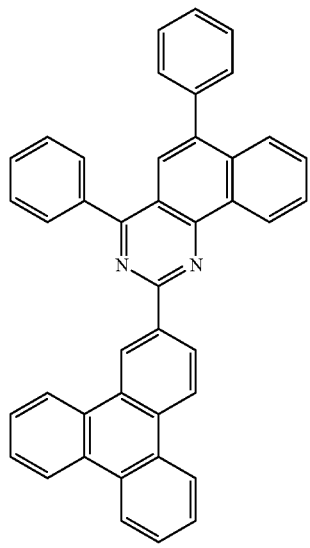
[Compound 12]
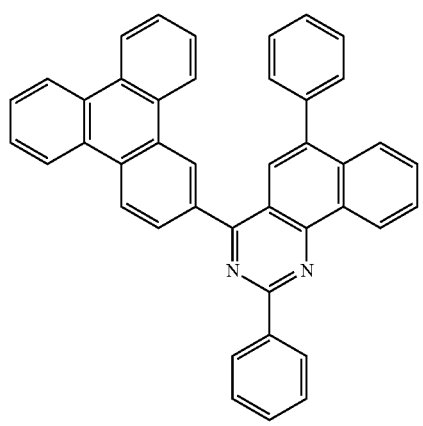
[Compound 13]
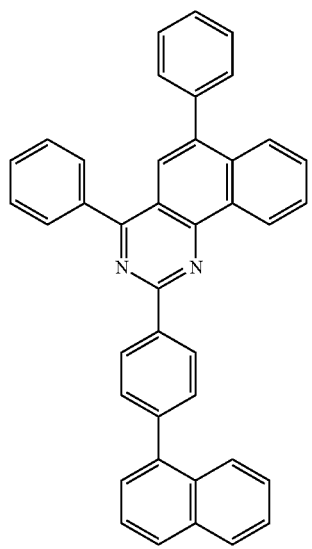
[Compound 14]
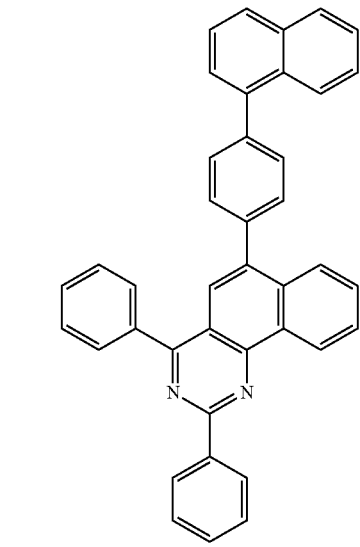
[Compound 15]
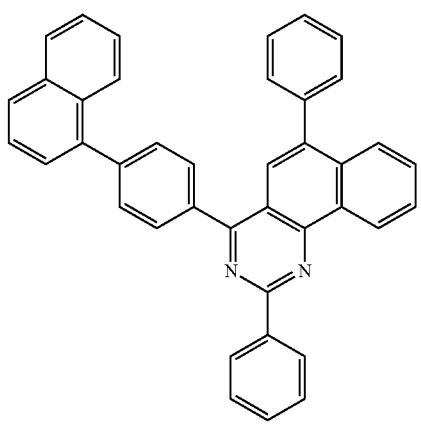
[Compound 16]
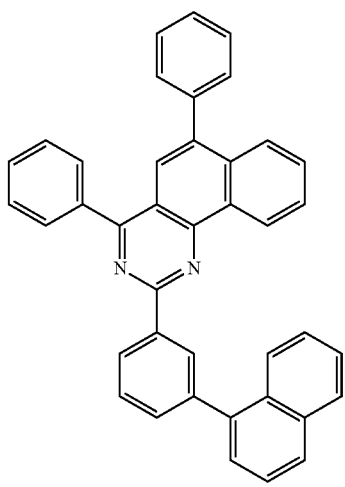

[Compound 17]
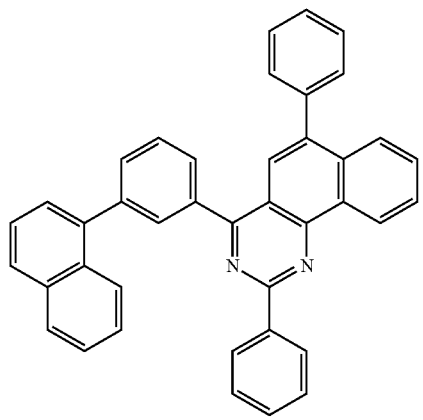
[Compound 18]
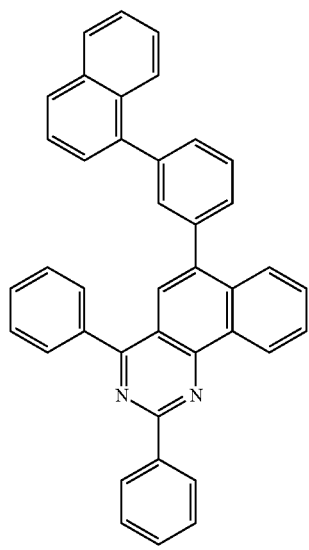
[Compound 19]
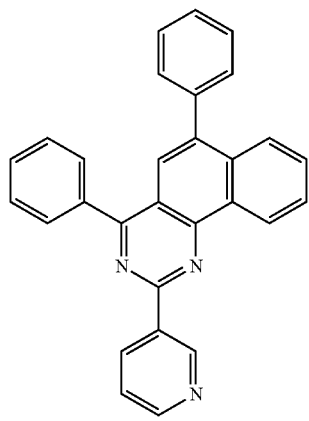
[Compound 20]
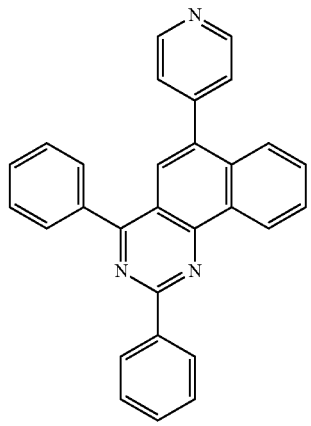
[Compound 21]
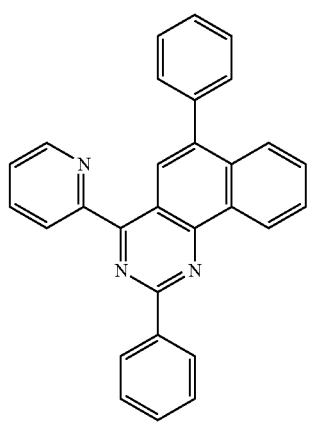
[Compound 22]
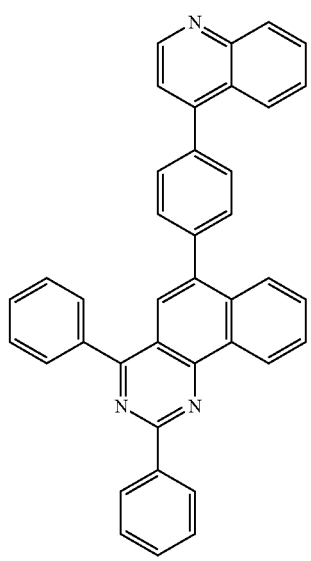

[Compound 23]
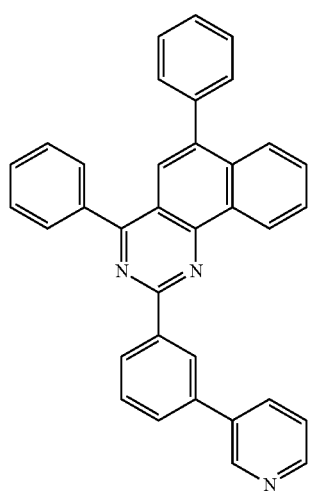
[Compound 24]
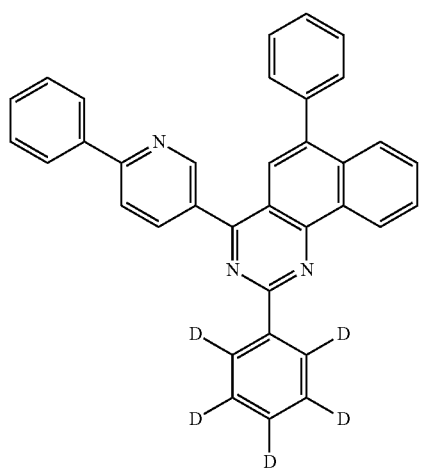
[Compound 25]
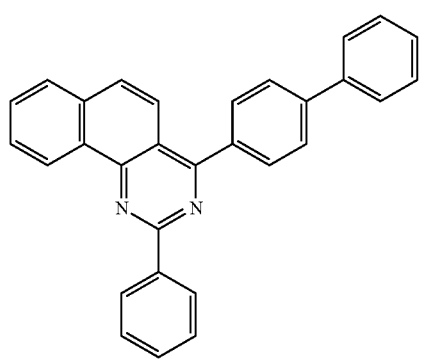
[Compound 26]
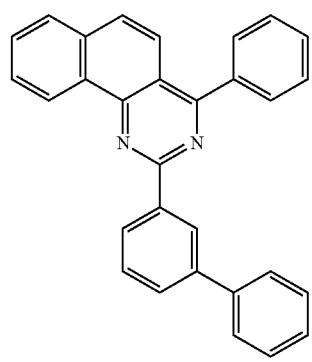
[Compound 27]
[Compound 28]
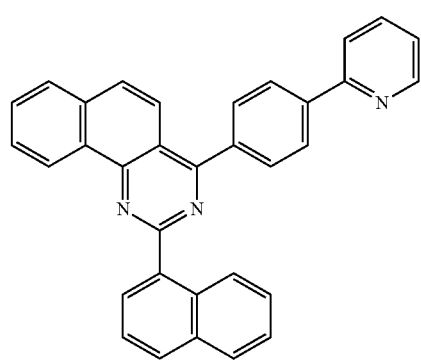
[Compound 29]

[Compound 30]

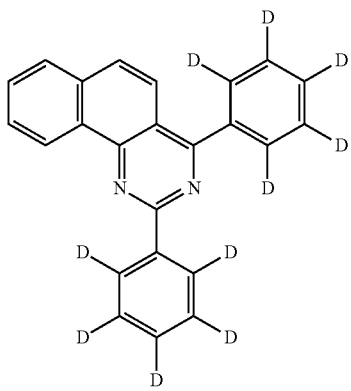

[Compound 101]

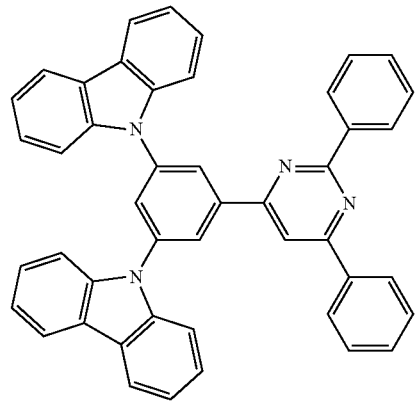

In the compound represented by Chemical Formula G, which is available for the electron density control layer in the present disclosure, at least one of $Z_1$ and $Z_2$ may be represented by the following Structural Formula B:

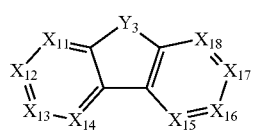    [Structural Formula B]

wherein, Cz is a substituted or unsubstituted carbazole, $L_{19}$ is selected from among a single bond, a substituted or unsubstituted alkylene of 1 to 30 carbon atoms, a substituted or unsubstituted cycloalkylene of 3 to 30 carbon atoms, a substituted or unsubstituted arylene of 6 to 50 carbon atoms, and a substituted or unsubstituted heteroarylene of 3 to 50 carbon atoms, with preference for a single bond, a substituted or unsubstituted arylene of 6 to 50 carbon atoms, and a substituted or unsubstituted heteroarylene of 3 to 50 carbon atoms, o is an integer of 0 to 2.

In Structural Formula A of Chemical Formula G, HAr may be a substituent represented by the following Structural Formula C:

[Structural Formula C]

[Compound 102]

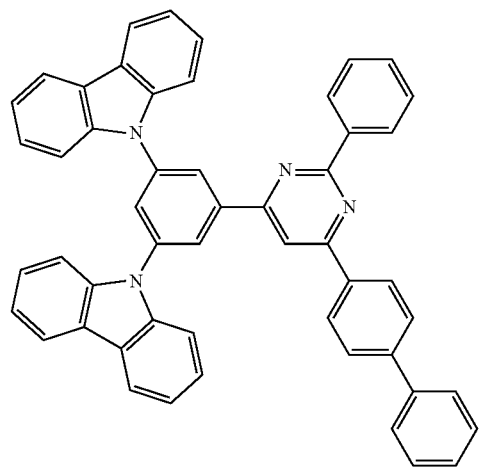

wherein, $X_{11}$ to $X_{18}$ may be the same or different and are each independently N or $CR_{31}$, with the proviso that one of them may be a carbon atom linked to the substituent $L_{13}$ in Structural Formula A via a single bond, $Y_3$ is O or S, $R_{31}$ is as defined for R' in Chemical Formula G, with the proviso that when two or more $CR_{31}$'s exist, they are the same or different.

According to some embodiments of the present disclosure, at least two or $X_1$ to $X_3$ in Chemical Formula G may be N. That is, the material for an electron density control layer, represented by Chemical Formula G, may have a pyrimidine structure.

Concrete examples of the compound represented by Chemical Formula G include, but are not limited to, the following Compounds 101 to 132:

[Compound 103]

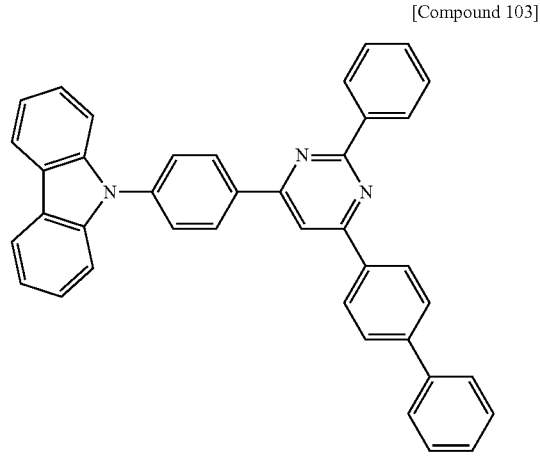

[Compound 104]
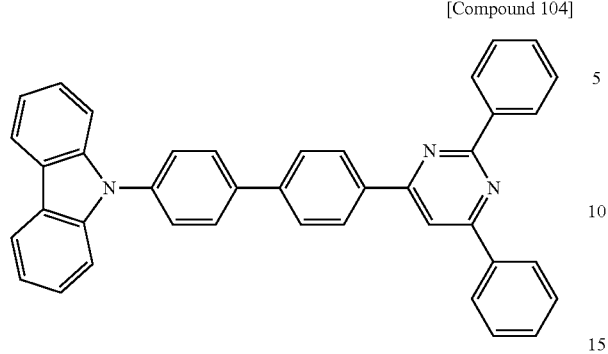
[Compound 108]
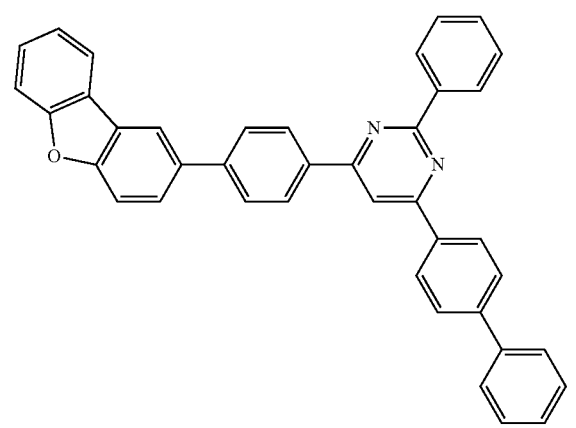
[Compound 105]
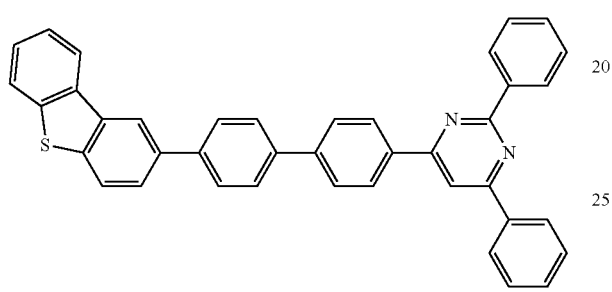
[Compound 106]
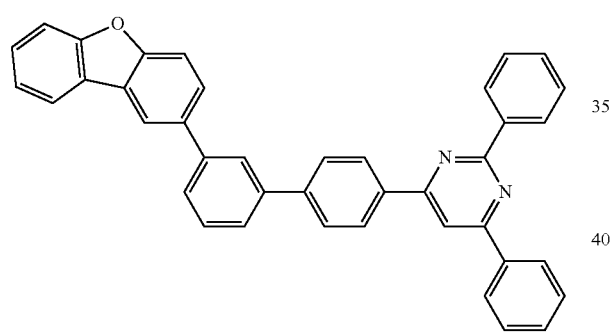
[Compound 109]
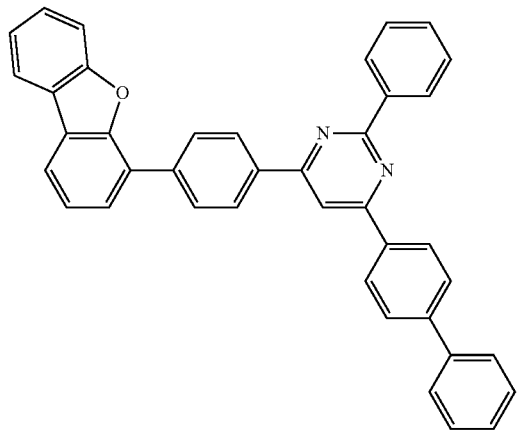
[Compound 107]
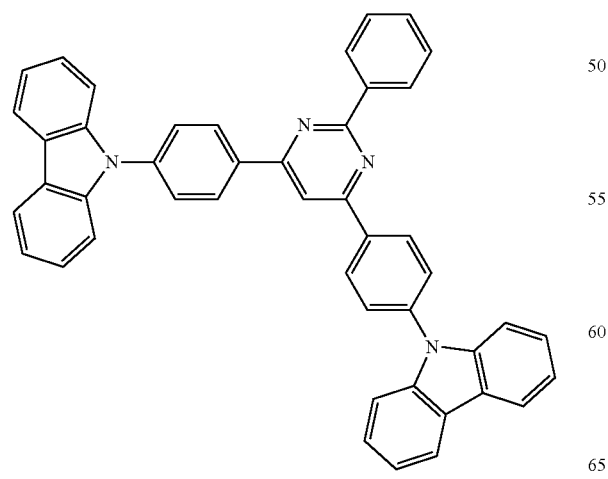
[Compound 110]
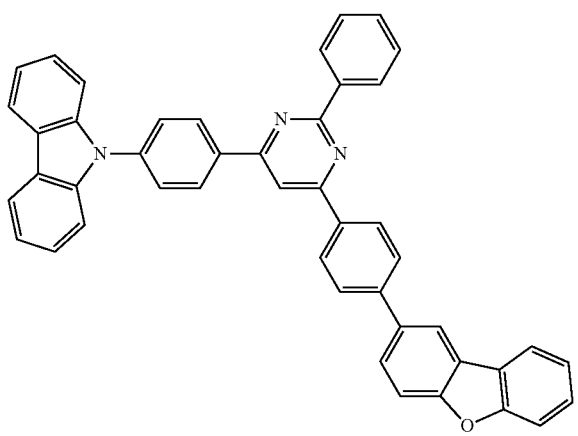

[Compound 111]
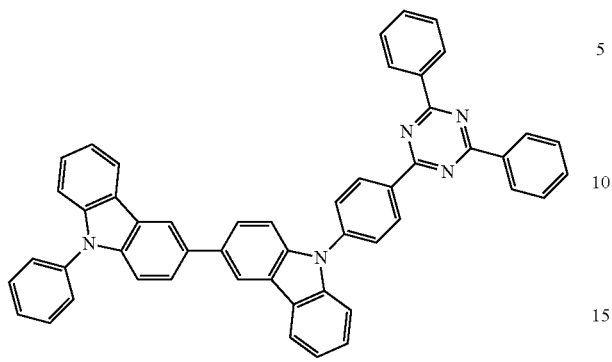
[Compound 112]
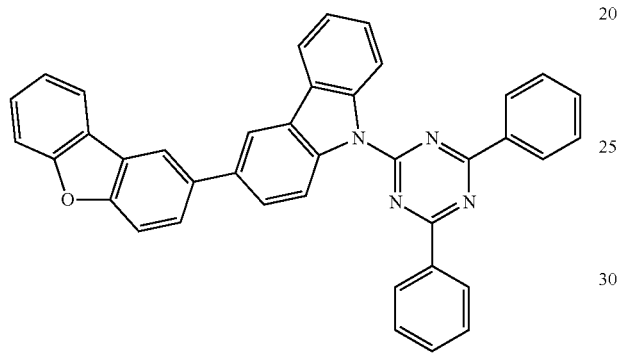
[Compound 113]
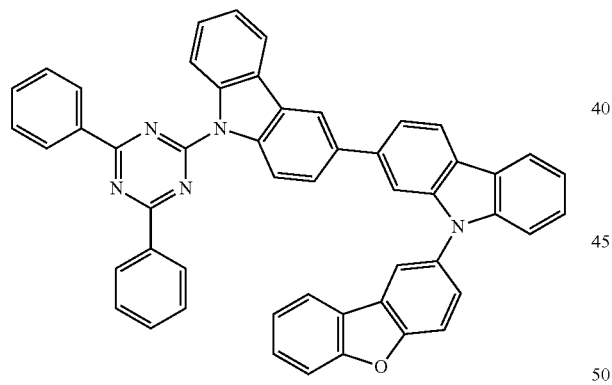
[Compound 114]
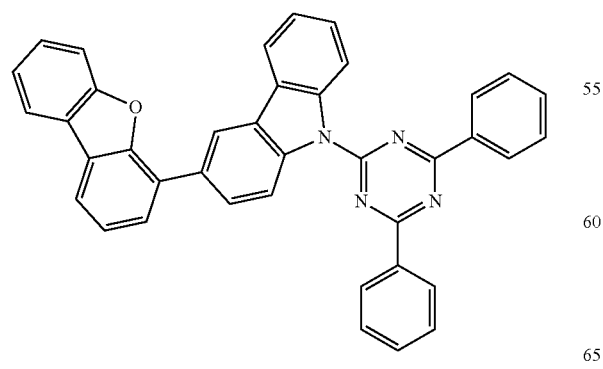
[Compound 115]
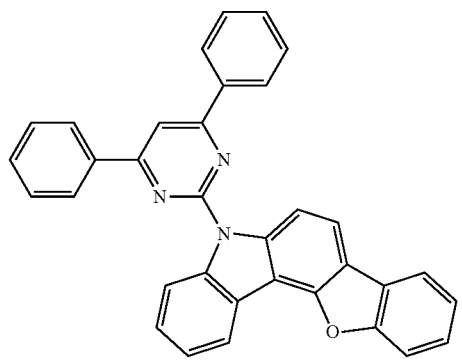
[Compound 116]
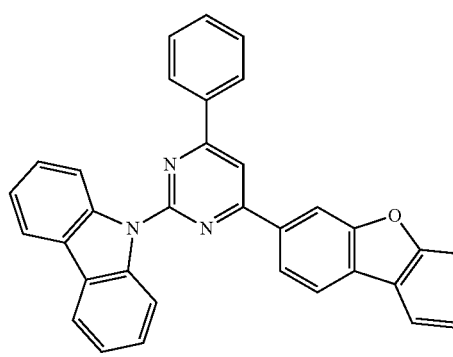
[Compound 117]
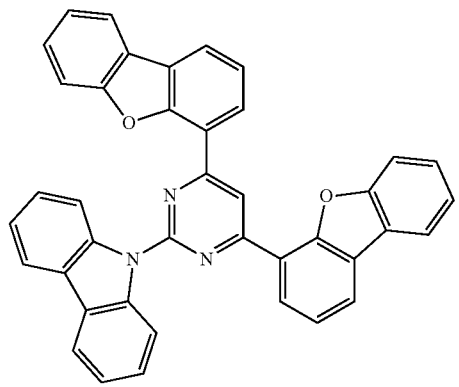
[Compound 118]
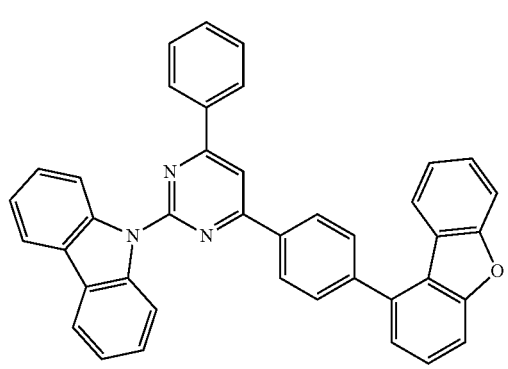

[Compound 119]
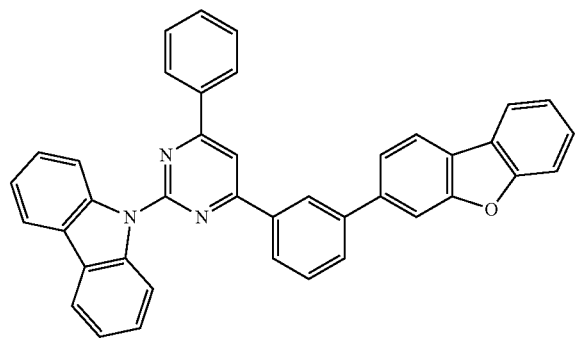
[Compound 120]
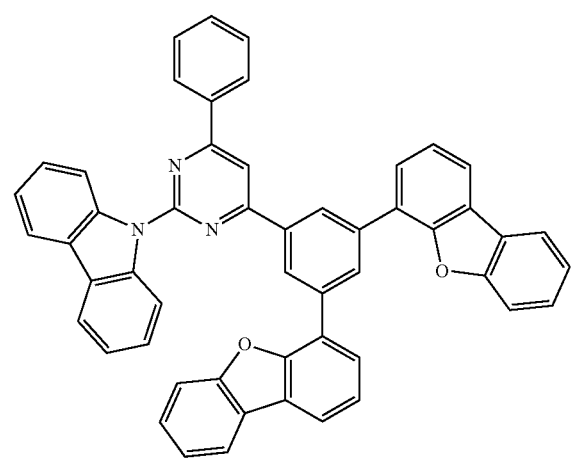
[Compound 121]
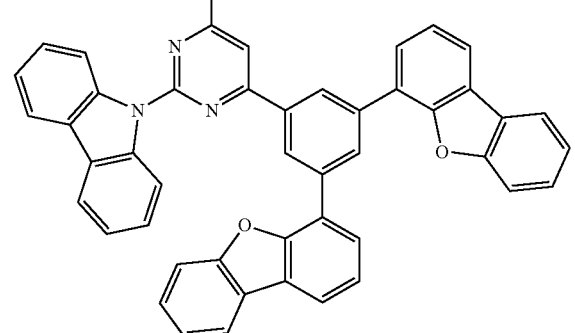
[Compound 122]
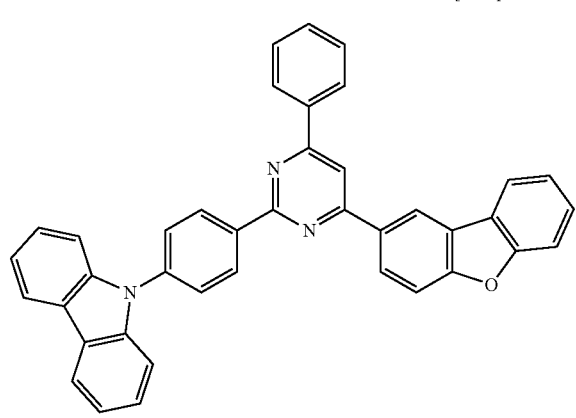
[Compound 123]
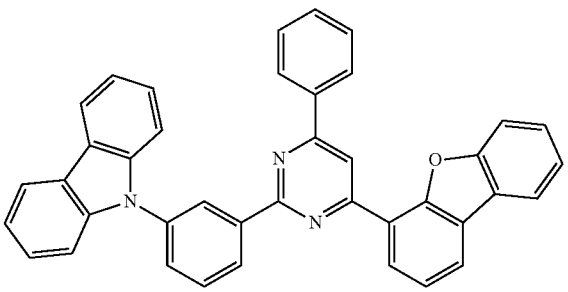
[Compound 124]
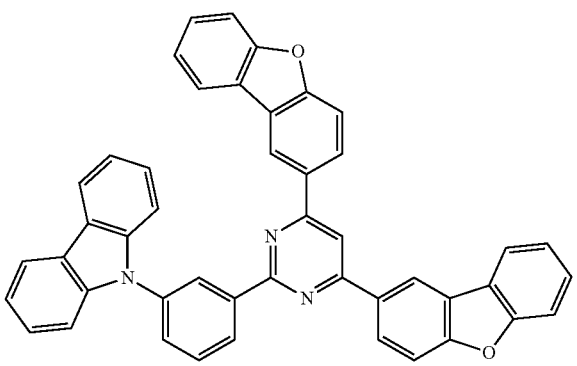
[Compound 125]
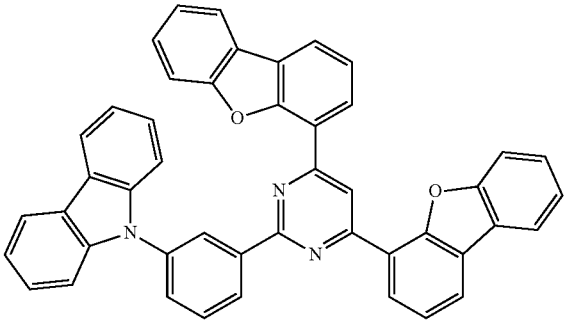
[Compound 126]
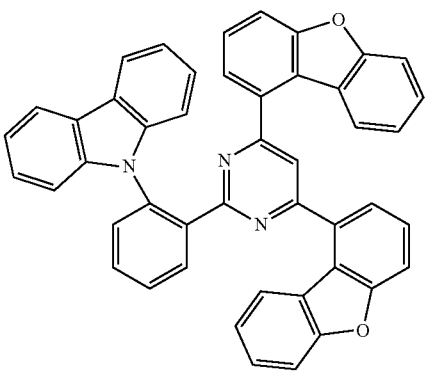

[Compound 127]

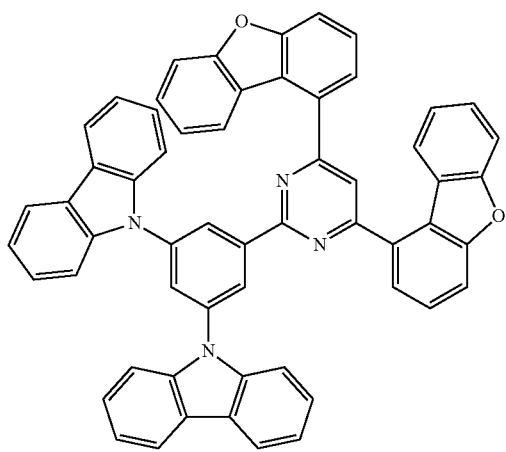

[Compound 128]

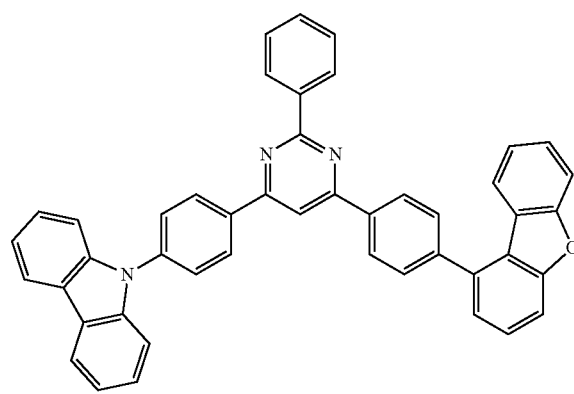

[Compound 129]

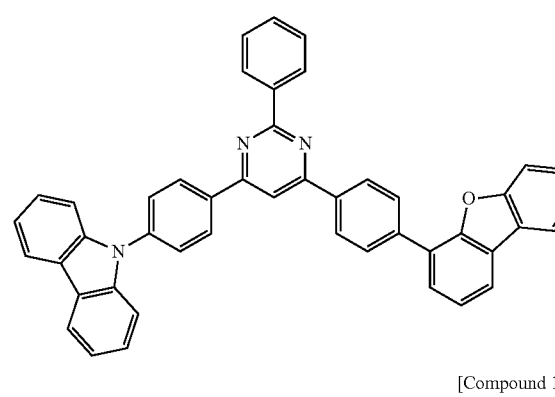

[Compound 130]

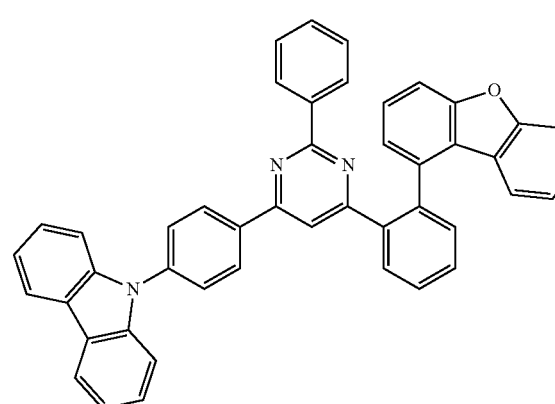

[Compound 131]

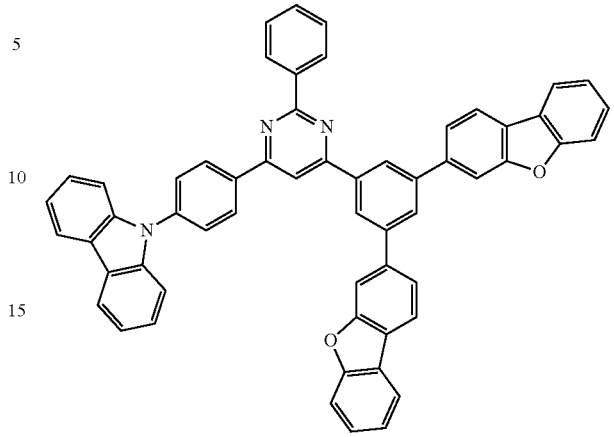

[Compound 132]

In the compound represented by Chemical Formula H, available for the electron density control layer in the present disclosure, the anthracene ring moiety may have a substituent $Z_{11}$ bonded thereto at position 10 and a linker $L_{14}$ bonded thereto at position 9 while the substituent $L_{14}$ is linked to a substituted or unsubstituted arylene of 6 to 50 carbon atoms or a substituted or unsubstituted heteroaryl of 2 to 50 carbon atoms.

In Chemical Formula H, according to one embodiment of the present disclosure, $L_{14}$ is a single bond or an aryl of 6 to 18 carbon atoms, substituents $Z_{11}$ and $Z_{12}$ may be the same or different and are each independently a substituted or unsubstituted aryl of 6 to 20 carbon atoms or a substituted or unsubstituted heteroaryl of 2 to 20 carbon atoms, with the proviso that at least one of $Z_{11}$ and $Z_{12}$ is a substituted or unsubstituted heteroaryl of 3 to 20 carbon atoms.

In greater detail, the compound represented by Chemical Formula H may be any one of the compounds represented by Chemical Formulas H-1 to H-4:

[Chemical Formula H-1]

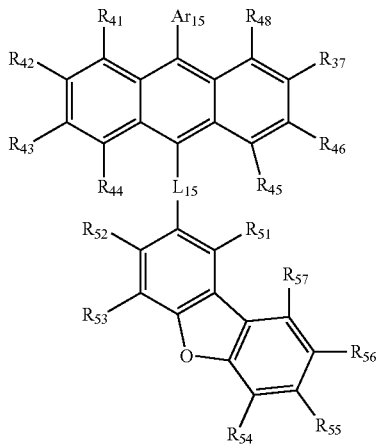

[Chemical Formula H-2]

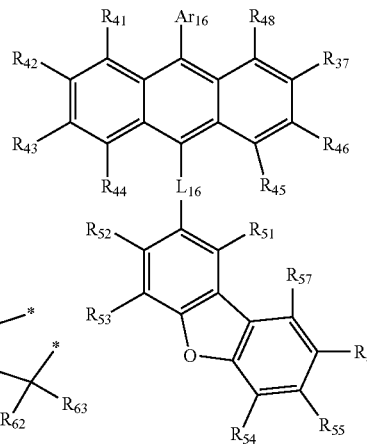

[Chemical Formula H-3]

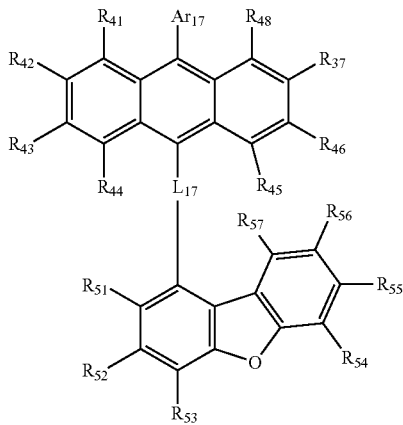

[Chemical Formula H-4]

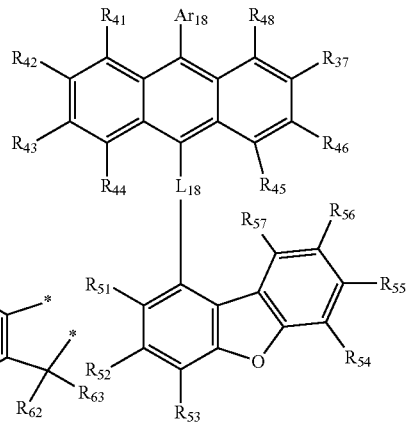

wherein, substituents $R_{41}$ to $R_{48}$ and $R_{51}$ to $R_{63}$ may be the same or different and are each independently selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 2 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen, a substituted or unsubstituted silyl of 1 to 30 carbon atoms, a substituted or unsubstituted alkyl germanium of 1 to 30 carbon atoms, a substituted or unsubstituted alkyl boron of 1 to 30 carbon atoms, a substituted or unsubstituted alkyl aluminum of 1 to 30 carbon atoms, a carbonyl, a phosphoryl, an amino, a thiol, a hydroxy, a selenium, a tellurium, an amide, an ether, and an ester, substituents $Ar_{15}$ to $Ar_{18}$ are each a substituted or unsubstituted aryl of 6 to 50 carbon atoms or a substituted or unsubstituted heteroaryl of 2 to 50 carbon atoms;

linkers $L_{15}$ to $L_{18}$ are each independently selected from among a single bond, a substituted or unsubstituted alkylene of 1 to 30 carbon atoms, a substituted or unsubstituted cycloalkylene of 3 to 30 carbon atoms, a substituted or unsubstituted arylene of 6 to 50 carbon atoms, and a substituted or unsubstituted heteroarylene of 3 to 50 carbon atoms.

$R_{52}$ and $R_{53}$, or two adjacent substituents of $R_{54}$ to $R_{57}$ in Chemical Formula H-2 are respectively single bonds involved in forming a 5-membered ring as a fused ring with the carbon atom to which substituents $R_{62}$ and $R_{63}$ in $Q_3$ are both bonded, two adjacent substituents of $R_{51}$ to $R_{53}$ or of $R_{54}$ to $R_{57}$ in Chemical Formula H-4 are respectively single bonds involved in forming a 5-membered ring as a fused ring with the carbon atom to which substituents $R_{62}$ and $R_{63}$ in $Q_4$ are both bonded, $R_{62}$ and $R_{63}$ may be linked to each other to form a ring, wherein the term 'substituted' in the expression 'substituted or unsubstituted' means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 2 to 24 carbon atoms, an alkylsilyl of 1 to 24 carbon atoms, an arylsilyl of 6 to 24 carbon atoms, and an aryloxy of 6 to 24 carbon atoms.

In Chemical Formula H according to the present disclosure, $Z_{11}$ may be a substituted or unsubstituted aryl of 6 to 18 carbon atoms.

That is, the compounds, represented by Chemical Formulas H-1 to H-4, available for the electron density control layer, are technically characterized in that a linker is bonded to the compounds at position 9 of the anthracene moiety and is connected to a dibenzofuran ring represented by the following Diagram 1 at position 1 or 2 of the dibenzofuran moiety.

[Diagram 1]

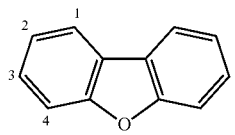

As shown in Chemical Formulas H-2 and H-4, $R_{52}$ and $R_{53}$, or two adjacent substituents of $R_{54}$ to $R_{57}$ in Chemical Formula H-2 are respectively single bonds involved in forming a 5-membered ring as a fused ring with the carbon atom to which substituents $R_{62}$ and $R_{63}$ in Structural Formula $Q_3$ are both bonded, and two adjacent substituents of $R_{51}$ to $R_{53}$ or of $R_{54}$ to $R_{57}$ in Chemical Formula H-4 are respectively single bonds involved in forming a 5-membered ring as a fused ring with the carbon atom to which substituents $R_{62}$ and $R_{63}$ in Structural Formula $Q_4$ are both bonded.

According to some embodiments of the present disclosure, substituents $R_{62}$ and $R_{63}$ of Structural Formula $Q_3$ in Chemical Formula H-2 may be the same or different and are each independently a substituted or unsubstituted aryl of 6 to 24 carbon atoms, and substituents $R_{62}$ and $R_{63}$ of Structural Formula $Q_4$ in Chemical Formula H-4 may be the same or different and are each independently a substituted or unsubstituted aryl of 6 to 24 carbon atoms.

Meanwhile, a connection may be formed between substituents $R_{62}$ and $R_{63}$ in Chemical Formula H-2 and between substituents $R_{62}$ and $R_{63}$ in Chemical Formula H-4 to form additional fused rings, respectively.

By way of example, when the substituents $R_{62}$ and $R_{63}$ are connected to each other, the compound represented by Chemical Formula H-4 may include a substituted or unsubstituted spirobisfluorene ring as illustrated in the following Diagram 2. Likewise, the compound represented by Chemical Formula H-2 may include a substituted or unsubstituted spirobisfluorene ring when the substituents $R_{62}$ and $R_{63}$ are connected to each other.

[Diagram 2]

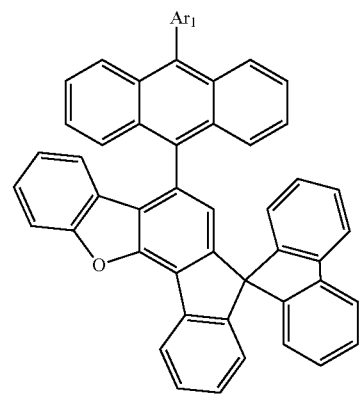

In greater detail, the compound, represented by one of Chemical Formulas H, available for the electron density control layer, may be selected from among the following Compounds 201 to 348, but is not limited thereto.

<Compound 201>

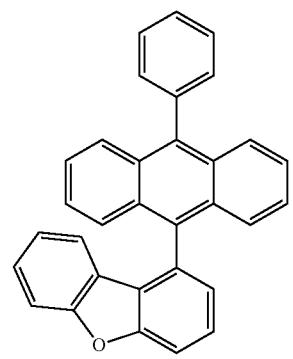

<Compound 202>

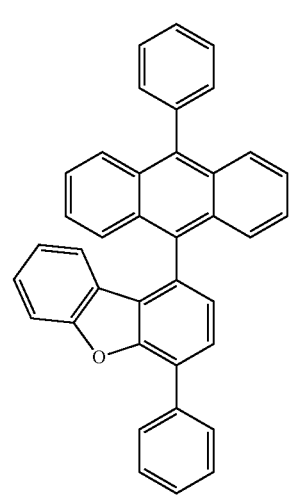

<Compound 203>
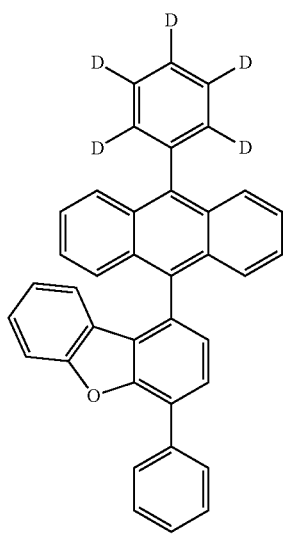
<Compound 204>
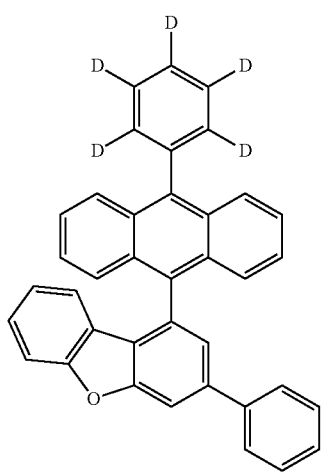
<Compound 205>
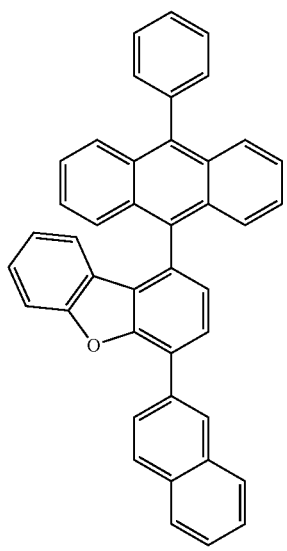
<Compound 206>
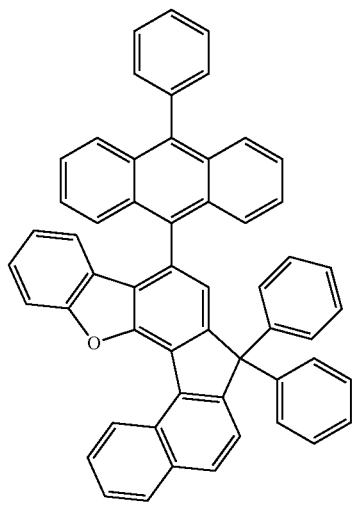
<Compound 207>
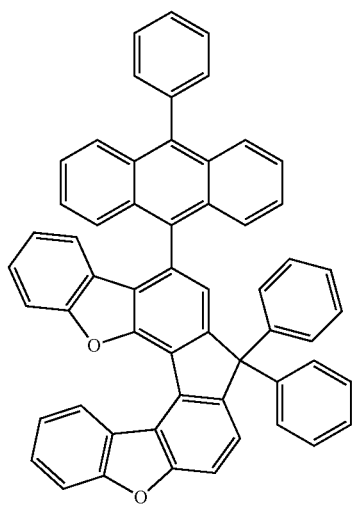
<Compound 208>
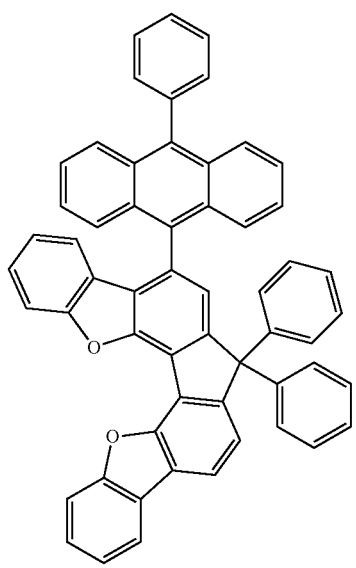

<Compound 209>
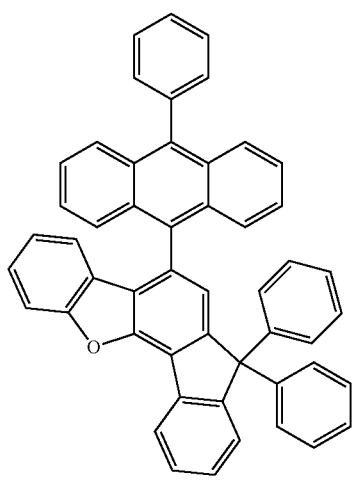
<Compound 210>
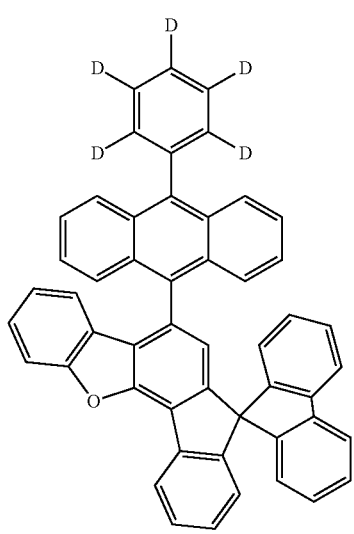
<Compound 211>
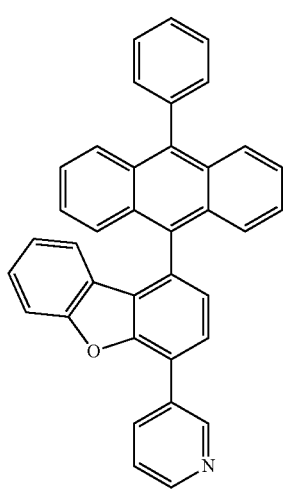
<Compound 212>
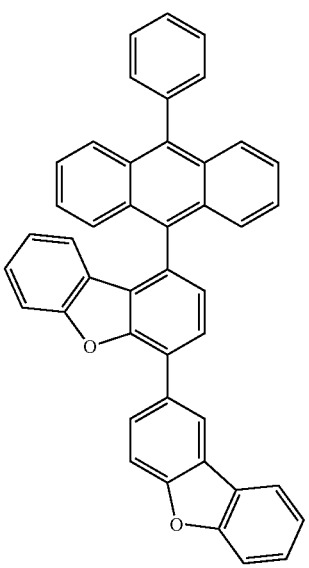
<Compound 213>
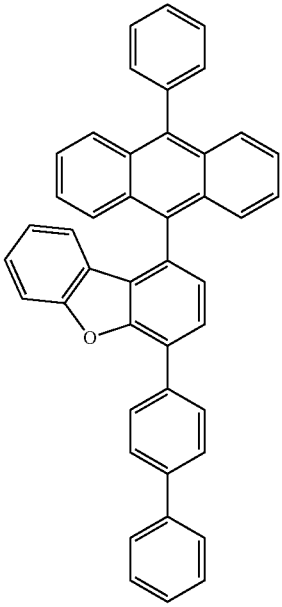

-continued
<Compound 214>
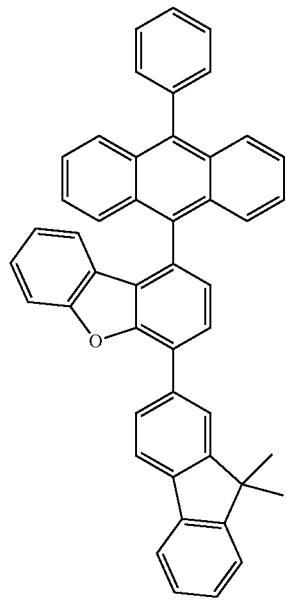
<Compound 215>
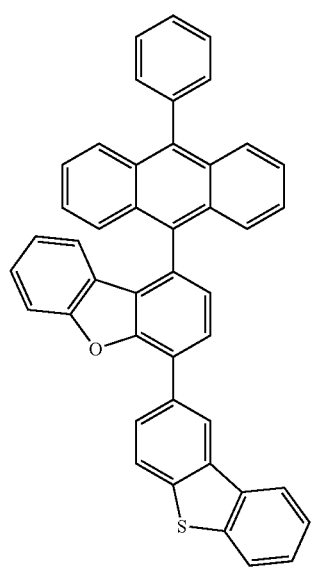
-continued
<Compound 216>
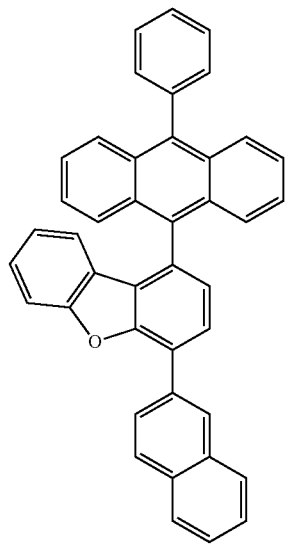
<Compound 217>
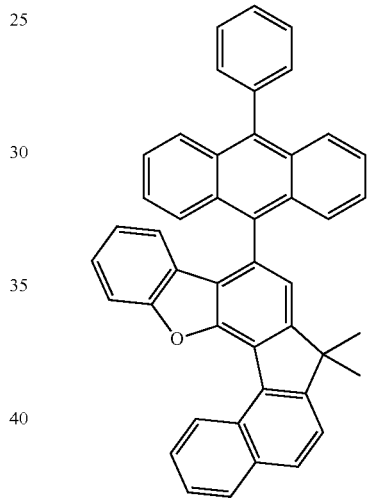
<Compound 218>
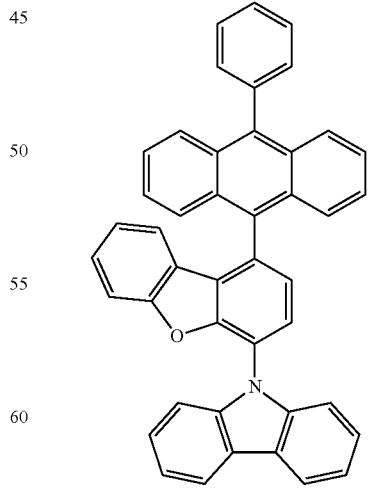

<Compound 219>
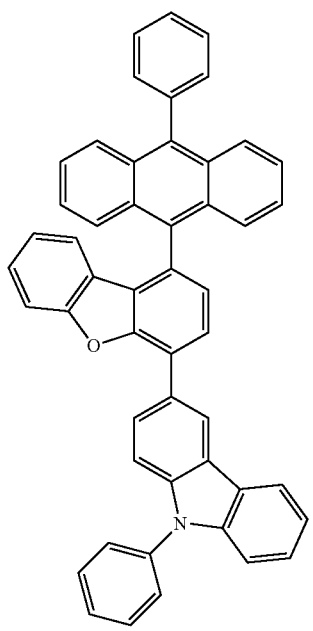
<Compound 220>
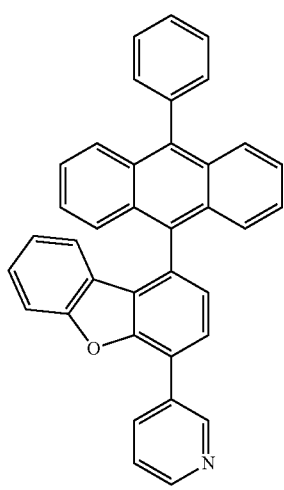
<Compound 221>
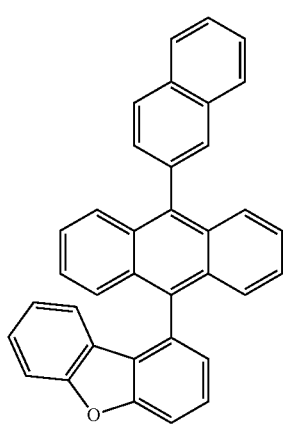
<Compound 222>
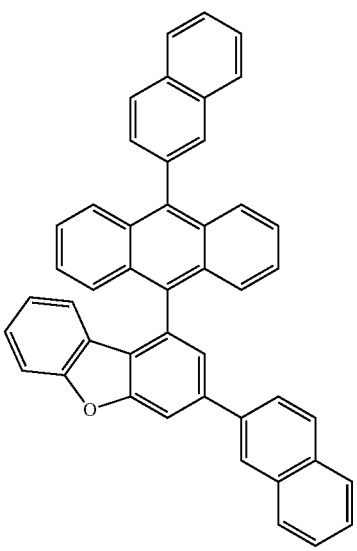
<Compound 223>
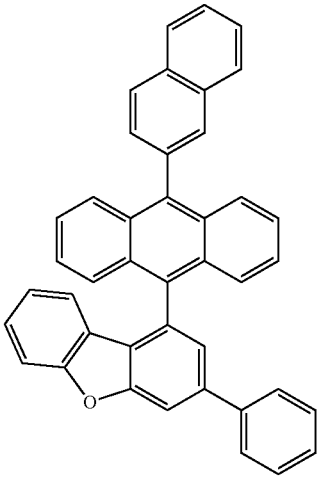
<Compound 224>

<Compound 225>
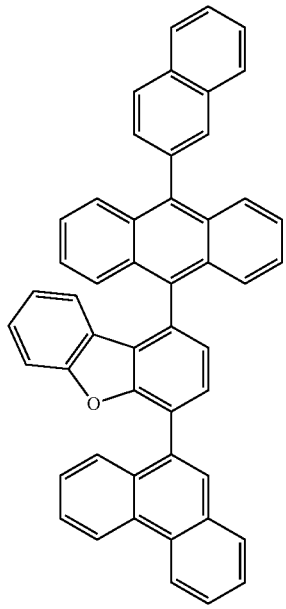
<Compound 226>
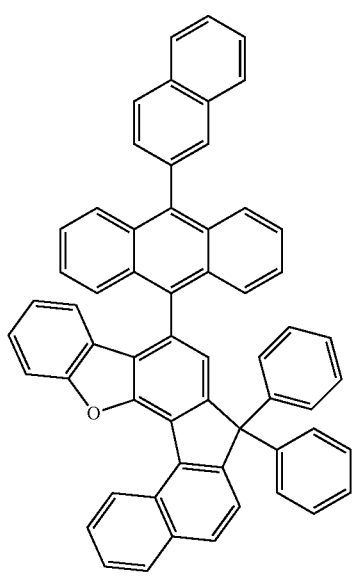
<Compound 227>
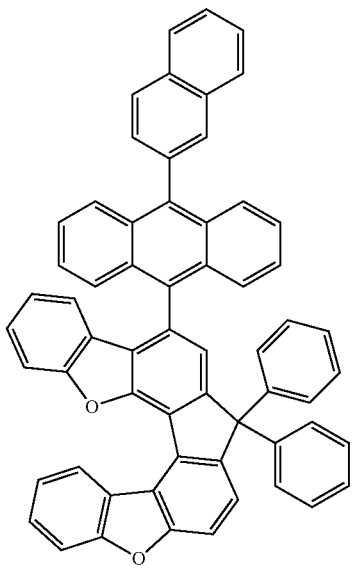
<Compound 228>

<Compound 229>
<Compound 230>
<Compound 231>
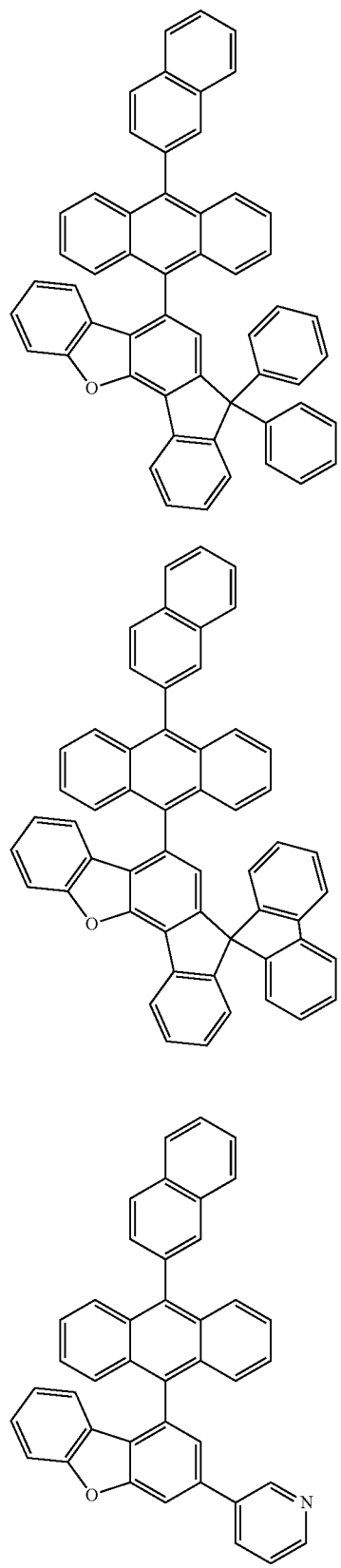
<Compound 232>
<Compound 233>
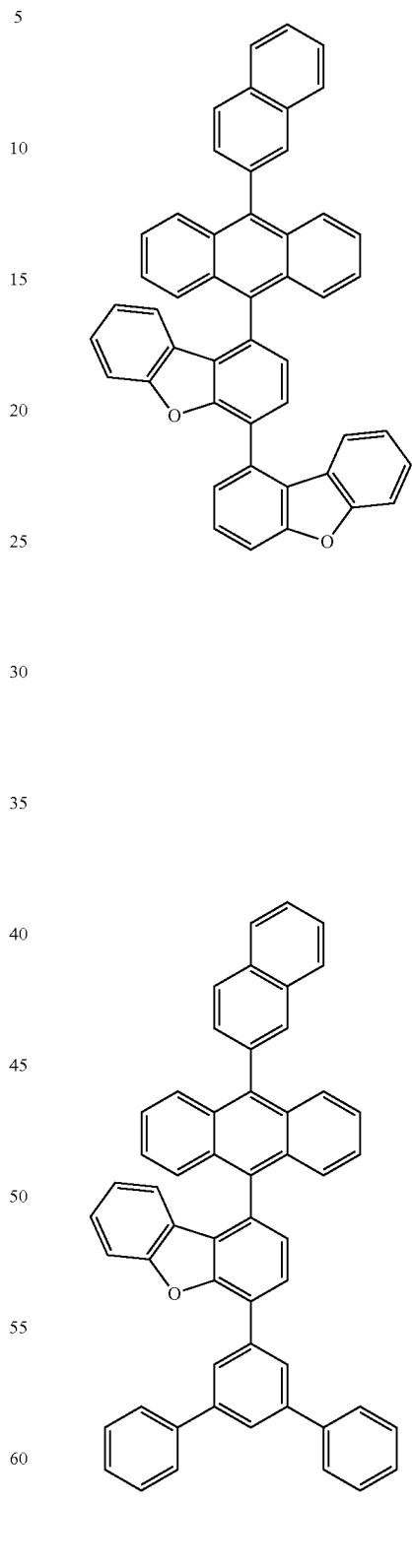

<Compound 234>
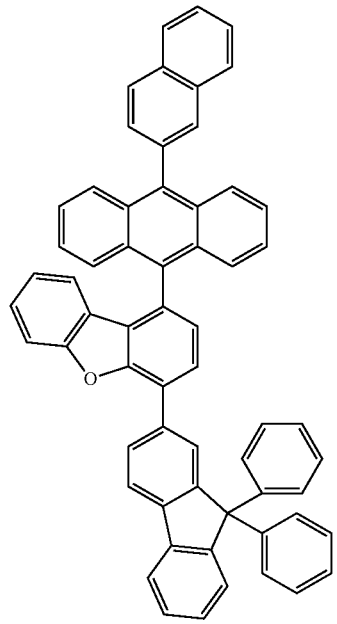
<Compound 236>
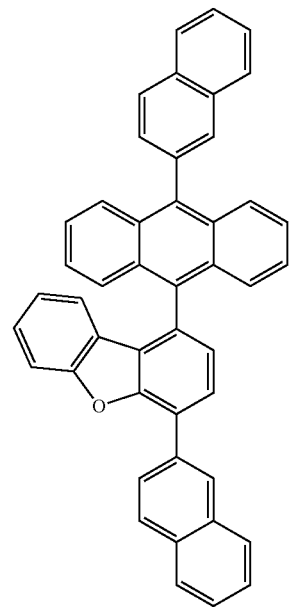
<Compound 235>
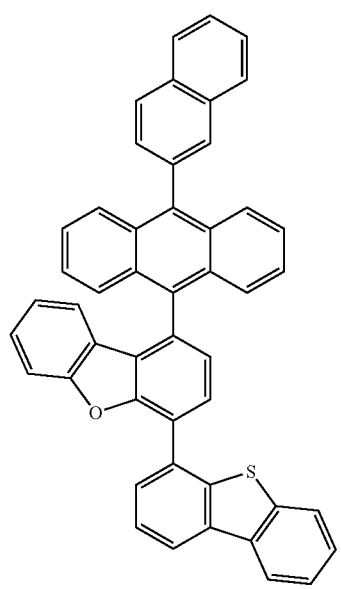
<Compound 237>
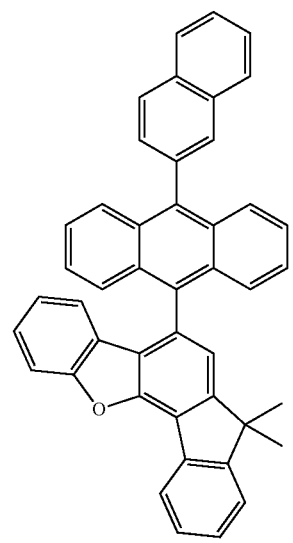

<Compound 238>
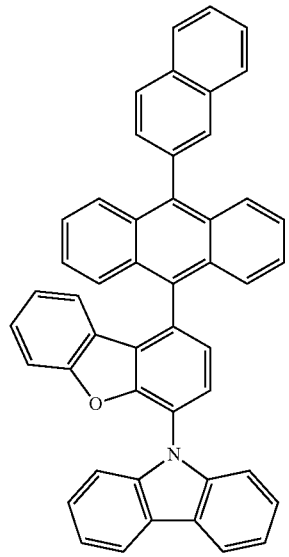
<Compound 239>
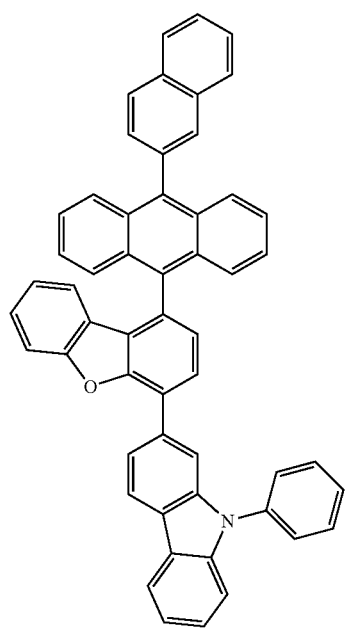
<Compound 240>
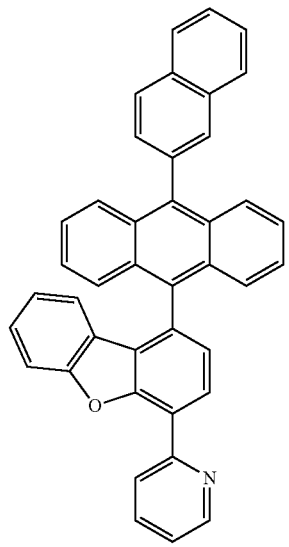
<Compound 241>
<Compound 242>
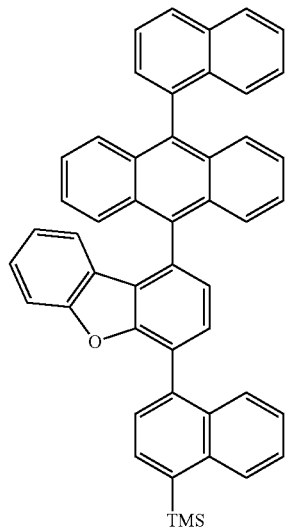

<Compound 243>
<Compound 244>
<Compound 245>
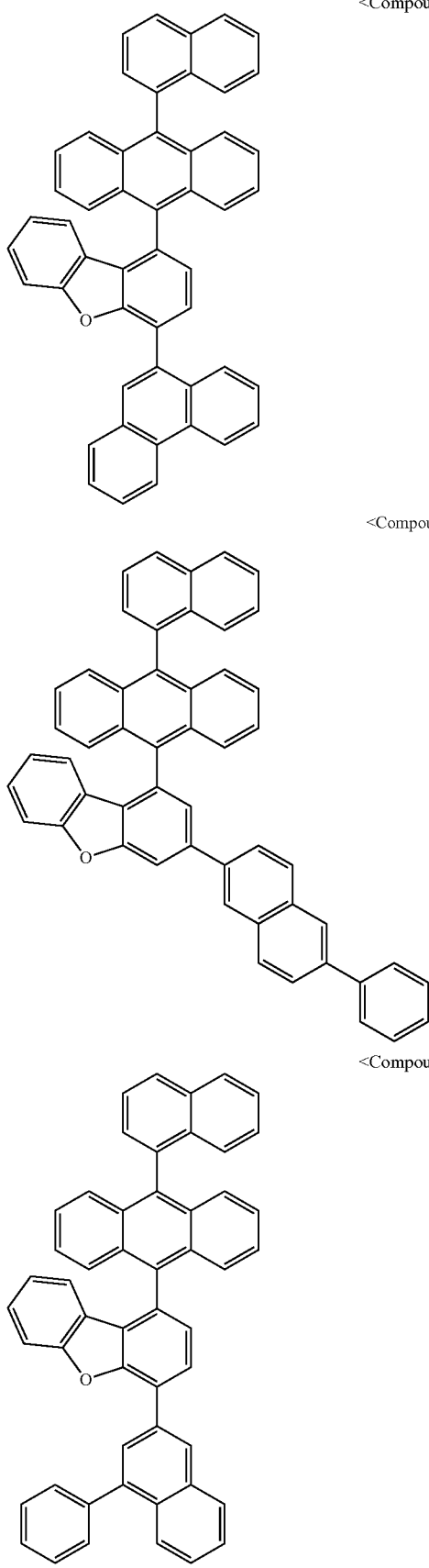
<Compound 246>
<Compound 247>
<Compound 248>
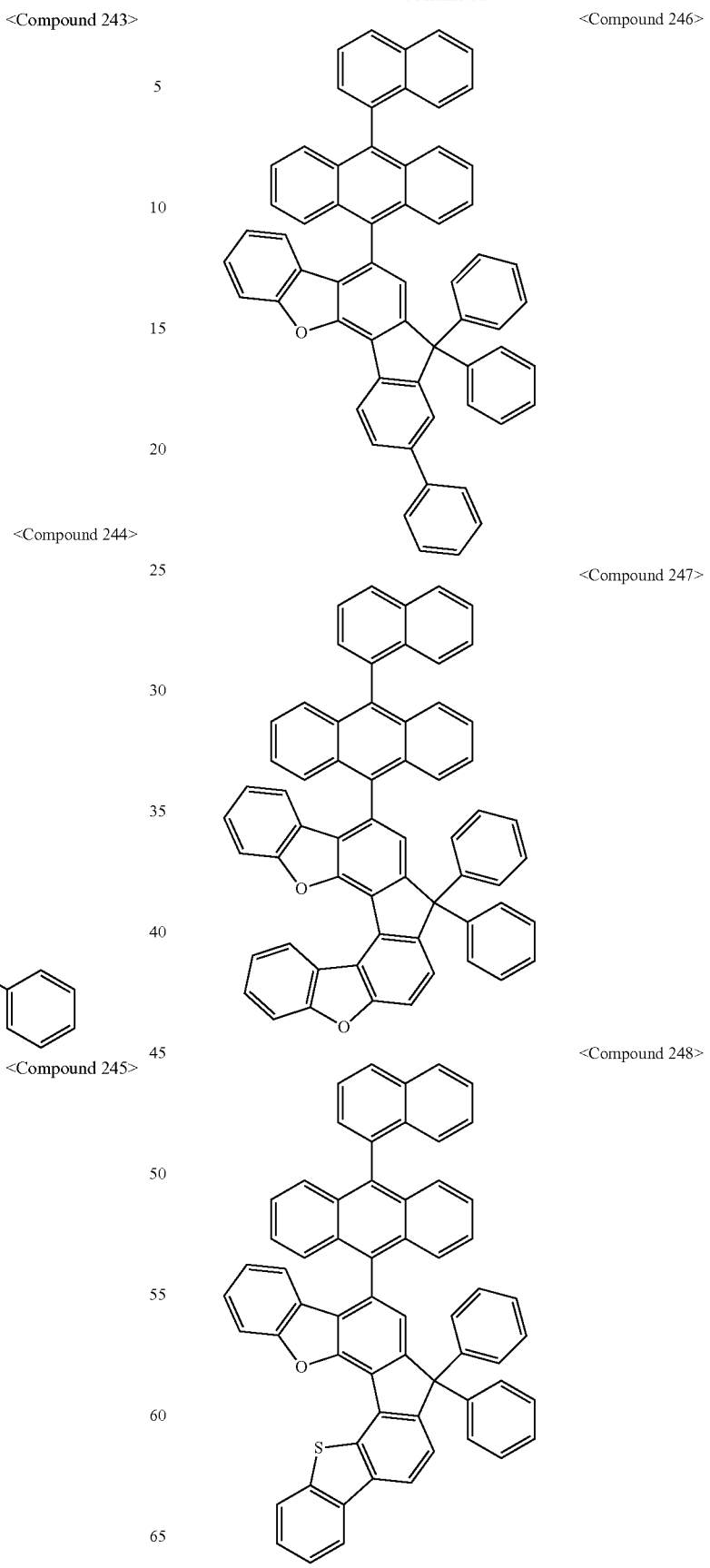

<Compound 249>
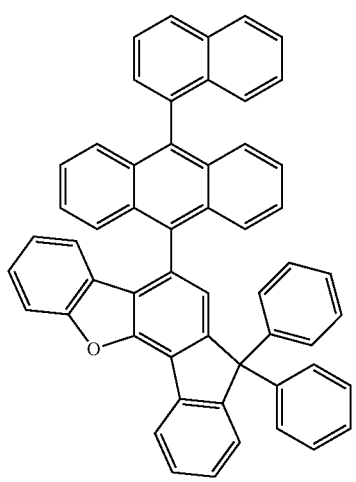
<Compound 250>
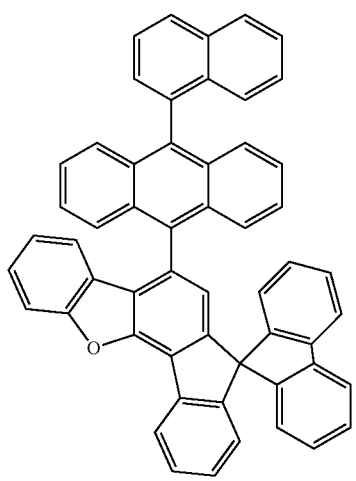
<Compound 251>
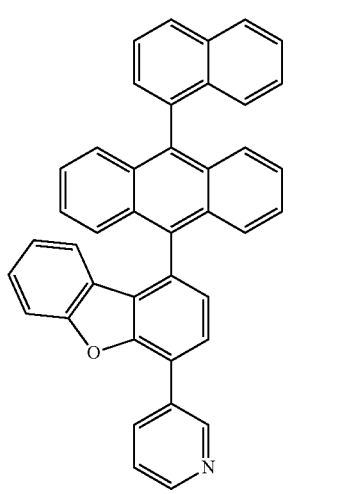
<Compound 252>
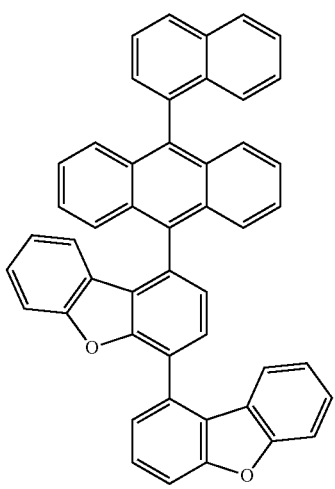
<Compound 253>
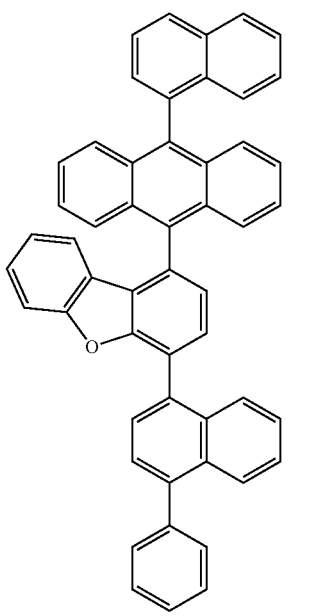
<Compound 254>
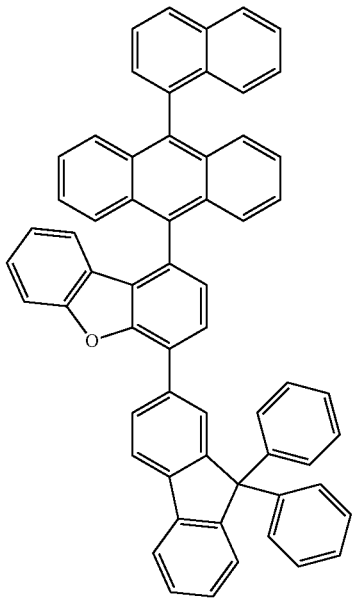

<Compound 255>
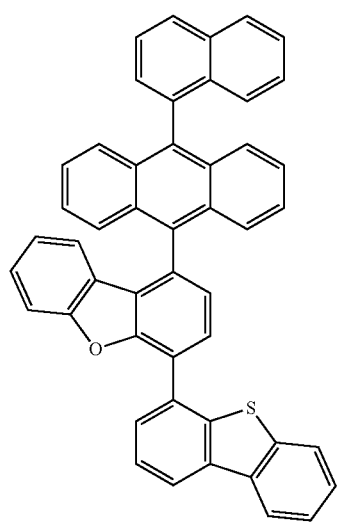
<Compound 256>
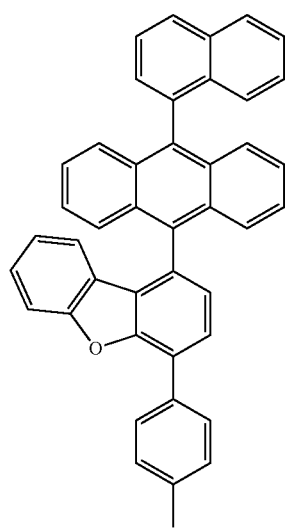
<Compound 257>
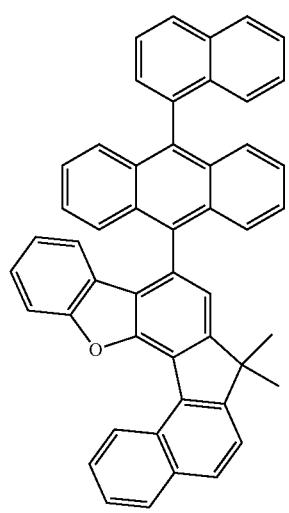
<Compound 258>
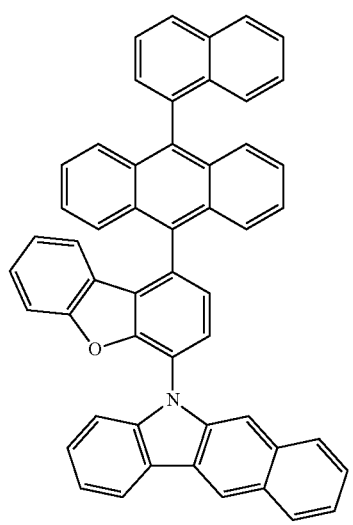
<Compound 259>
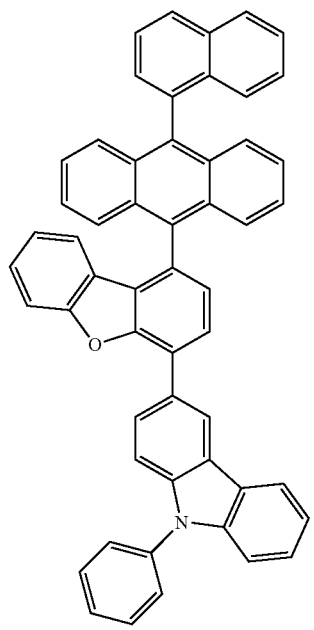
<Compound 260>
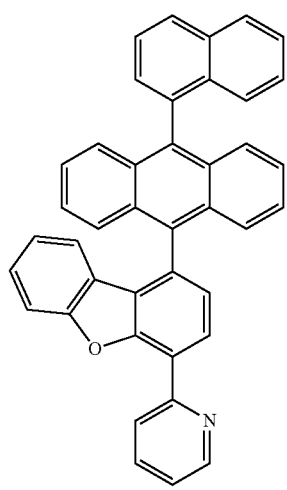

<Compound 261>
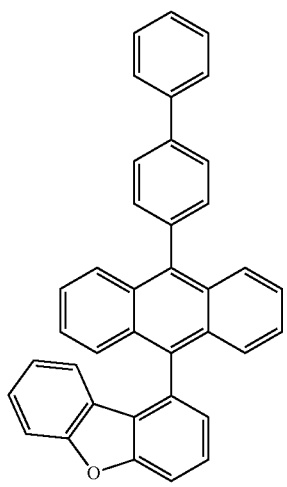
<Compound 262>
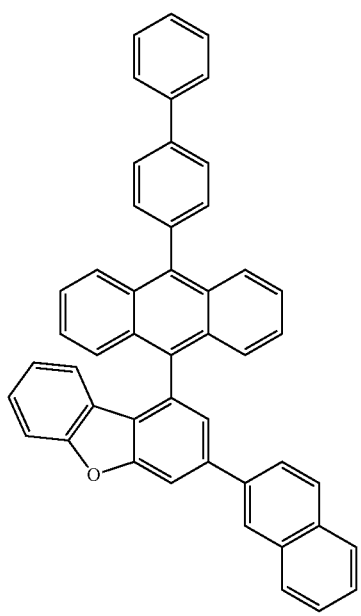
<Compound 263>
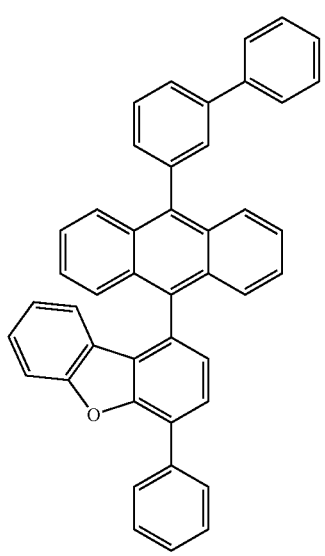
<Compound 264>
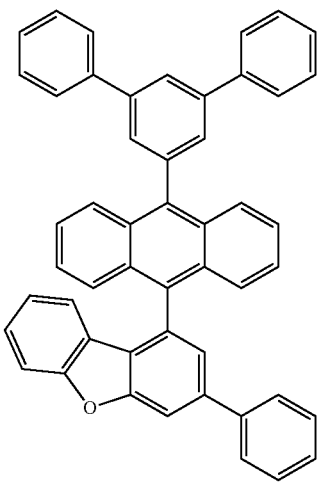
<Compound 265>
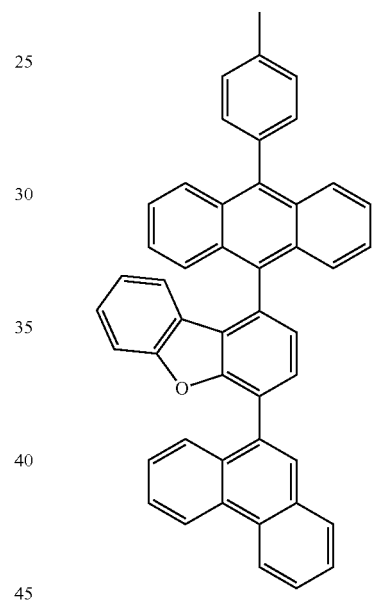
<Compound 266>
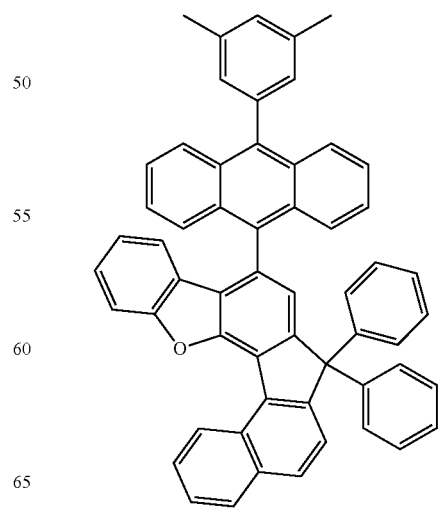

<Compound 267>
<Compound 268>
<Compound 269>
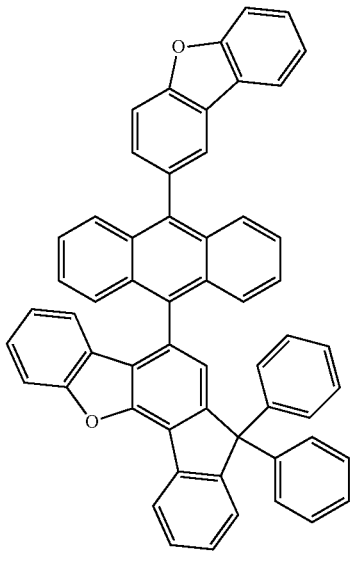
<Compound 270>
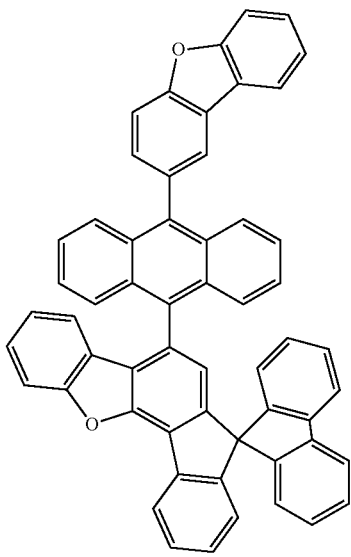
<Compound 271>
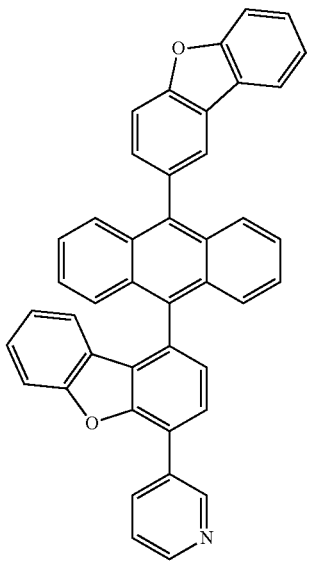

<Compound 272>
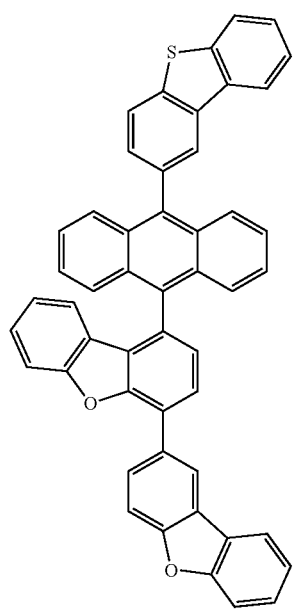
<Compound 274>
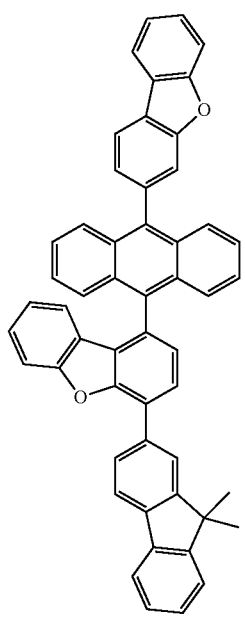
<Compound 273>
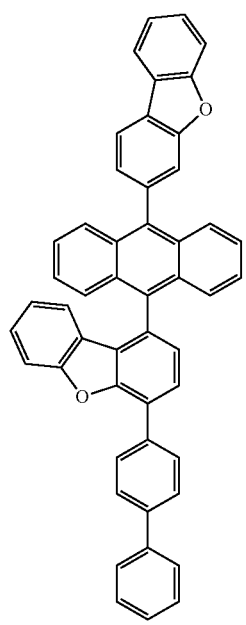
<Compound 275>

<Compound 276>
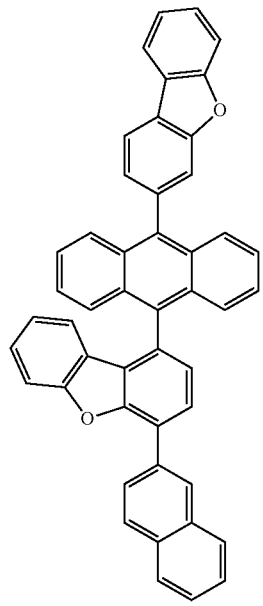
<Compound 277>
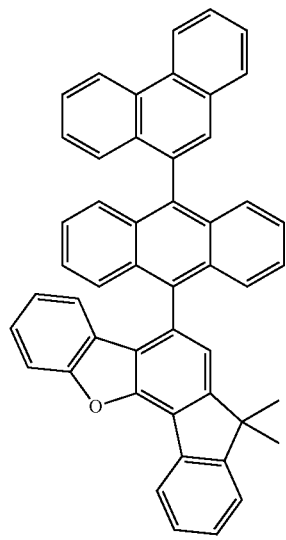
<Compound 278>
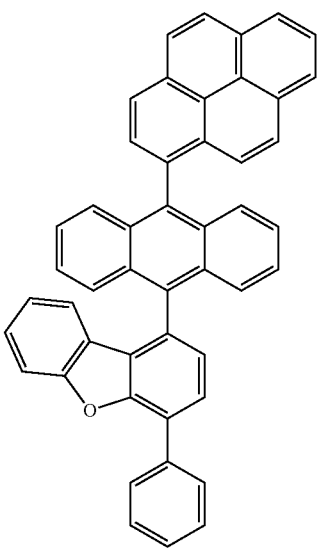
<Compound 279>
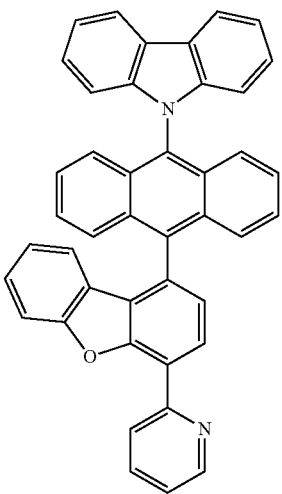
<Compound 280>

<Compound 281>
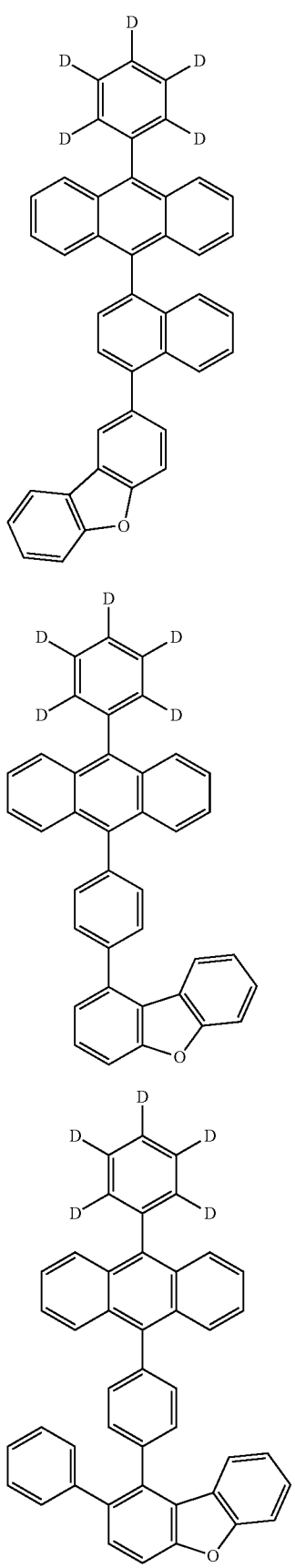
<Compound 282>
<Compound 284>
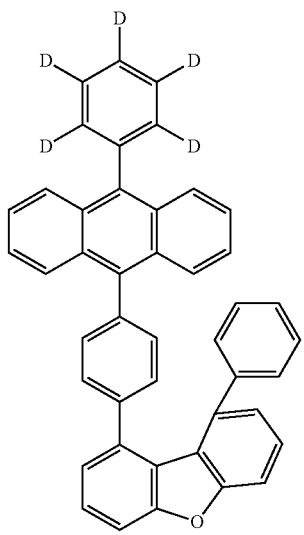
<Compound 285>
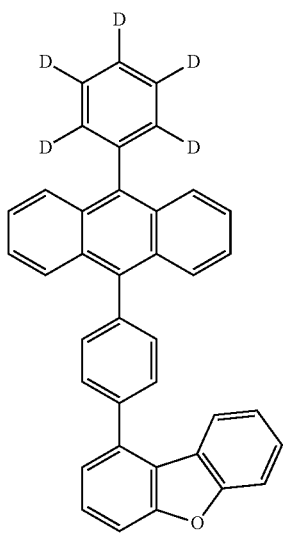
<Compound 283>
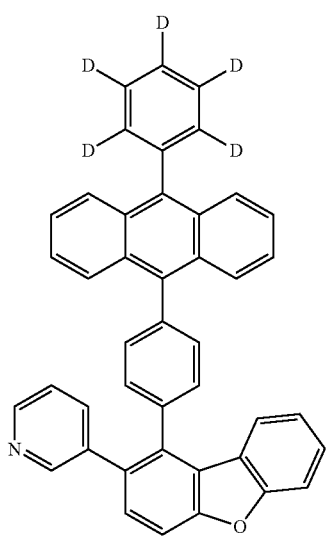
<Compound 286>
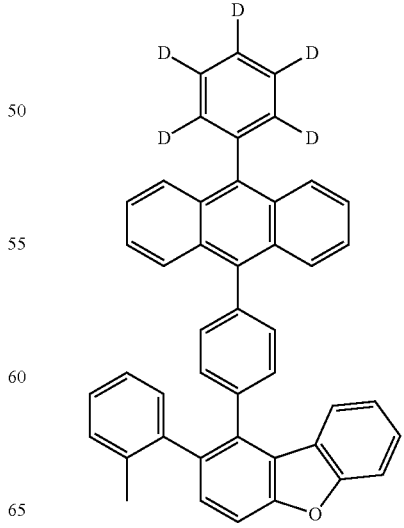

<Compound 287>
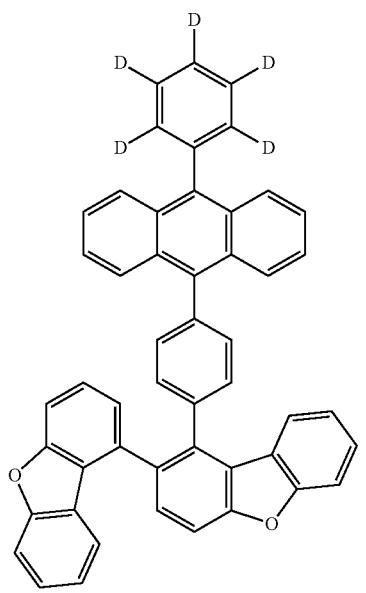
<Compound 288>
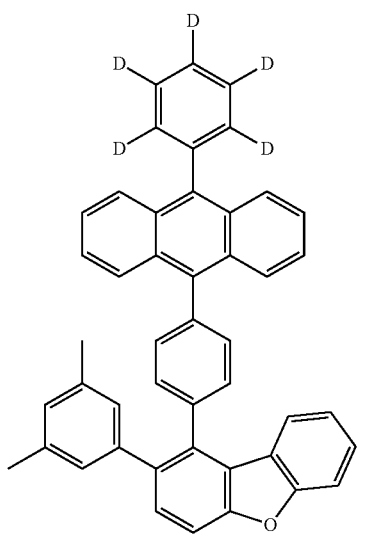
<Compound 289>
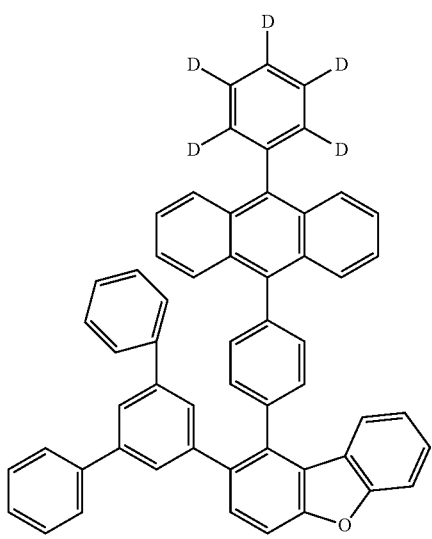
<Compound 290>
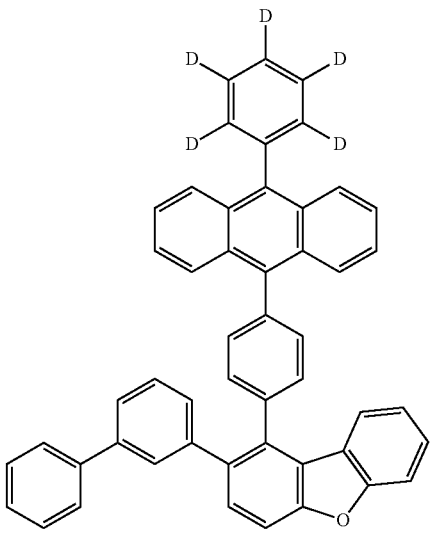
<Compound 291>
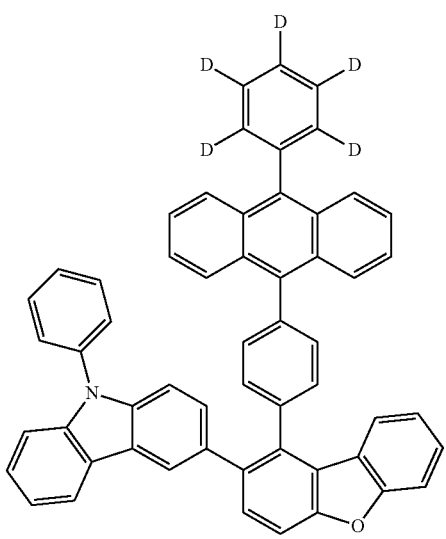
<Compound 292>
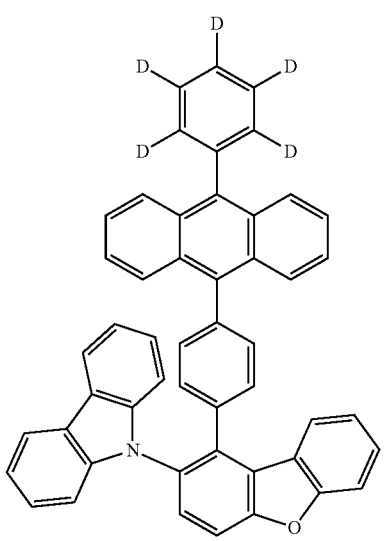

<Compound 293>
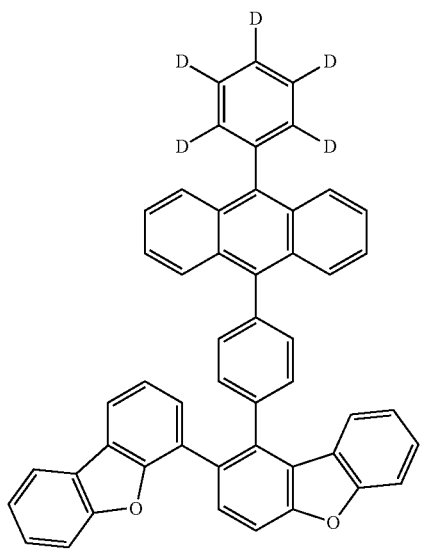
<Compound 294>
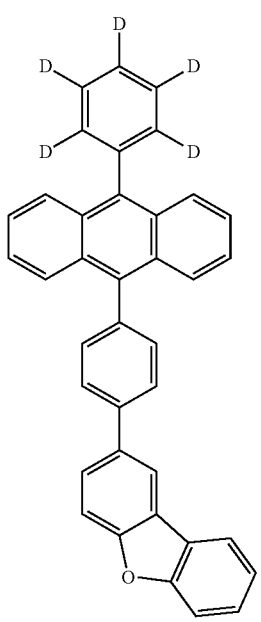
<Compound 295>
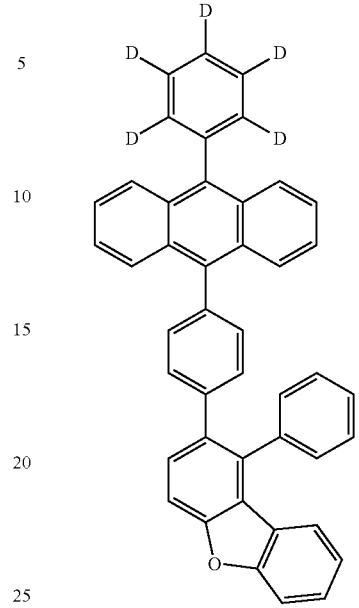
<Compound 296>
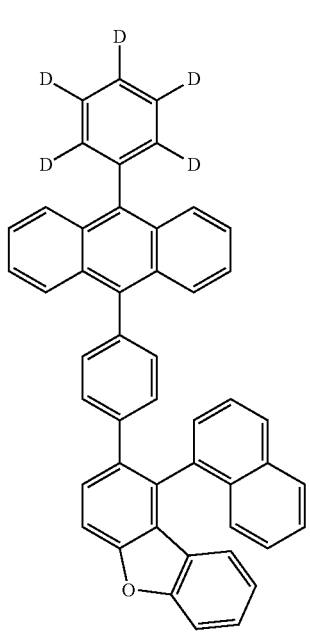

<Compound 297>
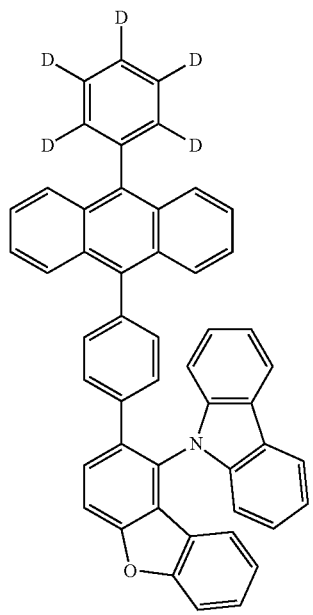
<Compound 299>
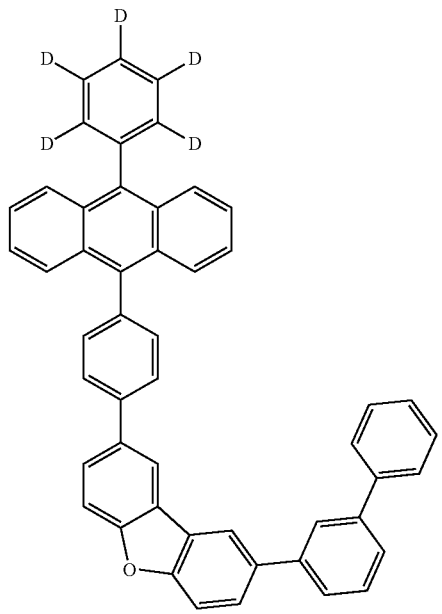
<Compound 298>
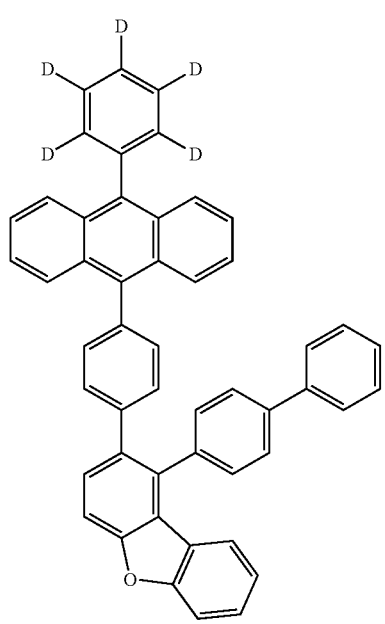
<Compound 300>
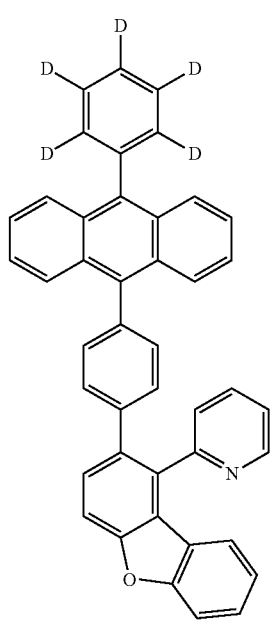

<Compound 301>
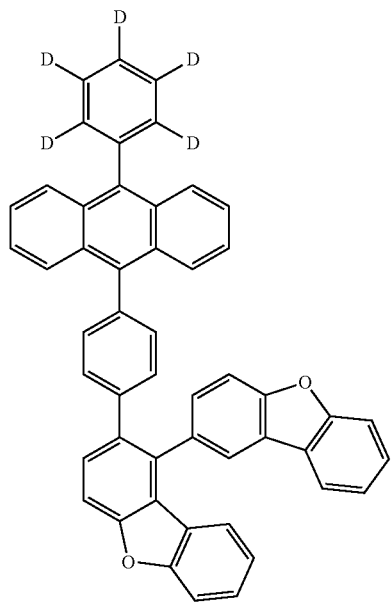
<Compound 302>
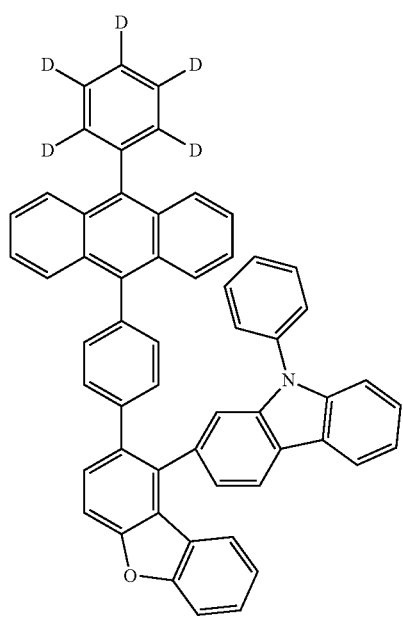
<Compound 303>
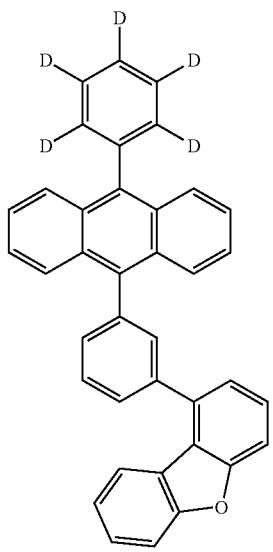
<Compound 304>
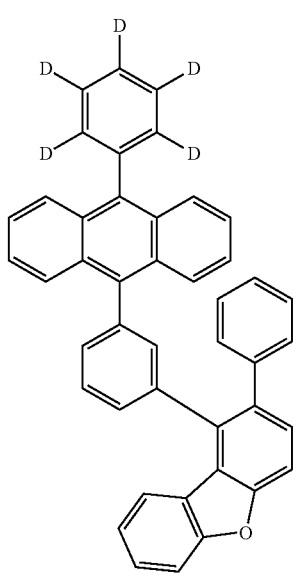

<Compound 305>
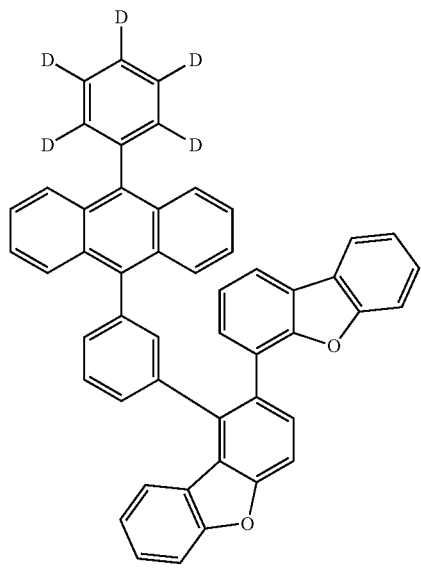
<Compound 307>
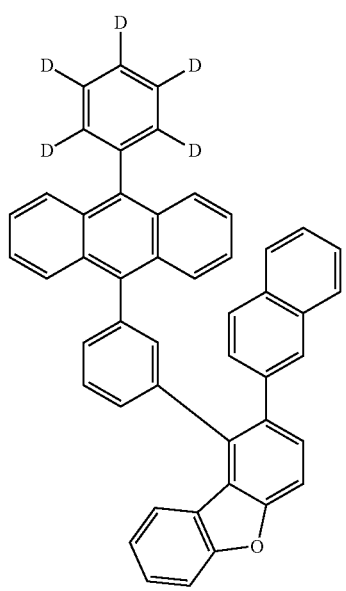
<Compound 306>
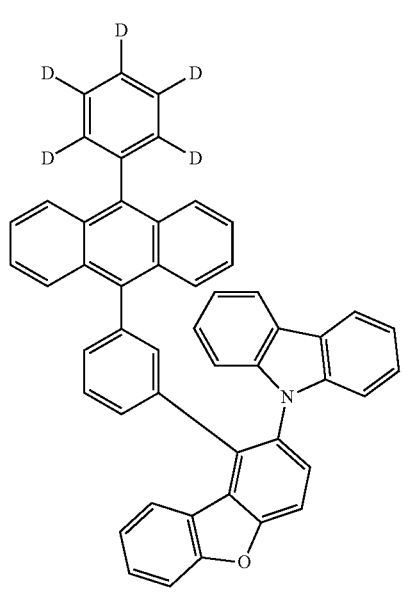
<Compound 308>
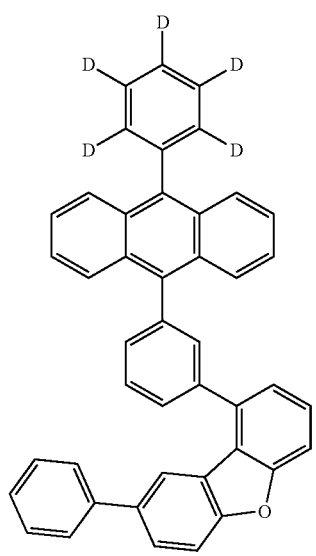

<Compound 309>
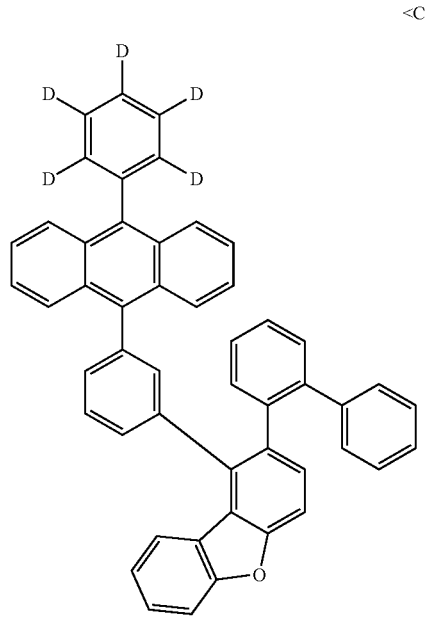
<Compound 311>
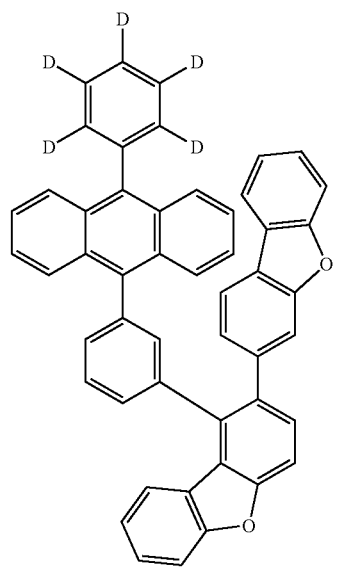
<Compound 310>
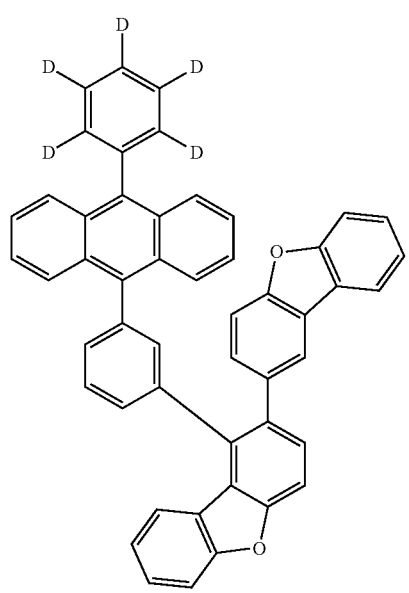
<Compound 312>
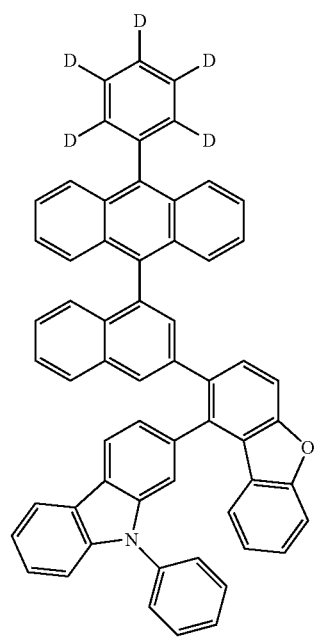

<Compound 313>
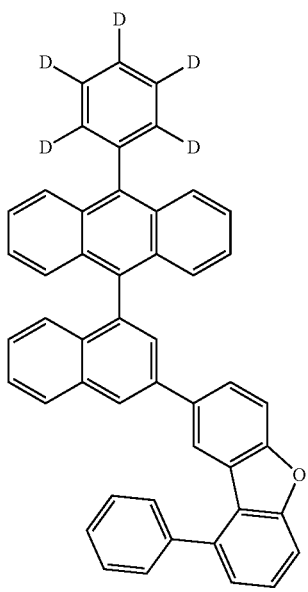
<Compound 314>
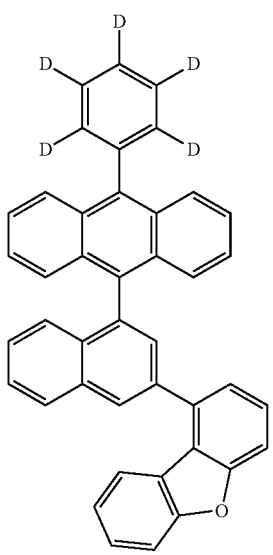
<Compound 315>
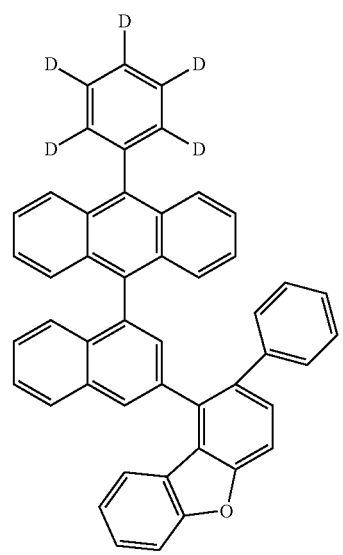
<Compound 316>
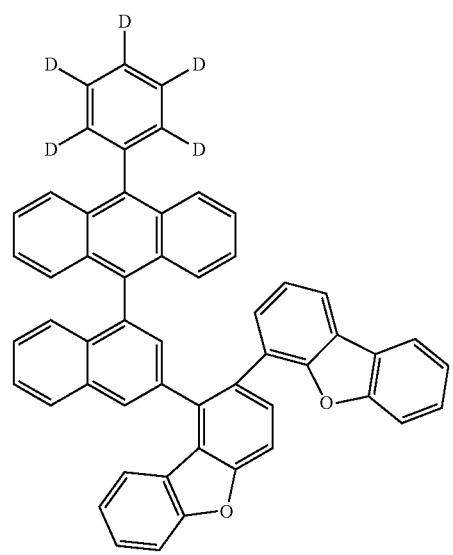

<Compound 317>
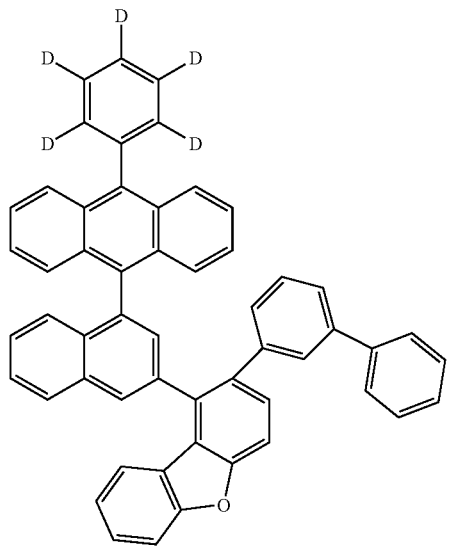
<Compound 318>
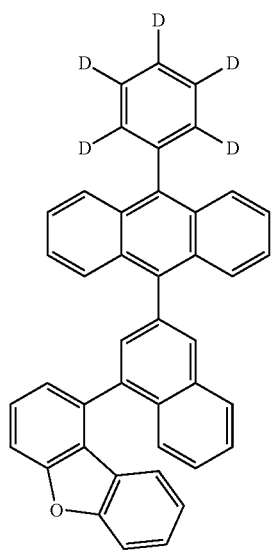
<Compound 319>
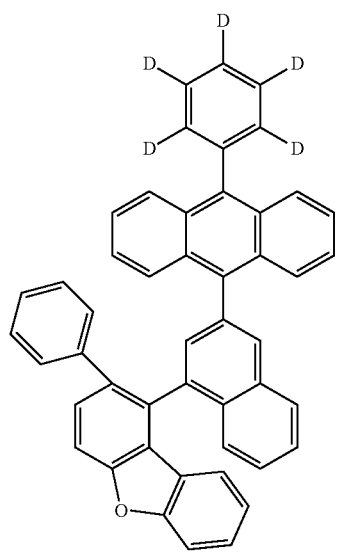
<Compound 320>
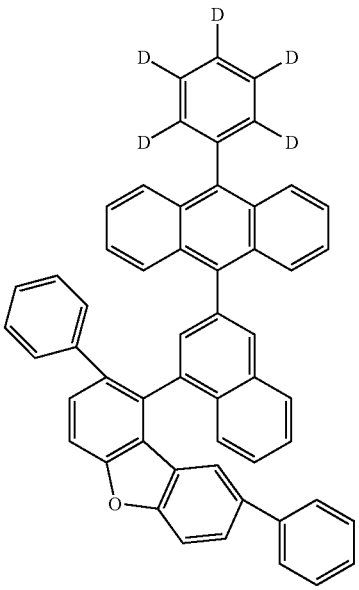
<Compound 321>
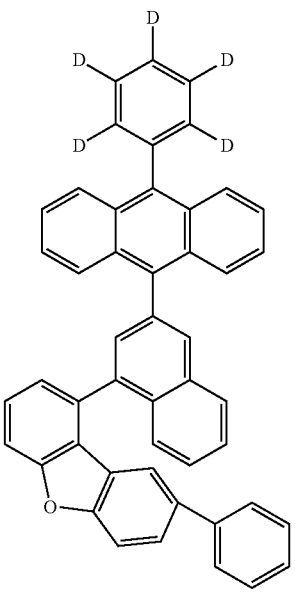

<Compound 322>
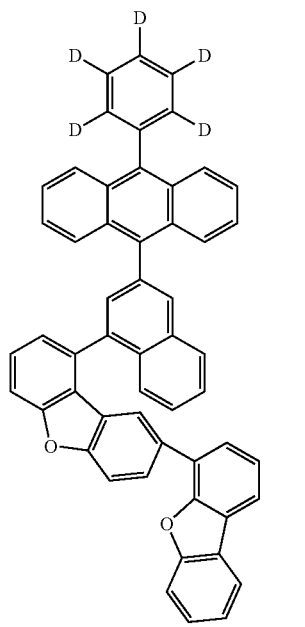
<Compound 323>
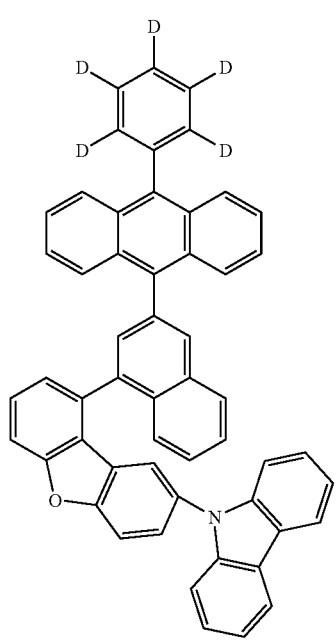
<Compound 324>
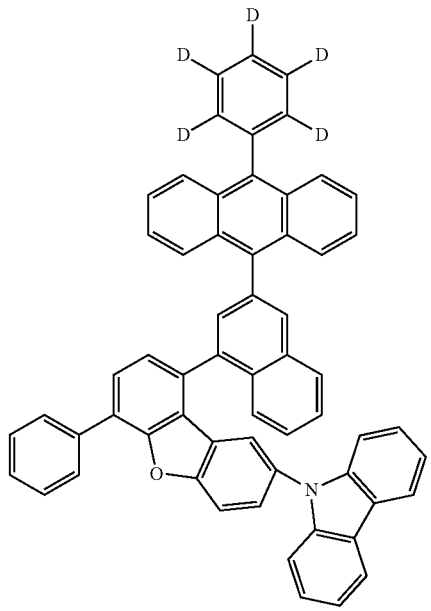
<Compound 325>
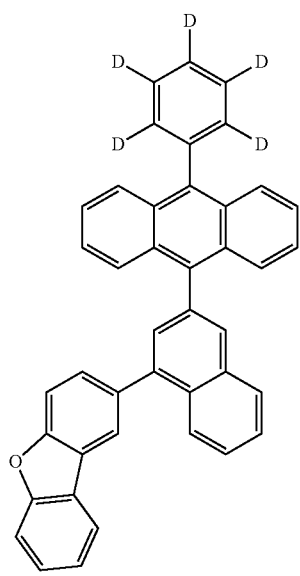

<Compound 326>
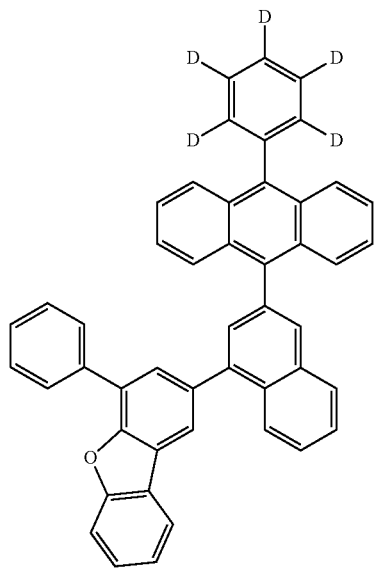
<Compound 327>
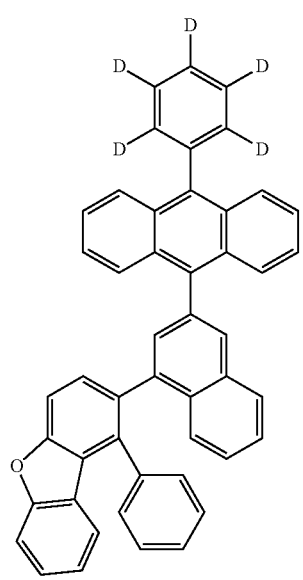
<Compound 328>
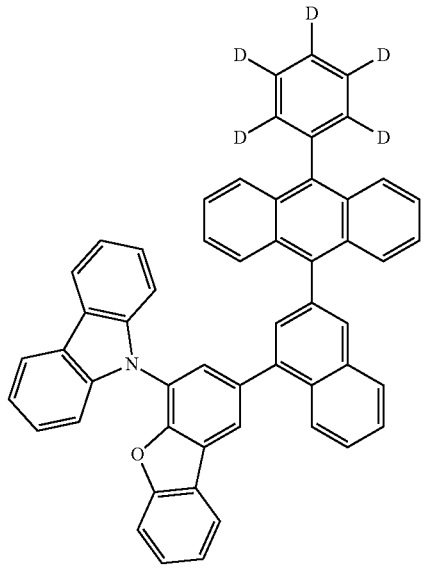
<Compound 329>
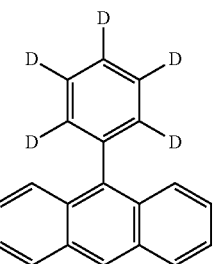
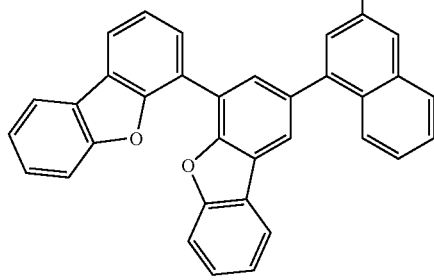
<Compound 330>
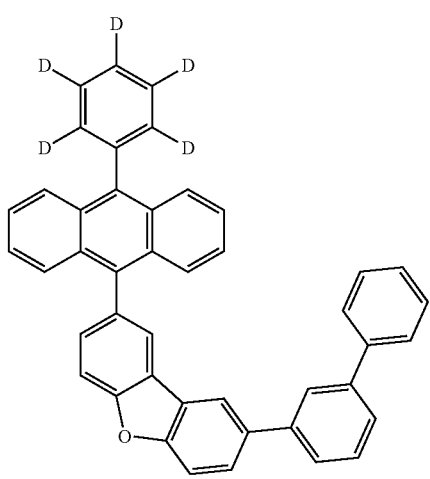

<Compound 331>
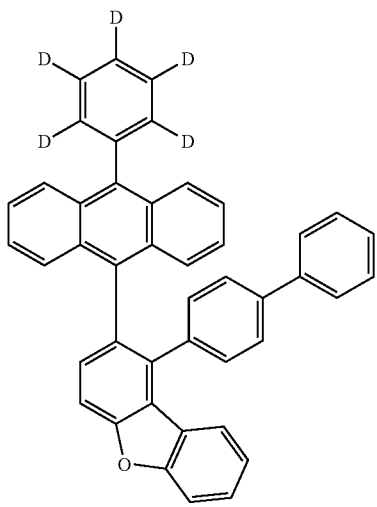
<Compound 332>
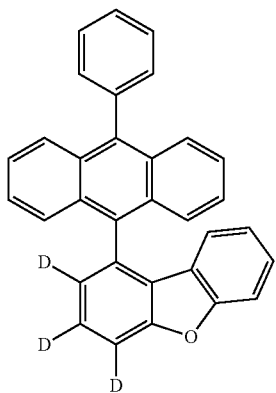
<Compound 333>
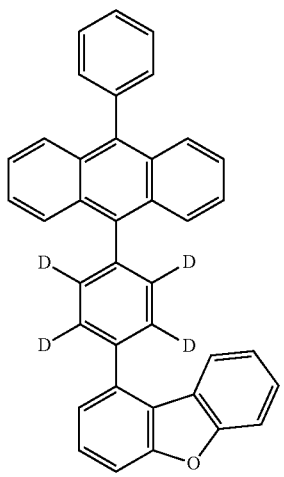
<Compound 334>
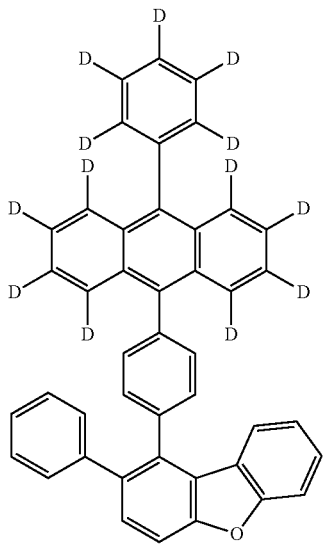
<Compound 335>
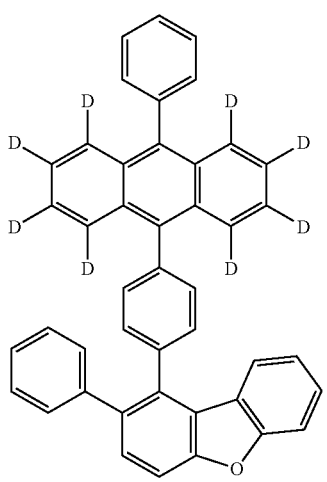
<Compound 336>
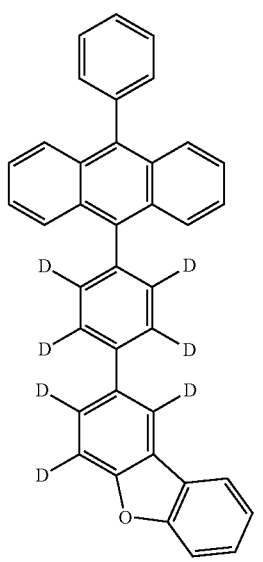

<Compound 337>
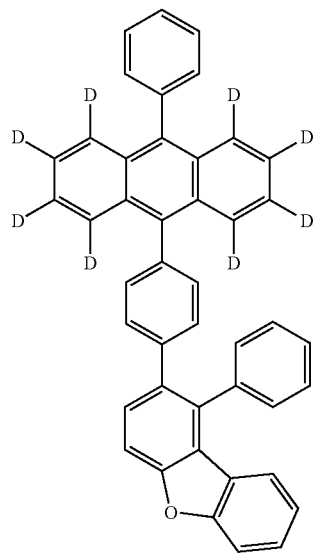
<Compound 338>
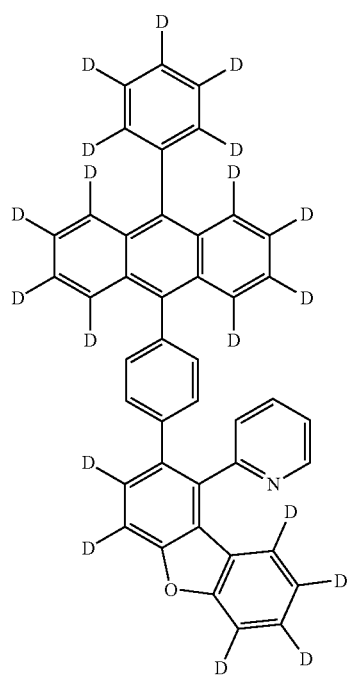
[Compound 339]
[Compound 340]
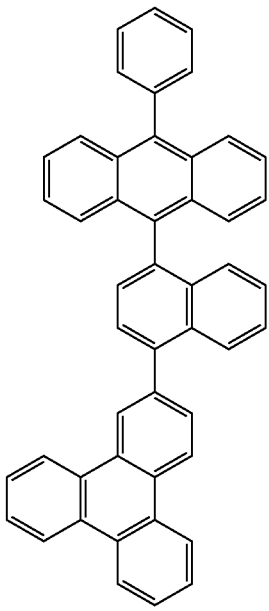
[Compound 341]
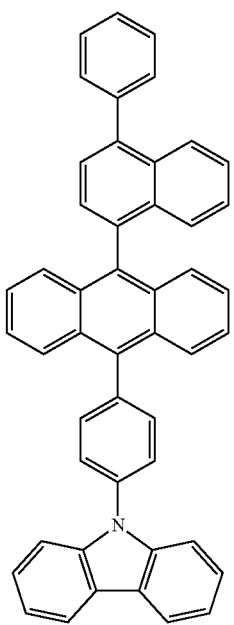

[Compound 342]
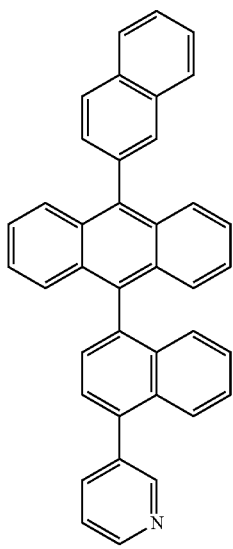
[Compound 343]
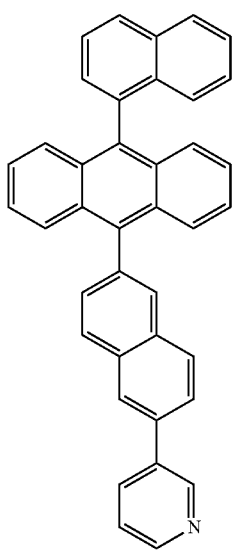
[Compound 344]
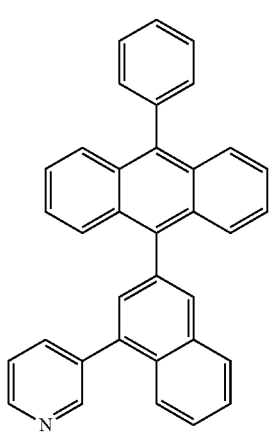
[Compound 345]
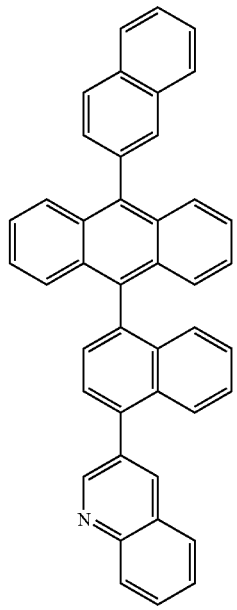
[Compound 346]
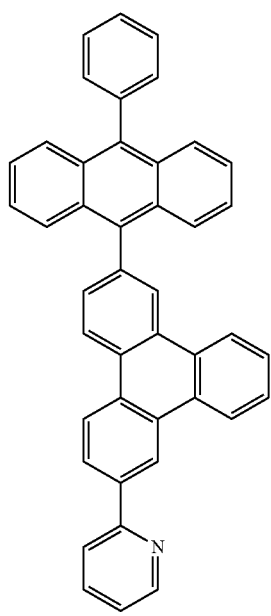

[Compound 347]

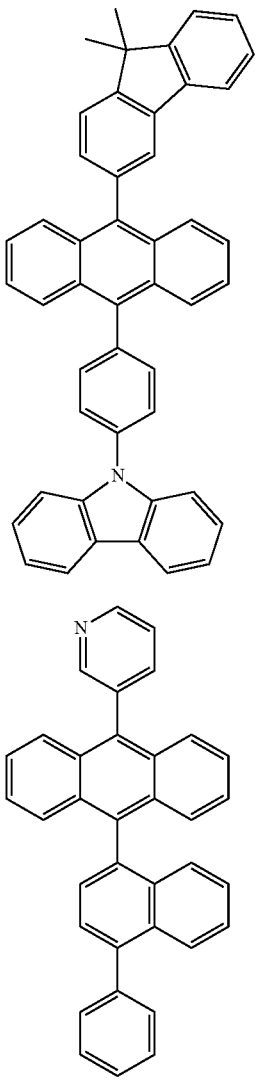

[Compound 348]

Below, the organic light-emitting diode according to an embodiment of the present disclosure is explained with reference to FIG. 1.

FIG. 1 is a schematic cross-sectional view of the structure of an organic light-emitting diode according to some embodiments of the present disclosure.

As shown in FIG. 1, the organic light-emitting diode comprises an anode 20, a hole transport layer 40, an organic light-emitting layer 50 including a host and a dopant, an electron density control layer 55, an electron transport layer 60, and a cathode 80, sequentially, which corresponds to an organic light-emitting diode in which an anode and a cathode serve as a first and a second electrode, respectively, and a hole transport layer disposed between the anode and a light-emitting layer and an electron transport layer is disposed between an electron density control and the cathode.

That is, an electron density control layer 55 including at least one of the compounds represented by Chemical Formulas F to H is disposed between the light-emitting layer 50 and the electron transport layer 60, and the light-emitting layer includes at least one of the compounds represented by Chemical Formula A or B as a dopant.

In addition, the organic light-emitting diode according to an embodiment of the present disclosure may comprise a hole injection layer 30 between the anode 20 and the hole transport layer 40 and an electron injection layer between the electron transport layer 60 and the cathode 80.

Reference is made to FIG. 1 with regard to the fabrication of the organic light-emitting diode of the present disclosure.

First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, ease of handling, and water resistance. As the anode electrode material, indium tin oxide (ITO), indium zinc oxide (IZO), tin oxide ($SnO_2$), or zinc oxide (ZnO), which are transparent and superior in terms of conductivity, may be used.

A hole injection layer material is applied on the anode electrode 20 by thermal deposition in a vacuum or by spin coating to form a hole injection layer 30. Subsequently, thermal deposition in a vacuum or by spin coating may also be conducted to form a hole transport layer 40 with a hole transport layer material on the hole injection layer 30.

No particular limitations are imposed on the hole injection layer material, as long as it is one that is typically used in the art. For example, mention may be made of 2-TNATA [4,4',4"-tris(2-naphthylphenyl-phenylamino)-triphenylamine], NPD [N,N'-di(1-naphthyl)-N,N'-diphenylbenzidine)], TPD [N,N'-diphenyl-N,N'-bis(3-methylphenyl)-1,1'-biphenyl-4,4'-diamine], and DNTPD [N,N'-diphenyl-N,N'-bis-[4-(phenyl-m-tolyl-amino)-phenyl]-biphenyl-4,4'-diamine], but is not limited thereto.

So long as it is typically used in the art, any material may be selected for the hole transport layer without particular limitation. Examples include, but are not limited to, N,N'-bis(3-methylphenyl)-N,N'-diphenyl-[1,1-biphenyl]-4,4'-diamine (TPD) and N,N'-di(naphthalen-1-yl)-N,N'-diphenyl-benzidine (a-NPD).

Then, an organic light-emitting layer 50 is deposited on the hole transport layer 40, followed by the formation of an electron density control layer 55 according to the present disclosure on the organic light-emitting layer 50 by deposition in a vacuum or by spin coating.

Here, the light-emitting layer may be composed of a host and a dopant the materials of which are as described above.

In some embodiments of the present disclosure, the light-emitting layer particularly ranges in thickness from 50 to 2,000 Å.

In the light-emitting layer according to the present disclosure, a dopant material may be used in combination with a host material. When the light-emitting layer includes a host and a dopant, the content of the dopant in the light-emitting layer may range from about 0.01 to 20 parts by weight based on 100 parts by weight of the host, but is not limited thereto.

Following the formation of the electron density control layer 55 according to the present disclosure on the light-emitting layer, an electron transport layer 60 may be deposited using a vacuum deposition method or a spin coating method and then overlaid with an electron injection layer 70. A cathode metal is deposited on the electron injection layer 70 by thermal deposition in a vacuum to form a cathode 80, thus obtaining an organic light-emitting diode (OLED).

So long as it functions to stably transport the electrons from a cathode, any known material may be used for the electron transport layer. Examples of the known electron transport material include quinoline derivatives, particularly tris(8-quinolinolate)aluminum ($AlQ_3$), Liq, TAZ, Balq, beryllium bis(benzoquinoline-10-olate) ($Bebq_2$), compound 401, compound 402, BCP, and the oxadiazole derivatives PBD, BMD, and BND, but are not limited thereto.

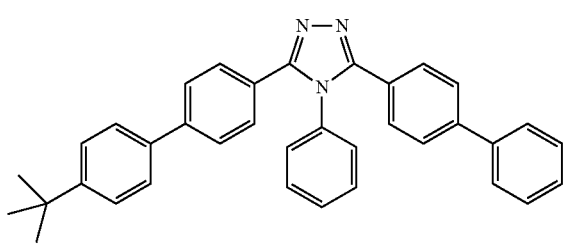

TAZ

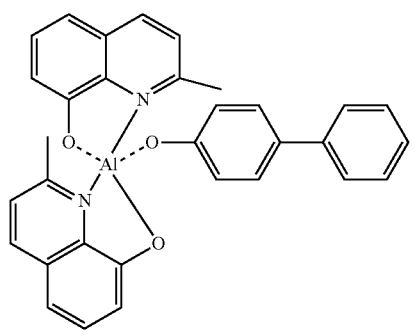

Balq

<Compound 401>

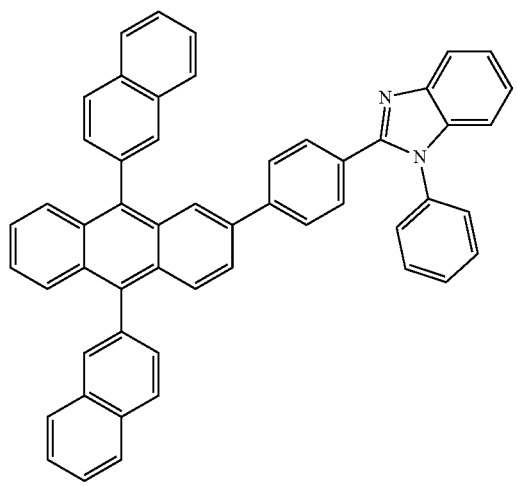

<Compound 402>

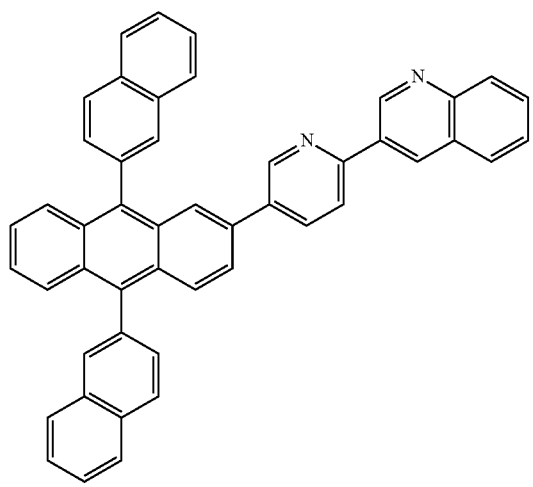

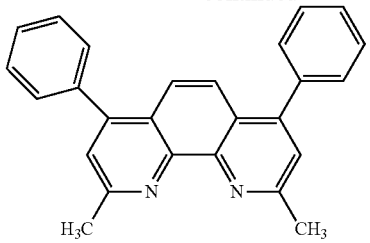

BCP

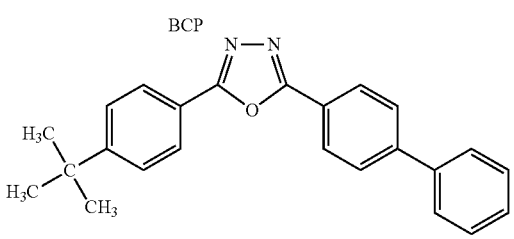

PBD

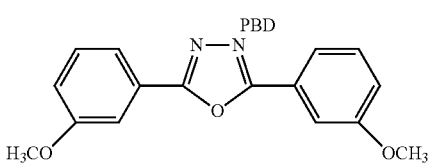

BMD

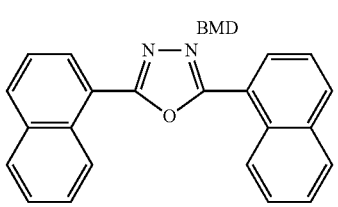

BND

In addition, an electron injection layer (EIL) is positioned on the electron transport layer in the organic light-emitting diode of the present disclosure. So long as it functions to facilitate the injection of electrons from the cathode, any known material may be available for forming the electron injection layer, without particular limitations.

By way of example, a material for the electron injection layer may be CsF, NaF, LiF, NaCl, Li$_2$O, or BaO. The condition for depositing the electron injection layer is dependent on the compound that is employed, but may fall within the range of conditions for the formation of the hole injection layer.

The electron injection layer may range in thickness from about 1 Å to about 100 Å, and particularly from about 3 Å to about 90 Å. Given this thickness range, the electron injection layer can exhibit satisfactory electron injection properties without an actual increase in driving voltage.

The cathode may be made of a metal or metal alloy such as lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be employed to form a transparent cathode for a top-emitting organic light-emitting diode.

In another embodiment, the light-emitting device of the present disclosure may further comprise a light-emitting layer, made of a blue light-emitting material, a green light-emitting material, or a red light-emitting material, which can emit light in a wavelength range of 380 nm to 800 nm. That is, the light-emitting layer in the organic light-emitting device of the present disclosure may have a multilayer structure in which the additional blue, green, and/or red light-emitting layer may be made of a fluorescent or phosphorescent material.

Further, one or more layers selected from among a hole injection layer, a hole transport layer, a light-emitting layer, an electron density control layer, an electron transport layer, and an electron injection layer may be deposited using a single-molecule deposition process or a solution process.

Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices; flexible display devices; monochrome or grayscale flat illumination devices; and monochrome or grayscale flexible illumination devices.

A better understanding of the present disclosure may be obtained through the following examples which are set forth to illustrate, but are not to be construed as limiting the present disclosure.

EXAMPLES

Preparation Example of Dopant Material for Light-Emitting Layer

Synthesis Example 1: Synthesis of Compound of Chemical Formula 1

Synthesis Example 1-(1): Synthesis of [Intermediate 1-a]

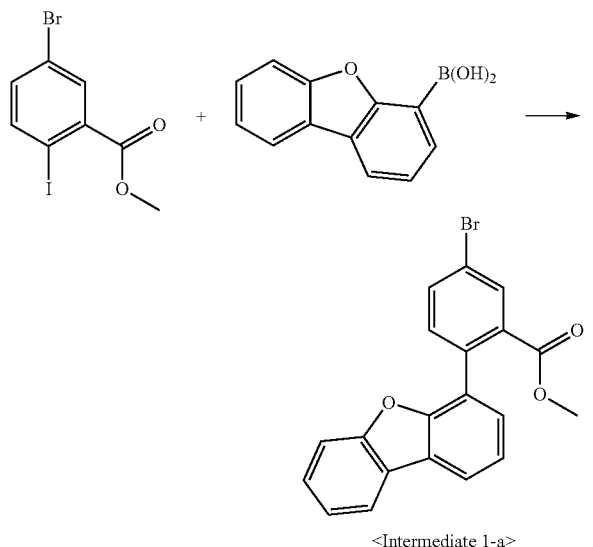

<Intermediate 1-a>

In a 500-mL round-bottom flask reactor, methyl 5-bromo-2-iodobenzoate (25.0 g, 73 mmol), 4-dibenzofuran boronic acid (18.7 g, 88 mmol), tetrakis (triphenylphosphine)palladium (1.7 g, 0.15 mmol), and potassium carbonate (20.2 g, 146.7 mmol) were stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 1-a> (75.0 g, 60.1%).

Synthesis Example 1-(2): Synthesis of Intermediate 1-b

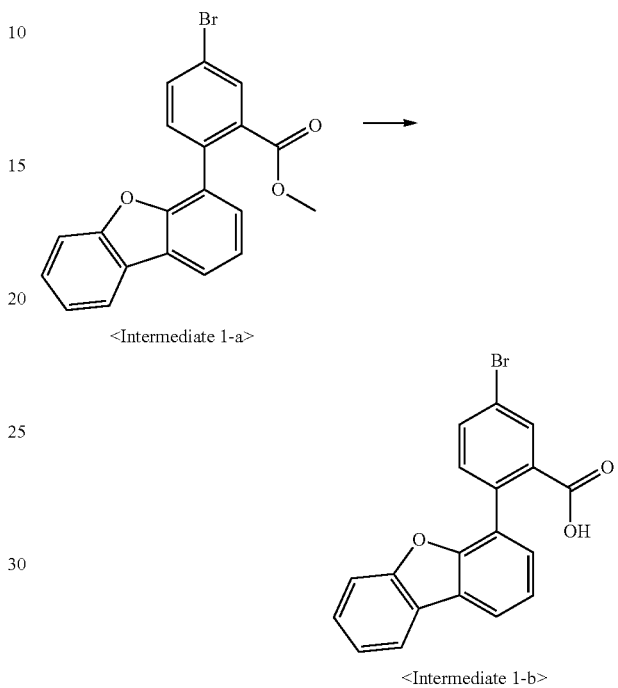

<Intermediate 1-a>

<Intermediate 1-b>

In a 500-mL round-bottom flask reactor, <Intermediate 1-a> (17.0 g, 45 mmol), sodium hydroxide (2.14 g, 54 mmol) and ethanol (170 ml) were stirred together for 48 hrs under reflux. After the completion of the reaction was confirmed using thin-layer chromatography, the reaction mixture was cooled to room temperature. The chilled solution was acidified with drops of 2-N HCl, followed by stirring for 30 min. The solid thus formed was filtered and then recrystallized in dichloromethane and n-hexane to afford <Intermediate 1-b>. (14.5 g, 88.6%)

Synthesis Example 1-(3): Synthesis of Intermediate 1-c

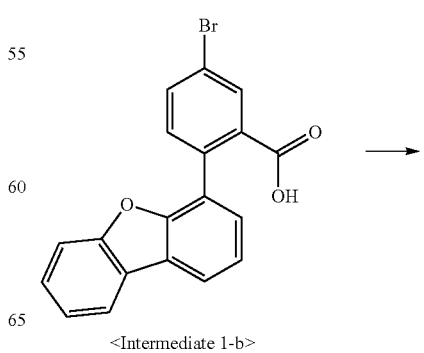

<Intermediate 1-b>

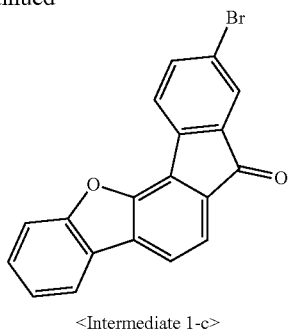

<Intermediate 1-c>

In a 250-mL round-bottom flask reactor, <Intermediate 1-b> (14.5 g, 39 mmol) and methanesulfonic acid (145 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the solid thus formed was filtered and washed with water and methanol to afford <Intermediate 1-c> (11.50 g, 83.4%).

Synthesis Example 1-(4): Synthesis of [Intermediate 1-d]

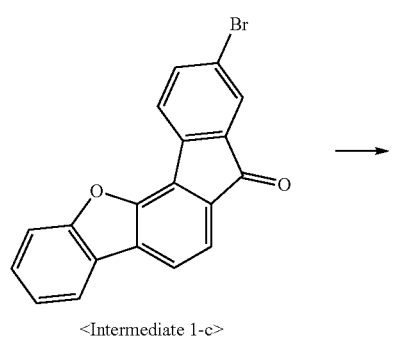

<Intermediate 1-c>

<Intermediate 1-d>

In a 1-L round-bottom flask reactor, <Intermediate 1-c> (11.5 g, 33 mmol) and dichloromethane (300 ml) were stirred together at room temperature. A dilution of bromine (3.4 ml, 66 mmol) in dichloromethane (50 ml) was dropwise added, followed by stirring at room temperature for 8 hrs. After completion of the reaction, the reaction mixture was stirred together with acetone (100 ml). The solid thus formed was filtered and washed with acetone. Recrystallization in monochlorobenzene afforded <Intermediate 1-d> (11.0 g, 78%).

Synthesis Example 1-(5): Synthesis of [Intermediate 1-e]

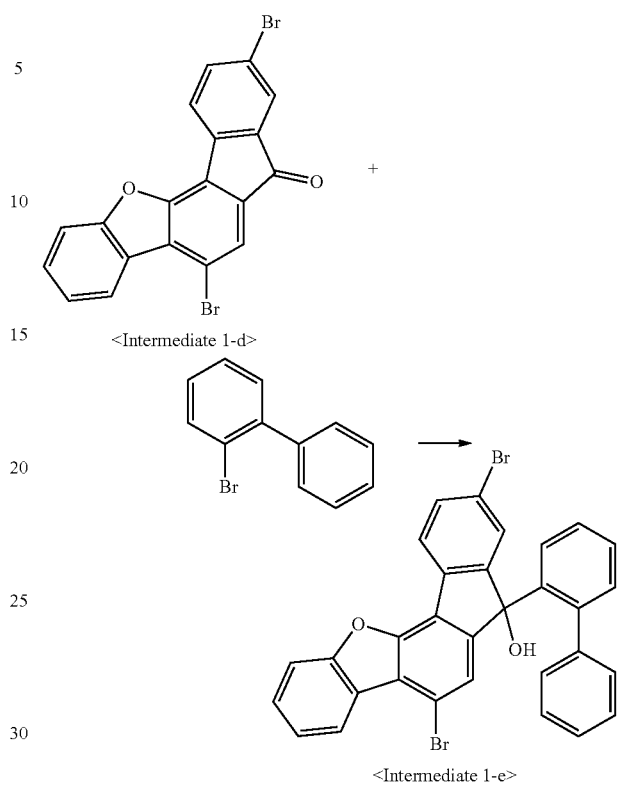

<Intermediate 1-d>

<Intermediate 1-e>

In a 250-ml round-bottom flask reactor, 2-bromobiphenyl (8.4 g, 0.036 mol) and tetrahydrofuran (110 ml) were cooled at −78° C. in a nitrogen atmosphere. At the same temperature, n-butyl lithium (19.3 ml, 0.031 mol) was dropwise added to the reaction solution, which was then stirred for 2 hrs. Thereafter, <Intermediate 1-d> (11.0 g, 0.026 mol) was added little by little to the reaction solution and stirred at room temperature. When the reaction mixture started to change color, the reaction was monitored via TLC. After the reaction was stopped with H₂O (50 ml), extraction was conducted with ethyl acetate and water. The organic layer was separated, concentrated in a vacuum, and recrystallized in acetonitrile to afford <Intermediate 1-e> (12.2 g, 81.5%).

Synthesis Example 1-(6): Synthesis of [Intermediate 1-f]

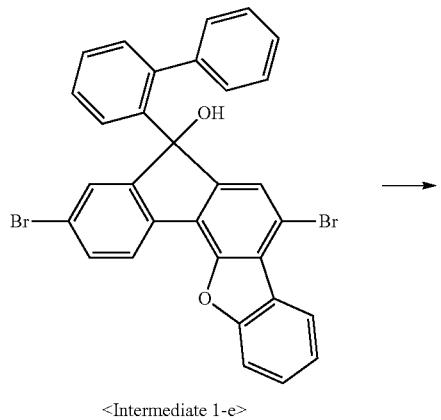

<Intermediate 1-e>

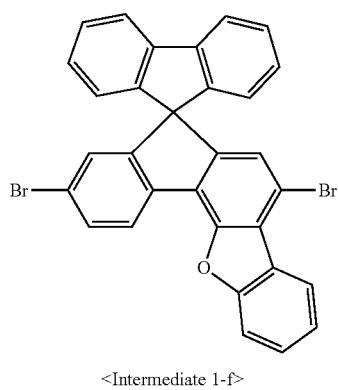

<Intermediate 1-f>

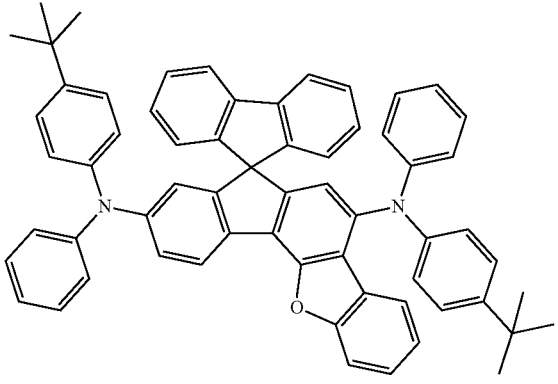

<Chemical Formula 1>

In a 250-ml round-bottom flask reactor, a mixture of <Intermediate 1-e> (12.0 g, 0.021 mol), acetic acid (120 ml), and sulfuric acid (2 ml) was stirred for 5 hrs under reflux. When a precipitate was formed, the completion of the reaction was monitored using thin-layer chromatography. The reaction mixture was then cooled to room temperature and filtered. The filtrate was washed with $H_2O$ and methanol and dissolved in monochlorobenzene. Following silica gel filtration, the fraction was concentrated and cooled to room temperature to give <Intermediate 1-f> (10.7 g, 90%).

Synthesis Example 1-(7): Synthesis of Compound of [Chemical Formula 1]

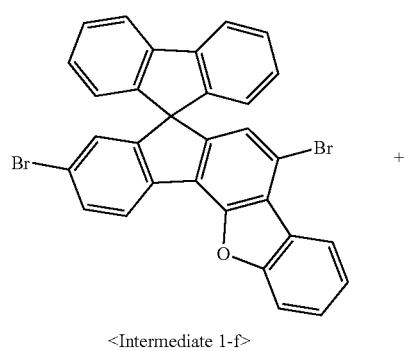

<Intermediate 1-f>

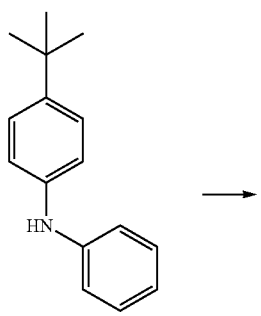

In a 250-ml round-bottom flask reactor, a mixture of <Intermediate 1-f> (5.0 g, 0.009 mol), (4-tert-butylphenyl) amine (4.7 g, 0.021 mol), palladium (II) acetate (0.08 g, 0.4 mmol), sodium tert-butoxide (3.4 g, 0.035 mol), tri-tert-butyl phosphine (0.07 g, 0.4 mmol), and toluene (60 ml) was stirred for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield the compound of Chemical Formula 1 (2.9 g, 38%).

MS (MALDI-TOF): m/z 852.41 [M+]

Synthesis Example 2: Synthesis of Compound of Chemical Formula 33

Synthesis Example 2-(1): Synthesis of Intermediate 2-a

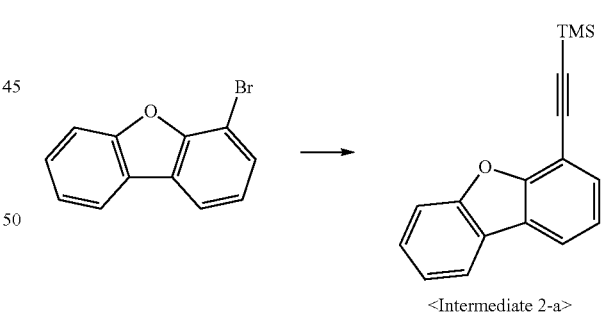

<Intermediate 2-a>

In a 2-L round bottom flask, 4-bromodibenzofuran (100.0 g, 0.405 mol), ethynyl trimethylsilane (47.7 g, 0.486 mol), [1,1'-bis(diphenylphosphino)ferrocene] dichloropalladium (9.92 g, 0.012 mol), copper iodide (2.31 g, 0.012 mol), triphenylphosphine (10.6 g, 0.040 mol), and triethylamine (700 ml) were stirred for 5 hrs under reflux in a nitrogen atmosphere. After completion of the reaction, the reaction mixture was cooled to room temperature and added with heptane (500 ml) to terminate the reaction. Filtration was conducted through a silica gel pad topped with celite. The filtrate was concentrated in a vacuum to afford <Intermediate 2-a> (130 g, 84%).

Synthesis Example 2-(2): Synthesis of Intermediate 2-b

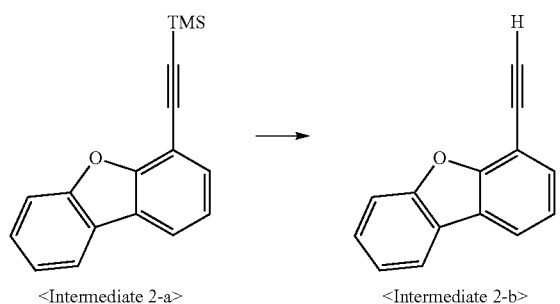 [SMILES: C[Si](C)(C)C#Cc1cccc2c1oc1ccccc12 ; C#Cc1cccc2c1oc1ccccc12]

<Intermediate 2-a>        <Intermediate 2-b>

In a 2-L round-bottom flask reactor, <Intermediate 2-a> (130 g, 0.492 mol), potassium carbonate (101.9 g, 0.738 mol), methanol (650 ml), and tetrahydrofuran (650 ml) were stirred together for 2 hrs at room temperature. After completion of the reaction, heptane (500 ml) was added to terminate the reaction. The reaction mixture was filtered and the filtrate was extracted with ethyl acetate and water. The organic layer thus formed was isolated and dried over magnesium sulfate. Filtration and vacuum concentration afforded <Intermediate 2-b> as an oil (82 g, 84%).

Synthesis Example 2-(3): Synthesis of Intermediate 2-c

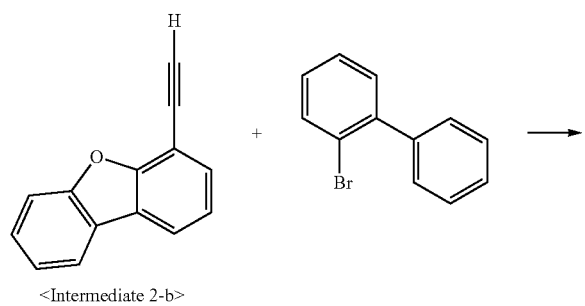

<Intermediate 2-b>

<Intermediate 2-c>

In a 2-L round-bottom flask reactor, 2-bromobiphenyl (66.0 g, 0.283 mol), <Intermediate 2-b> (65.3 g, 0.340 mol), [1,1'-bis(diphenylphosphino)ferrocene]dichloropalladium (6.94 g, 0.008 mol), copper iodide (1.62 g, 0.008 mol), triphenylphosphine (7.4 g, 0.028 mol), and triethylamine (500 ml) were stirred for 5 hrs under reflux in a nitrogen atmosphere. After completion of the reaction, the reaction mixture was cooled to room temperature and added with heptane (500 ml) to terminate the reaction. Filtration was conducted through a silica gel pad topped with celite. The filtrate was concentrated in a vacuum to afford <Intermediate 2-c> (80 g, 82%).

Synthesis Example 2-(4): Synthesis of Intermediate 2-d

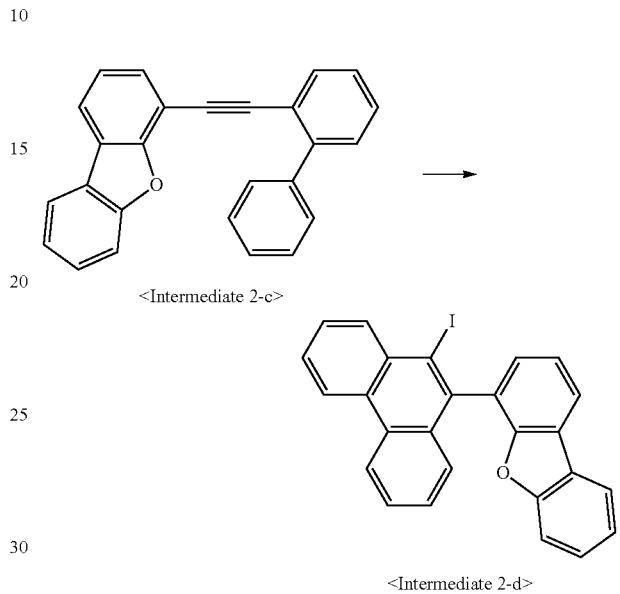

<Intermediate 2-c>

<Intermediate 2-d>

In a 2-L round-bottom flask reactor, a solution of <Intermediate 2-c> (80.0 g, 0.232 mol) in dichloromethane (960 ml) was cooled to −78° C. under a nitrogen atmosphere. Iodine monochloride (278.4 ml, 0.279 mol) was dropwise added to the chilled solution, which was then stirred at room temperature for 12 hrs. After completion of the reaction, the reaction mixture was stirred together with an aqueous saturated sodium thiosulfate solution. Following extraction with dichloromethane and water, the organic layer was isolated, concentrated in a vacuum, and washed with methanol to afford <Intermediate 2-d> as a crystal (67 g, 61.3%).

Synthesis Example 2-(5): Synthesis of Intermediate 2-e 57

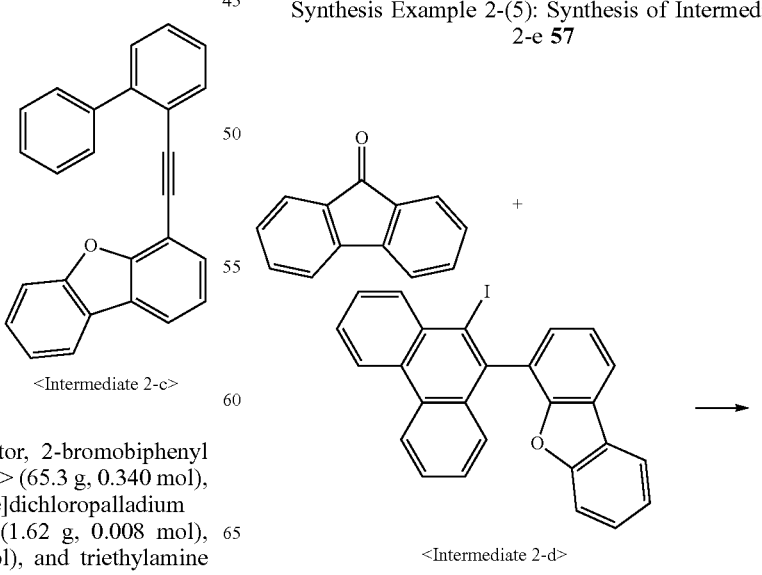

<Intermediate 2-d>

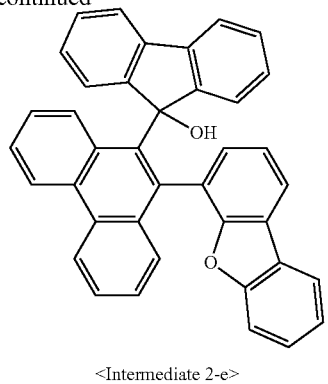

<Intermediate 2-e>

In a 500-mL round-bottom flask reactor, a solution of <Intermediate 2-d> (54.8 g, 0.117 mol) in tetrahydrofuran (150 ml) was cooled to −78° C. under a nitrogen atmosphere. At the same temperature, 1.6 M n-butyl lithium (62.4 ml, 0.1 mol) was dropwise added to the chilled solution and stirred for 1 hr. Then, a solution of 9-fluorenone (15.0 g, 0.083 mol) in tetrahydrofuran (50 ml) was dropwise added before stirring at room temperature for 8 hrs. After completion of the reaction, extraction was performed with ethyl acetate and water. The organic layer thus formed was isolated and dried over magnesium sulfate. Vacuum concentration subsequent to filtration afforded <Intermediate 2-e> as an oil (33.2 g, 76%).

Synthesis Example 2-(6): Synthesis of Intermediate 2-f

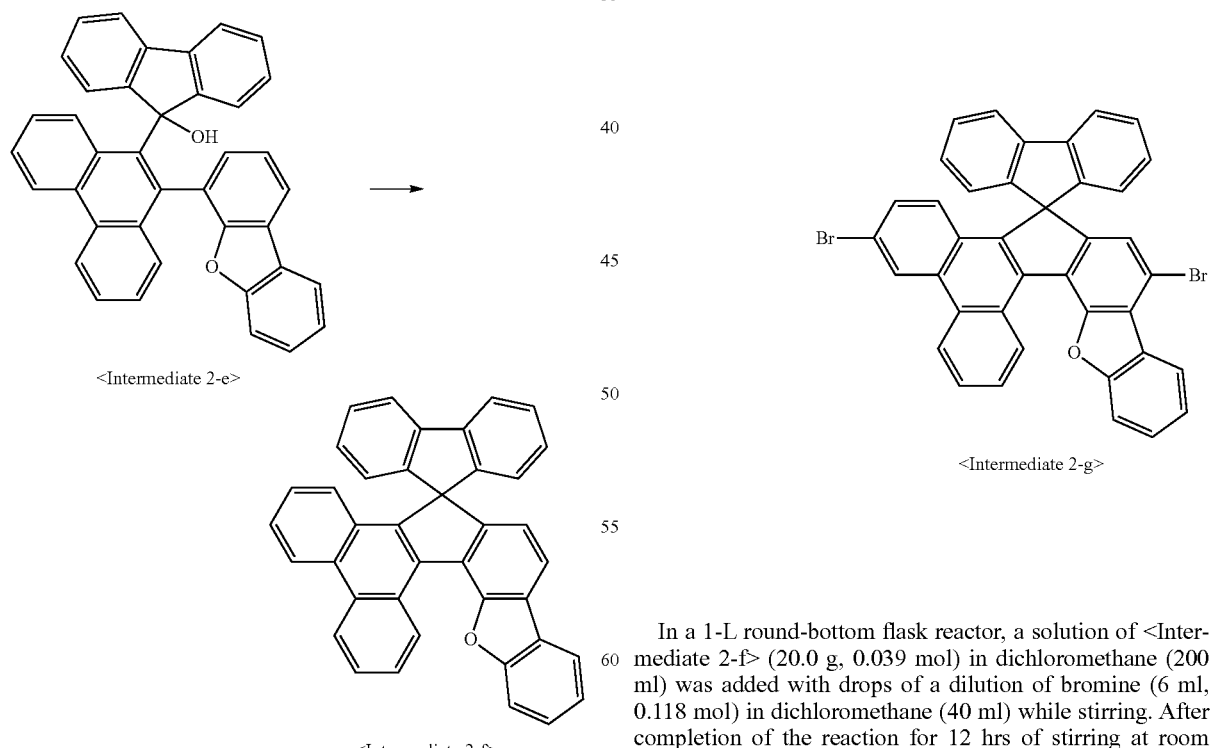

<Intermediate 2-e>

<Intermediate 2-f>

In a 1-L round-bottom flask reactor, <Intermediate 2-e> (33.3 g, 0.063 mol), acetic acid (330 ml), and sulfuric acid (3 ml) were stirred together for 3 hrs under reflux. After the completion of the reaction was confirmed using thin-layer chromatography, the reaction mixture was cooled to room temperature. The precipitates thus formed were filtered and washed with $H_2O$ and methanol to afford <Intermediate 2-f> (28.6 g, 88%).

Synthesis Example 2-(7): Synthesis of Intermediate 2-g

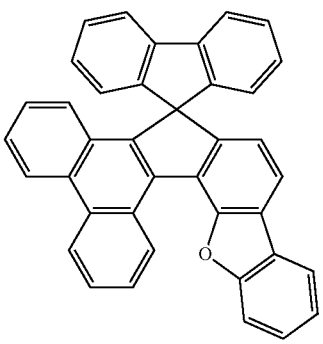

<Intermediate 2-f>

<Intermediate 2-g>

In a 1-L round-bottom flask reactor, a solution of <Intermediate 2-f> (20.0 g, 0.039 mol) in dichloromethane (200 ml) was added with drops of a dilution of bromine (6 ml, 0.118 mol) in dichloromethane (40 ml) while stirring. After completion of the reaction for 12 hrs of stirring at room temperature, the addition of methanol (100 ml) produced precipitates which were then washed with methanol. Recrystallization in 1,2-dichlorobenzene and acetone afforded <Intermediate 2-g> (16 g, 60%).

Synthesis Example 2-(8): Synthesis of Compound of Chemical Formula 33

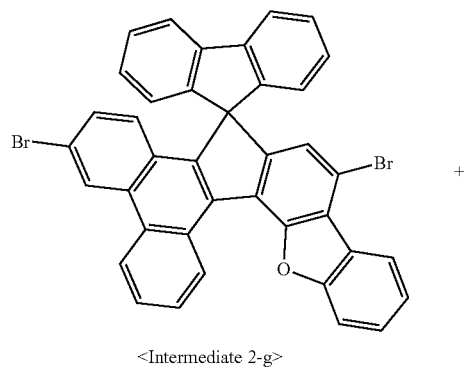

<Intermediate 2-g>

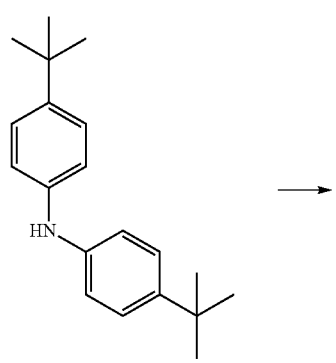

→

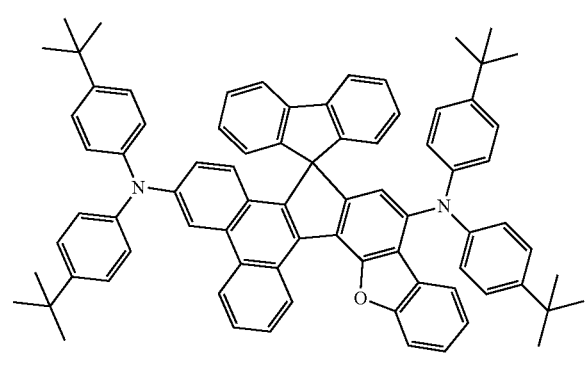

<Chemical Formula 33>

The same procedure was conducted as in Synthesis Example 1-(7), with the exception of using <Intermediate 2-g> instead of <Intermediate 1-f>, to synthesize the compound of <Chemical Formula 33> (2.5 g, 31%).

MS (MALDI-TOF): m/z 1064.5 [M+]

Synthesis Example 3: Synthesis of Compound of Chemical Formula 49

Synthesis Example 3-(1): Synthesis of Intermediate 3-a

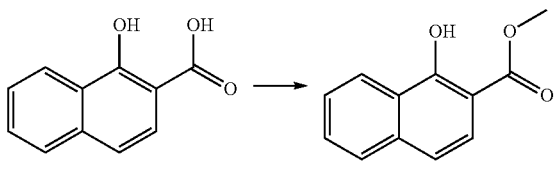

<Intermediate 3-a>

In a 2-L round-bottom flask reactor, 1-hydroxy 2-naphthalic acid (50 g, 266 mmol), methanol (1000 ml), and sulfuric acid (100 ml) were stirred together for 100 hrs under reflux. The completion of the reaction was confirmed by TLC before the reaction mixture was cooled to room temperature. The mixture was concentrated in a vacuum and extracted with dichloromethane and water. The organic layer was isolated, dried over magnesium sulfate, and filtered. The filtrate was concentrated at a reduced pressure and crystallized in an excess of heptane to afford <Intermediate 3-a> (39 g, 72.6%).

Synthesis Example 3-(2): Synthesis of Intermediate 3-b

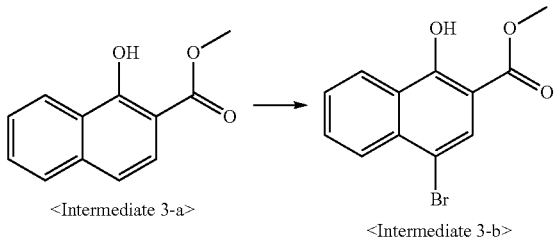 [SMILES: COC(=O)c1ccc2ccccc2c1O ; COC(=O)c1cc(Br)c2ccccc2c1O]

<Intermediate 3-a>     <Intermediate 3-b>

In a 1-L round-bottom flask reactor, <Intermediate 3-a> (39.0 g, 193 mmol) was stirred together with acetic acid (390 ml) at room temperature. A dilution of acetic acid (80 ml) in bromine (11.8 ml, 231 mmol) was added dropwise thereto. The resulting reaction solution was stirred for 5 hrs at room temperature. After completion of the reaction, the precipitates thus formed were filtered and slurried in heptane to afford <Intermediate 3-b> (50 g, 90%).

Synthesis Example 3-(3): Synthesis of Intermediate 3-c

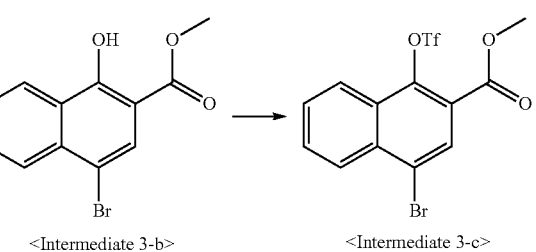

<Intermediate 3-b>     <Intermediate 3-c>

In a 2-L round-bottom flask reactor, <Intermediate 3-b> (50 g, 178 mmol) was stirred together with dichloromethane. Under a nitrogen atmosphere, pyridine (28.1 g, 356 mmol) was added and stirred at room temperature for 20 min. The resulting solution was cooled to 0° C. and then added with drops of trifluoromethanesulfonic anhydride (65.24 g, 231 mmol) under a nitrogen atmosphere. After 3 hrs of stirring, the completion of the reaction was confirmed by TLC. Water (20 ml) was added, and the mixture was stirred for 10 min. The reaction mixture was concentrated in a vacuum, followed by purification through column chromatography to afford <Intermediate 3-c> (45 g, 61%).

Synthesis Example 3-(4): Synthesis of Intermediate 3-d

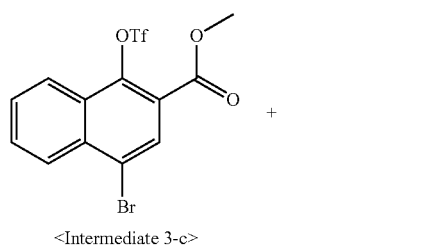

<Intermediate 3-c>

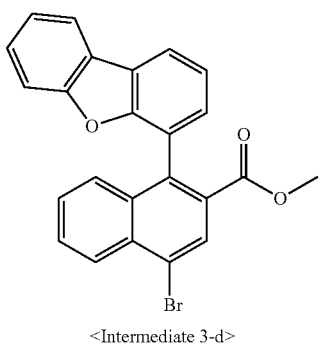

<Intermediate 3-d>

In a 1-L round-bottom flask reactor, a mixture of <Intermediate 3-c> (45.0 g, 0.109 mol), 4-dibenzofuran boronic acid (25.4 g, 0.120 mol), tetrakis (triphenylphosphine)palladium (2.5 g, 0.22 mmol), and potassium carbonate (30.1 g, 0.218 mol) was stirred together with toluene (300 mL), ethanol (130 mL) and water (90 mL) at 80° C. for 5 hrs. After completion of the reaction, the reaction mixture was cooled to room temperature and extracted with ethyl acetate. The organic layer was isolated and concentrated in a vacuum.

Purification through column chromatography afforded <Intermediate 3-d>. (22.0 g, 46.1%)

Synthesis Example 3-(5): Synthesis of Intermediate 3-e

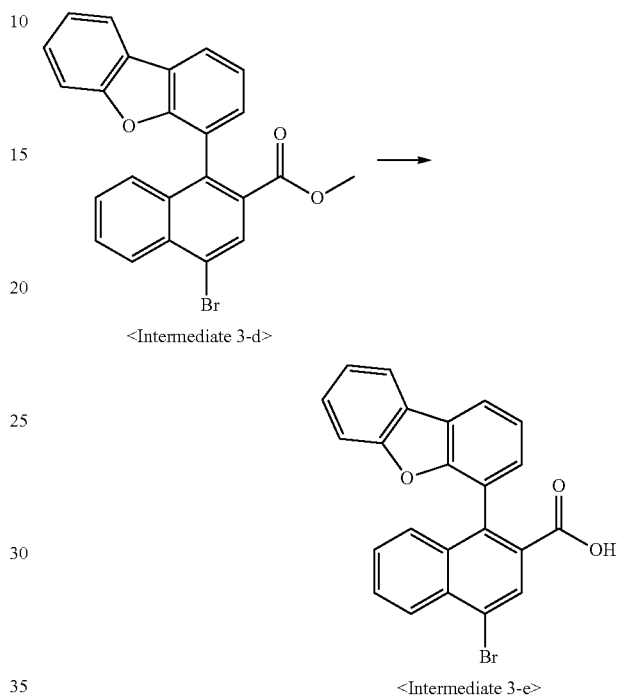

In a 1-L round-bottom flask reactor, <Intermediate 3-d> (22.0 g, 0.051 mol) was stirred together with sodium hydroxide (2.65 g, 0.066 mol) for 48 hrs under reflux. After completion of the reaction, the reaction mixture was cooled to room temperature. The chilled solution was acidified with drops of 2-N HCl, followed by stirring for 30 min. The solid thus formed was filtered and recrystallized in dichloromethane and n-hexane to afford <Intermediate 3-e> (17.6 g, 82.7%).

Synthesis Example 3-(6): Synthesis of Intermediate 3-f

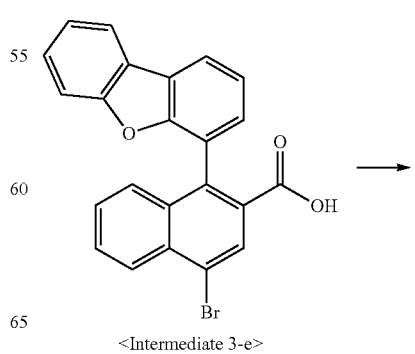

<Intermediate 3-e>

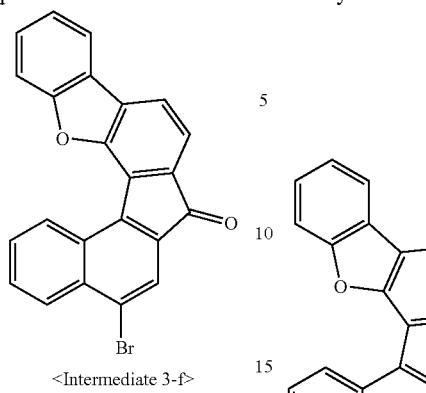

<Intermediate 3-f>

In a 500-mL round-bottom flask reactor, <Intermediate 3-e> (17.6 g, 0.042 mol) and methanesulfonic acid (170 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the precipitates thus formed were filtered and washed with water and methanol. They were dissolved in monochlorobenzene and filtered through a silica gel pad. The filtrate was concentrated by heating and recrystallized in acetone to afford <Intermediate 3-f> (12 g, 71%).

Synthesis Example 3-(7): Synthesis of Intermediate 3-g

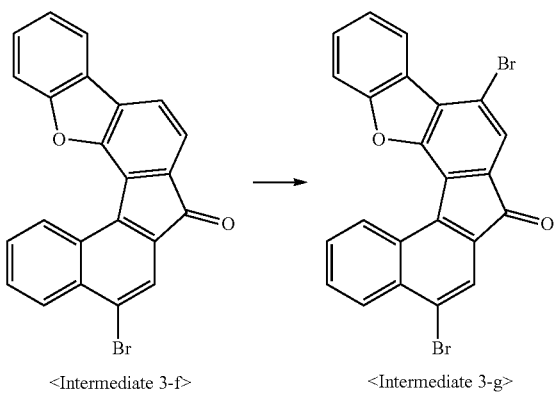 [SMILES: O=C1c2cc(Br)c3ccccc3c2-c2c1ccc1c2oc2ccccc21 ; O=C1c2cc(Br)c3ccccc3c2-c2c1cc(Br)c1c2oc2ccccc21]

<Intermediate 3-f>   <Intermediate 3-g>

In a 1-L round-bottom flask reactor, <Intermediate 3-f> (12.0 g, 0.030 mol) and dichloromethane (360 ml) were stirred together at room temperature. A dilution of bromine (3.1 ml, 0.06 mol) in dichloromethane (40 ml) was dropwise added, followed by stirring at room temperature for 12 hrs. After completion of the reaction, methanol (100 ml) was added to induce the formation of precipitates. They were then filtered and washed with methanol. Recrystallization in 1,2-dichlorobenzene and acetone afforded <Intermediate 3-g> (10.3 g, 71.7%).

Synthesis Example 3-(8): Synthesis of Intermediate 3-h

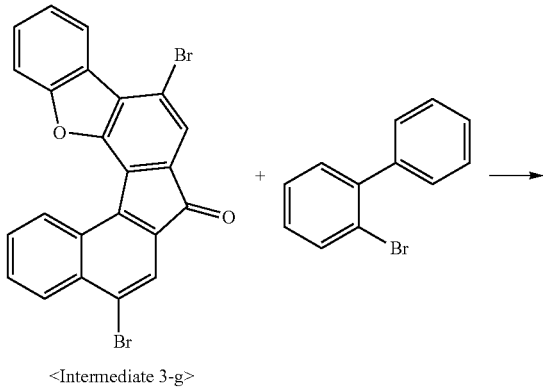

<Intermediate 3-g>

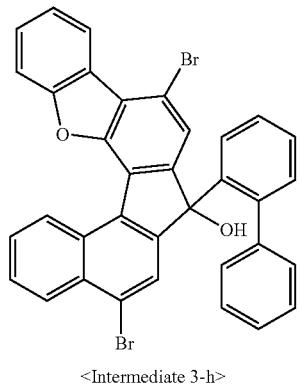

<Intermediate 3-h>

With the exception that <Intermediate 3-g> was used instead of <Intermediate 1-d>, the same procedure as in Synthesis Example 1-(5) was performed to afford <Intermediate 3-h> (10.0 g, 73.4%).

Synthesis Example 3-(9): Synthesis of Intermediate 3-i

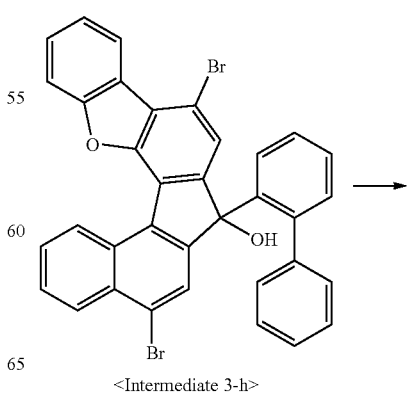

<Intermediate 3-h>

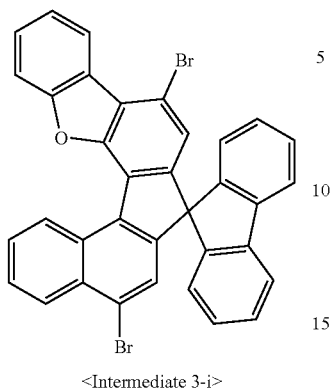

<Intermediate 3-i>

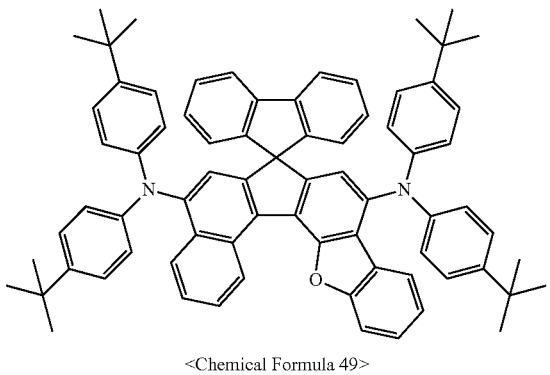

<Chemical Formula 49>

With the exception that <Intermediate 3-h> was used instead of <Intermediate 1-e>, the same procedure as in Synthesis Example 1-(6) was performed to afford <Intermediate 3-i> (6.3 g, 64.8%).

Synthesis Example 3-(10): Synthesis of Compound of Chemical Formula 49

With the exception that <Intermediate 3-i> and <Intermediate 3-h> were used, respectively, instead of <Intermediate 1-f> in Synthesis Example 1-(7) and <Intermediate 1-e> in Synthesis Example 1-(6), the same procedure as in Synthesis Examples 1-(7) and 1-(6) was performed to afford the compound of <Chemical Formula 49> (3.0 g, 36.1%).

MS (MALDI-TOF): m/z 1014.5 [M+]

Synthesis Example 4: Synthesis of Compound of Chemical Formula 76

Synthetic Example 4-(1): Synthesis of Intermediate 4-a

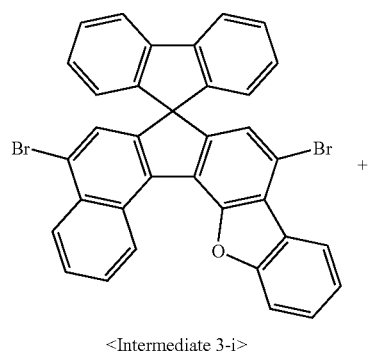

<Intermediate 3-i>

+

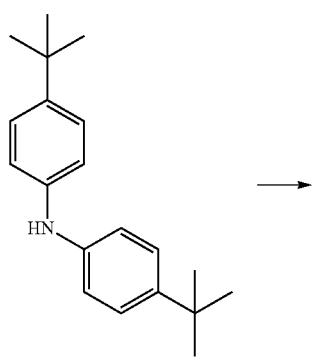

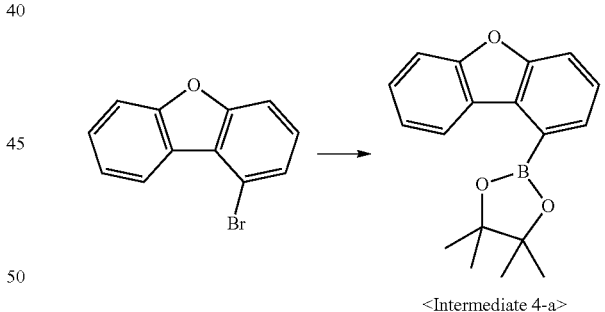

<Intermediate 4-a>

In a 500-mL round-bottom flask reactor, 1-bromodibenzofuran (20.0 g, 0.081 mmol), bis(pinacolato)diboron (26.7 g, 0.105 mol), [1,1'-bis(diphenylphosphino)ferrocene]dichloropalladium (1.3 g, 0.002 mol), potassium acetate (19.9 g, 0.202 mol), and 1,4-dioxane (200 ml) were stirred together for hrs under reflux. After completion of the reaction, filtration was performed through a celite pad. The filtrate was concentrated in a vacuum, purified by column chromatography, and recrystallized in dichloromethane and heptane to afford <Intermediate 4-a> (17.0 g, 70%).

Synthesis Example 4-(2): Synthesis of Intermediate 4-b

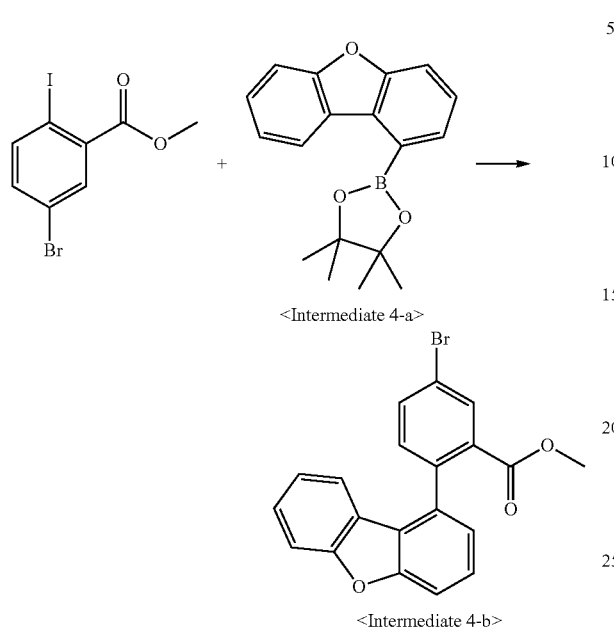

<Intermediate 4-a>

<Intermediate 4-b>

With the exception that <Intermediate 4-a> was used instead of 4-dibenzofuran boronic acid, the same procedure as in Synthesis Example 1-(1) was performed to afford <Intermediate 4-b> (13.1 g, 68.9%).

Synthesis Example 4-(3): Synthesis of Intermediate 4-c

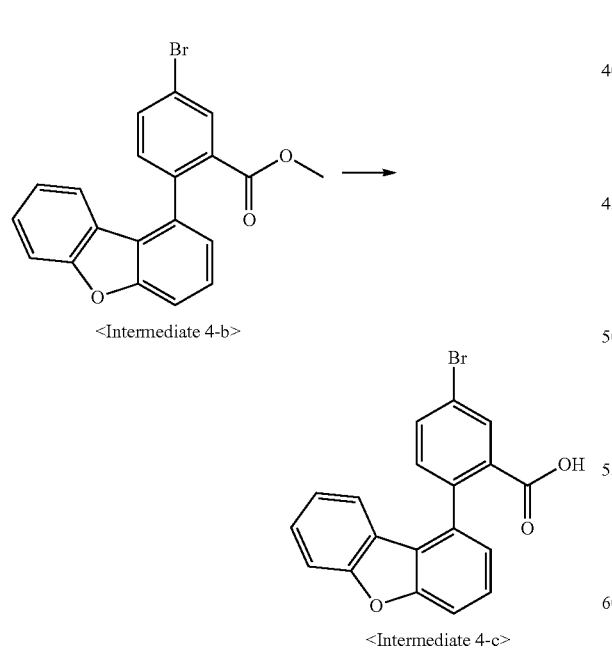

<Intermediate 4-b>

<Intermediate 4-c>

With the exception that <Intermediate 4-b> was used instead of <Intermediate 1-a>, the same procedure as in Synthesis Example 1-(2) was performed to afford <Intermediate 4-c> (11 g, 87%)

Synthesis Example 4-(4): Synthesis of Intermediate 4-d

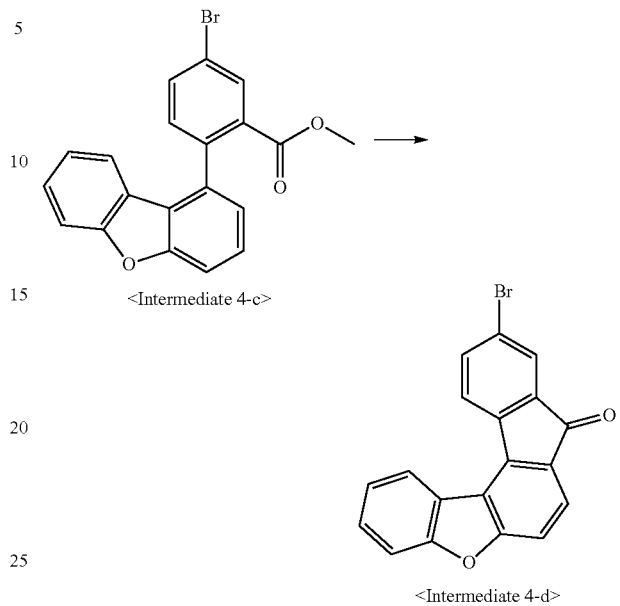

<Intermediate 4-c>

<Intermediate 4-d>

With the exception that <Intermediate 1-b> was used instead of <Intermediate 4-c>, the same procedure as in Synthesis Example 1-(3) was performed to afford <Intermediate 4-d> (9.0 g, 86%)

Synthesis Example 4-(5): Synthesis of Intermediate 4-e

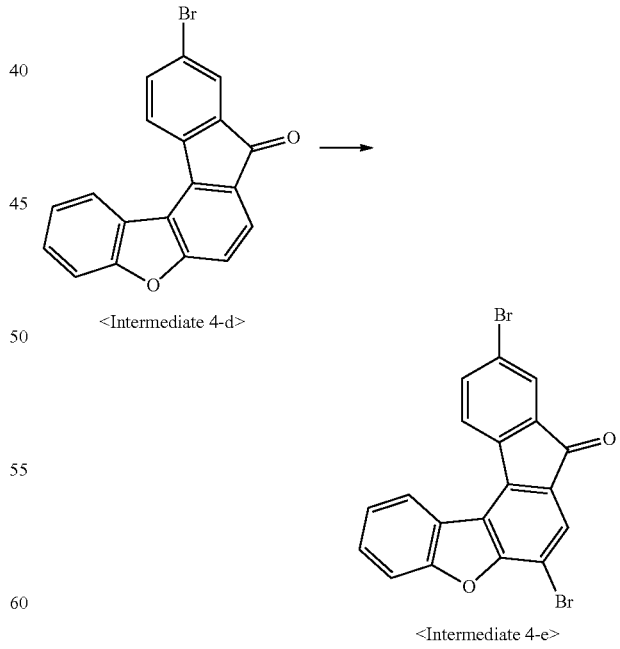

<Intermediate 4-d>

<Intermediate 4-e>

With the exception that <Intermediate 4-d> was used instead of <Intermediate 1-c>, the same procedure as in Synthesis Example 1-(4) was performed to afford <Intermediate 4-e> (6.7 g, 60.7%)

Synthesis Example 4-(6): Synthesis of Intermediate 4-f

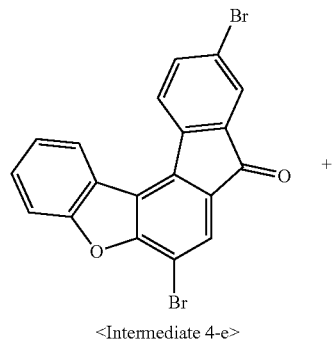

<Intermediate 4-e>

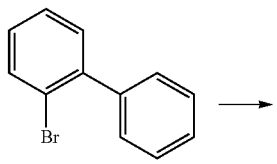

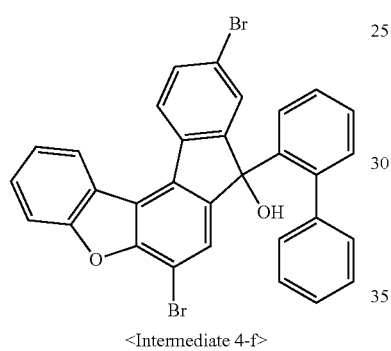

<Intermediate 4-f>

With the exception that <Intermediate 4-e> was used instead of <Intermediate 1-d>, the same procedure as in Synthesis Example 1-(5) was performed to afford <Intermediate 4-f> (5.2 g, 55%)

Synthesis Example 4-(7): Synthesis of Intermediate 4-g

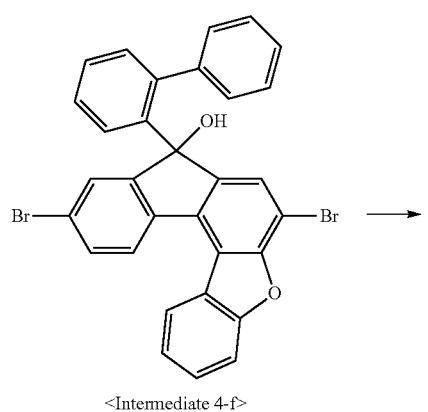

<Intermediate 4-f>

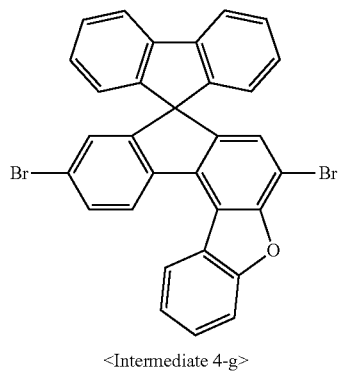

<Intermediate 4-g>

With the exception that <Intermediate 4-f> was used instead of <Intermediate 1-e>, the same procedure as in Synthesis Example 1-(6) was performed to afford <Intermediate 4-g> (4.3 g, 85.3%)

Synthesis Example 4-(8): Chemical Formula 76

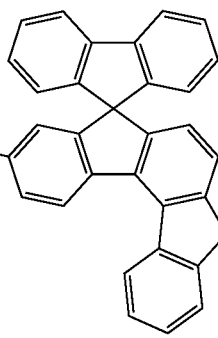

<Intermediate 4-g>

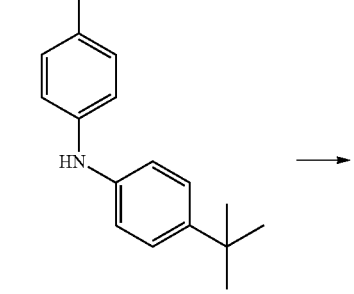

-continued

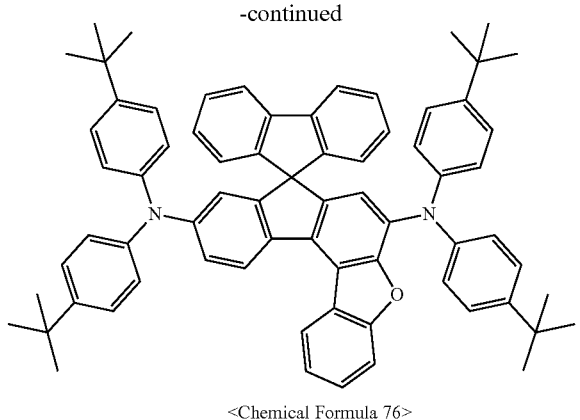

<Chemical Formula 76>

With the exception that <Intermediate 4-g> was used instead of <Intermediate 1-f>, the same procedure as in Synthesis Example 1-(7) was performed to afford the compound of <Chemical Formula 76> (2.5 g, 34%).

MS (MALDI-TOF): m/z 964.5 [M+]

Synthesis Example 5: Chemical Formula 231

Synthesis Example 5-(1): Synthesis of Intermediate 5-a

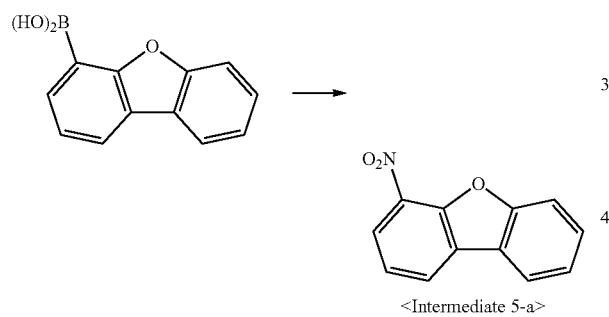

<Intermediate 5-a>

In a 1-L round-bottom flask reactor, 4-dibenzofuran boronic acid (85.0 g, 0.401 mol), bismuth (III) nitrate pentahydrate (99.2 g, 0.200 mol), and toluene (400 ml) were stirred together at 70° C. for 3 hrs under a nitrogen atmosphere. After completion of the reaction, the reaction mixture was cooled to room temperature, and the precipitates thus formed were filtered and washed with toluene to afford <Intermediate 5-a> (61.5 g, 72%).

Synthetic Example 5-(2): Synthesis of Intermediate 5-b

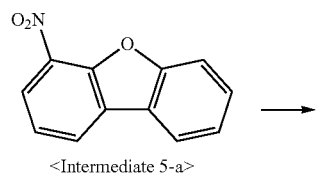

<Intermediate 5-a>

-continued

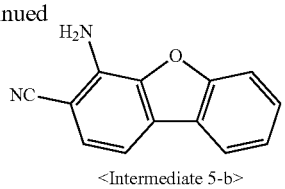

<Intermediate 5-b>

In a 2-L round-bottom flask reactor, ethyl cyanoacetate (202.9 g, 1.794 mol) and dimethylformamide (500 ml) were placed. Potassium hydroxide (67.10 g, 1.196 mol) and potassium cyanide (38.95 g, 0.598 mol) were added thereto, followed by dimethyl formamide (200 ml). The reaction solution was stirred at room temperature. <Intermediate 5-a> (127.5 g, 0.737 mol) was added little by little to the reaction solution, followed by stirring at 50° C. for 72 hrs. After completion of the reaction, an aqueous sodium hydroxide solution (25%, 200 ml) was added to the reaction solution, which was then stirred for 3 hrs under reflux and cooled to room temperature. Extraction was performed using ethyl acetate and water. The organic layer was isolated and concentrated in a vacuum. Purification through column chromatography afforded <Intermediate 5-b> (20.0 g, 16%).

Synthetic Example 5-(3): Synthesis of Intermediate 5-c

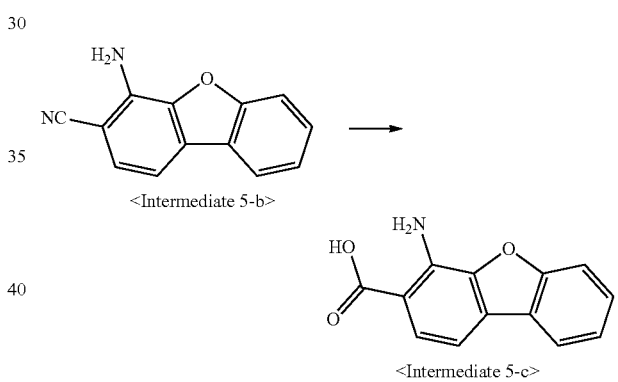

<Intermediate 5-b>

<Intermediate 5-c>

In a 2-L round-bottom flask reactor, <Intermediate 5-b> (20.0 g, 0.096 mol), ethanol (600 ml), and an aqueous potassium hydroxide solution (142.26 g, 2.53 mol, 170 ml) were stirred together for 12 hrs under reflux. After completion of the reaction, the reaction mixture was cooled to room temperature and acidified with 6-N HCl (400 ml). The solid thus formed was stirred for 20 min and filtered. The filtrate was washed with ethanol to afford <Intermediate 5-c> (17.0 g, 88.5%).

Synthetic Example 5-(4): Synthesis of Intermediate 5-d

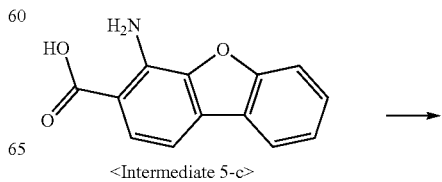

<Intermediate 5-c>

-continued

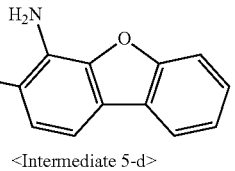

<Intermediate 5-d>

In a 2-L round-bottom flask reactor, <Intermediate 5-c> (17.0 g, 0.075 mol) and sulfuric acid (15 ml) were stirred together for 72 hrs under reflux. After completion of the reaction, the reaction mixture was cooled to room temperature and then extracted with ethyl acetate and water. The organic layer was isolated and washed with an aqueous sodium hydrogen carbonate, followed by concentration in a vacuum. The concentrate was crystallized in an excess of methanol and filtered to afford <Intermediate 5-d> (14.0 77.6%).

Synthetic Example 5-(5): Synthesis of Intermediate 5-e

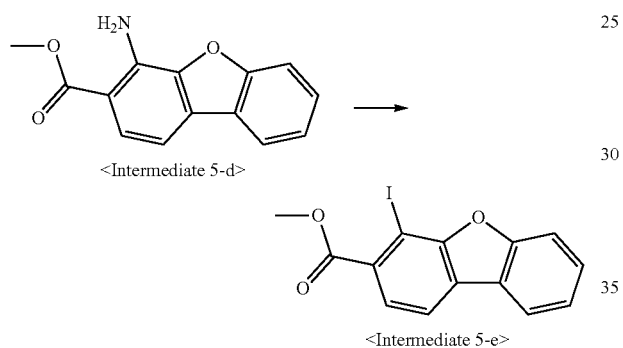

<Intermediate 5-d>

<Intermediate 5-e>

In a 500-mL round-bottom flask reactor, a mixture of <Intermediate 5-d> (14.0 g, 0.058 mol), HCl (20 ml), and water (100 ml) was cooled to 0° C. and stirred for 1 hr. At the same temperature, an aqueous solution (50 ml) of sodium nitrite (7.4 g, 0.116 mol) was dropwise added to the mixture and then stirred for 1 hr. An aqueous solution (100 ml) of potassium iodide (30.0 g, 0.180 mol) was dropwise added, taking care not to increase the temperature of the reaction solution above 5° C. Stirring was continued for 5 hrs at room temperature, and after completion of the reaction, the reaction mixture was washed with an aqueous sodium thiosulfate solution and extracted with ethyl acetate and water. The organic layer was separated and concentrated in a vacuum. Purification through column chromatography gave <Intermediate 5-e> (9.1 g, 48%).

Synthesis Example 5-(6): Synthesis of Intermediate 5-f

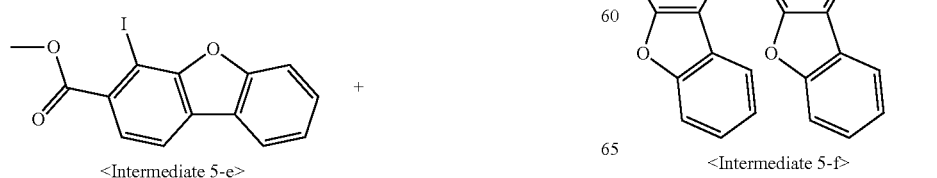

<Intermediate 5-e>

-continued

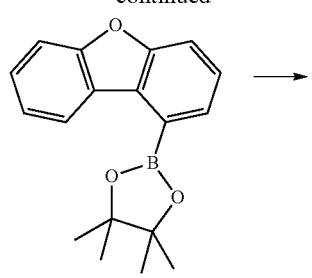

<Intermediate 5-f>

In a 250-mL round-bottom flask reactor, a mixture of <Intermediate 5-e> (9.3 g, 25 mmol), 4-dibenzofuran boronic acid (8.3 g, 28 mmol), tetrakis(triphenylphosphine) palladium (0.6 g, 0.05 mmol), and potassium carbonate (6.7 g, 50 mmol) was stirred together with toluene (50 mL), tetrahydrofuran (50 mL) and water (20 mL) at 80° C. for 10 hrs. After completion of the reaction, the reaction mixture was cooled to room temperature and extracted with ethyl acetate. The organic layer was isolated and concentrated in a vacuum. Purification through column chromatography afforded <Intermediate 5-f> (5.3 g, 52.3%).

Synthesis Example 5-(7): Synthesis of Intermediate 5-g

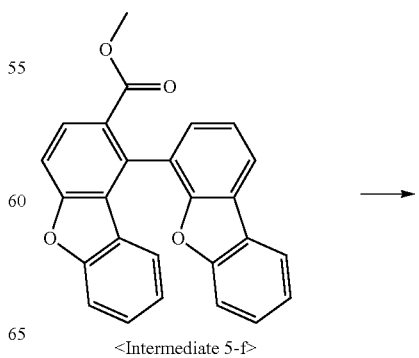

<Intermediate 5-f>

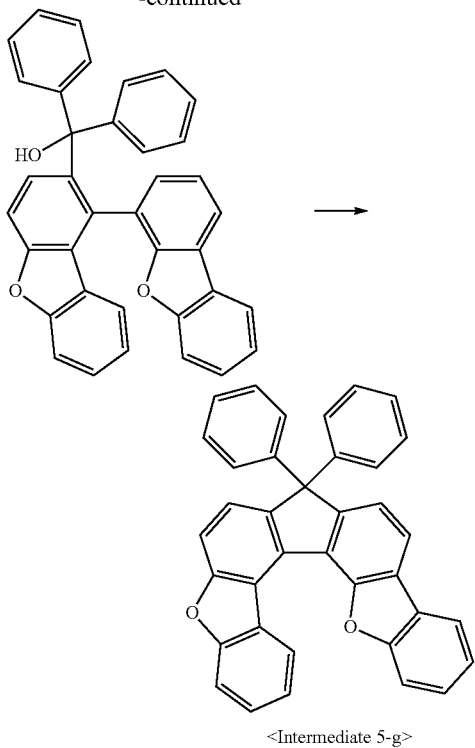

<Intermediate 5-g>

In a 500-mL round-bottom flask reactor, a mixture of bromobenzene (25.5 g, 0.163 mol) and tetrahydrofuran (170 ml) was cooled to −78° C. under a nitrogen atmosphere. N-butyl lithium (1.6 M) (95.6 ml, 0.153 mol) was dropwise added to the chilled solution, which was then stirred at the same temperature for 1 hr. <Intermediate 5-f> (20.0 g, 0.051 mol) was added, followed by stirring at room temperature for 3 hrs. After completion of the reaction, the reaction mixture was stirred together with water (50 ml) for 30 min. Extraction was made with ethyl acetate and water. The organic layer was isolated and concentrated in a vacuum. The concentrate was stirred together with acetic acid (200 ml) and HCl (1 ml) at 80° C. After the reaction was completed, the precipitate thus formed was filtered and washed with methanol to afford <Intermediate 5-g> (20.0 g, 78%).

Synthesis Example 5-(8): Synthesis of Intermediate 5-h

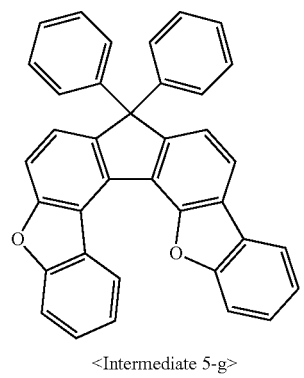

<Intermediate 5-g>

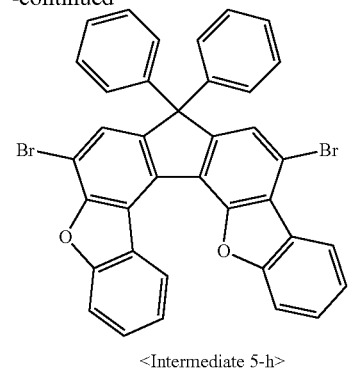

<Intermediate 5-h>

In a 100-mL round-bottom flask reactor, a mixture of <Intermediate 5-g> (20 g, 58 mmol) and dichloromethane (40 ml) was stirred at room temperature. A dilution of bromine (5.8 ml, 116 mmol) in dichloromethane (10 ml) was dropwise added to the reactor and stirred for 8 hours at room temperature. After completion of the reaction, acetone (20 ml) was added to the reactor and stirred. The solid thus formed was filtered and washed with acetone. Recrystallization in monochlorobenzene afforded <Intermediate 5-h> as a solid (15.8 g, 55%).

Synthesis Example 5-(9): Chemical Formula 231

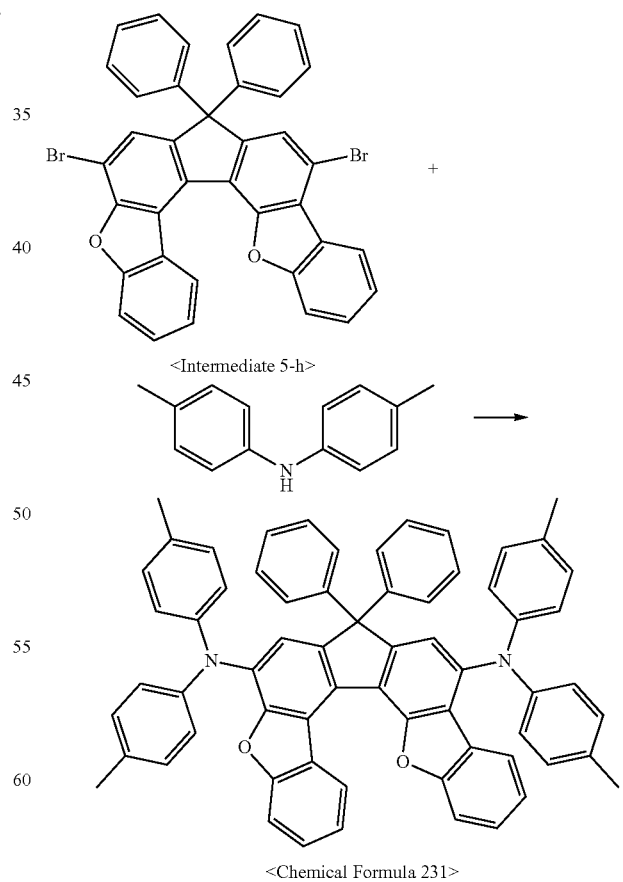

<Chemical Formula 231>

In a 100-ml round-bottom flask reactor, a mixture of <Intermediate 5-h> (4.0 g, 0.006 mol), di-p-tolyl amine (3.2 g, 0.016 mol), palladium(II) acetate (0.08 g, 0.4 mmol), sodium tert-butoxide (3.2 g, 0.032 mol), tri-tert-butyl phosphine (0.08 g, 0.4 mmol), and toluene (50 ml) was stirred for 2 hours under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to afford the compound of Chemical Formula 231 (2.1 g, 41%).

MS (MALDI-TOF): m/z 890.0 [M+]

Synthesis Example 6: Chemical Formula 98

Synthesis Example 6-(1): Synthesis of Intermediate 6-a

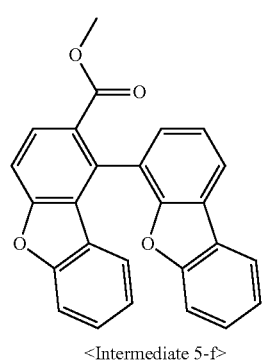

<Intermediate 5-f>

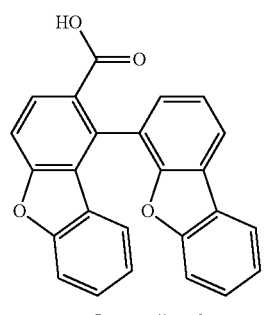

<Intermediate 6-a>

In a 100-mL round-bottom flask reactor, <Intermediate 5-f> (5.3 g, 15 mmol), sodium hydroxide (0.7 g, 17 mmol) and ethanol (50 ml) were stirred together for 48 hrs under reflux. After the completion of the reaction was confirmed using thin-layer chromatography, the reaction mixture was cooled to room temperature. The chilled solution was acidified with drops of 2-N HCl, followed by stirring for 30 min. The solid thus formed was filtered and then recrystallized in dichloromethane and n-hexane to afford <Intermediate 6-a> (4.5 g, 88.0%).

Synthesis Example 6-(2): Synthesis of Intermediate 6-b

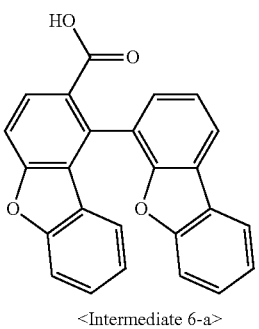

<Intermediate 6-a>

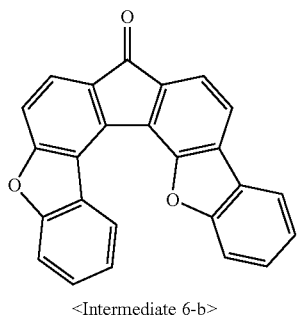

<Intermediate 6-b>

In a 100-mL round-bottom flask reactor, <Intermediate 6-a> (4.5 g, 12 mmol) and methanesulfonic acid (30 ml) were stirred together for 3 hrs at 80° C. After the completion of the reaction was confirmed using thin-layer chromatography, the reaction mixture was cooled to room temperature and dropwise added to ice water (50 ml). After stirring for 30 min, the solid thus formed was filtered and washed with water and methanol to afford <Intermediate 6-b> (3.8 g, 88.8%).

Synthesis Example 6-(3): Synthesis of Intermediate 6-c

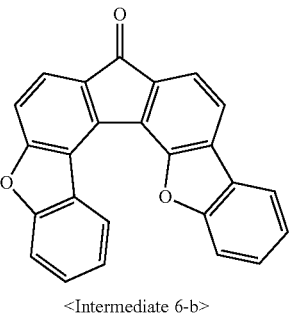

<Intermediate 6-b>

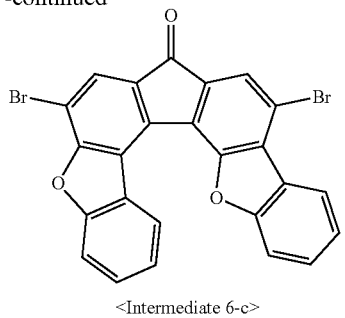

<Intermediate 6-c>

In a 100-mL round-bottom flask reactor, <Intermediate 6-b> (3.8 g, 11 mmol) and dichloromethane (40 ml) were stirred together at room temperature. A dilution of bromine (1.1 ml, 22 mmol) in dichloromethane (10 ml) was dropwise added, followed by stirring at room temperature for 8 hrs. After completion of the reaction, the reaction mixture was stirred together with acetone (20 ml). The solid thus formed was filtered and washed with acetone. Recrystallization in monochlorobenzene afforded <Intermediate 6-c> (3.0 g, 55%).

Synthesis Example 6-(4): Synthesis of Intermediate 6-d

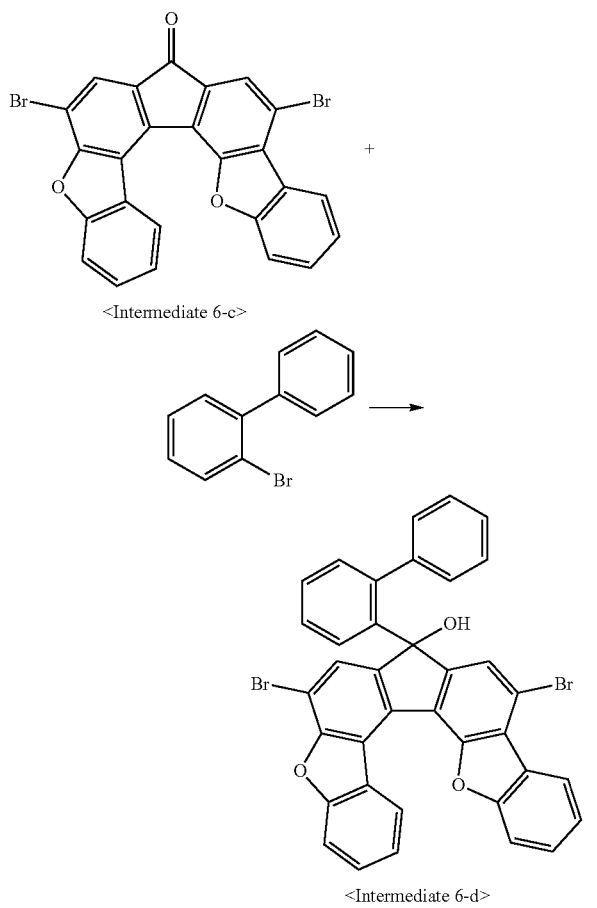

In a 100-ml round-bottom flask reactor, 2-bromobiphenyl (2.1 g, 0.009 mol) and tetrahydrofuran (30 ml) were cooled at −78° C. in a nitrogen atmosphere. At the same temperature, n-butyl lithium (4.8 ml, 0.008 mol) was dropwise added to the reaction solution, which was then stirred for 2 hrs. Thereafter, <Intermediate 6-c> (3.0 g, 0.006 mol) was added little by little to the reaction solution and stirred at room temperature. When the reaction mixture started to change color, the reaction was monitored via TLC. After the reaction was stopped with H₂O (10 ml), extraction was conducted with ethyl acetate and water. The organic layer was separated, concentrated in a vacuum, and recrystallized in acetonitrile to afford <Intermediate 6-d> (2.5 g, 64%).

Synthesis Example 6-(5): Synthesis of Intermediate 6-e

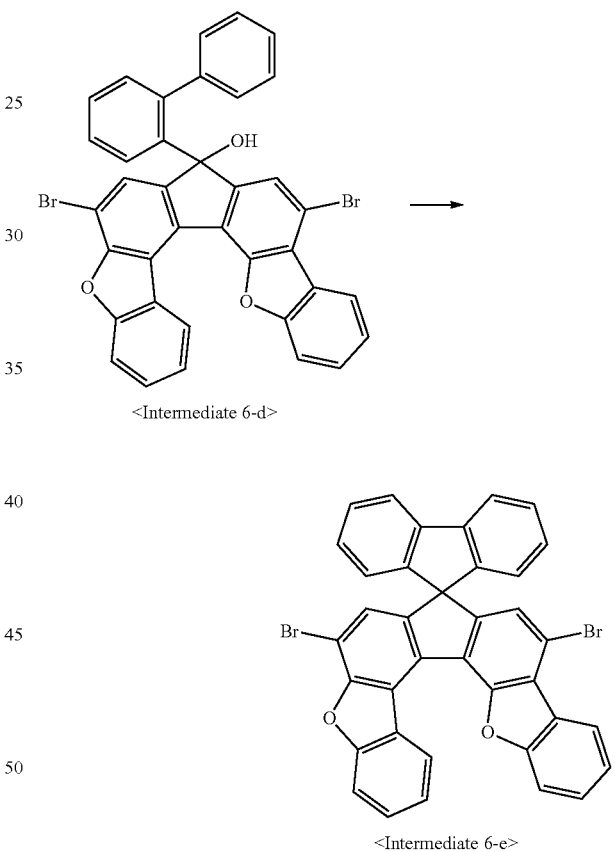

In a 100-ml round-bottom flask reactor, a mixture of <Intermediate 6-d> (2.5 g, 0.04 mol), acetic acid (25 ml), and sulfuric acid (0.5 ml) was stirred for 5 hrs under reflux. When a precipitate was formed, the completion of the reaction was monitored using thin-layer chromatography. The reaction mixture was then cooled to room temperature and filtered. The filtrate was washed with H₂O and methanol and dissolved in monochlorobenzene. Following silica gel filtration, the fraction was concentrated and cooled to room temperature to give <Intermediate 6-e> (2.2 g, 90%).

Synthesis Example 6-(6): Chemical Formula 98

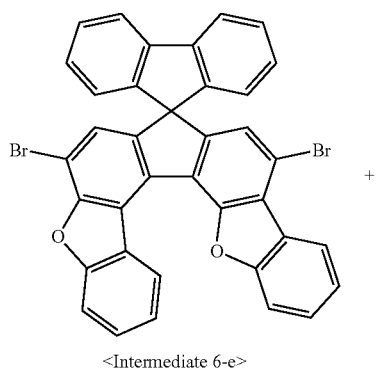

<Intermediate 6-e>

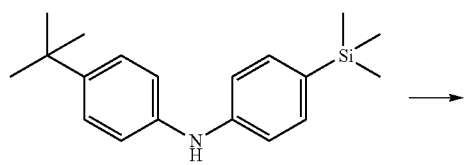

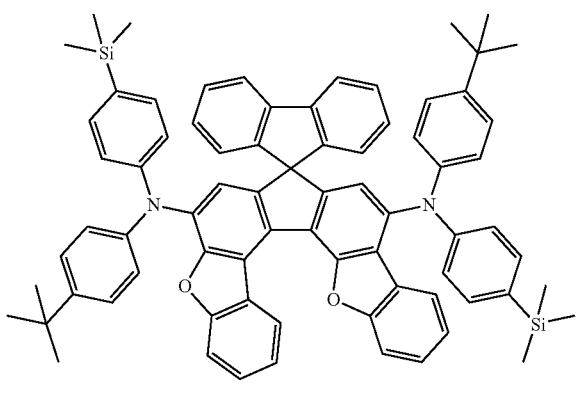

<Chemical Formula 98>

In a 100-ml round-bottom flask reactor, a mixture of <Intermediate 6-e> (2.2 g, 0.003 mol), 4-(tert-butyl)-N-(4-(trimethylsilyl)phenyl)amine (2.4 g, 0.008 mol), palladium (II) acetate (0.04 g, 0.2 mmol), sodium tert-butoxide (1.6 g, 0.016 mol), tri-tert-butylphosphine (0.04 g, 0.2 mmol), and toluene (30 ml) was stirred for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield the compound of Chemical Formula 98 (1.4 g, 43%).

MS (MALDI-TOF): m/z 1086.50 [M+]

Preparation Example of Compound for Electron Density Control Layer (EDCL)

Synthesis Example 7: Synthesis of Compound 10

Synthesis Example 7-(1): Synthesis of Intermediate 7-a

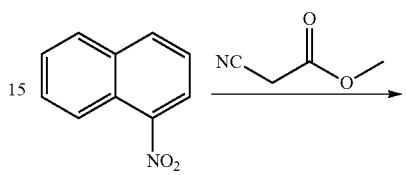

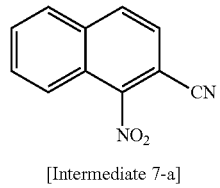

[Intermediate 7-a]

In a reactor, 1-nitronaphthalene (97 g, 0.56 mol), methyl cyanoacetate (166.5 g, 1.68 mol), potassium cyanide (40.1 g, 0.62 mol), and potassium hydroxide (62.9 g, 1.12 mol) were stirred together. To the reactants was added dimethylformamide (970 mL), followed by stirring at 60° C. overnight. The solvent was removed by vacuum concentration at room temperature, after which a 10% sodium hydroxide solution (500 mL) was added and refluxed for about 1 hr. Recrystallization in toluene and heptane subsequent to separation through column chromatography afforded [Intermediate 7-a] (50.8 g): yield 75%.

Synthesis Example 7-(2): Synthesis of Intermediate 7-b

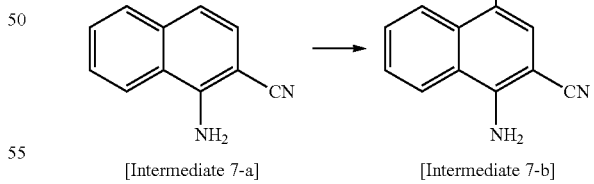

[Intermediate 7-a]     [Intermediate 7-b]

A solution of [Intermediate 7-a] (18.5 g, 0.11 mol) in dimethyl formamide (200 mL) was stirred at 0° C. Drops of a solution of N-bromosuccinimide (20.1 g, 0.11 mol) in dimethyl formamide (100 mL) were slowly added over 1 hr. The reaction mixture was warmed to room temperature and stirred for 12 hrs. Following filtration with an excess of distilled water, the filtrate was washed with methanol and recrystallized in toluene and methanol to afford [Intermediate 7-b] (18.7 g): yield 69%.

Synthesis Example 7-(3): Synthesis of Intermediate 7-c

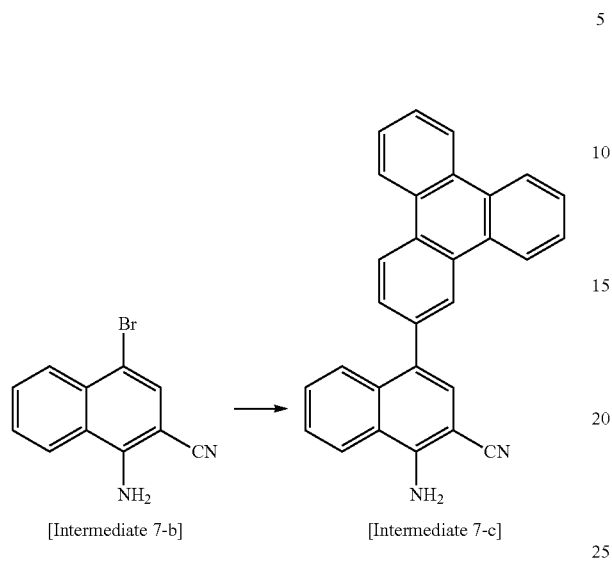

[Intermediate 7-b]    [Intermediate 7-c]

With the exception that [Intermediate 7-b] and triphenylene-2-yl boronic acid were used, respectively, instead of <Intermediate 6-e> and 4-dibenzofuran boronic acid, the same procedure as in Synthesis Example 6-(6) was performed to afford [Intermediate 7-c] (15.7 g): yield 57%.

Synthesis Example 7-(4): Synthesis of Intermediate 7-d

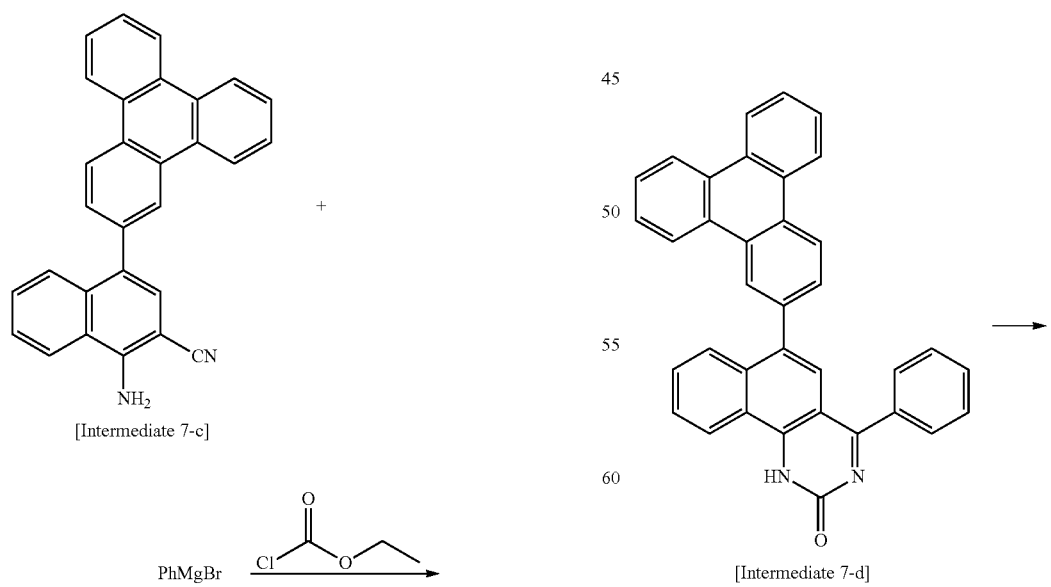

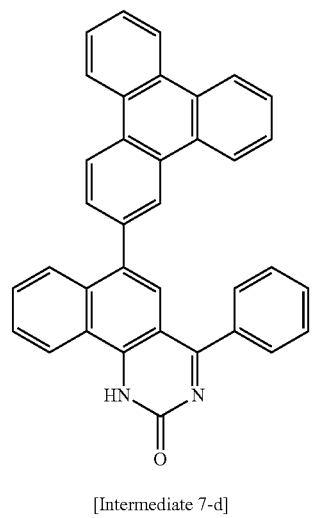

[Intermediate 7-d]

[Intermediate 7-c] (29.3 g, 75 mmol) was added to tetrahydrofuran (100 mL) and stirred. Drops of phenyl magnesium bromide (3.0 M in Et$_2$O) (43.7 mL, 148 mmol) were added, followed by refluxing at 0° C. for about 1 hour. Ethyl chloroformate (9.7 g, 89 mmol) was dropwise added and then refluxed for about 1 hour. The reaction mixture was added with an aqueous ammonium chloride solution until weak acidity was obtained, followed by washing with water and heptane to afford [Intermediate 7-d] (29.9 g): yield 80%.

Synthesis Example 7-(5): Synthesis of Intermediate 7-e

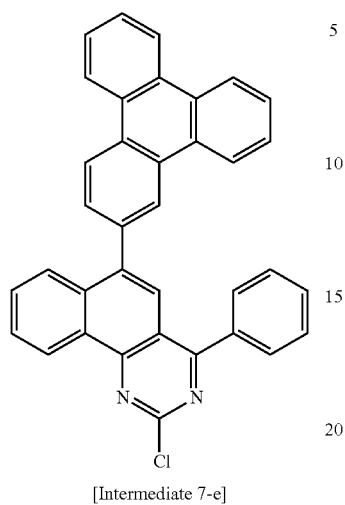

[Intermediate 7-e]

In a reactor, [Intermediate 7-d] (27.4 g, 55 mmol) and phosphorous oxychloride (ca. 80 mL) were placed and refluxed overnight. The temperature was lowered to −20° C. before addition of drops of distilled water (ca. 300 mL). The reaction mixture was washed with water, methanol, and heptane and recrystallized in toluene and heptane to afford [Intermediate 7-e] (12.7 g): yield 45%

Synthesis Example 7-(6): Synthesis of Compound 10

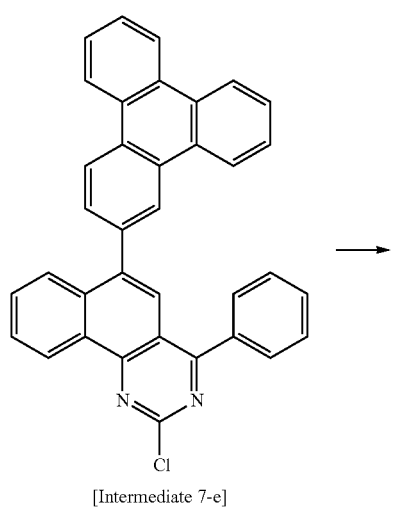

[Intermediate 7-e]

→

[Compound 10]

With the exception that [Intermediate 7-e] and phenyl boronic acid were used, respectively, instead of <Intermediate 6-e> and 4-dibenzofuran boronic acid, the same procedure as in Synthesis Example 6-(6) was performed to afford [Compound 10] (9.2 g): yield 68%.

MS (MALDI-TOF): m/z 558.21 [M+]

Synthesis Example 8: Synthesis of Compound 11

Synthesis Example 8-(1): Synthesis of Intermediate 8-a

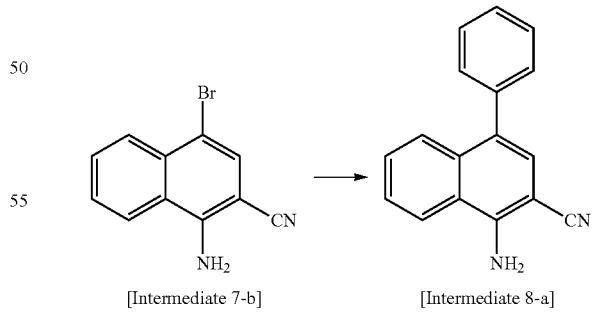

[Intermediate 7-b]  [Intermediate 8-a]

With the exception that <Intermediate 7-b> and phenyl boronic acid were used, respectively, instead of <Intermediate 6-e> and 4-dibenzofuran boronic acid, the same procedure as in Synthesis Example 6-(6) was performed to afford [Intermediate 8-a] (22.2 g): yield 66%.

Synthesis Example 8-(2): Synthesis of Intermediate 8-b

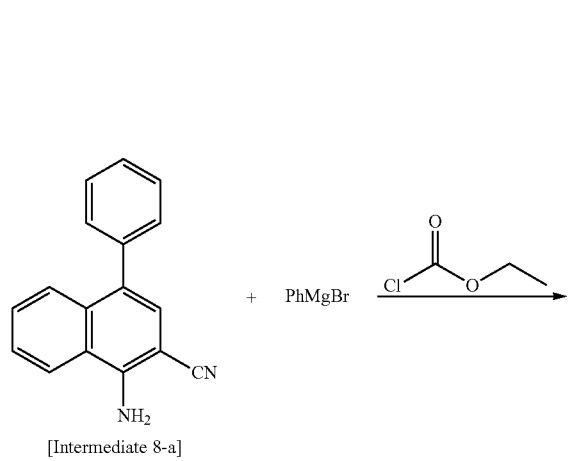

[Intermediate 8-a]

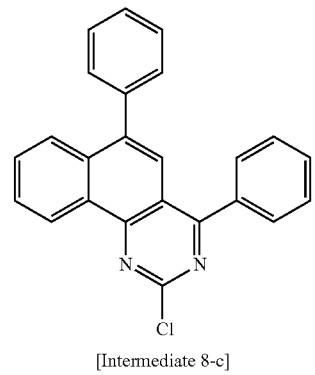

[Intermediate 8-c]

With the exception that [Intermediate 8-b] was used instead of [Intermediate 7-d], the same procedure as in Synthesis Example 7-5 was performed to afford [Intermediate 8-c] (9.7 g): yield 44%.

Synthesis Example 8-(4): Synthesis of Compound 11

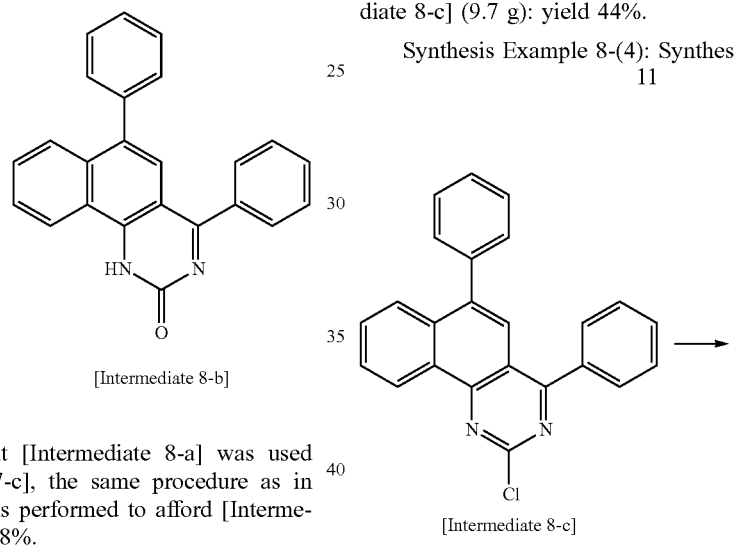

[Intermediate 8-b]

With the exception that [Intermediate 8-a] was used instead of [Intermediate 7-c], the same procedure as in Synthesis Example 7-4 was performed to afford [Intermediate 8-b] (16.5 g): yield 78%.

Synthesis Example 8-(3): Synthesis of Intermediate 8-c

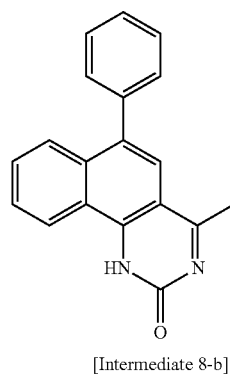

[Intermediate 8-b]

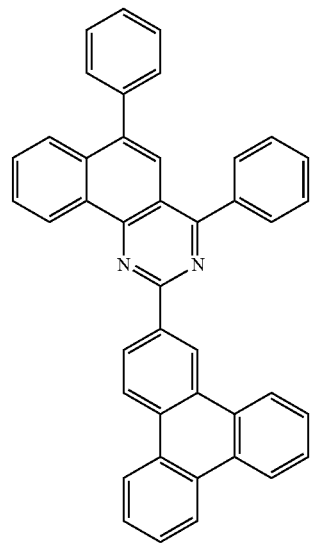

[Compound 11]

With the exception that [Intermediate 8-c] and triphenylene-2-yl boronic acid were used, respectively, instead of <Intermediate 6-e> and 4-dibenzofuran boronic acid, the same procedure as in Synthesis Example 6-(6) was performed to afford [Compound 11] 4.9 g (yield 64%).

MS (MALDI-TOF): m/z 558.21 [M+]

Synthesis Example 9: Synthesis of Compound 16

Synthesis Example 9-(1): Synthesis of Compound 16

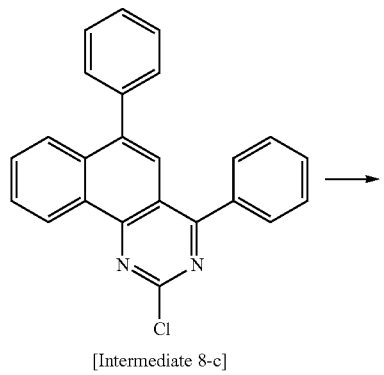

[Intermediate 8-c]

[Compound 16]

With the exception that [Intermediate 8-e] and 3-(naphthalene-1-yl)phenyl boronic acid were used, respectively, instead of <Intermediate 6-e> and 4-dibenzofuran boronic acid, the same procedure as in Synthesis Example 6-(6) was performed to afford [Compound 16] (5.6 g): yield 66%.

MS (MALDI-TOF): m/z 534.21 [M+]

Synthesis Example 10: Synthesis of Compound 18

Synthesis Example 10-(1): Synthesis of Intermediate 10-a

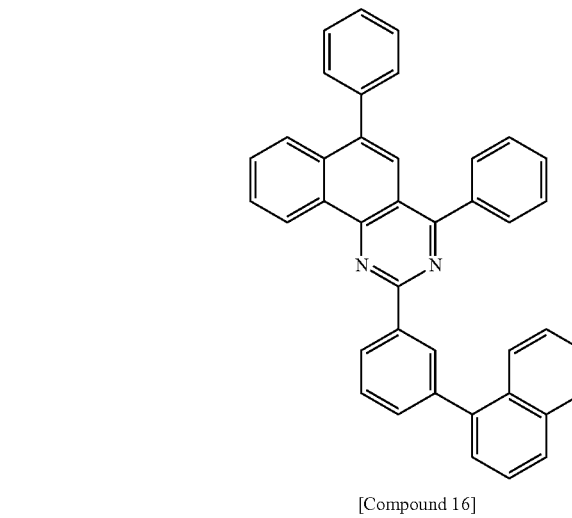

[Intermediate 7-b]    [Intermediate 10-a]

With the exception that [Intermediate 7-b] and 3-(naphthalene-1-yl)phenyl boronic acid were used, respectively, instead of <Intermediate 6-e> and 4-dibenzofuran boronic acid, the same procedure as in Synthesis Example 6-(6) was performed to afford [Intermediate 10-a] (16.8 g): yield 53%.

Synthesis Example 10-(2): Synthesis of Intermediate 10-b

[Intermediate 10-a]

PhMgBr

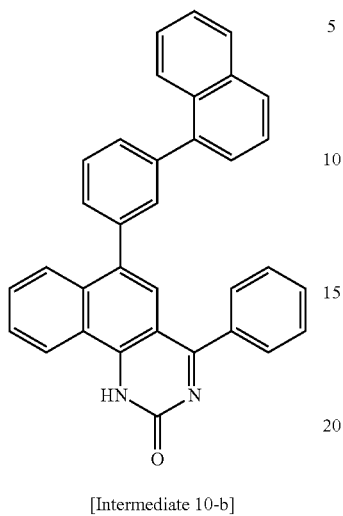

[Intermediate 10-b]

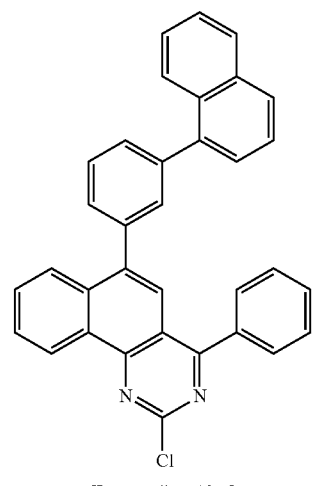

[Intermediate 10-c]

With the exception that [Intermediate 10-a] was used instead of [Intermediate 7-c], the same procedure as in Synthesis Example 7-(4) was performed to afford [Intermediate 10-b] (13.7 g): yield 76%.

With the exception that [Intermediate 10-b] was used instead of [Intermediate 7-d], the same procedure as in Synthesis Example 7-(5) was performed to afford [Intermediate 10-c] (10.3 g): yield 47%.

Synthesis Example 10-(3): Synthesis of Intermediate 10-c

Synthesis Example 10-(4): Synthesis of Compound 18

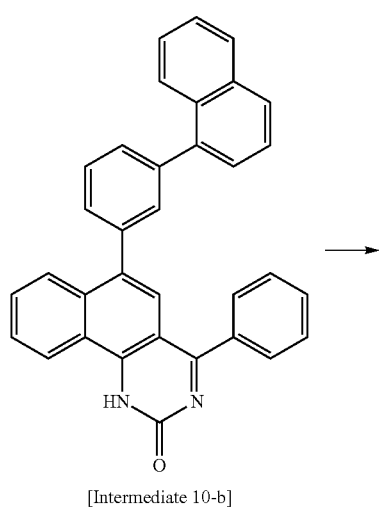

[Intermediate 10-b]

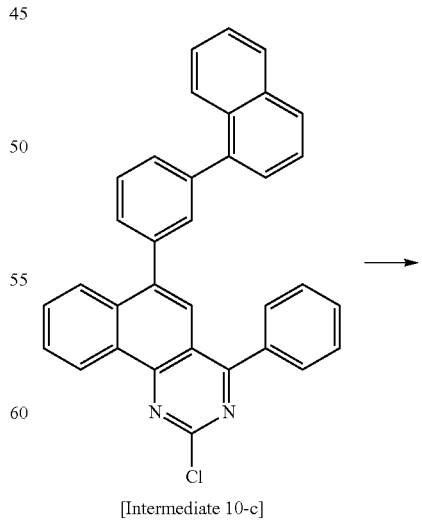

[Intermediate 10-c]

-continued

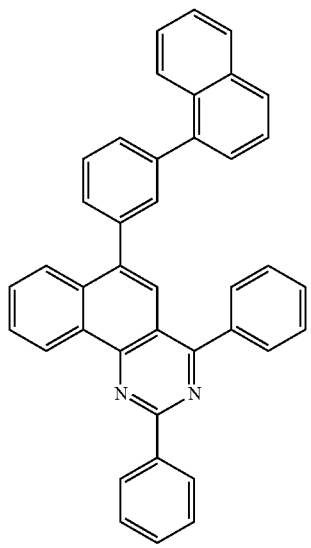

[Compound 18]

With the exception that [Intermediate 10-c] and phenyl boronic acid were used, respectively, instead of <Intermediate 6-e> and 4-dibenzofuran boronic acid, the same procedure as in Synthesis Example 6-(6) was performed to afford [Compound 18] (5.9 g): yield 72%.

MS (MALDI-TOF): m/z 534.21 [M+]

Synthesis Example 11: Synthesis of Compound 203

Synthesis Example 11-(1): Synthesis of Intermediate 11-a

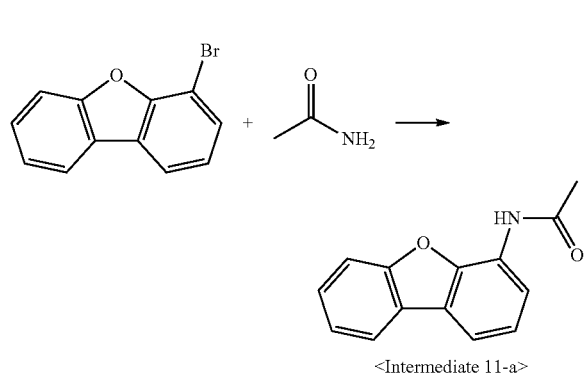

<Intermediate 11-a>

In a 2 L-round-bottom flask reactor, 4-bromodibenzofuran (150.0 g, 0.607 mol), acetamide (53.8 g, 0.911 mol), copper iodide (57.8 g, 0.30 mol), (±)trans-1,2-diaminocyclohexane (63.9 g, 0.60 mol), and potassium carbonate (167.8 g, 1.21 mol), and toluene (1500 ml) were together stirred overnight under reflux. After completion of the reaction, filtration through a silica gel pad was carried out, and the filtrate was washed many times with hot toluene. The filtrate was concentrated in a vacuum, and the concentrate was crystallized in acetonitrile, followed by filtration to afford <Intermediate 11-a>. (70.0 g, 51%)

Synthesis Example 11-(2): Synthesis of Intermediate 11-b

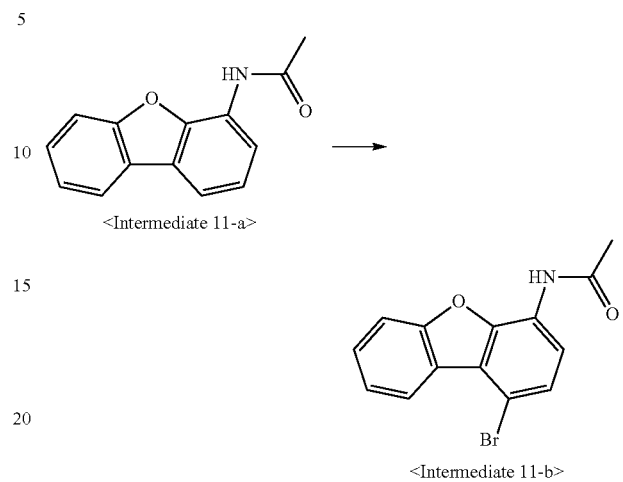

In a 2-L round-bottom flask reactor, <Intermediate 11-a> (70.0 g, 0.311 mol) was dissolved in acetic acid (630 ml). A mixture of bromine (49.7 g, 0.311 mol) and acetic acid (280 ml) was dropwise added into the reactor. At room temperature, the mixture was stirred for 2 hrs, and then water (100 ml) was added and stirred. The gray solid thus formed was slurried in ethanol (500 ml), stirred, and filtered. Dehydration of the filtrate afforded <Intermediate 11-b>. (86.0 g, 91%)

Synthesis Example 11-(3): Synthesis of Intermediate 11-c

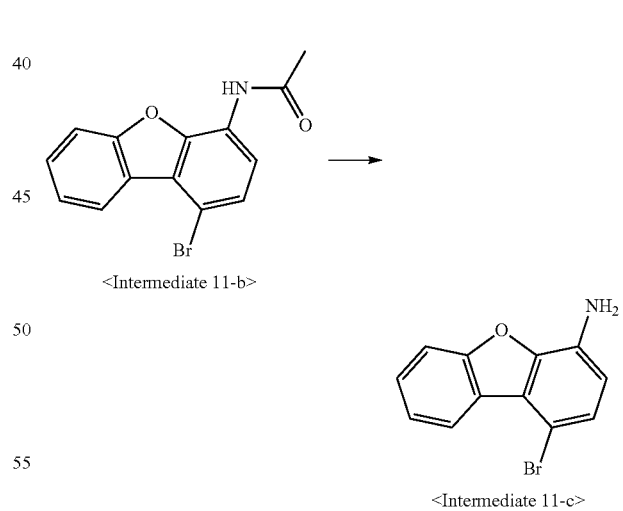

In a 2-L round-bottom flask reactor, <Intermediate 11-b> (86.0 g, 0.283 mol) was dissolved in ethanol (600 ml) and tetrahydrofuran (430 ml) and stirred. A solution of potassium hydroxide (47.6 g, 0.848 mol) in water (260 ml) was slowly added to the reactor, followed by stirring overnight under reflux. After completion of the reaction, the reaction mixture was cooled to room temperature. Extraction with ethyl acetate and water gave an organic layer which was then concentrated in a vacuum. The concentrate was stirred in excess ethanol and filtered. Recrystallization in methylene chloride and heptane afforded <Intermediate 11-c>. (73.0 g, 98%)

Synthesis Example 11-(4): Synthesis of Intermediate 11-d

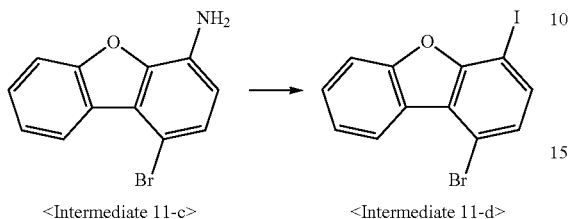

In a 2-L round-bottom flask reactor, a mixture of <Intermediate 11-c> (73.0 g, 0.279 mol), HCl (90 ml), and water (440 ml) was cooled to 0° C. and stirred. At the same temperature, a solution of sodium nitrite (25.0 g, 0.362 mol) in water (90 ml) was dropwise added and then stirred for 1 hour. A solution of potassium iodide (92.5 g, 0.557 mol) in water (90 ml) was dropwise added to the reaction solution and then stirred at room temperature. After completion of the reaction, the reaction mixture was extracted with ethylacetate and water. The organic layer was washed with an aqueous sodium thiosulfate pentahydrate solution, separated, and concentrated in a vacuum. Purification by column chromatography afforded <Intermediate 11-d> (52.3 g, 50.3%).

Synthesis Example 11-(5): Synthesis of Intermediate 11-e

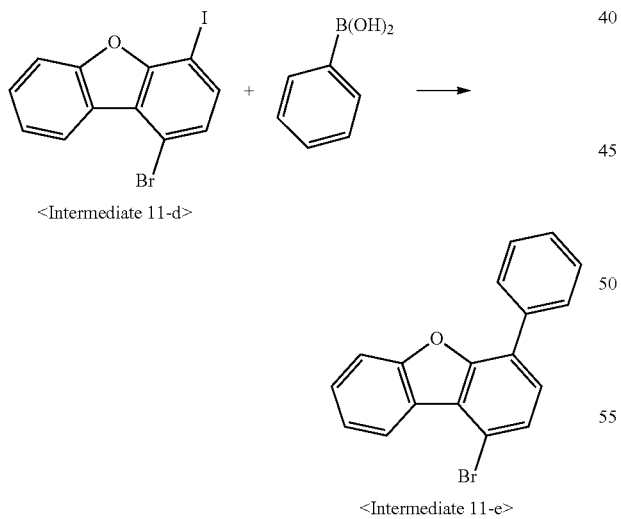

In a 2-L round-bottom flask reactor were placed <Intermediate 11-d> (15.0 g, 40 mmol), phenyl boronic acid (5.4 g, 44 mmol), tetrakis(triphenylphosphine)palladium (0.9 g, 1 mmol), and potassium carbonate (11.1 g, 80 mmol), followed by toluene (100 mL), methanol (45 mL), and water (30 mL). The mixture was stirred overnight under reflux. After completion of the reaction, the reaction mixture was cooled to room temperature, and extracted with ethyl acetate. The organic layer thus formed was concentrated in a vacuum. Following purification by column chromatography, recrystallization in heptane afforded <Intermediate 11-e> (7.0 g, 53.9%).

Synthesis Example 11-(6): Synthesis of Compound 203

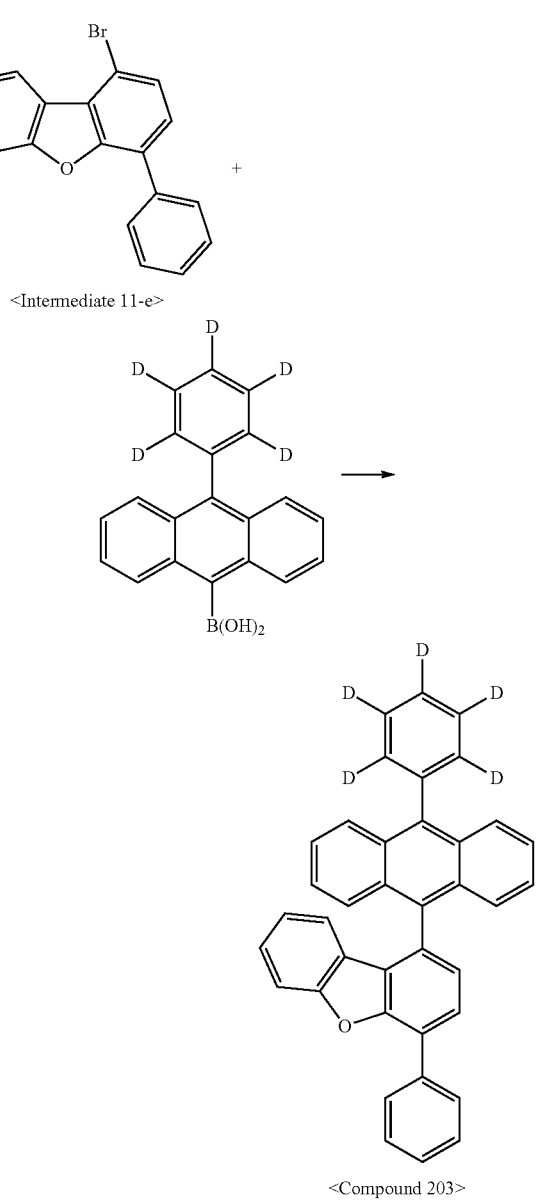

In a 250-ml round bottom flask reactor were placed <Intermediate 11-e> (7.0 g, 22 mmol), 10-phenyl(d5)-anthracene-9-boronic acid (7.9 g, 26 mmol), tetrakis(triphenylphosphine) palladium (0.5 g, 1 mmol), and potassium carbonate (6.0 g, 43 mmol), followed by toluene (50 ml), ethanol (21 ml), and water (14 ml). The mixture was heated to 90° C. and stirred overnight. After completion of the reaction, the reaction mixture was cooled to room temperature and stirred together with methanol (50 mL) at room temperature. The solid thus formed was filtered and washed with methanol. The solid was recrystallized in toluene and acetone to afford <Compound 203.>

MS (MALDI-TOF): m/z 501.21 [M+]

Synthesis Example 12: Synthesis of Compound 209

Synthesis Example 12-(1): Synthesis of Intermediate 12-a

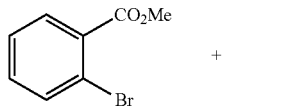

+

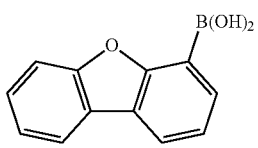

→

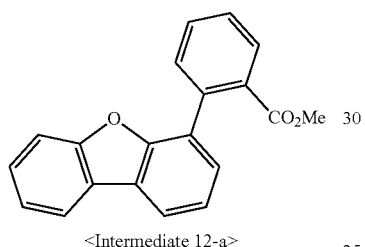

<Intermediate 12-a>

In a 500-mL round-bottom flask reactor were placed methyl 2-bromobenzoate (30.0 g, 0.140 mol), 4-dibenzofuran boronic acid (32.5 g, 0.153 mol), tetrakis(triphenylphosphine)palladium (3.2 g, 3 mmol), and potassium carbonate (38.6 g, 0.279 mol), followed by toluene (210 mL), methanol (90 mL), and water (60 mL). The mixture was stirred overnight under reflux. After completion of the reaction, the reaction mixture was cooled to room temperature and extracted with ethyl acetate. The organic layer thus formed was separated, concentrated in a vacuum, and purified by column chromatography to afford <Intermediate 12-a>. (25.0 g, 59.1%).

Synthesis Example 12-(2): Synthesis of Intermediate 12-b

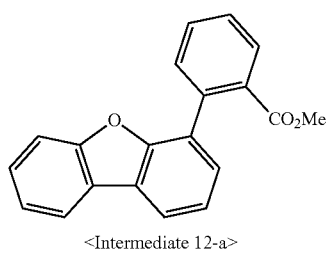 + 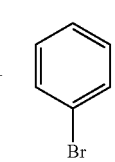 →

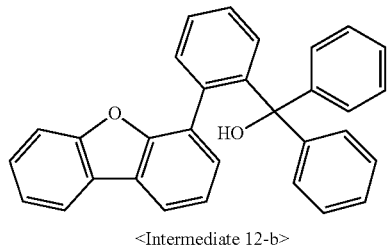

<Intermediate 12-b>

In a 500-ml round-bottom flask reactor, bromobenzene (28.6 g, 182 mmol) and tetrahydrofuran (220 ml) were cooled to −78° C. under a nitrogen atmosphere. At the same temperature, n-butyl lithium (104.6 ml, 167 mmol) was dropwise added to the chilled solution, and stirred for 2 hrs. Then, <Intermediate 12-a> (22.0 g, 73 mmol) was added little by little at room temperature while stirring. After completion of the reaction, the reaction was stopped with H₂O (50 ml), and extraction with ethyl acetate and water was conducted. The organic layer thus formed was concentrated in a vacuum to afford <Intermediate 12-b>. (28.0 g, 90%)

Synthesis Example 12-(3): Synthesis of Intermediate 12-c

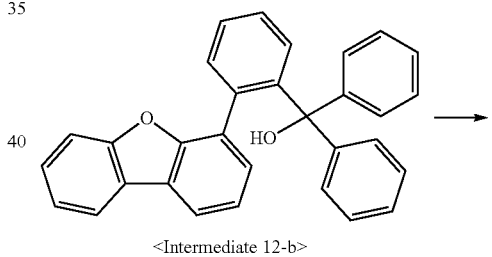

<Intermediate 12-b>

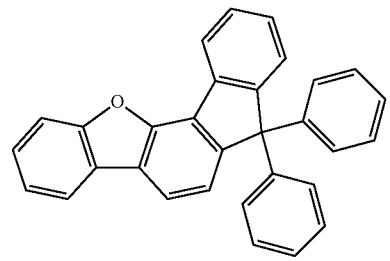

<Intermediate 12-c>

In a 500-ml round-bottom flask reactor, <Intermediate 12-b> (28.0 g, 66 mmol), acetic acid (310 ml) and HCl (2 ml) were stirred together for 1 hr under reflux. When a solid was formed, the completion of the reaction was confirmed by thin layer chromatography. After the reaction mixture was cooled to room temperature, the solid thus formed was filtered. The filtrate washed H₂O and methanol, and dried to afford <Intermediate 12-c>. (22.3 g, 83.2%)

227

Synthesis Example 12-(4): Synthesis of Intermediate 12-d

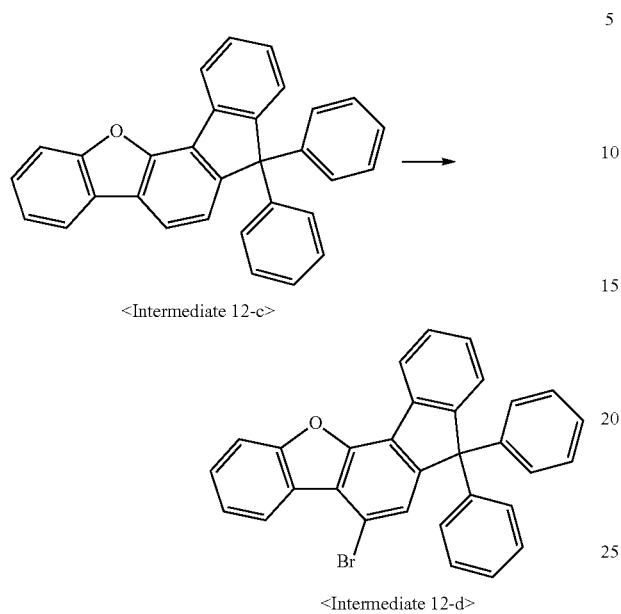

In a 2-L round-bottom flask reactor, <Intermediate 12-c> (22.3 g, 55 mmol) was dissolved in methylene chloride (500 ml). A mixture of bromine (8.72 g, 55 mmol) and methylene chloride (250 ml) was dropwise added to the reactor, followed by stirring at room temperature for 3 hrs. After completion of the reaction, the reaction mixture was washed with an aqueous sodium hydrogen carbonate solution. The solid thus formed was filtered and recrystallized in toluene and acetone to afford <Intermediate 12-d>. (25.0 g, 94%)

Synthesis Example 12-(5): Synthesis of Compound 209

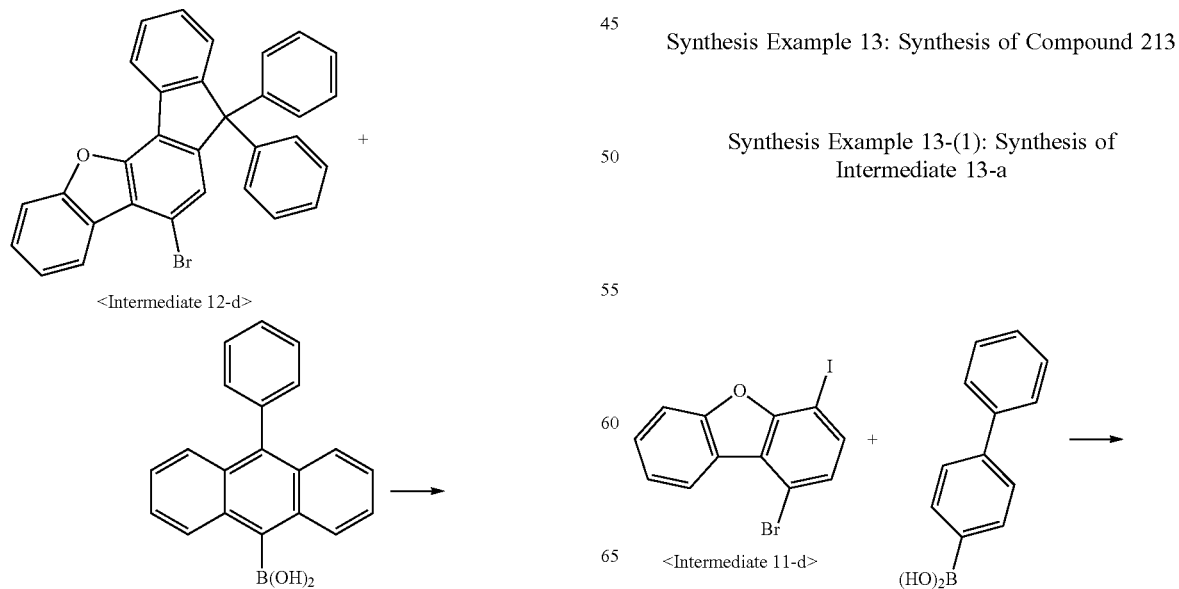

In a 250-ml round bottom flask reactor were placed <Intermediate 12-d> (7.0 g. mmol), 10-phenyl-anthracene-9-boronic acid (5.1 g, 17 mmol), tetrakis(triphenylphosphine) palladium (0.3 g, 3 mmol), and potassium carbonate (4.0 g, 29 mmol), followed by toluene (49 ml), ethanol (21 ml), and water (14 ml). The mixture was heated to 90° C. and stirred overnight. After completion of the reaction, the reaction mixture was cooled to room temperature and extracted with ethyl acetate. The organic layer was isolated, and concentrated in a vacuum. Following purification by column chromatography, recrystallization in methylene chloride and acetone afforded <Compound 209>.

MS (MALDI-TOF): m/z 660.25 [M+]

Synthesis Example 13: Synthesis of Compound 213

Synthesis Example 13-(1): Synthesis of Intermediate 13-a

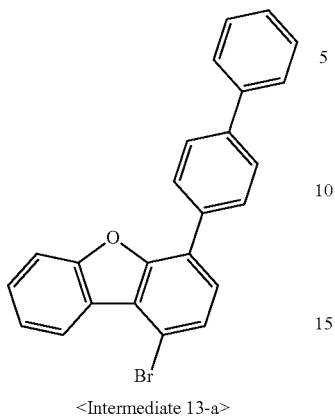

<Intermediate 13-a>

With the exception that 4-biphenyl boronic acid was used instead of phenyl boronic acid, the same procedure as in Synthesis Example 11-(5) was performed to afford <Intermediate 13-a> (8.5 g, 55.9%).

Synthesis Example 13-(2): Synthesis of Compound 213

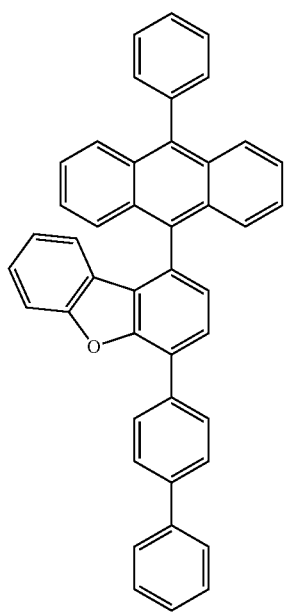

<Compound 213>

With the exception that <Intermediate 13-a> was used instead of <Intermediate 12-d>, the same procedure as in Synthesis Example 12-(5) was carried out to afford <Compound 213> (6.3 g, 51%).

MS (MALDI-TOF): m/z 572.21 [M$^+$]

Synthesis Example 14: Synthesis of Compound 281

Synthesis Example 14-(1): Synthesis of Intermediate 14-a

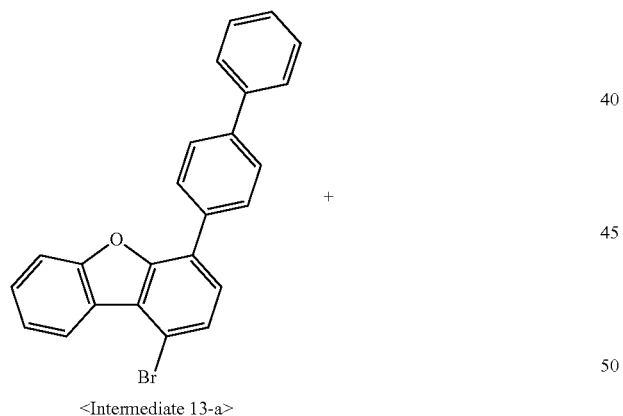

<Intermediate 13-a>

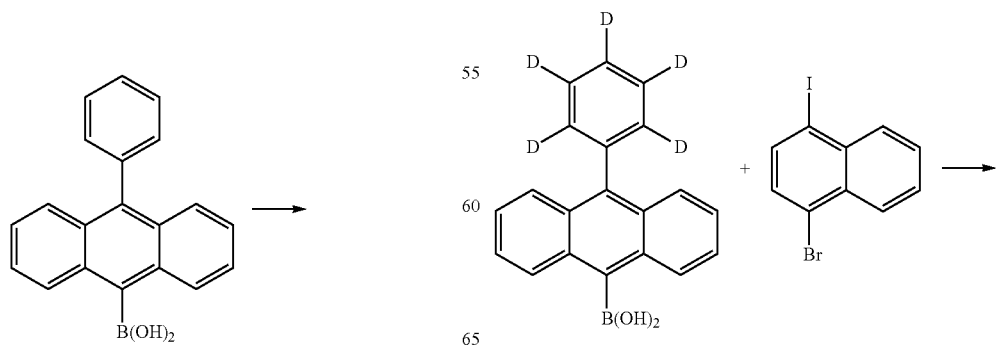

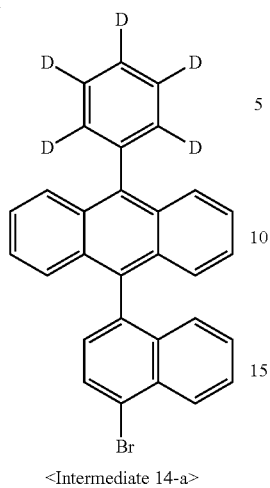

<Intermediate 14-a>

In a 500-mL round-bottom flask reactor were placed (10-phenyl(d5)-anthracene-9-boronic acid (38.6 g, 127 mmol), 1-bromo-4-iodonaphthalene (35.3 g, 106 mmol), tetrakis(triphenylphosphine)palladium (3.43 g, 3 mmol), and potassium carbonate (27.35 g, 197.9 mmol), followed by toluene (150 mL), tetrahydrofuran (150 mL), and water (60 mL). The reactor was heated to 90° C. before stirring overnight. After completion of the reaction, the reaction mixture was cooled to room temperature and extracted with ethyl acetate. The organic layer thus formed was isolated, concentrated in a vacuum, and purified by column chromatography to afford <Intermediate 14-a>. (39.2 g, 79.7%)

Synthesis Example 14-(2): Synthesis of Intermediate 14-b

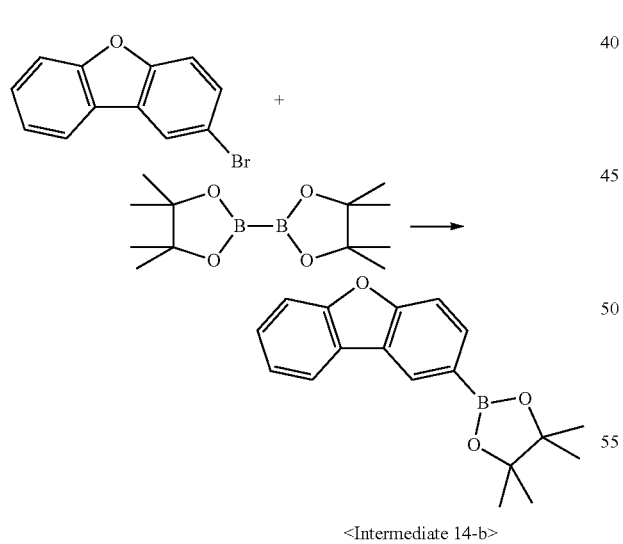

<Intermediate 14-b>

In a 2-L round-bottom flask reactor, 2-bromodibenzofuran (70.0 g, 0.283 mol), bis(pinacolato)diboron (86.3 g, 0.340 mol), 1,1'-bis(diphenylphosphino)ferrocene-dichloropalladium (II) dichloride (4.6 g, 0.006 mol), potassium acetate (56.6 g, 0.567 mol), and 1,4-dioxane (700 ml) were stirred together overnight under reflux. After completion of the reaction, filtration through a celite pad was conducted. The filtrate was concentrated in a vacuum, purified by column chromatography, and filtered to afford <Intermediate 14-b> (66.4 g, 79%).

Synthesis Example 14-(3): Synthesis of Compound 281

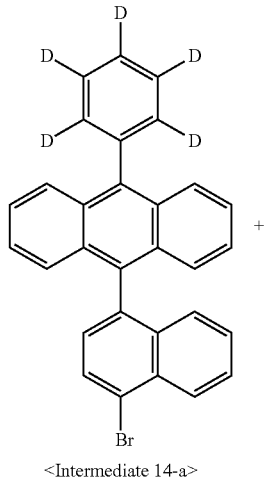

<Intermediate 14-a>

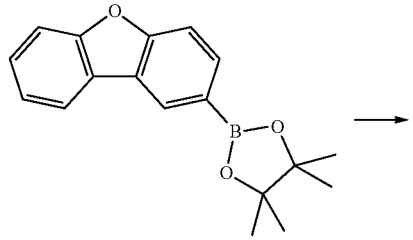

<Intermediate 14-b>

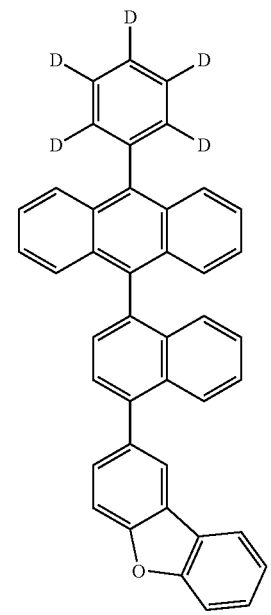

<Compound 281>

With the exception that <Intermediate 14-b> and <Intermediate 11-a> were used instead of 10-phenyl(d5)-anthracene-9-boronic acid and 1-bromo-4-iodonaphthalene, respectively, the same procedure as in Synthesis Example 14-(1) was carried out to afford <Compound 281> (8.5 g, 66.5%).

MS (MALDI-TOF): m/z 551.23 [M⁺]

Synthesis Example 15: Synthesis of Compound 106

Synthesis Example 15-(1): Intermediate 15-a

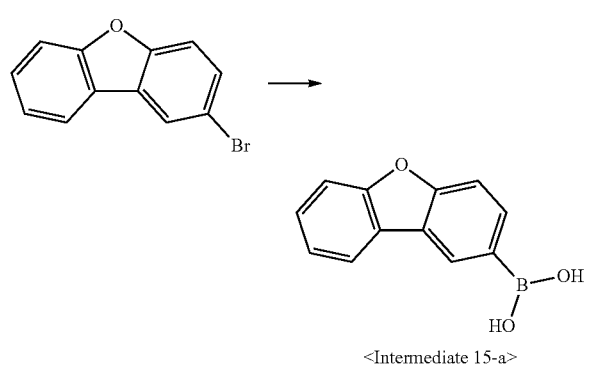

<Intermediate 15-a>

In a 1-L reactor, tetrahydrofuran (500 mL) was added with 2-bromodibenzofuran (33 g, 133.6 mmol) and then cooled to −78° C. in a nitrogen atmosphere. After 30 min, drops of 1.6 M n-butyl lithium (50 mL, 80 mmol) were slowly added and stirred at −78° C. for 1 hr. At −78° C., trimethyl borate (9.05 g, 87.1 mmol) was dropwise added before being heated to room temperature. Stirring for 2 hrs was followed by terminating the reaction with an aqueous HCl solution. The organic layer thus formed was extracted and distilled in a vacuum. Recrystallization in hexane gave a solid which was then filtered and dried to afford <Intermediate 15-a>. (22 g, 78%)

Synthesis Example 15-(2): Intermediate 15-b

<Intermediate 15-a>

<Intermediate 15-b>

In a 2-L reactor, 3-bromoiodobenzene (50 g, 159 mmol), <Intermediate 15-a> (22 g, 104 mmol), tetrakis(triphenylphosphine)palladium (3.7 g, 3.17 mmol), potassium carbonate (65.7 g, 476 mmol), toluene (700 mL), and distilled water (200 mL) were stirred together at 100° C. for 12 hrs. The reaction mixture was cooled to room temperature and treated with ethyl acetate. The organic layer thus formed was extracted and concentrated in a vacuum, followed by column chromatography to afford <Intermediate 15-b> (16 g, 48%).

Synthesis Example 15-(3): Intermediate 15-c

<Intermediate 15-b>

<Intermediate 15-c>

With the exception that <Intermediate 15-b> was used instead of 2-bromo dibenzofuran, the same procedure as in Synthesis Example 15-(1) was performed to afford <Intermediate 15-c> (9.5 g, 67%).

Synthesis Example 15-(4): Synthesis of Compound 106

<Intermediate 15-c>

-continued

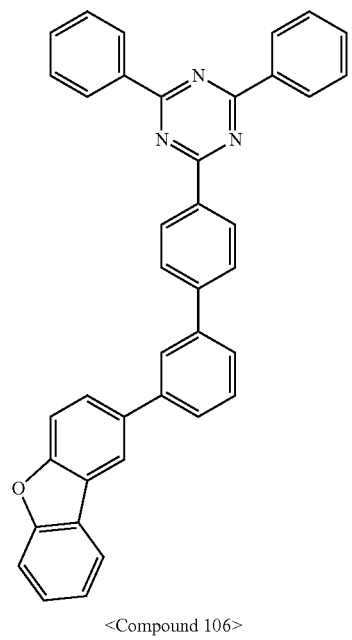

<Compound 106>

With the exception that 2-(4-bromophenyl)-4,6-diphenyl-1,3,5-triazine and <Intermediate 15-c> were used, respectively, instead of 3-bromoiodobenzene and <Intermediate 15-a>, the same procedure as in Synthesis Example 15-(2) was performed to afford Compound 106. (11 g, 61%)

MS (MALDI-TOF): m/z 551.20 [M+]

Synthesis Example 16: Synthesis of Compound 115

Synthesis Example 16-(1): Intermediate 16-a

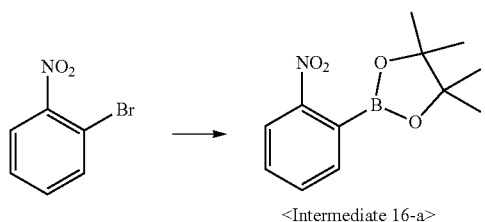 [SMILES: O=[N+]([O-])c1ccccc1Br ; CC1(C)OB(c2ccccc2[N+](=O)[O-])OC1(C)C]

<Intermediate 16-a>

In a 1-L round-bottom flask reactor, 1-bromo-2-nitrobenzene (50 g, 248 mmol), bis(pinacolato)diboron (81.7 g, 322 mmol), 1,1'-bis(diphenylphosphino)ferrocene-palladium(II) dichloride (4.03 g, 5 mmol), potassium acetate (48.6 g, 495 mmol), and toluene (500 ml) were stirred together overnight under reflux. After completion of the reaction, the reaction mixture was filtered through a celite pad and the filtrate was concentrated in a vacuum. Isolation and purification by column chromatography afforded <Intermediate 16-a>. (46.8 g, 75.9%)

Synthesis Example 16-(2): Intermediate 16-b

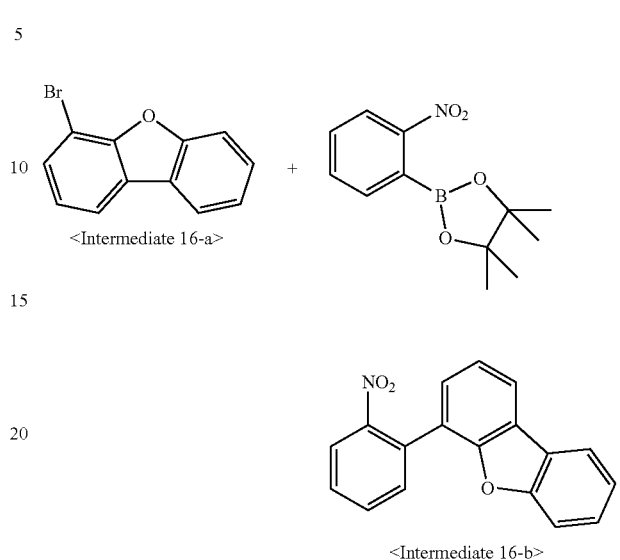

With the exception that 4-bromodibenzofuran and <Intermediate 16-a> were used, respectively, instead of 3-bromoiodobenzene and <Intermediate 15-a>, the same procedure as in Synthesis Example 15-(2) was performed to afford <Intermediate 16-b>. (10.4 g, 59.8%)

Synthesis Example 16-(3): Intermediate 16-c

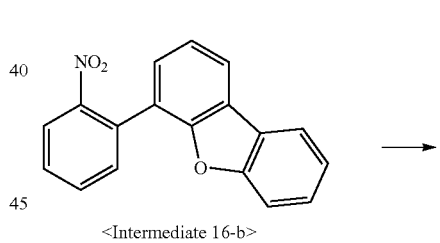

<Intermediate 16-b>

<Intermediate 16-c>

In a 250-ml reactor, <Intermediate 16-b> (10.4 g, 36 mmol) and triphenyl phosphine (17.9 g, 2 mmol) were placed, followed by 1,2-dichlorobenzene (80 ml). The reactor was heated to 120° C. at which stirring was conducted overnight. After completion of the reaction, the reaction mixture was concentrated by heating. Isolation and purification by column chromatography afforded <Intermediate 16-c>. (8.5 g, 92%)

Synthesis Example 16-(4): Synthesis of Compound 115

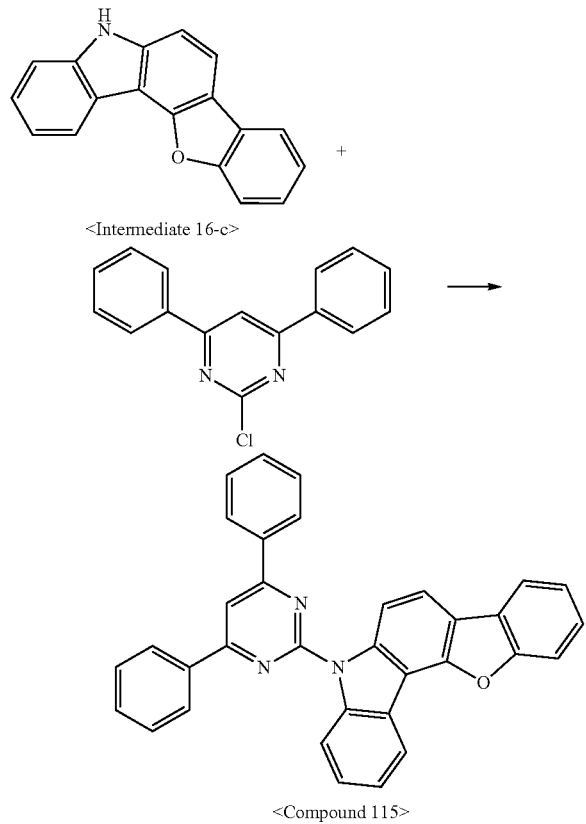

<Intermediate 16-c>

+

<Compound 115>

In a 250-ml round-bottom flask reactor, <Intermediate 16-c> (8.5 g, 40 mmol), 2-chloro-4,6-diphenylpyrimidine (7.6 g, 37 mmol), bis(dibenzylideneacetone) palladium(0) (0.4 g, 0.6 mmol), tri-tert-butyl phosphine tetrahydroborate (0.9 g, 3 mmol), sodium tert-butoxide (6 g, 62 mmol), and xylene (85 ml) were heated and stirred overnight together under reflux. The reaction mixture was filtered and concentrated in a vacuum. Following purification by column chromatography, recrystallization in toluene and acetone afforded <Compound 115>. (8.1 g, 50%)

MS (MALDI-TOF): m/z 487.17 [M+]

Examples 1 to 20: Fabrication of Organic Light-Emitting Diode—Efficiency

An ITO glass substrate was patterned to have a translucent area of 2 mm×2 mm and cleansed. The ITO glass was mounted in a vacuum chamber that was then set to have a base pressure of $1\times10^{-7}$ torr. On the ITO glass substrate, films were formed of DNTPD (400 Å) and a-NPD (200 Å) in that order. A light-emitting layer (200 Å) was formed of a mixture including [BH] and each of the compounds shown as a dopant in Table 1 according to the present disclosure (weight ratio 97:3). Then, the compounds shown in Table 1 were deposited to form an electron density control layer (50 Å), on which [Chemical Formula E-1] for an electron transport layer (250 Å), [Chemical Formula E-2] for an electron injection layer (5 Å), and Al (1000 Å) were deposited in the order to fabricate an organic light-emitting diode. The organic light-emitting diode thus obtained was measured at 10 mA/cm² for luminescence properties.

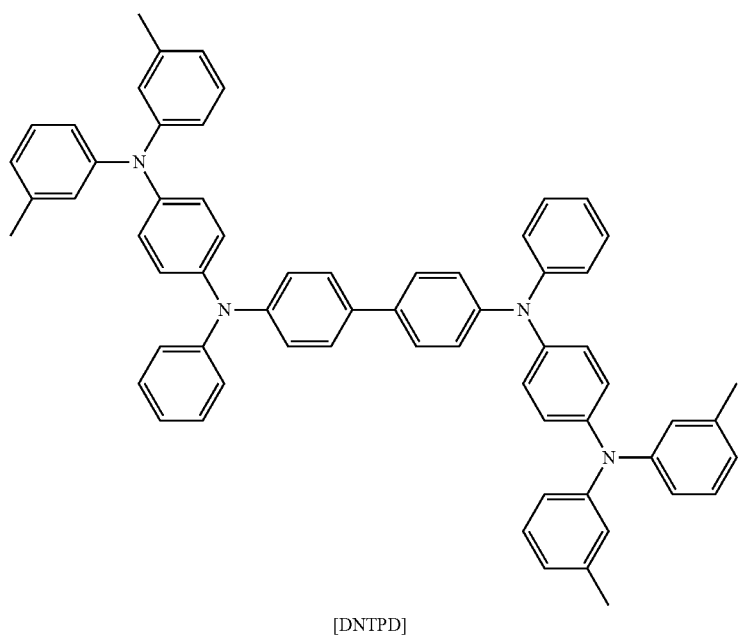

[DNTPD]

-continued

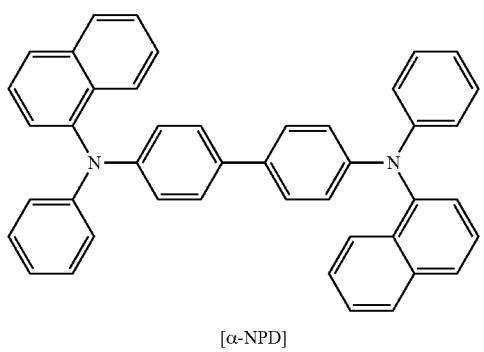

[α-NPD]

[Chemical Formula E-1]

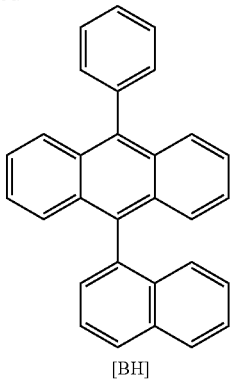

[BH]

[Chemical Formula E-2]

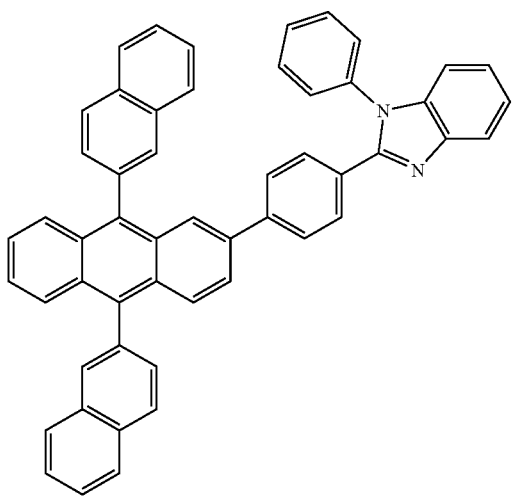

Comparative Example 1

Comparative Examples 2 and 3

An organic light-emitting diode was fabricated in the same manner as in Example 7, with the exception that [BD1], a conventional compound for a dopant in a light-emitting layer, was used, instead of the compounds used in Example 7. The luminescence of the organic light-emitting diodes was measured at 10 mA/cm². The structure of [BD1] is as follows.

[BD1]

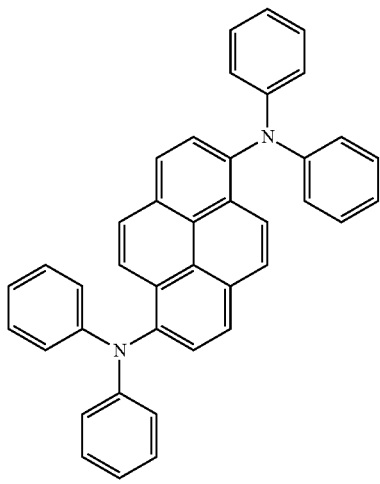

An ITO glass substrate was patterned to have a translucent area of 2 mm×2 mm and cleansed. The ITO glass was mounted in a vacuum chamber that was then set to have a base pressure of 1×10⁻⁷ torr. On the ITO glass substrate, films were formed of DNTPD (400 Å) and a-NPD (200 Å) in that order. A light-emitting layer (200 Å) was formed of a mixture including [BH] and each of the compounds shown as a dopant in Table 1 according to the present disclosure (weight ratio 97:3). Without forming an electron density control layer according to the present disclosure, [Chemical Formula E-1] for an electron transport layer (300 Å), [Chemical Formula E-2] for an electron injection layer (5 Å), and Al (1000 Å) were deposited in the order on the light-emitting layer to fabricate organic light-emitting diodes. The organic light-emitting diodes thus obtained were measured at 10 mA/cm² for luminescence properties.

TABLE 1

| | Dopant | Electron Density Control Layer | V | CIEx | CIEy | EQE |
|---|---|---|---|---|---|---|
| Ex. 1 | Chemical Formula 1 | Compound 10 | 3.68 | 0.138 | 0.107 | 11.34 |
| Ex. 2 | Chemical Formula 1 | Compound 18 | 3.73 | 0.138 | 0.107 | 11.46 |
| Ex. 3 | Chemical Formula 1 | Compound 106 | 3.84 | 0.138 | 0.108 | 12.00 |

TABLE 1-continued

| | Dopant | Electron Density Control Layer | V | CIEx | CIEy | EQE |
|---|---|---|---|---|---|---|
| Ex. 4 | Chemical Formula 1 | Compound 203 | 3.79 | 0.138 | 0.106 | 11.44 |
| Ex. 5 | Chemical Formula 1 | Compound 209 | 3.74 | 0.138 | 0.104 | 11.67 |
| Ex. 6 | Chemical Formula 1 | Compound 213 | 3.85 | 0.138 | 0.104 | 11.74 |
| Ex. 7 | Chemical Formula 1 | Compound 339 | 3.79 | 0.137 | 0.111 | 10.95 |
| Ex. 8 | Chemical Formula 1 | Compound 340 | 3.78 | 0.137 | 0.109 | 11.56 |
| Ex. 9 | Chemical Formula 1 | Compound 341 | 3.76 | 0.138 | 0.105 | 12.24 |
| Ex. 10 | Chemical Formula 33 | Compound 10 | 3.76 | 0.138 | 0.104 | 11.55 |
| Ex. 11 | Chemical Formula 33 | Compound 106 | 3.77 | 0.138 | 0.107 | 11.73 |
| Ex. 12 | Chemical Formula 33 | Compound 115 | 3.71 | 0.137 | 0.108 | 11.23 |
| Ex. 13 | Chemical Formula 49 | Compound 106 | 3.61 | 0.137 | 0.109 | 11.97 |
| Ex. 14 | Chemical Formula 49 | Compound 115 | 3.65 | 0.137 | 0.108 | 12.01 |
| Ex. 15 | Chemical Formula 49 | Compound 213 | 3.69 | 0.137 | 0.100 | 11.00 |
| C. Ex. 1 | BD1 | Compound 339 | 3.79 | 0.135 | 0.109 | 10.54 |
| C. Ex. 2 | Chemical Formula 1 | — | 3.94 | 0.137 | 0.111 | 10.62 |
| Ex. 16 | Chemical Formula231 | Compound 106 | 3.47 | 0.137 | 0.108 | 11.94 |
| Ex. 17 | Chemical Formula231 | Compound 203 | 3.43 | 0.138 | 0.106 | 12.31 |
| Ex. 18 | Chemical Formula231 | Compound 209 | 3.45 | 0.137 | 0.110 | 12.05 |
| Ex. 19 | Chemical Formula231 | Compound 213 | 3.42 | 0.138 | 0.105 | 12.12 |
| Ex. 20 | Chemical Formula231 | Compound 281 | 3.44 | 0.137 | 0.109 | 11.61 |
| C. Ex. 3 | Chemical Formula231 | — | 3.51 | 0.138 | 0.107 | 10.44 |

Examples 21 to 32: Fabrication of Organic Light-Emitting Diode—Life Span

An ITO glass substrate was patterned to have a translucent area of 2 mm×2 mm and cleansed. The ITO glass was mounted in a vacuum chamber that was then set to have a base pressure of $1 \times 10^{-7}$ torr. On the ITO glass substrate, films were formed of DNTPD (400 Å) and TPD (200 Å) in that order. A light-emitting layer (200 Å) was formed of a mixture including [BH1] and each of the compounds shown as a dopant in Table 2 according to the present disclosure (weight ratio 97:3). Then, the compounds shown in Table 2 were deposited to form an electron density control layer (50 Å), on which [Chemical Formula E-1] for an electron transport layer (250 Å), [Chemical Formula E-2] for an electron injection layer (5 Å), and Al (1000 Å) were deposited in the order to fabricate an organic light-emitting diode.

The organic light-emitting diode thus obtained was measured at 10 mA/cm² for luminescence properties.

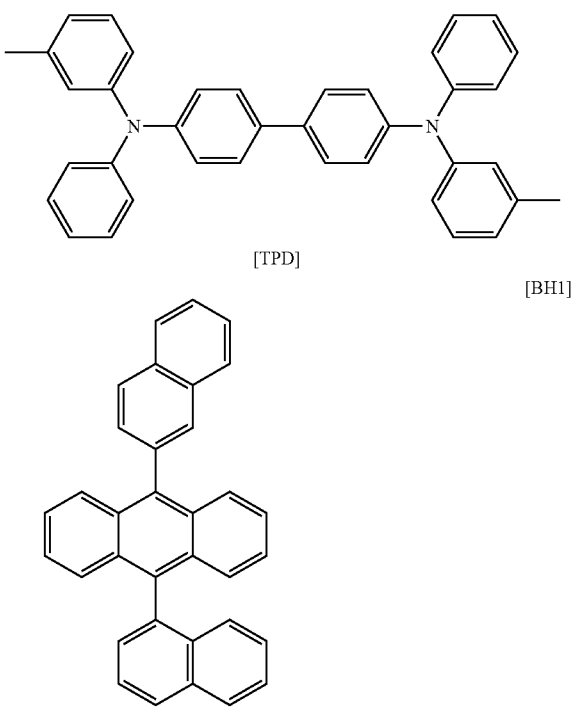

Comparative Example 4

An organic light-emitting diode was fabricated in the same manner as in Example 2, with the exception that [BD1] of Comparative Example 1 was used as a dopant in the light-emitting layer. The organic light-emitting diode thus obtained was measured at 10 mA/cm² for luminescence properties.

Comparative Examples 5 and 6

An ITO glass substrate was patterned to have a translucent area of 2 mm×2 mm and cleansed. The ITO glass was mounted in a vacuum chamber that was then set to have a base pressure of $1 \times 10^{-7}$ torr. On the ITO glass substrate, films were formed of DNTPD (400 Å) and TPD (200 Å) in that order. A light-emitting layer (200 Å) was formed of a mixture including [BH1] and each of the compounds shown as a dopant in Table 2 according to the present disclosure (weight ratio 97:3). Without forming an electron density control layer according to the present disclosure, [Chemical Formula E-1] for an electron transport layer (300 Å), [Chemical Formula E-2] for an electron injection layer (5 Å), and Al (1000 Å) were deposited in the order on the light-emitting layer to fabricate organic light-emitting diodes.

The organic light-emitting diode thus obtained was measured at 10 mA/cm² for luminescence properties.

TABLE 2

| | Dopant | Electron Density Control Layer | V | CIEx | CIEy | T90 |
|---|---|---|---|---|---|---|
| Ex. 21 | Chemical Formula 1 | Compound 11 | 3.92 | 0.136 | 0.106 | 450 |
| Ex. 22 | Chemical Formula 1 | Compound 16 | 3.87 | 0.136 | 0.107 | 400 |

TABLE 2-continued

| | Dopant | Electron Density Control Layer | V | CIEx | CIEy | T90 |
|---|---|---|---|---|---|---|
| Ex. 23 | Chemical Formula 1 | Compound 345 | 3.79 | 0.137 | 0.111 | 368 |
| Ex. 24 | Chemical Formula 1 | Compound 346 | 3.78 | 0.137 | 0.109 | 460 |
| Ex. 25 | Chemical Formula 1 | Compound 347 | 3.76 | 0.138 | 0.105 | 744 |
| Ex. 26 | Chemical Formula 49 | Compound 11 | 3.88 | 0.137 | 0.107 | 511 |
| Ex. 27 | Chemical Formula 49 | Compound 16 | 3.67 | 0.137 | 0.106 | 490 |
| Ex. 28 | Chemical Formula 76 | Compound 106 | 3.71 | 0.136 | 0.108 | 580 |
| Ex. 29 | Chemical Formula 76 | Compound 115 | 3.75 | 0.137 | 0.109 | 470 |
| C. Ex. 4 | BD1 | Compound 346 | 3.78 | 0.135 | 0.109 | 282 |
| C. Ex. 5 | Chemical Formula 1 | — | 3.94 | 0.137 | 0.111 | 284 |
| Ex. 30 | Chemical Formula 98 | Compound 11 | 3.93 | 0.139 | 0.100 | 480 |
| Ex. 31 | Chemical Formula 98 | Compound 16 | 3.91 | 0.139 | 0.100 | 590 |
| Ex. 32 | Chemical Formula 98 | Compound 346 | 3.88 | 0.138 | 0.100 | 465 |
| C. Ex. 6 | Chemical Formula 98 | — | 3.87 | 0.138 | 0.103 | 260 |

As is understood from data of Tables 1 and 2, the organic light-emitting diodes according to the present disclosure exhibited low-voltage operation, excellent external quantum efficiency, and long lifespan, compared to those of the Comparative Examples, which did not include an electron density control layer. In addition, the organic light-emitting diode according to the present disclosure was observed to have superior properties, compared to those proposed in Comparative Examples 1 and 4, which did not employ the dopant according to the present disclosure, but conventional dopants in the light-emitting layer, although including an electron density control layer. Consequently, the present disclosure provides an organic light-emitting diode of further improved efficiency.

INDUSTRIAL APPLICABILITY

Capable of fabricating organic light-emitting diodes that exhibit excellent diode properties including high luminous efficiency, low-voltage operation, and long lifespan, the present disclosure is industrially available.

The invention claimed is:

1. An organic light-emitting diode, comprising: a first electrode; a second electrode facing the first electrode; and a light-emitting layer and an electron density control layer sequentially arranged between the first electrode and the second electrode wherein the light-emitting layer includes at least one of the amine compounds represented by the following Chemical Formulas A and B and the electron density control layer includes at least one of the compounds represented by the following Chemical Formulas F to H:

[Chemical Formula A]

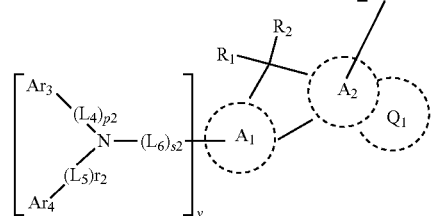
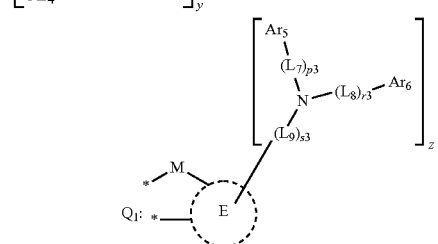
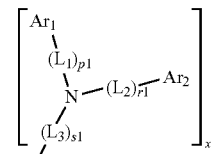

[Chemical Formula B]

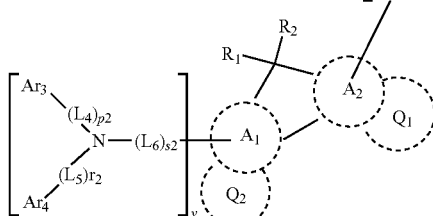
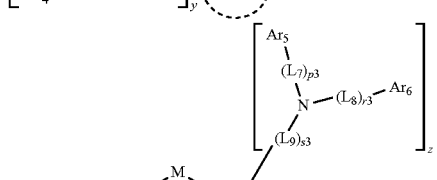
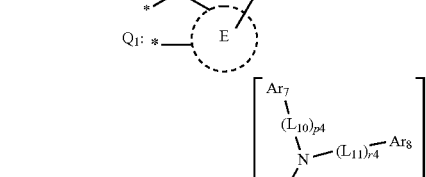
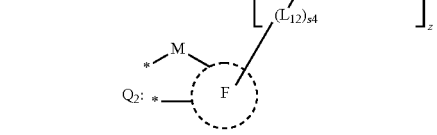

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms, wherein two adjacent carbon atoms of the aromatic ring $A_1$ and two adjacent carbon atoms of the aromatic ring A₂ form a 5-membered fused ring together with a carbon atom connected to both substituents R₁ and R₂;

linkers L₁ to L₁₂ may be the same or different and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—R₃, CR₄R₅, SiR₆R₇, GeR₈R₉, O, S, and Se;

R₁ to R₉ and Ar₁ to Ar₈ may be the same or different and are each independently any one selected from among a hydrogen atom, an deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 1 to 30 carbon atoms, a cyano, a nitro, and a halogen, with the proviso that R₁ and R₂ may be bonded to each other to form a mono- or polycyclic aliphatic or aromatic ring, which may be a heterocyclic ring bearing a heteroatom selected from among N, O, P, Si, S, Ge, Se, and Te as a ring member;

p1 to p4, r1 to r4, and s1 to s4 are each independently an integer of 1 to 3, with the proviso that when any of them is 2 or greater, the corresponding linkers may be the same or different;

x is an integer of 1 or 2, and y and z may be the same or different and are each independently an integer of 0 to 3; and Ar₁ may form a ring with Ar₂, Ar₃ may form a ring with Ar₄, Ar₅ may form a ring with Ar₆, and Ar₇ may form a ring with Ar₈;

two adjacent carbon atoms of the A₂ ring moiety of Chemical Formula A may occupy respective positions * of Structural Formula Q₁ to form a fused ring, and two adjacent carbon atoms of the A₁ ring moiety of Chemical Formula B may occupy respective positions * of structural Formula Q₂ to form a fused ring, and two adjacent carbon atoms of the A₂ ring moiety of Chemical Formula B may occupy respective positions * of Structural Formula Q₁ to form a fused ring;

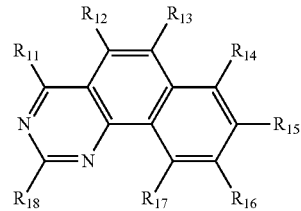

[Chemical Formula F]

wherein, substituents R11 to R₁₈ may be the same or different and are each independently selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted aryl of 6 to 50 carbon atoms, a substituted or unsubstituted heteroaryl of 3 to 50 carbon atoms, a substituted or unsubstituted alkoxy of 2 to 30 carbon atoms, a substituted or unsubstituted aryloxy of 6 to 50 carbon atoms, a substituted or unsubstituted alkylamine of 1 to 30 carbon atoms, a substituted or unsubstituted arylamine of 6 to 50 carbon atoms, a substituted or unsubstituted silyl, a halogen, and a cyano;

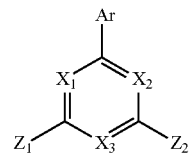

[Chemical Formula G]

wherein,

X₁ to X₃ may be the same or different and are each independently a nitrogen atom or CR', with the proviso that at least one of X₁ to X₃ is a nitrogen atom, wherein R' is selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted aryl of 6 to 50 carbon atoms, a substituted or unsubstituted heteroaryl of 3 to 50 carbon atoms, a substituted or unsubstituted alkoxy of 2 to 30 carbon atoms, a substituted or unsubstituted aryloxy of 6 to 50 carbon atoms, a substituted or unsubstituted alkylamine of 1 to 30 carbon atoms, a substituted or unsubstituted arylamine of 6 to 50 carbon atoms, a substituted or unsubstituted silyl, a halogen, and a cyano;

Ar is selected from among a substituted or unsubstituted alkyl of 1 to 20 carbon atoms, a substituted or unsubstituted cycloalkyl of 3 to 30 carbon atoms, a substituted or unsubstituted aryl of 6 to 50 carbon atoms, and a substituted or unsubstituted heteroaryl of 3 to 50 carbon atoms;

Z₁ and Z₂ may be the same or different and are each independently a substituted or unsubstituted aryl of 6 to 30 carbon atoms, a substituted or unsubstituted heteroaryl of 3 to 30 carbon atoms, or a substituent represented by the following Structural Formula A:

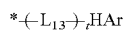  [Structural Formula A]

wherein,
$L_{13}$ is selected from among a single bond, a substituted or unsubstituted alkylene of 1 to 30 carbon atoms, a substituted or unsubstituted cycloalkylene of 3 to 30 carbon atoms, a substituted or unsubstituted arylene of 6 to 50 carbon atoms, and a substituted or unsubstituted heteroarylene of 3 to 50 carbon atoms,
HAr is a substituted or unsubstituted heteroaryl of 3 to 50 carbon atoms, and
t is an integer of 0 to 3, with the proviso that when t is 2 or greater, the corresponding substituents $L_{13}$'s may be the same or different; and

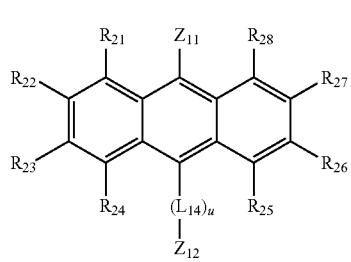  [Chemical Formula H]

wherein,
substituents $Z_{11}$ and $Z_{12}$ may be the same or different and are each independently a substituted or unsubstituted aryl of 6 to 50 carbon atoms or a substituted or unsubstituted heteroaryl of 3 to 50 carbon atoms,
linker $L_{14}$ is a single bond or a substituted or unsubstituted aryl of 6 to 50 carbon atoms,
u is an integer of 0 to 2, with the proviso that when u is 2, the corresponding linkers $L_{14}$'s may be the same or different, and
substituents $R_{21}$ to $R_{28}$ may be the same or different and are each independently selected from a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 2 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atom, a substituted or unsubstituted alkylgermanium of 1 to 30 carbon atoms, a substituted or unsubstituted arylgermanium of 1 to 30 carbon atoms, a cyano, a nitro, and a halogen;
wherein the term 'substituted' in the expression 'substituted or unsubstituted' used in Chemical Formulas A, B, and F to H means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 2 to 24 carbon atoms, an alkylsilyl of 1 to 24 carbon atoms, an arylsilyl of 6 to 24 carbon atoms, and an aryloxy of 6 to 24 carbon atoms.

2. The organic light-emitting diode of claim 1, wherein $A_1$, $A_2$, E, and F in Chemical Formula A or B may be the same or different and are each independently substituted or unsubstituted aromatic hydrocarbon rings of 6 to 50 carbon atoms.

3. The organic light-emitting diode of claim 2, wherein the substituted or unsubstituted aromatic hydrocarbon rings of 6 to 50 carbon atoms in Chemical Formula A or B may be the same or different and are each independently selected from among compounds represented by Structural Formulas 10 to 21:

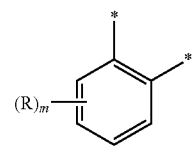  [Structural Formula 10]

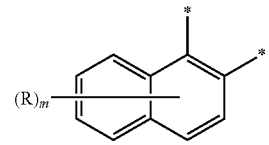  [Structural Formula 11]

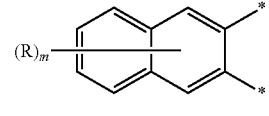  [Structural Formula 12]

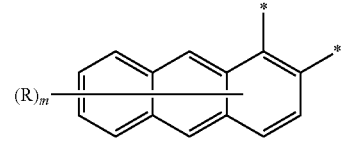  [Structural Formula 13]

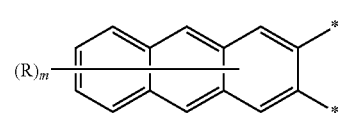  [Structural Formula 14]

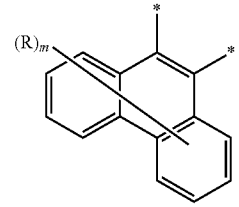  [Structural Formula 15]

-continued

[Structural Formula 16]

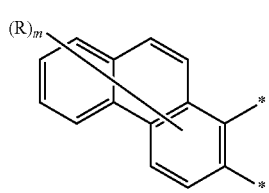

[Structural Formula 17]

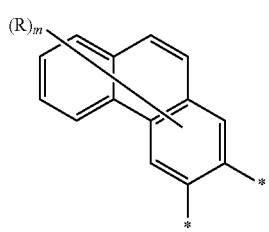

[Structural Formula 18]

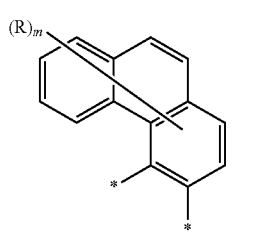

[Structural Formula 19]

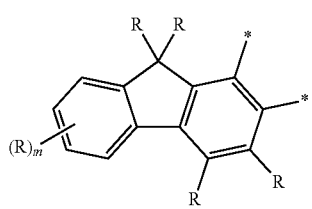

[Structural Formula 20]

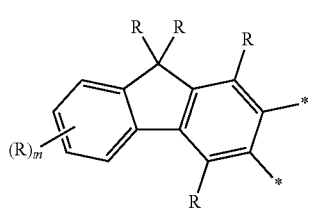

[Structural Formula 21]

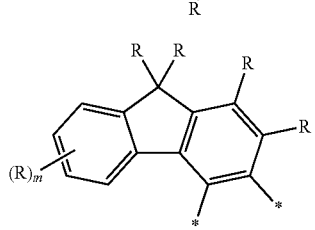

wherein

"-*" denotes a bonding site for forming a 5-membered ring bearing the carbon atom connected to the substituents $R_1$ and $R_2$ or a bonding site for forming a 5-membered ring bearing M of Structural Formula $Q_1$ and $Q_2$;

when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring;

R's are the same as defined above for $R_1$ and $R_2$, and m is an integer of 1 to 8, with the proviso that when m is 2 or greater or when two or more R's exist, the corresponding R's may be the same or different.

4. The organic light-emitting diode of claim 1, wherein the first electrode is an anode and the second electrode is a cathode, with the interposition of a hole transport layer between the cathode and the light-emitting layer and an electron transport layer between the electron density control layer and the anode.

5. The organic light-emitting diode of claim 1, wherein $R_{18}$ in Chemical Formula F is a substituted or unsubstituted aryl of 6 to 18 carbon atoms.

6. The organic light-emitting diode of claim 1, wherein at least one of $Z_1$ and $Z_2$ in Chemical Formula G is represented by the following Structural Formula B:

   [Structural Formula B]

wherein, Cz is a substituted or unsubstituted carbazole, $L_{13}$ is selected from among a single bond, a substituted or unsubstituted arylene of 6 to 50 carbon atoms, and a substituted or unsubstituted heteroarylene of 3 to 50 carbon atoms, and o is an integer of 0 to 2.

7. The organic light-emitting diode of claim 1, wherein HAr in Structural Formula A is a substituent represented by the following Structural Formula C:

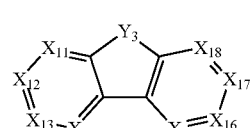   [Structural Formula C]

wherein, $X_{11}$ to $X_{18}$ may be the same or different and are each independently N or $CR_{31}$, with the proviso that one of them may be a carbon atom linked to the substituent $L_{13}$ in Structural Formula A via a single bond and that when two or more $CR_{31}$'s exist, they are the same or different, $Y_3$ is O or S, and $R_{31}$ is as defined for R' in Chemical Formula G.

8. The organic light-emitting diode of claim 1, wherein at least two of $X_1$ to $X_3$ in Chemical Formula G] are N.

9. The organic light-emitting diode of claim 1, wherein, in Chemical Formula H, $L_{14}$ is a single bond or an aryl of 6 to 18 carbon atoms, and substituents $Z_{11}$ and $Z_{12}$ may be the same or different and are each independently a substituted or unsubstituted aryl of 6 to 20 carbon atoms or a substituted or unsubstituted heteroaryl of 2 to 20 carbon atoms, with the proviso that at least one of $Z_{11}$ and $Z_{12}$ is a substituted or unsubstituted heteroaryl of 3 to 20 carbon atoms.

10. The organic light-emitting diode of claim 1, wherein the compound represented by Chemical Formula H is one of the compounds represented by Chemical Formulas H-1 to H-4:

[Chemical Formula H-1]

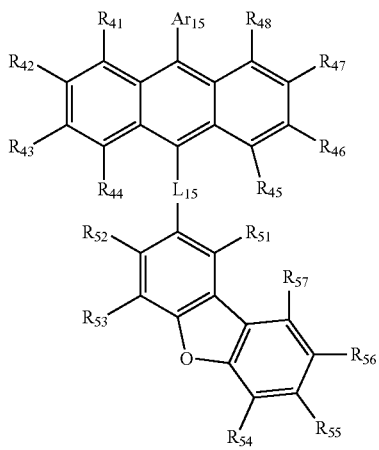

[Chemical Formula H-2]

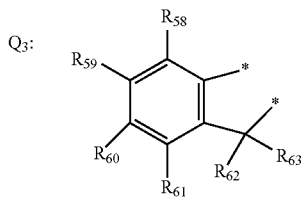

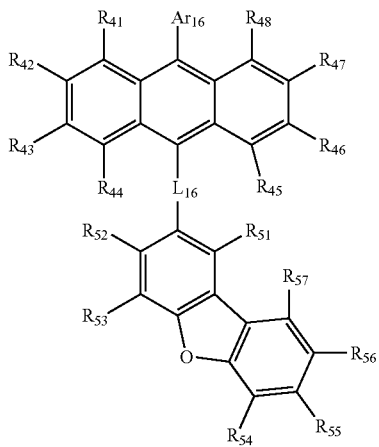

[Chemical Formula H-3]

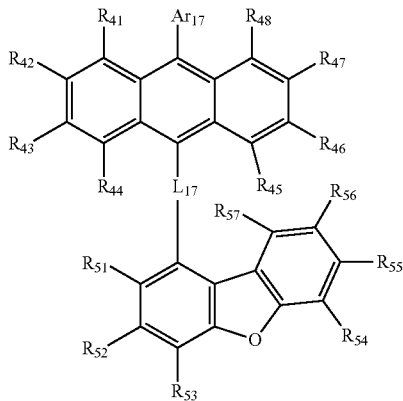

[Chemical Formula H-4]

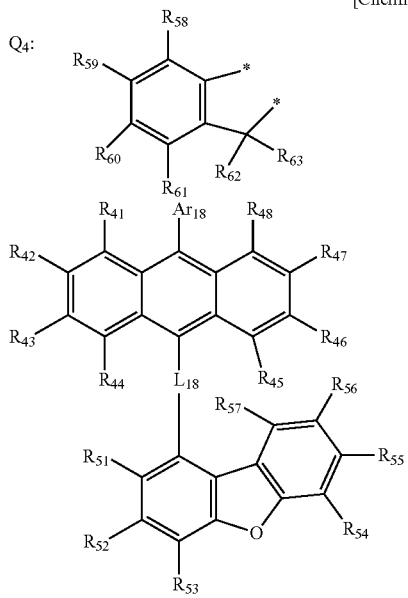

wherein, substituents $R_{41}$ to $R_{48}$ and $R_{51}$ to $R_{63}$ may be the same or different and are each independently selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 2 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen, a substituted or unsubstituted silyl of 1 to 30 carbon atoms, a substituted or unsubstituted alkyl germanium of 1 to 30 carbon atoms, a substituted or unsubstituted alkyl boron of 1 to 30 carbon atoms, a substituted or unsubstituted alkyl aluminum of 1 to 30 carbon atoms, a carbonyl, a phosphoryl, an amino, a thiol, a hydroxy, a selenium, a tellurium, an amide, an ether, and an ester, substituents $Ar_{15}$ to $Ar_{18}$ are each a substituted or unsubstituted aryl of 6 to 50 carbon atoms or a substituted or unsubstituted heteroaryl of 2 to 50 carbon atoms;

linkers $L_{15}$ to $L_{16}$ are each independently selected from among a single bond, a substituted or unsubstituted alkylene of 1 to 30 carbon atoms, a substituted or unsubstituted cycloalkylene of 3 to 30 carbon atoms, a substituted or unsubstituted arylene of 6 to 50 carbon atoms, and a substituted or unsubstituted heteroarylene of 3 to 50 carbon atoms;

$R_{52}$ and $R_{53}$, or two adjacent substituents of $R_{54}$ to $R_{57}$ in Chemical Formula H-2 are respectively single bonds involved in forming a 5-membered ring as a fused ring with the carbon atom to which substituents $R_{62}$ and $R_{63}$ in $Q_3$ are both bonded, two adjacent substituents of $R_{51}$ to $R_{53}$ or of $R_{54}$ to $R_{57}$ in Chemical Formula H-4 are respectively single bonds involved in forming a 5-membered ring as a fused ring with the carbon atom to which substituents $R_{62}$ and $R_{63}$ in $Q_4$ are both bonded, $R_{62}$ and $R_{63}$ may be linked to each other to form a ring, wherein the term 'substituted' in the expression 'substituted or unsubstituted' means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 2 to 24 carbon atoms, an alkylsilyl of 1 to 24 carbon atoms, an arylsilyl of 6 to 24 carbon atoms, and an aryloxy of 6 to 24 carbon atoms.

11. The organic light-emitting diode of claim 1, wherein the compound represented by Chemical Formula F is one selected from the group consisting of the following Compounds 1 to 30:

[Compound 1]

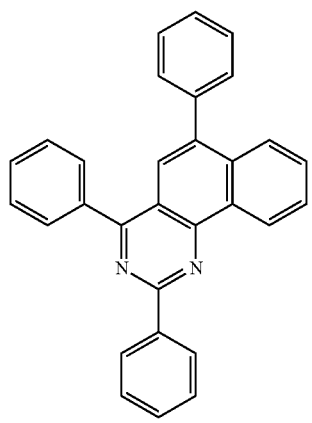

[Compound 2]

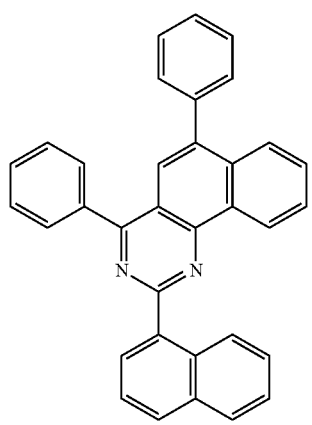

[Compound 3]

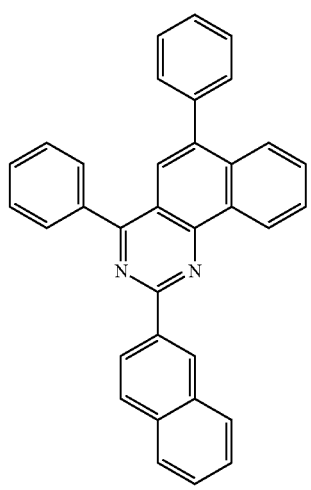

[Compound 4]

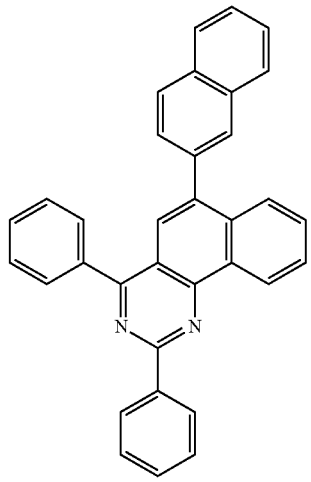

[Compound 5]

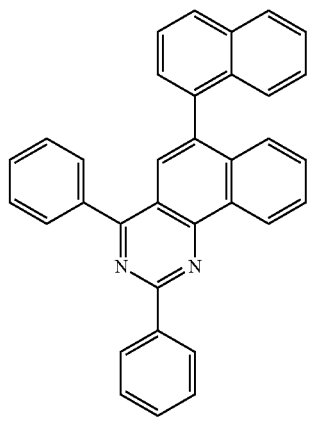

[Compound 6]
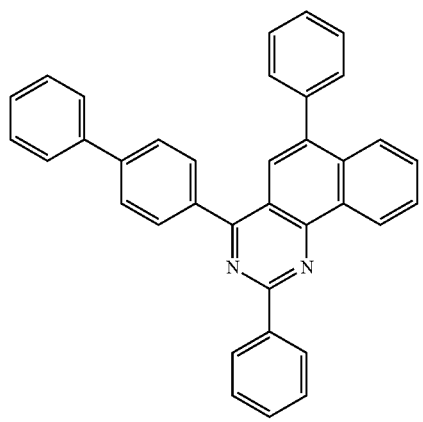
[Compound 9]
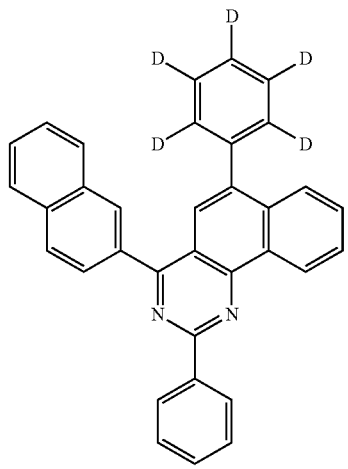
[Compound 7]
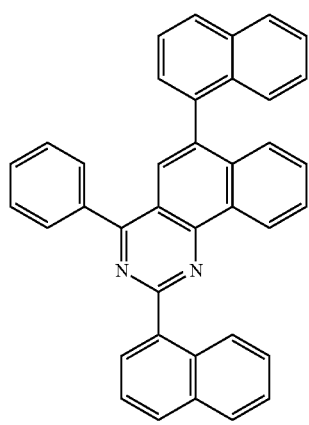
[Compound 10]
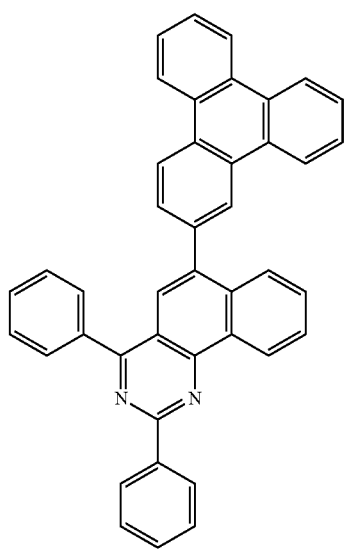
[Compound 8]
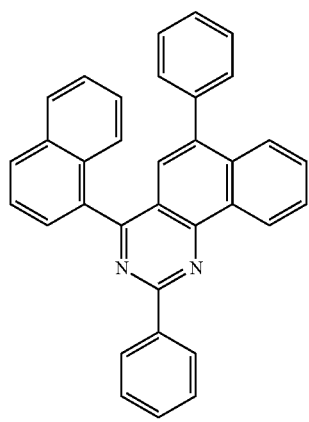
[Compound 11]
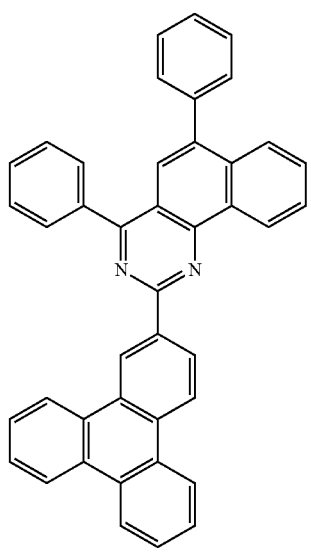

[Compound 12]
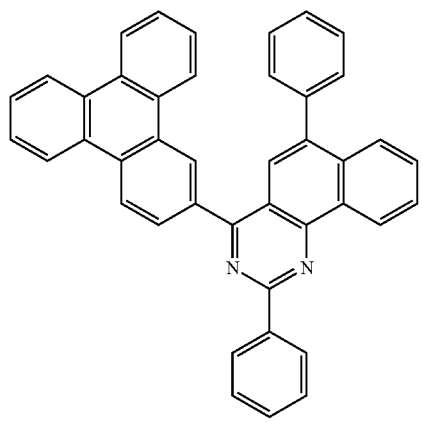
[Compound 15]
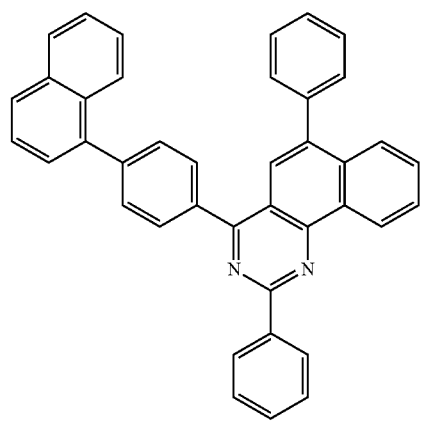
[Compound 13]
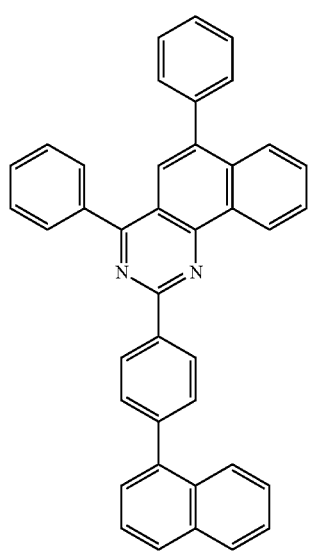
[Compound 16]
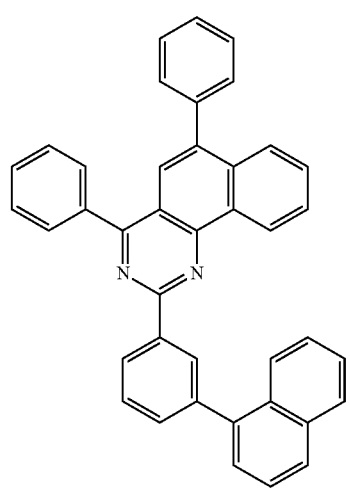
[Compound 14]
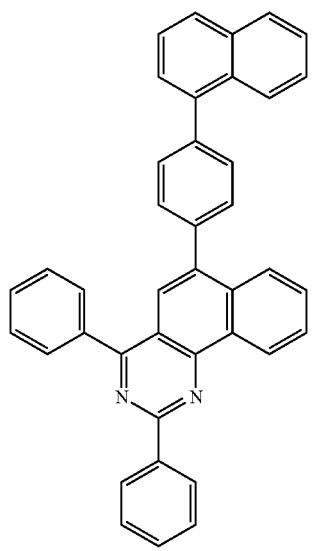
[Compound 17]
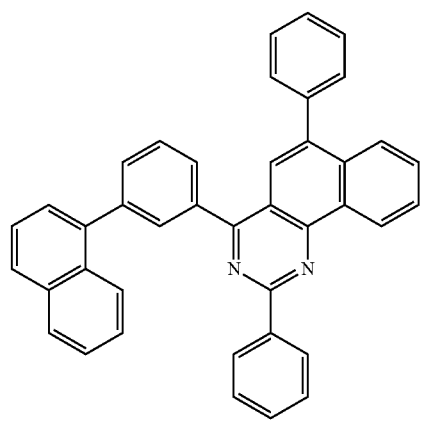

[Compound 18]
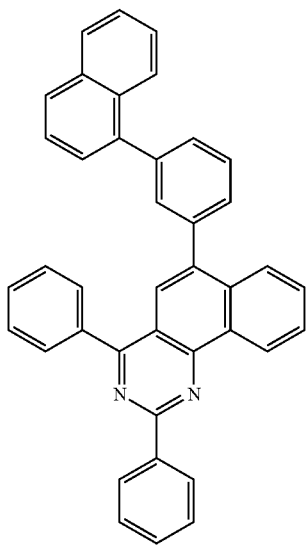
[Compound 19]
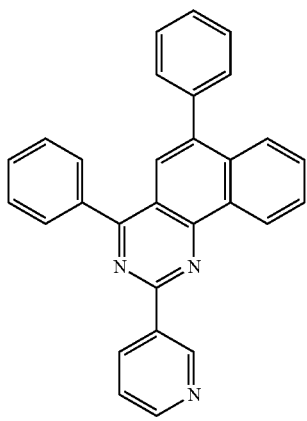
[Compound 20]
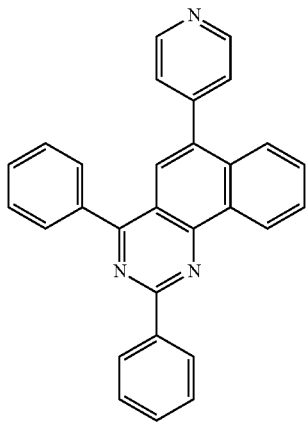
[Compound 21]
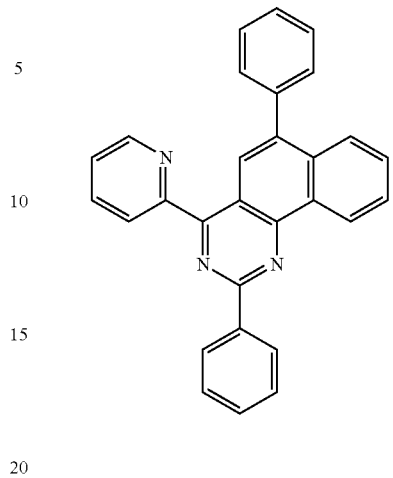
[Compound 22]
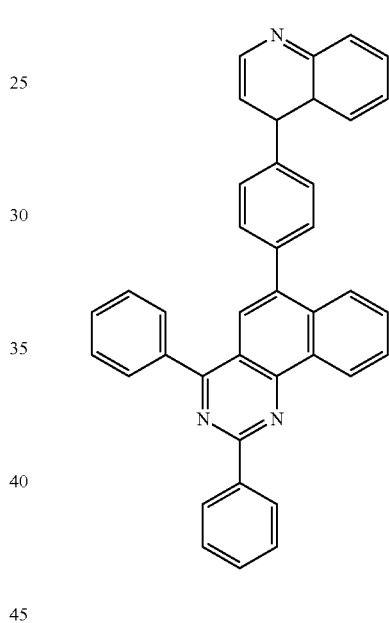
[Compound 23]
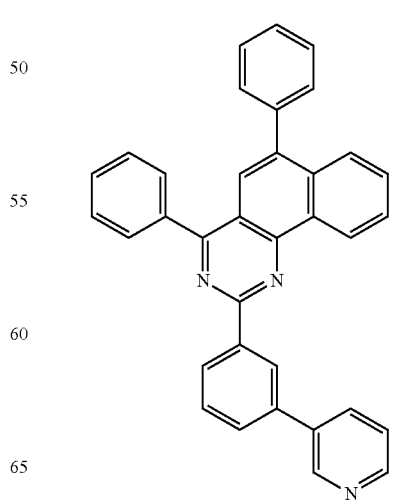

[Compound 24]
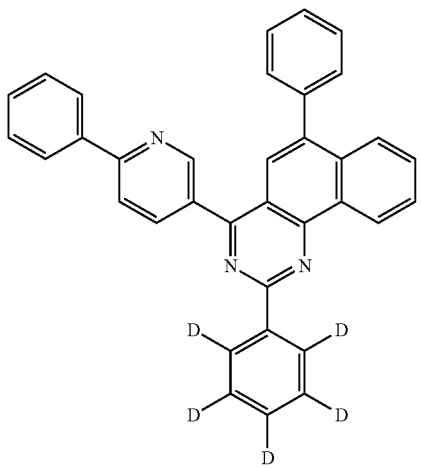
[Compound 25]
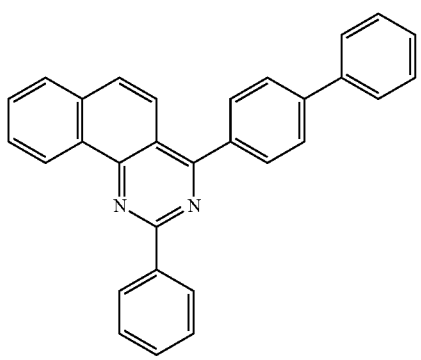
[Compound 26]
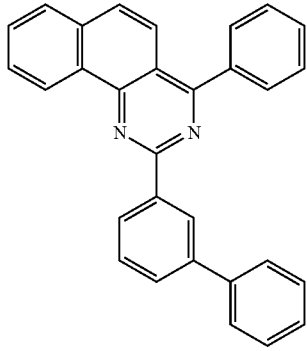
[Compound 27]
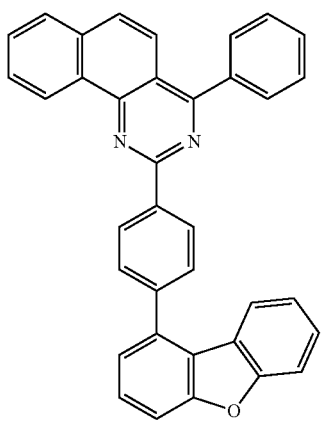
[Compound 28]
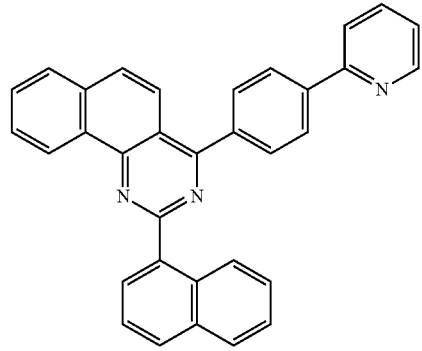
[Compound 29]
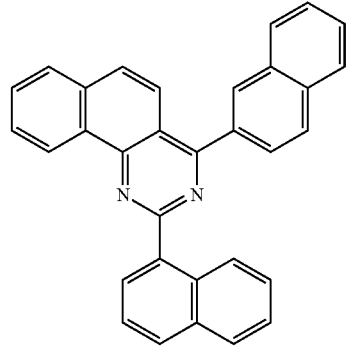
[Compound 30]
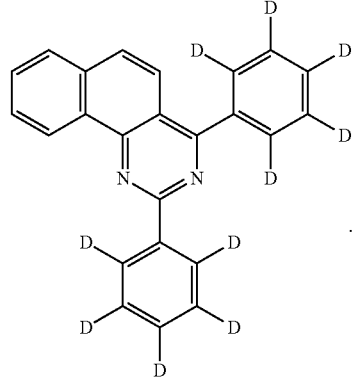
12. The organic light-emitting diode of claim 1, wherein the compound represented by Chemical Formula G is one selected from the group consisting of the following Compounds 101 to 132:
[Compound 101]
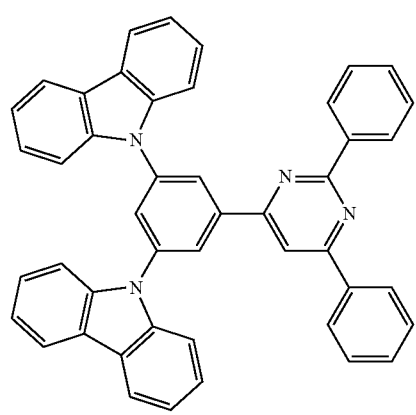

[Compound 102]
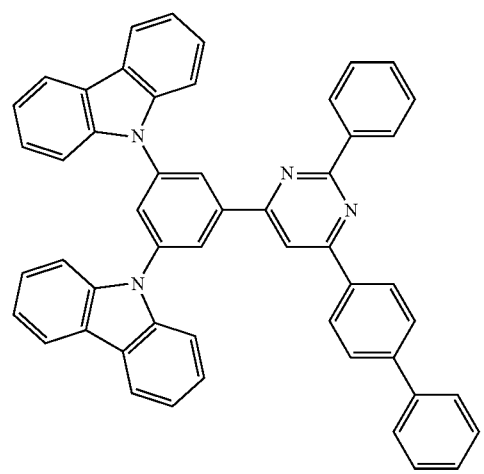
[Compound 106]
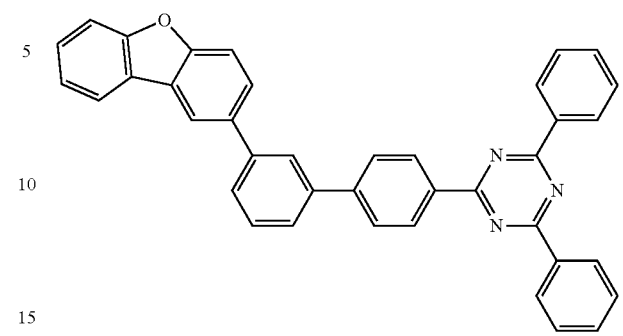
[Compound 103]
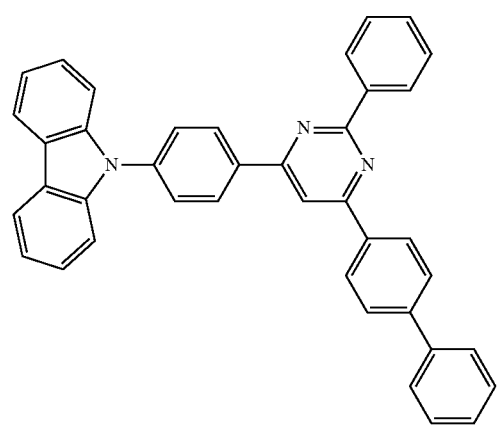
[Compound 107]
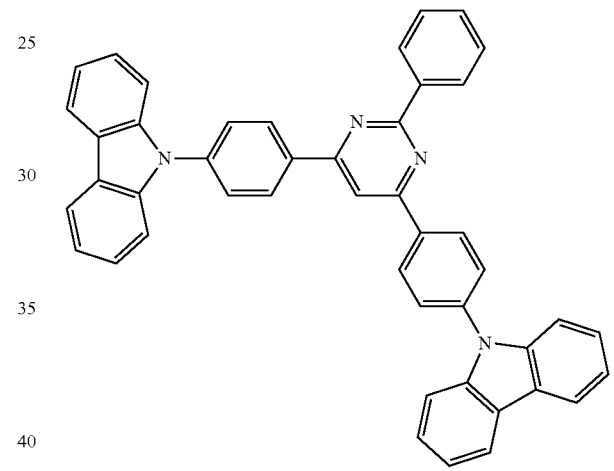
[Compound 104]
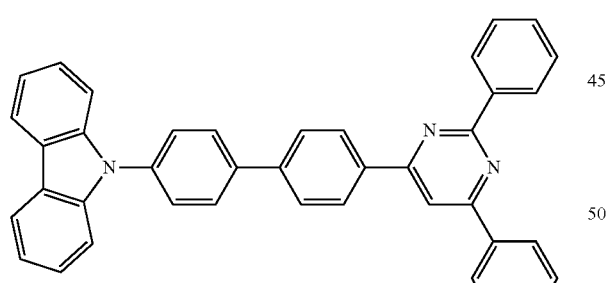
[Compound 105]
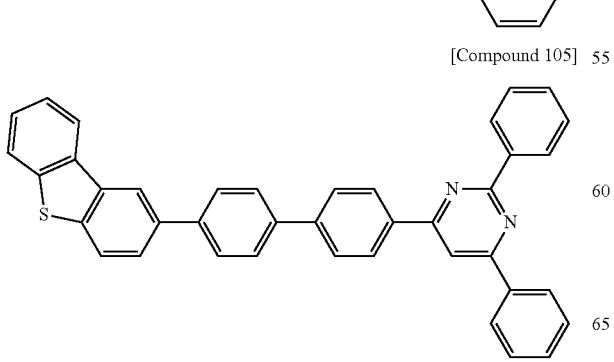
[Compound 108]
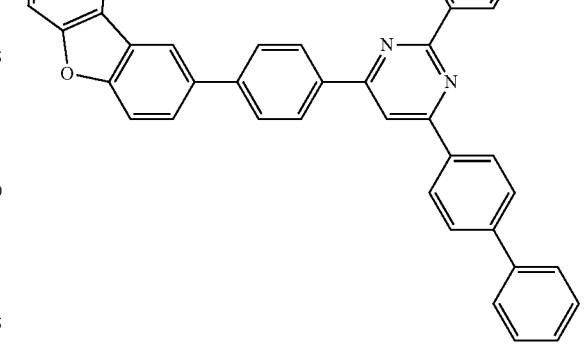

[Compound 109]
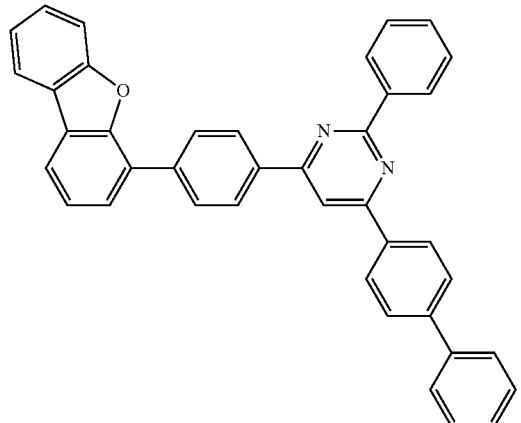
[Compound 110]
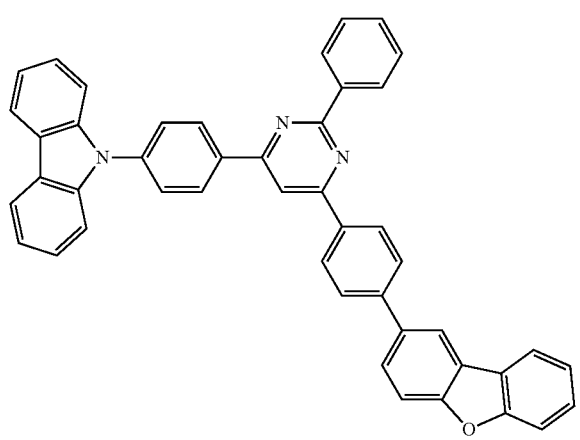
[Compound 111]
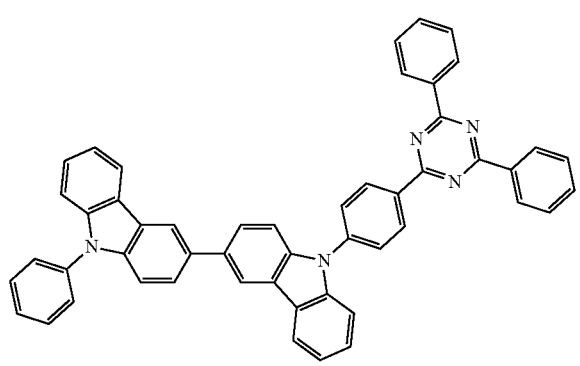
[Compound 112]
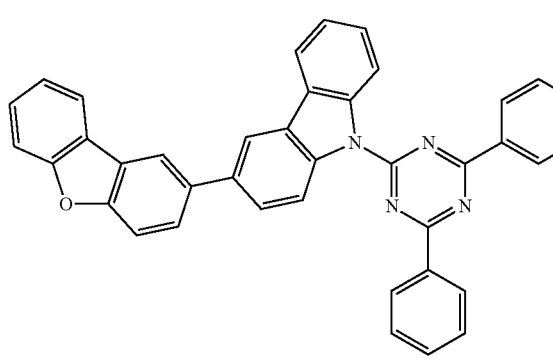
[Compound 113]
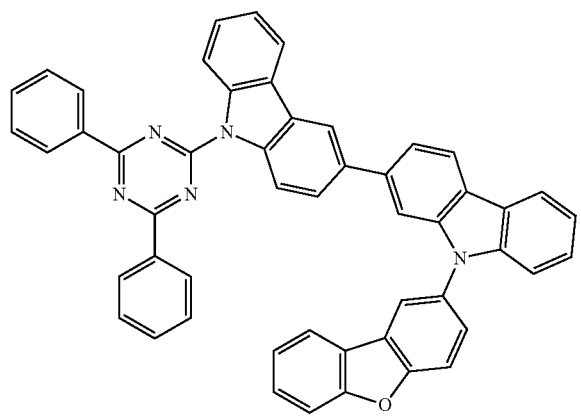
[Compound 114]
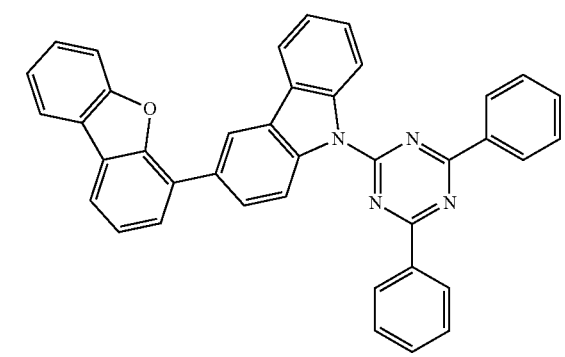
[Compound 115]
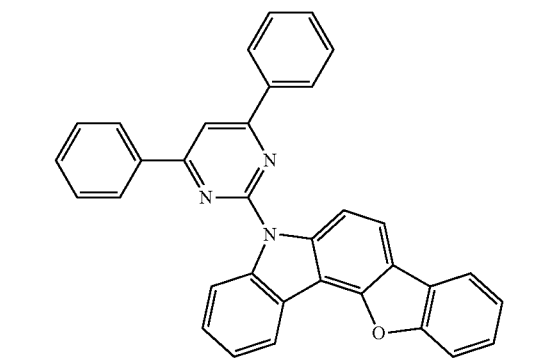
[Compound 116]
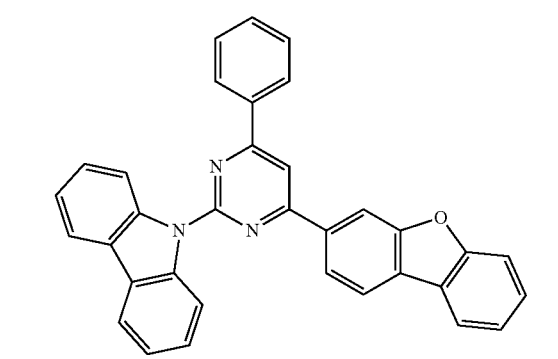

[Compound 117]
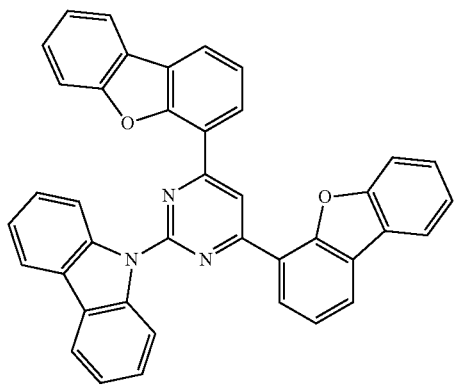
[Compound 118]
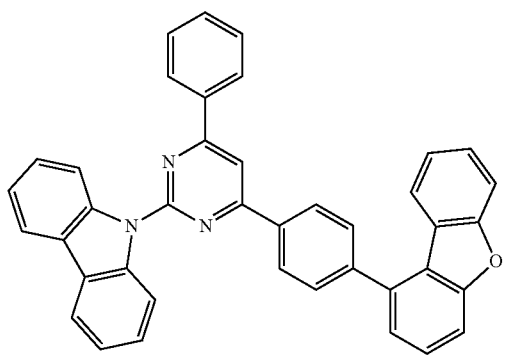
[Compound 119]
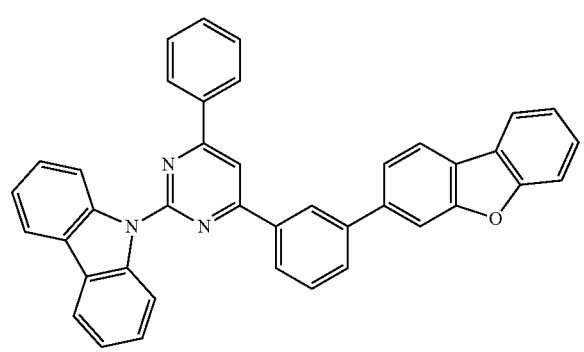
[Compound 120]
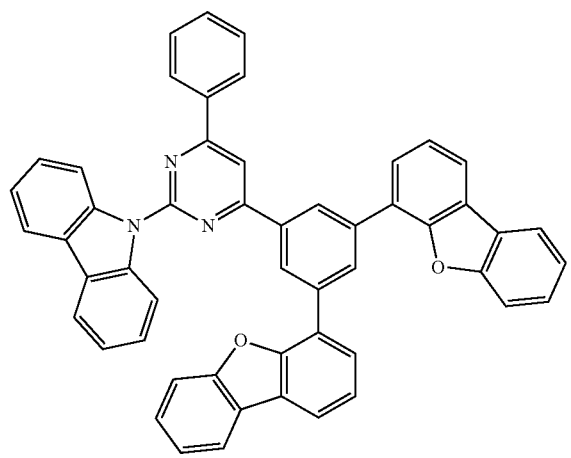
[Compound 121]
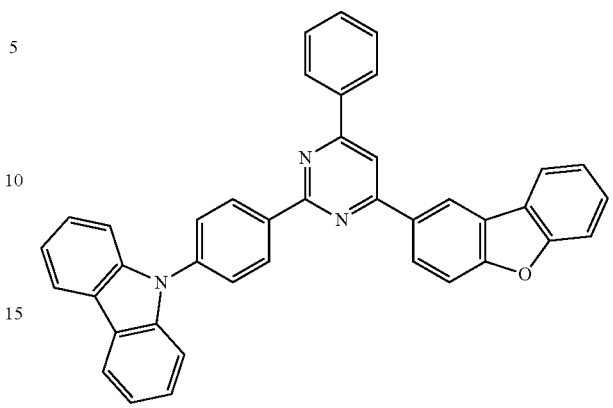
[Compound 122]
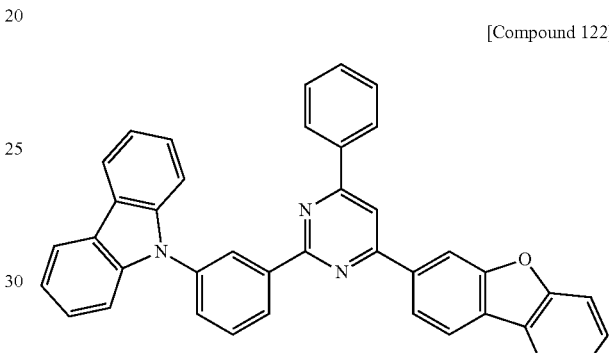
[Compound 123]
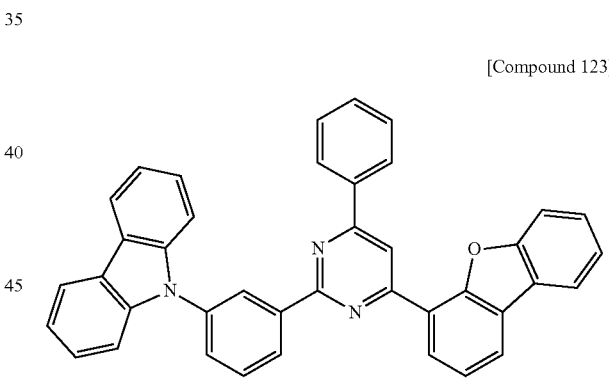
[Compound 124]
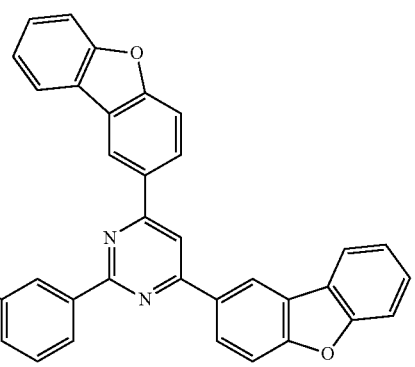

[Compound 125]
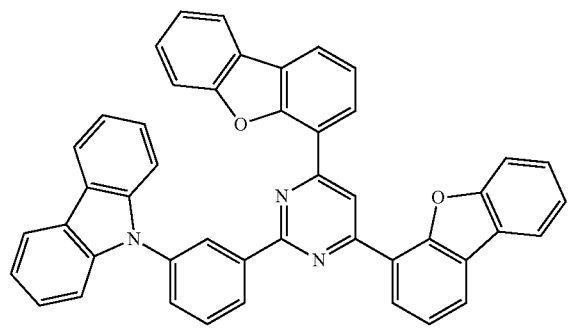
[Compound 126]
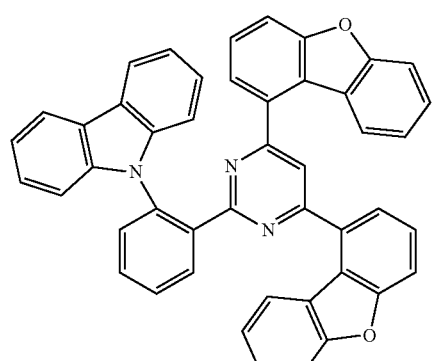
[Compound 127]
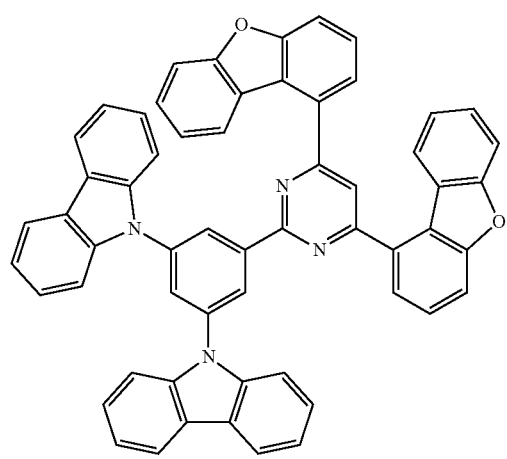
[Compound 128]
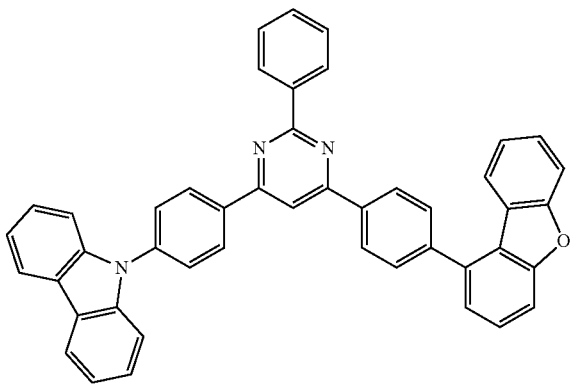
[Compound 129]
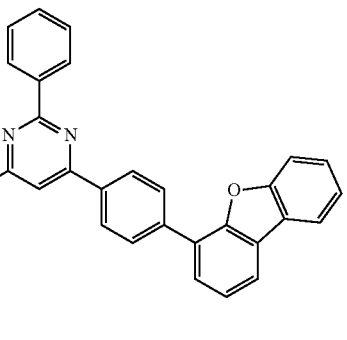
[Compound 130]
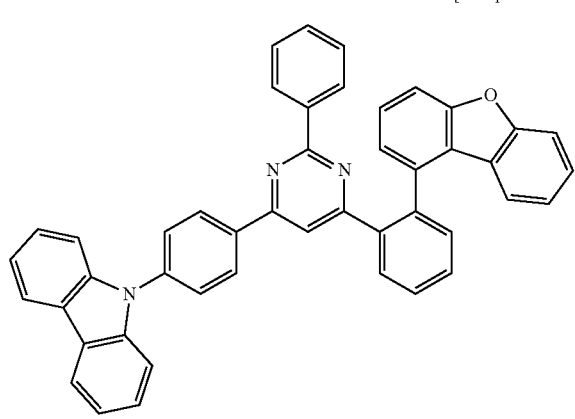
[Compound 131]
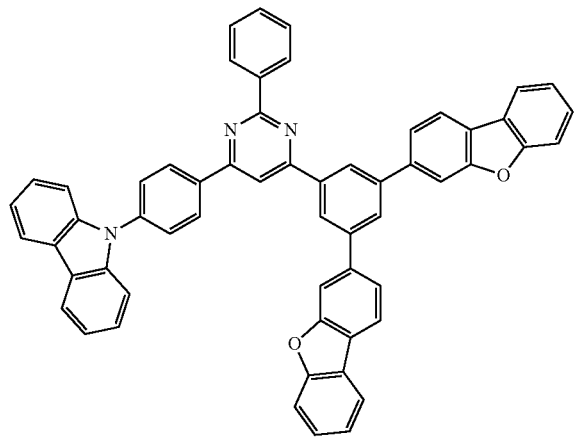
[Compound 132]

13. The organic light-emitting diode of claim 1, wherein the substituents $Z_{11}$'s in Chemical Formula H are each a substituted or unsubstituted aryl of 6 to 18 carbon atoms.

14. The organic light-emitting diode of claim 1, wherein the compound, represented by Chemical Formulas H is one selected from the group consisting of the following Compounds 201 to 348:

<Compound 201>

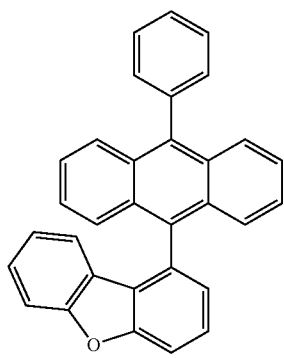

<Compound 202>

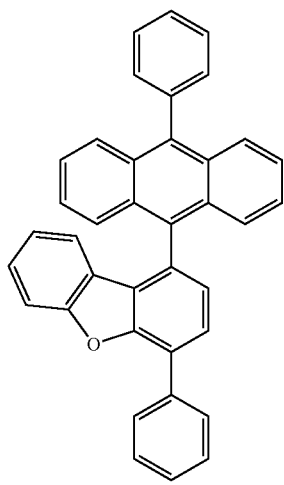

<Compound 203>

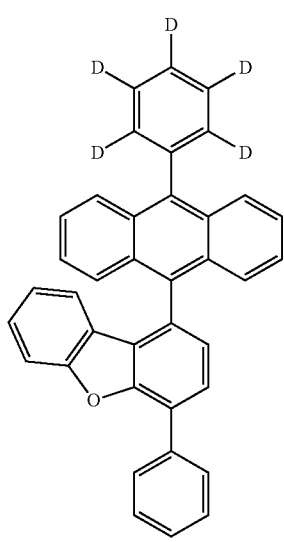

-continued

<Compound 204>

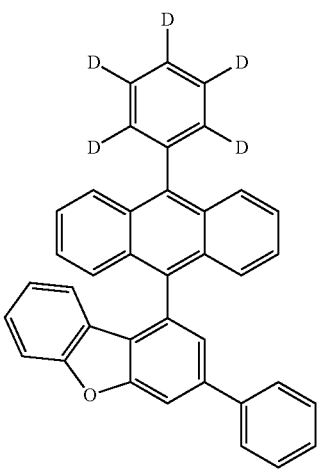

<Compound 205>

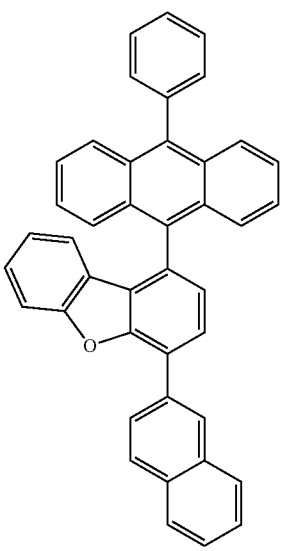

<Compound 206>

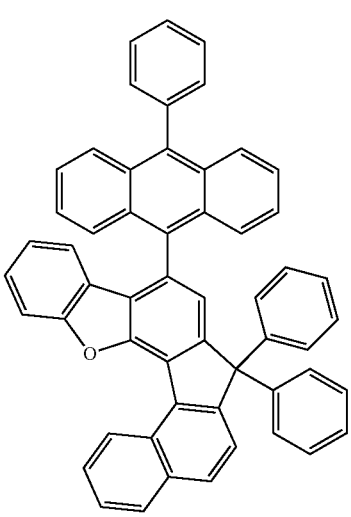

<Compound 207>
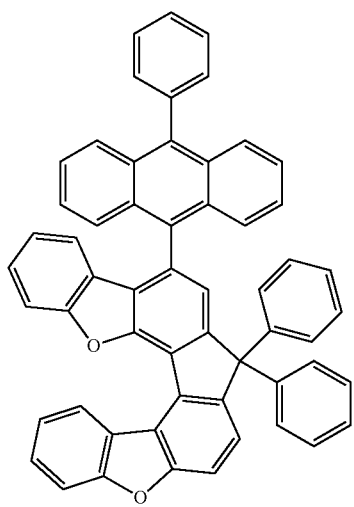
<Compound 208>
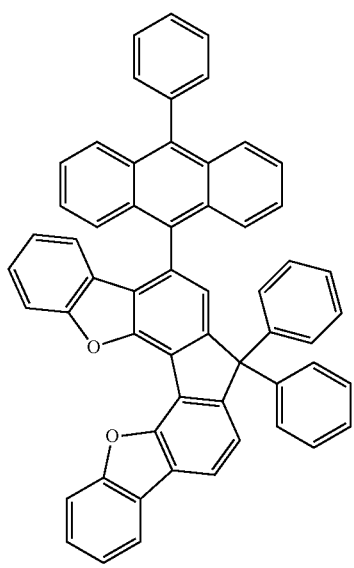
<Compound 209>
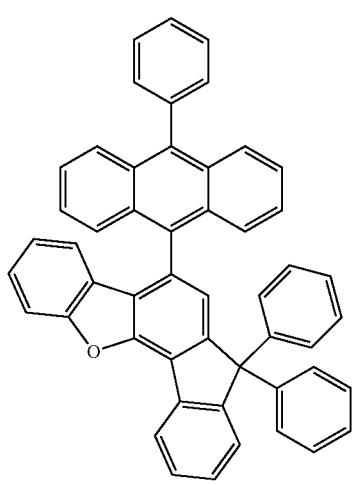
<Compound 210>
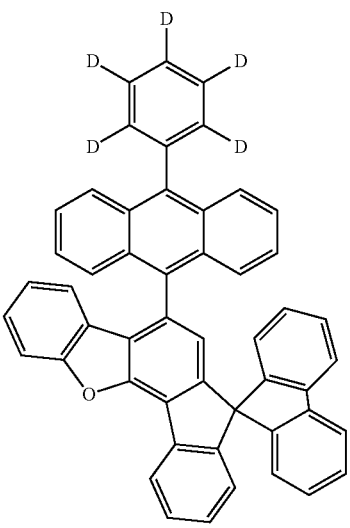
<Compound 211>
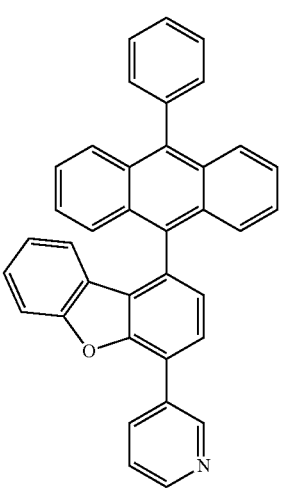
<Compound 212>
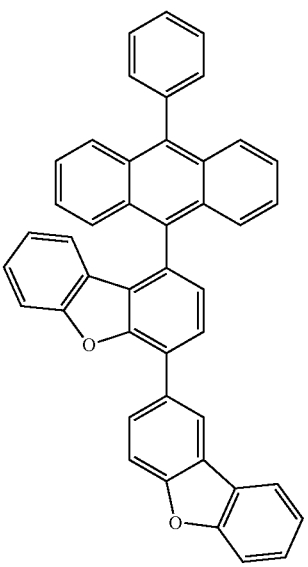

<Compound 213>
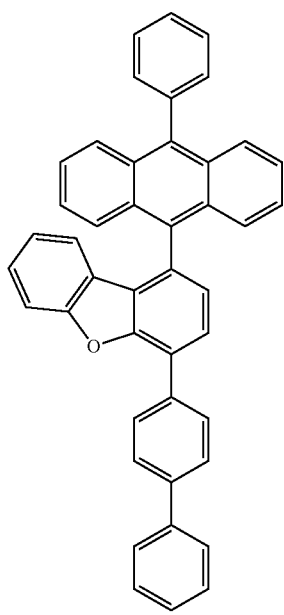
<Compound 214>
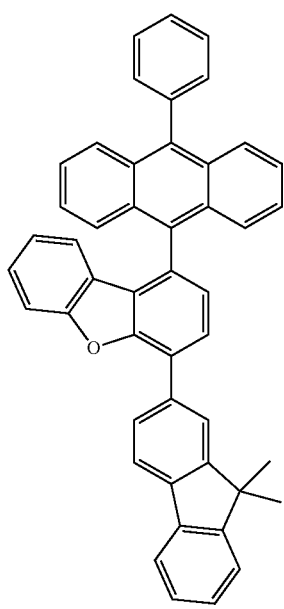
<Compound 215>
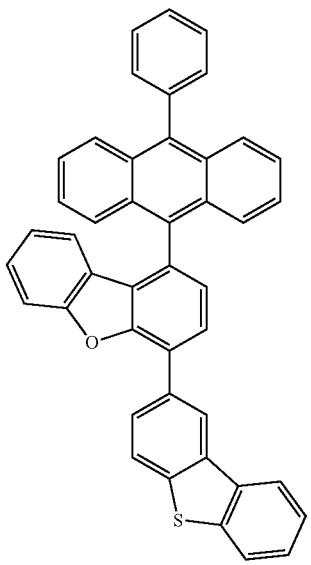
<Compound 216>
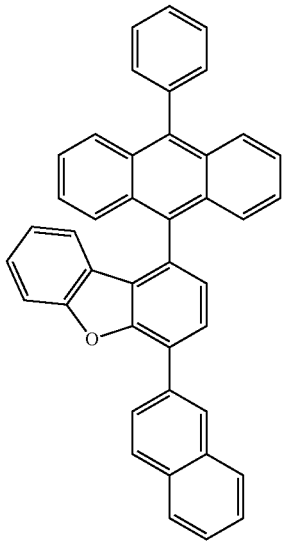
<Compound 217>
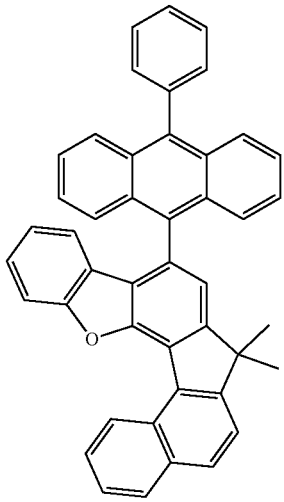

<Compound 218>
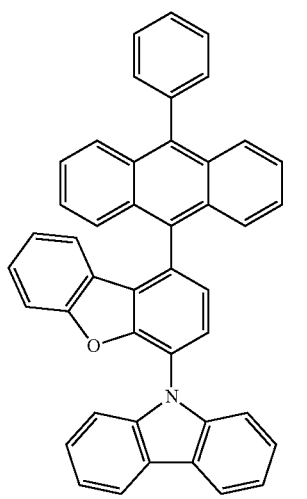
<Compound 219>
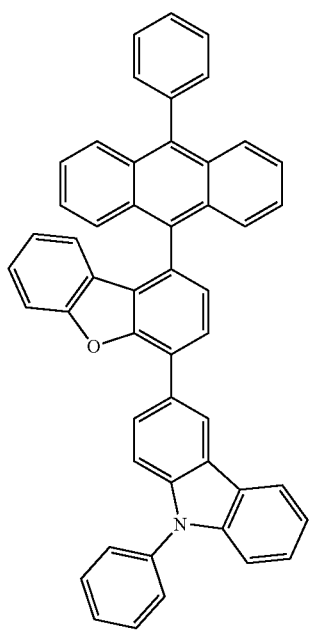
<Compound 220>
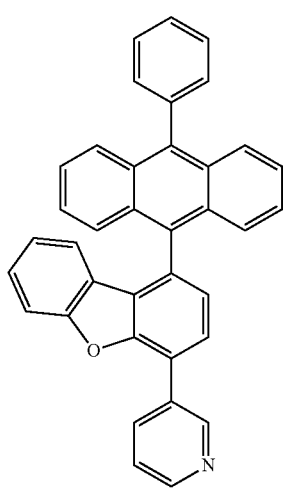
<Compound 221>
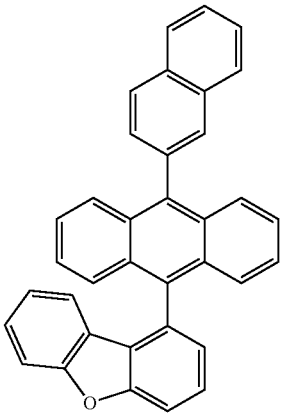
<Compound 222>
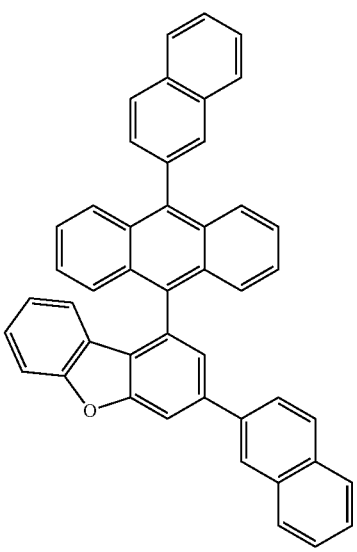
<Compound 223>
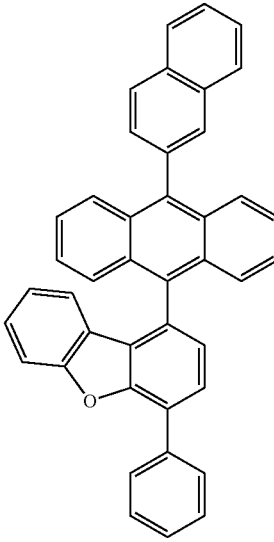

<Compound 224>
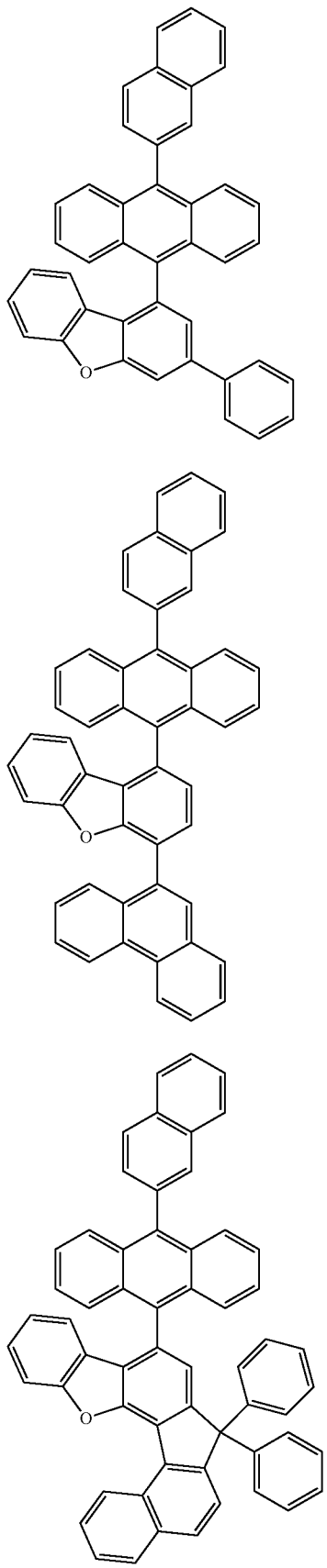
<Compound 225>
<Compound 226>
<Compound 227>
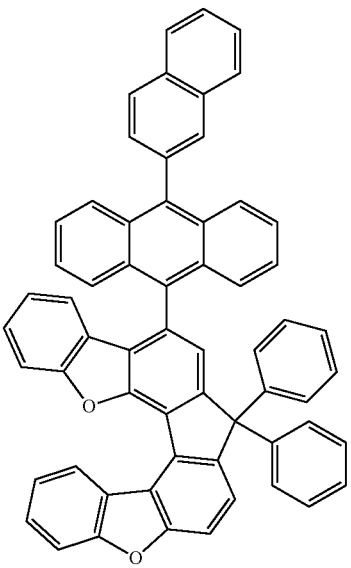
<Compound 228>
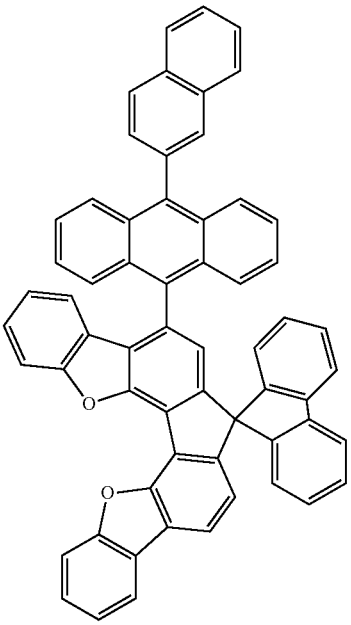

-continued
<Compound 229>
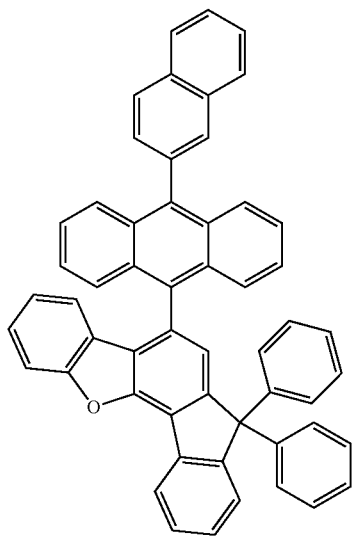
<Compound 230>
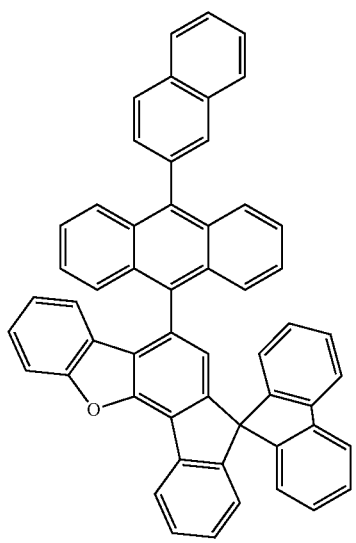
<Compound 231>
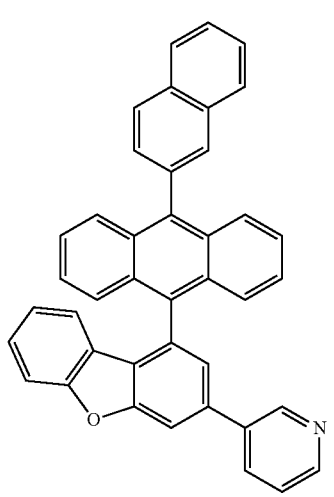
-continued
<Compound 232>
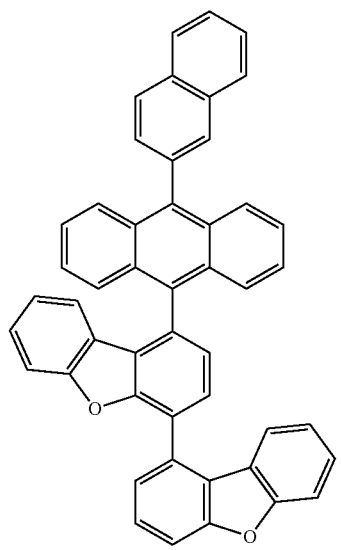
<Compound 233>
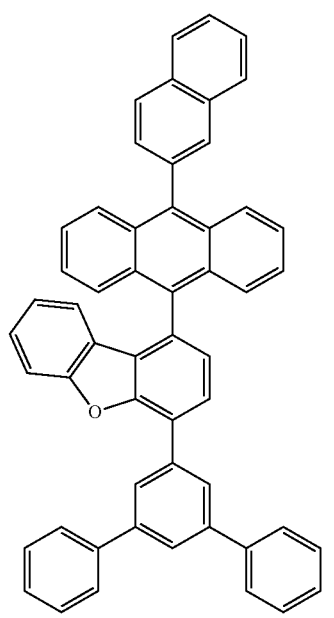

<Compound 234>
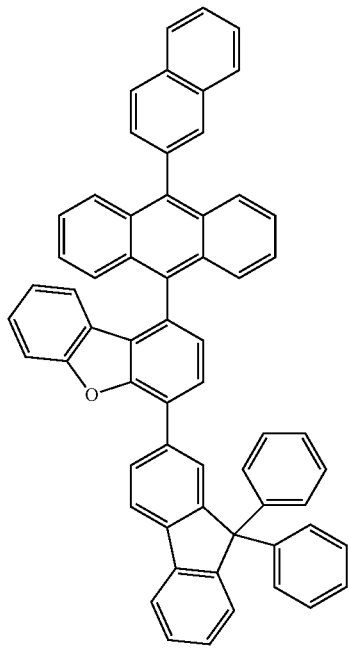
<Compound 235>
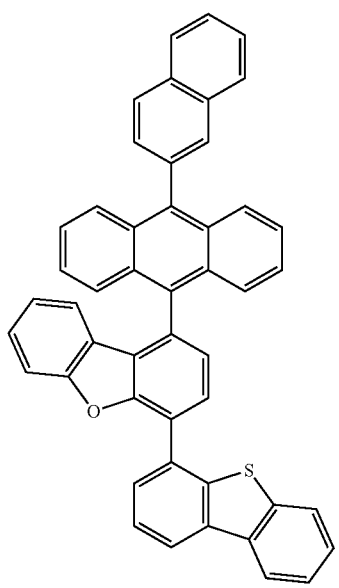
<Compound 236>
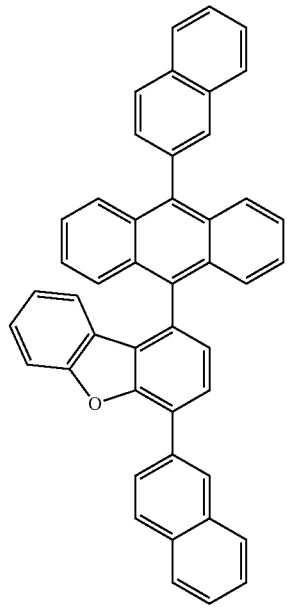
<Compound 237>
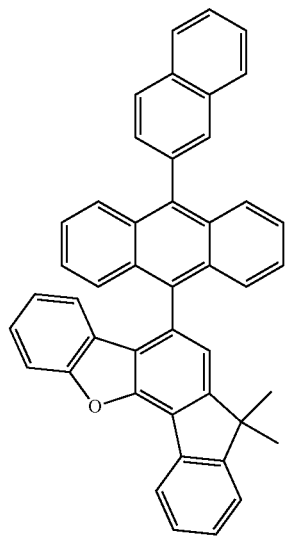

<Compound 238>
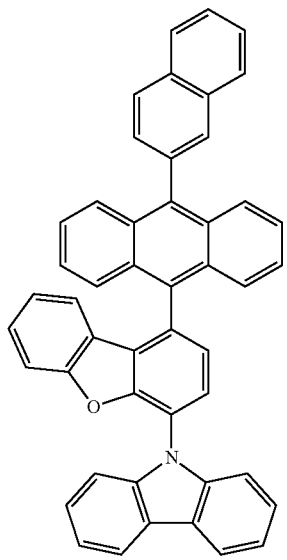
<Compound 239>
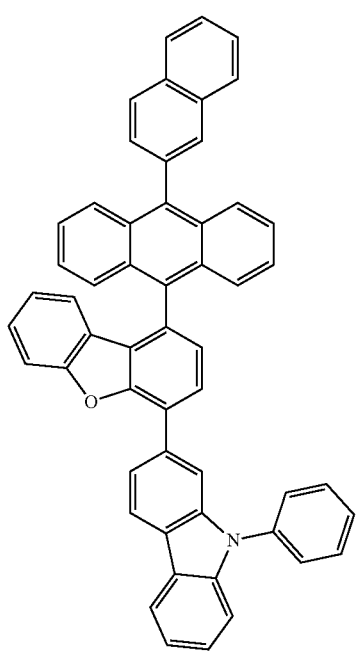
<Compound 240>
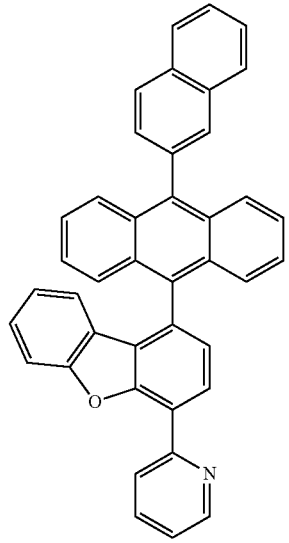
<Compound 241>
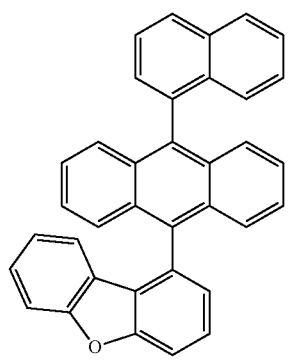
<Compound 242>
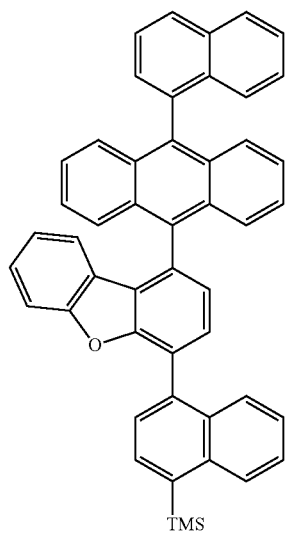

<Compound 243>
<Compound 244>
<Compound 245>
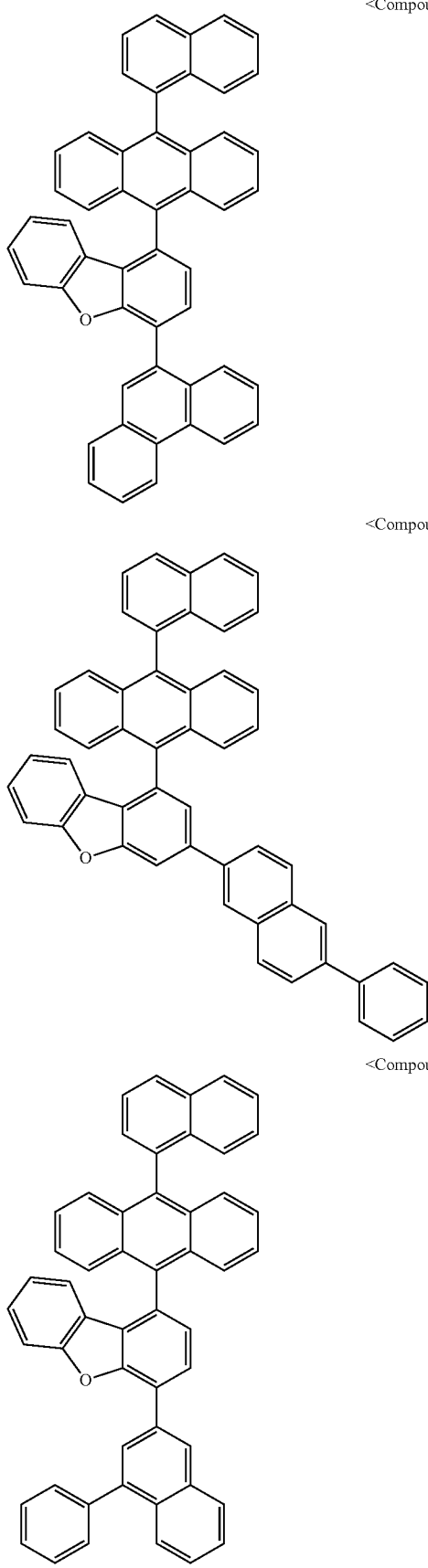
<Compound 246>
<Compound 247>
<Compound 248>
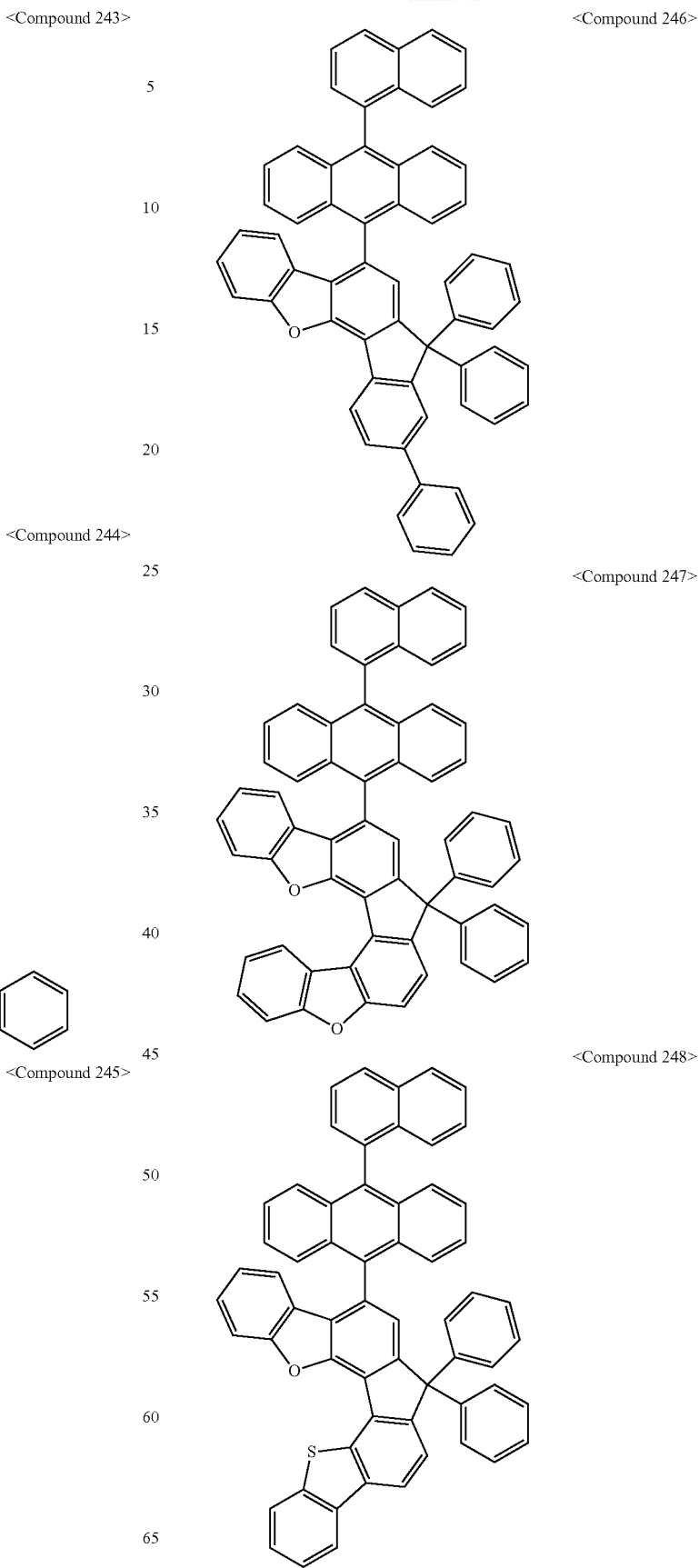

<Compound 249>
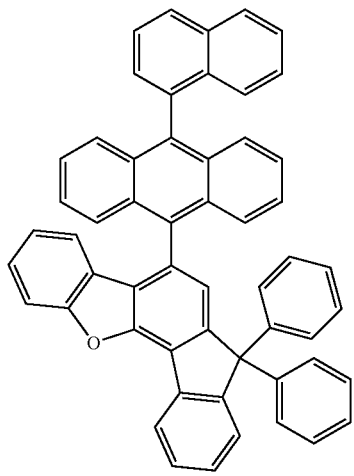
<Compound 250>
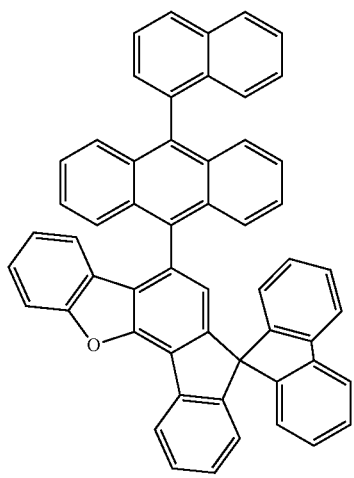
<Compound 251>
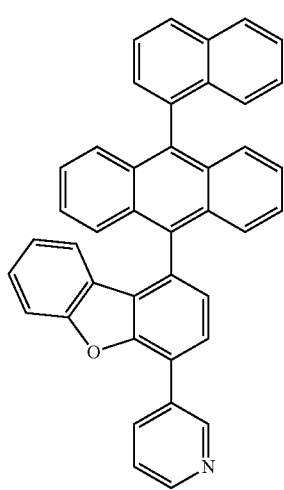
<Compound 252>
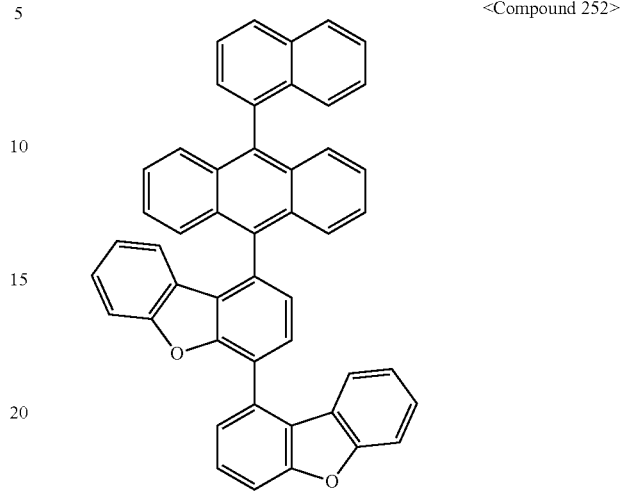
<Compound 253>
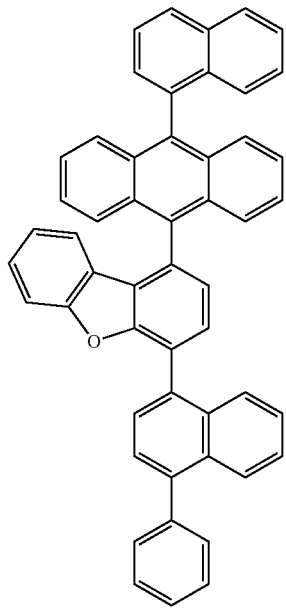

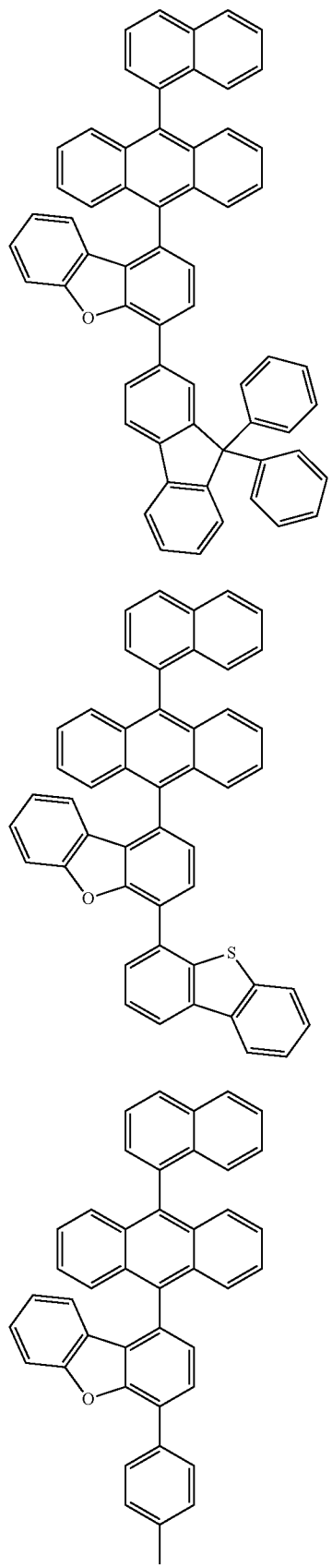
<Compound 254>
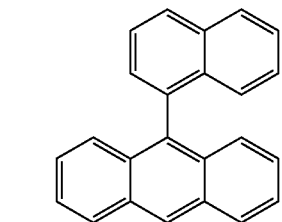
<Compound 255>
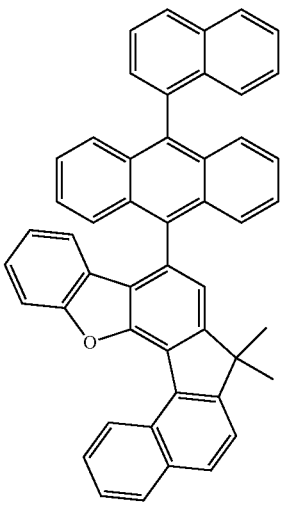
<Compound 256>
<Compound 257>
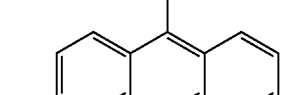
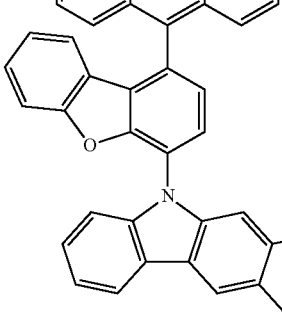
<Compound 258>
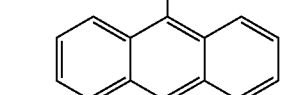
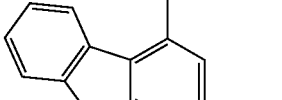
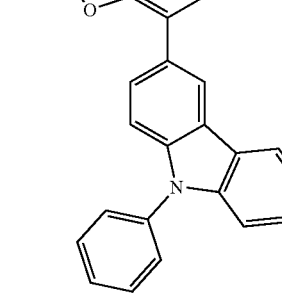
<Compound 259>

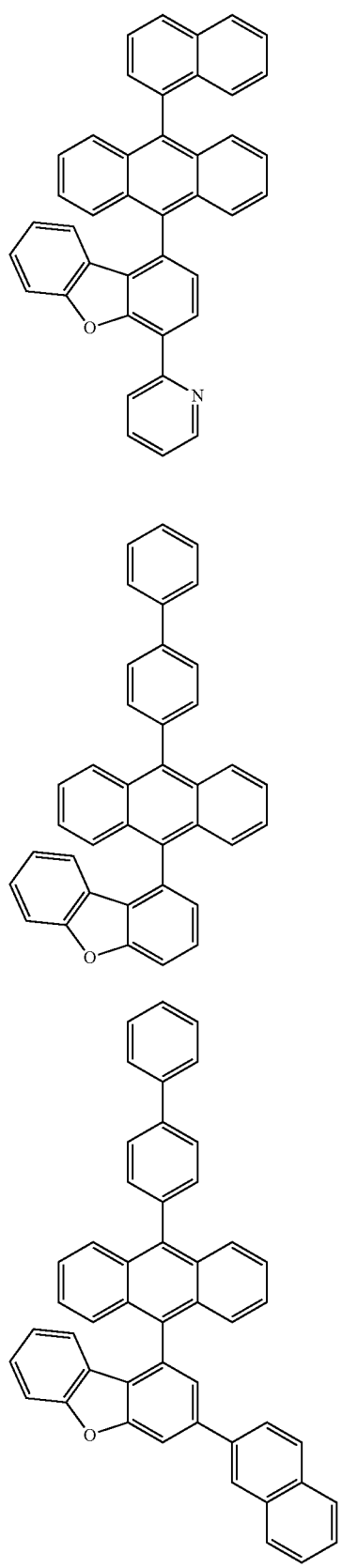
<Compound 260>
<Compound 261>
<Compound 262>
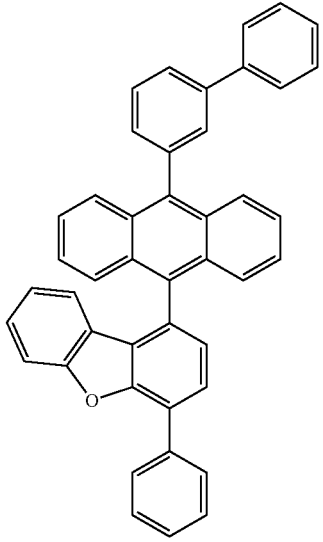
<Compound 263>
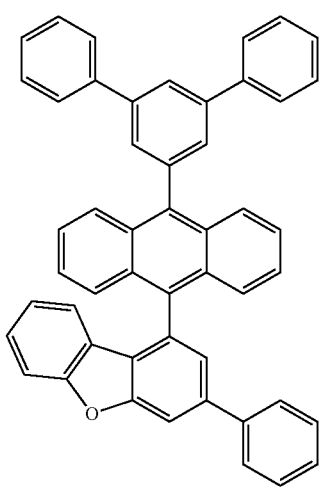
<Compound 264>
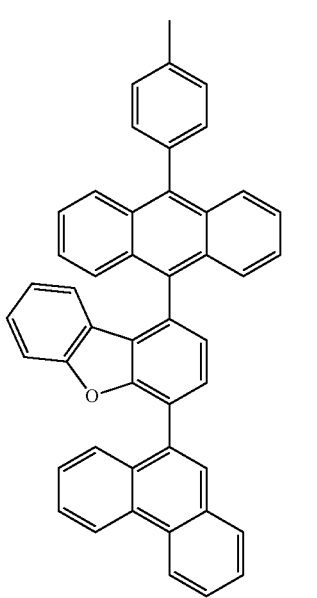
<Compound 265>

<Compound 266>
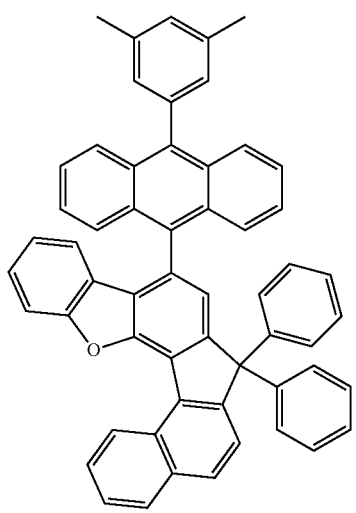
<Compound 267>
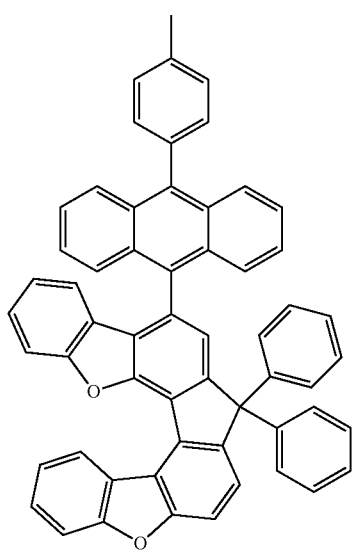
<Compound 268>
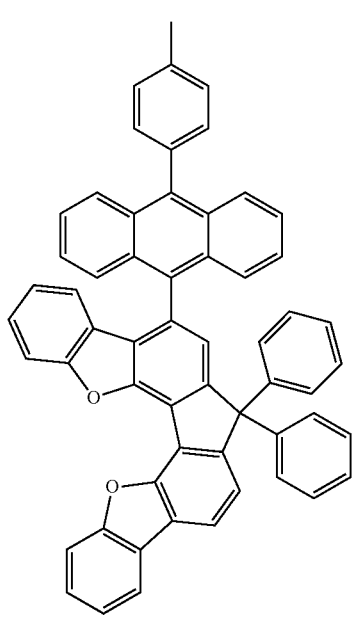
<Compound 269>
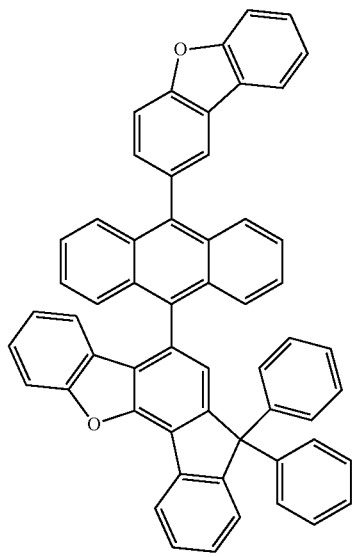
<Compound 270>
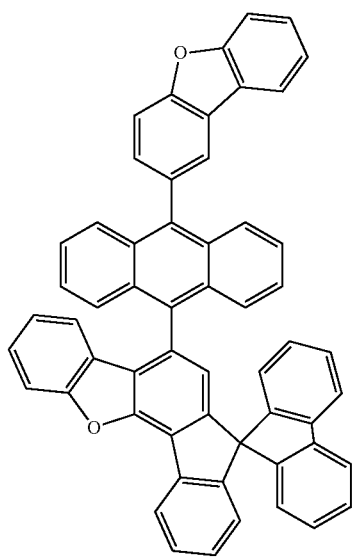
<Compound 271>
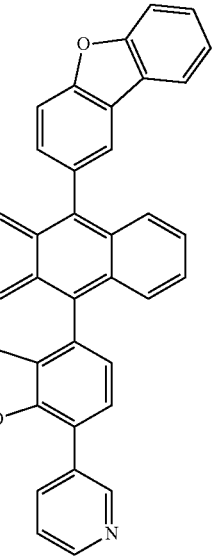

<Compound 272>
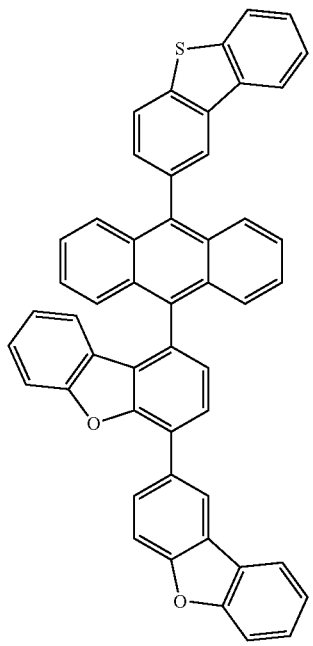
<Compound 274>
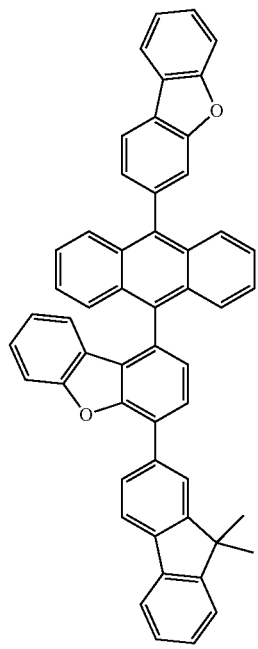
<Compound 273>
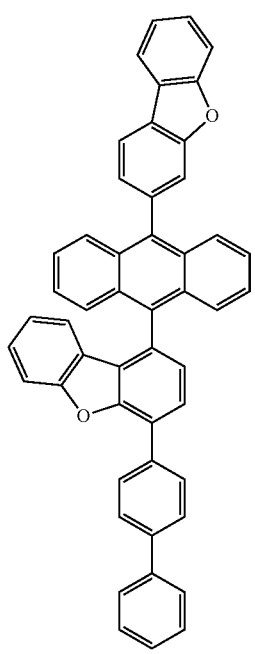
<Compound 275>
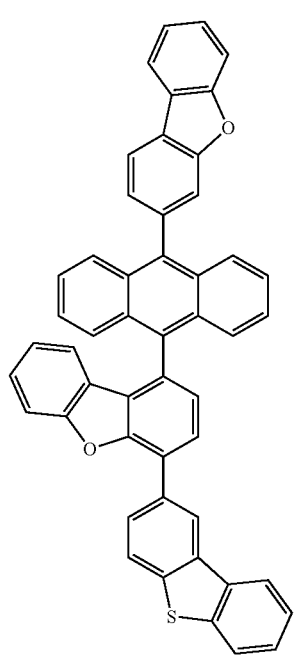

299
-continued
<Compound 276>
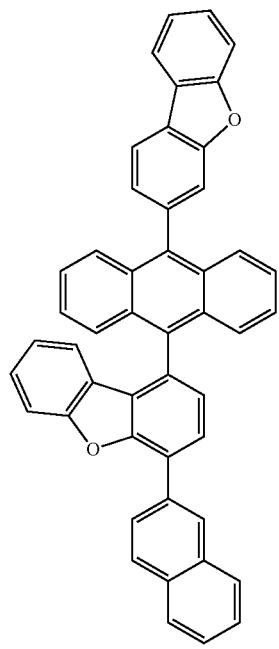
<Compound 277>
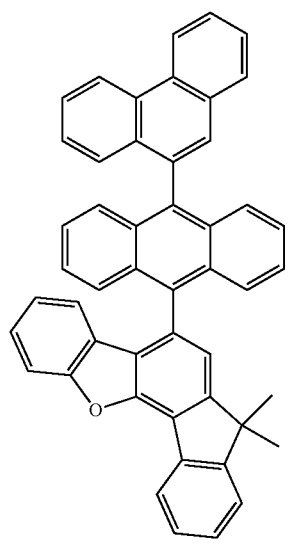
300
-continued
<Compound 278>
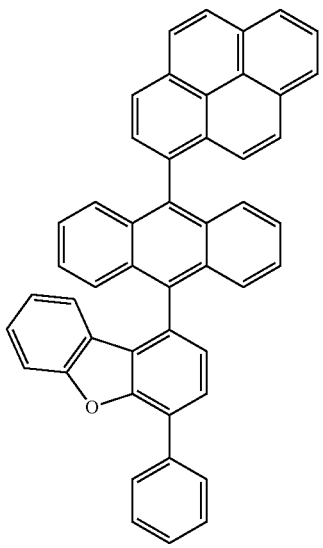
<Compound 279>
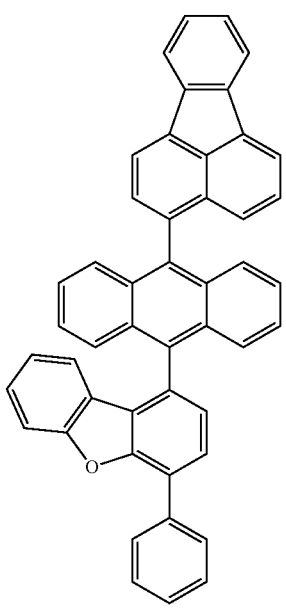
<Compound 280>
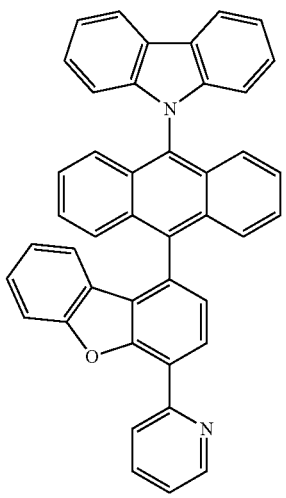

<Compound 281>
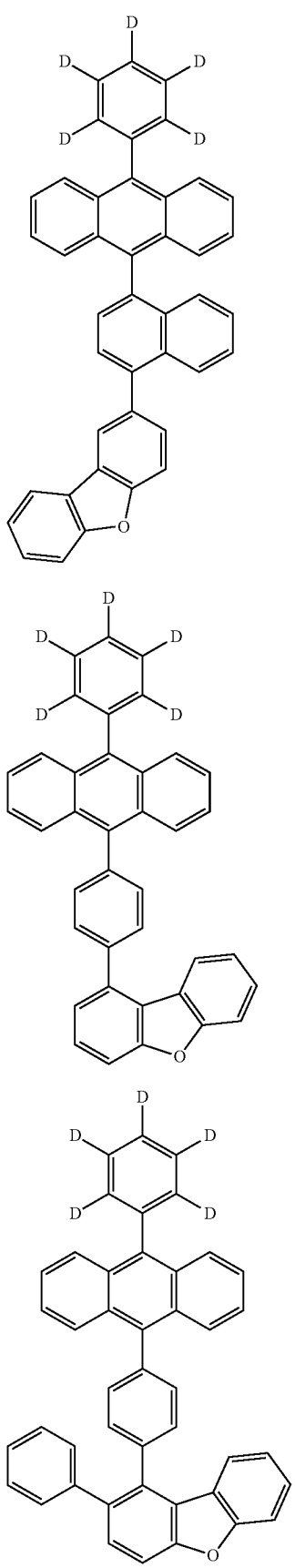
<Compound 282>
<Compound 283>
<Compound 284>
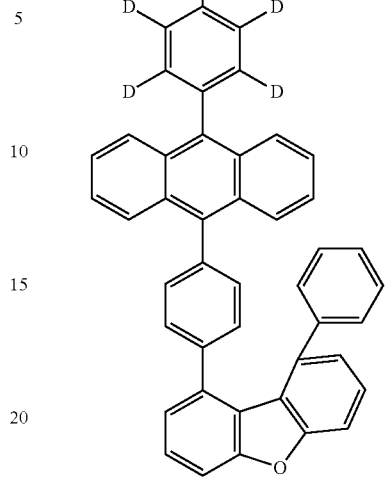
<Compound 285>
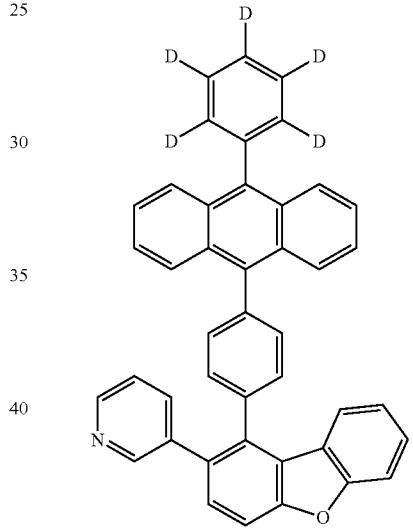
<Compound 286>
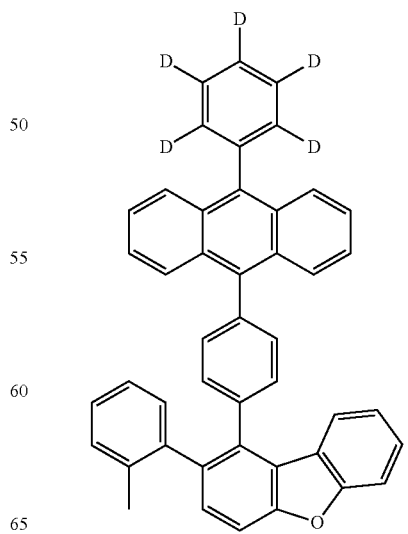

-continued
<Compound 287>
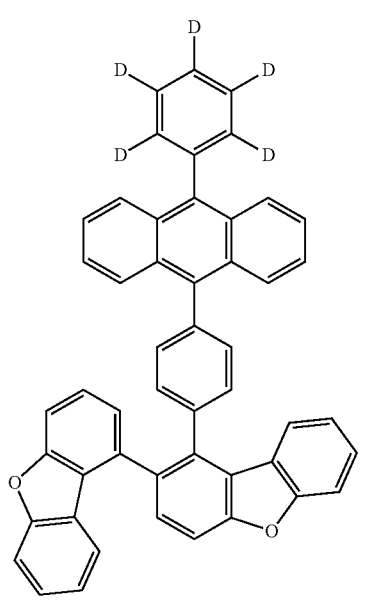
<Compound 288>
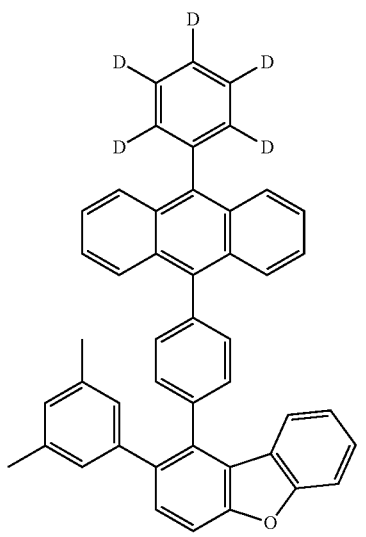
-continued
<Compound 290>
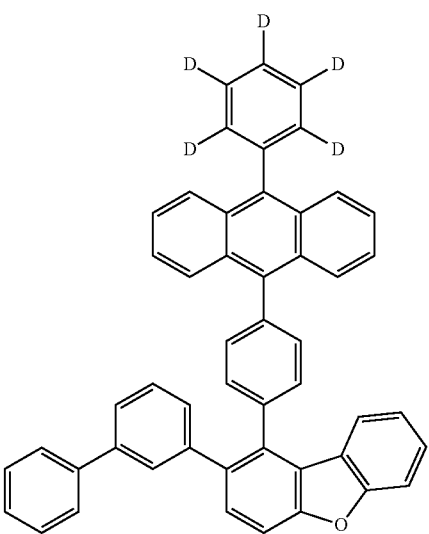
<Compound 291>
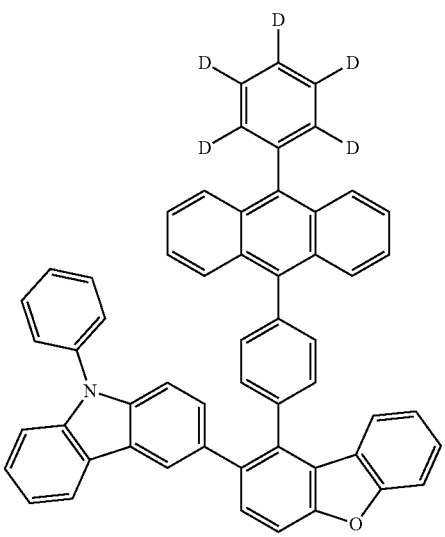
<Compound 289>
<Compound 292>
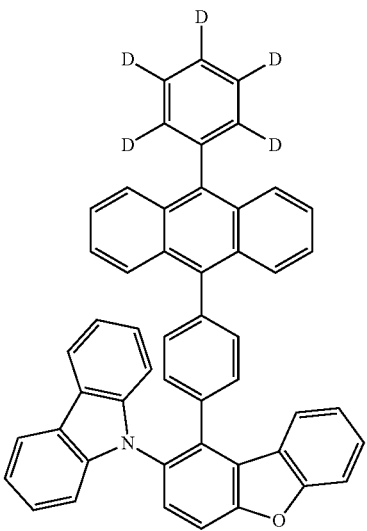

<Compound 293>
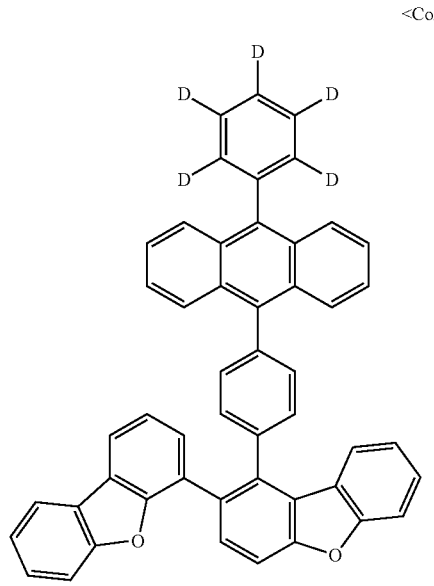
<Compound 294>
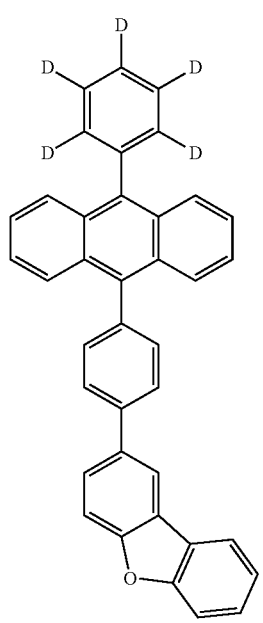
<Compound 295>
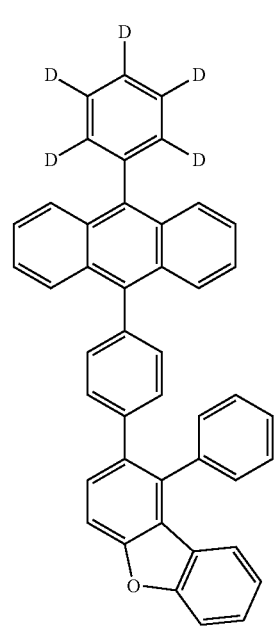
<Compound 296>
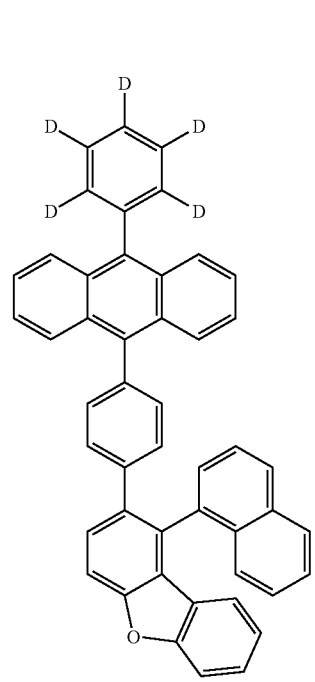

<Compound 297>
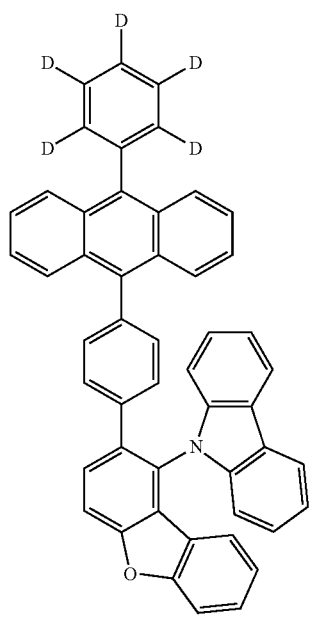
<Compound 299>
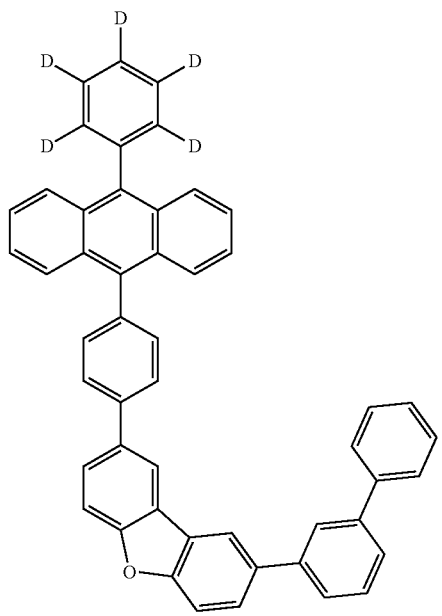
<Compound 298>
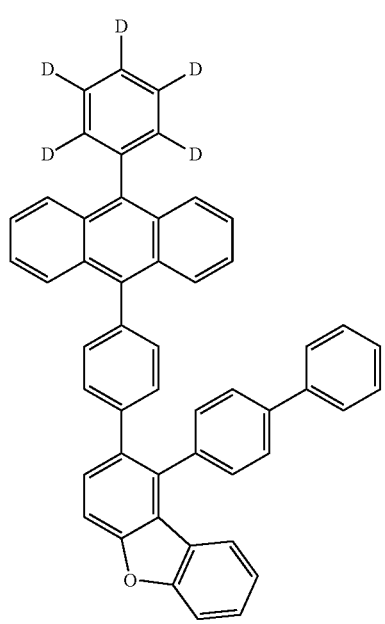
<Compound 300>
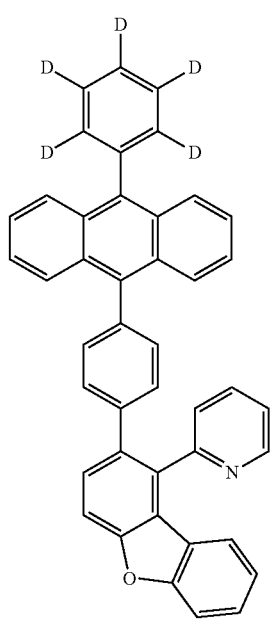

<Compound 301>
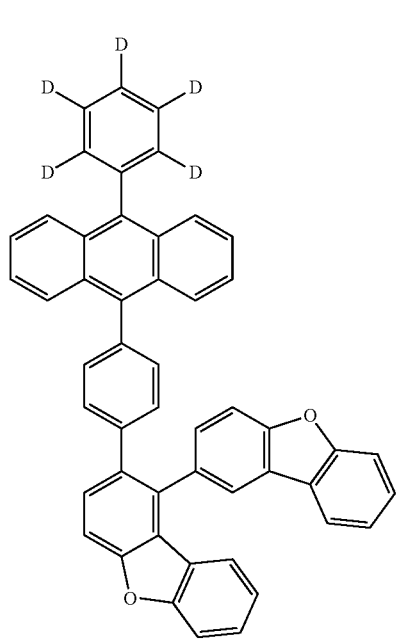
<Compound 303>
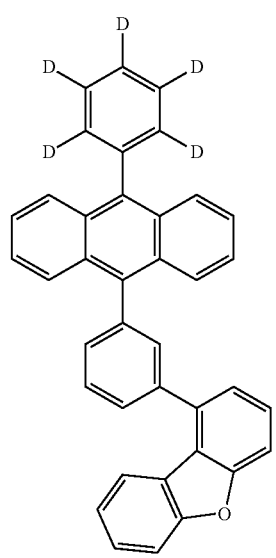
<Compound 302>
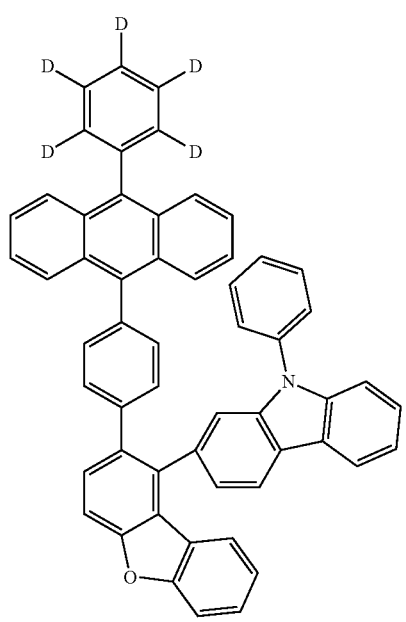
<Compound 304>
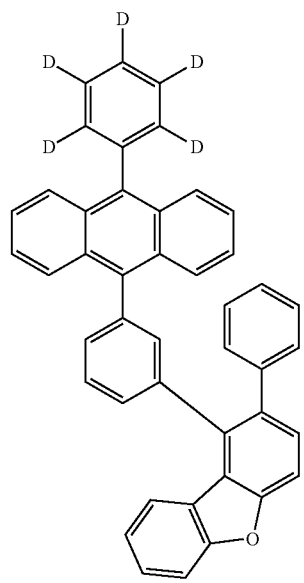

<Compound 305>
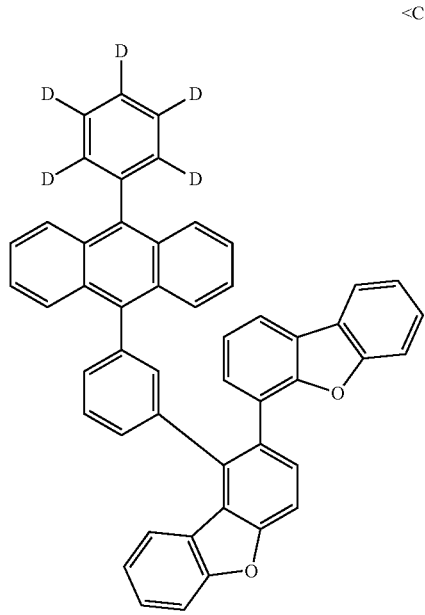
<Compound 307>
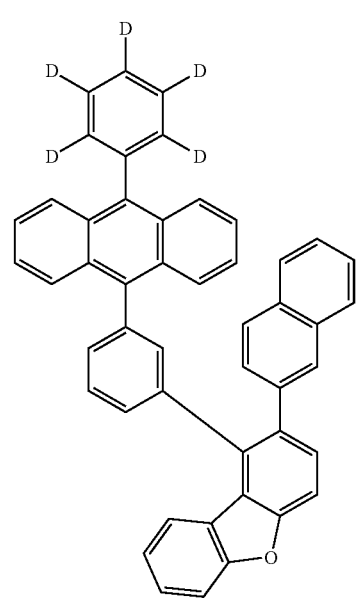
<Compound 306>
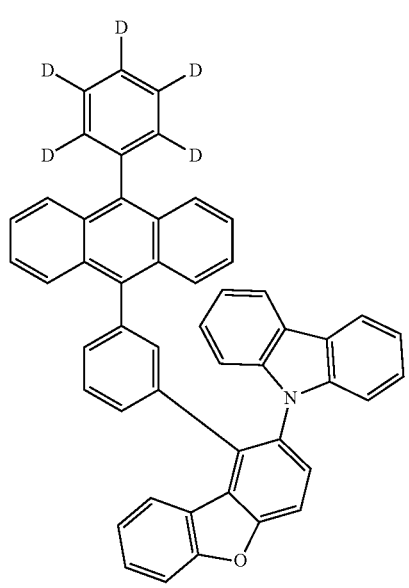
<Compound 308>
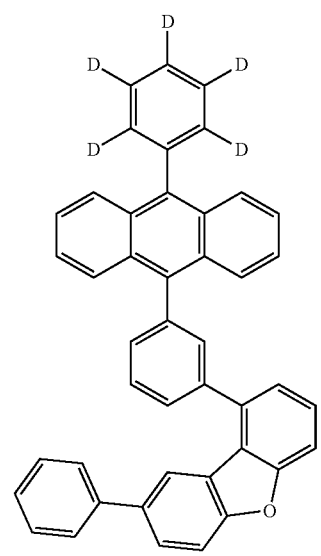

<Compound 309>
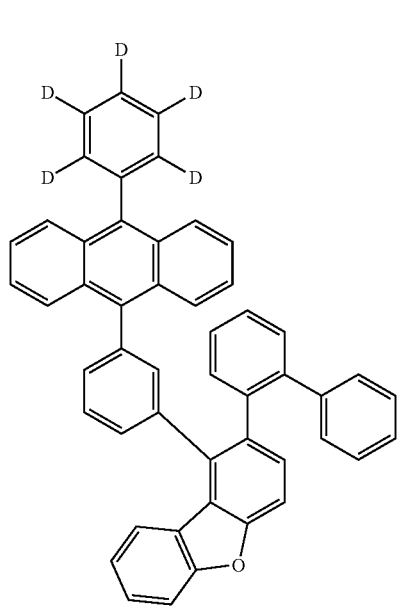
<Compound 311>
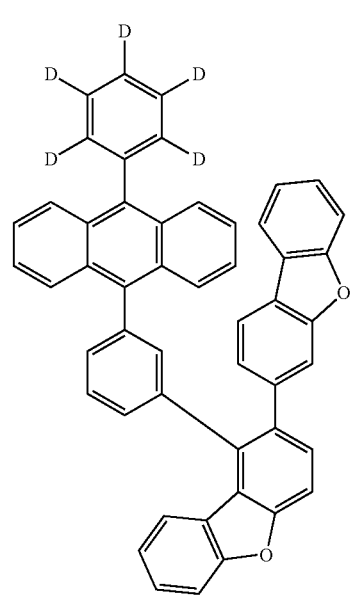
<Compound 310>
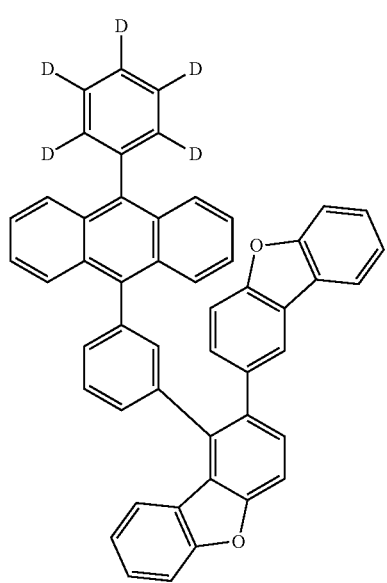
<Compound 312>
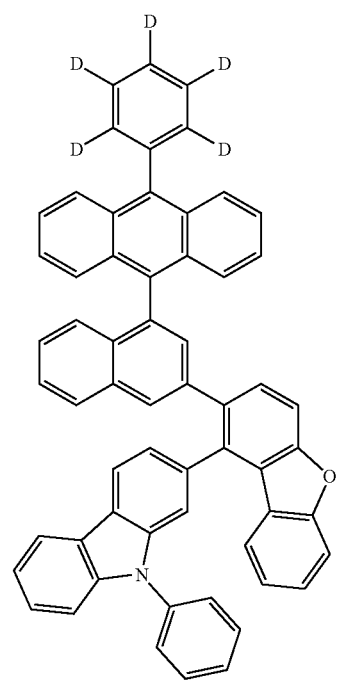

<Compound 313>
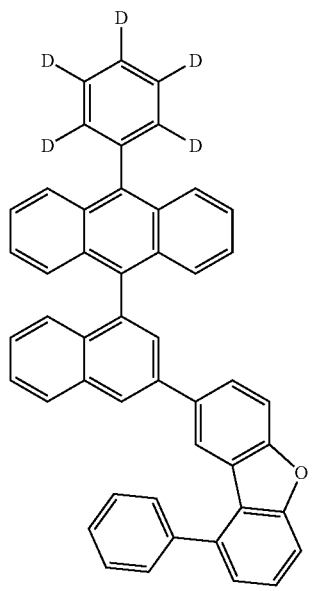
<Compound 314>
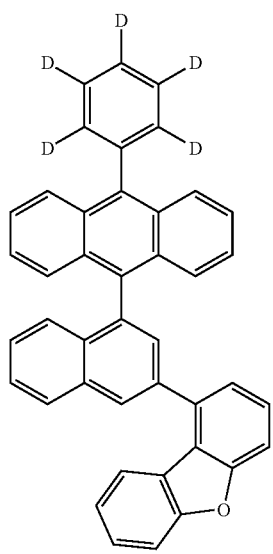
<Compound 315>
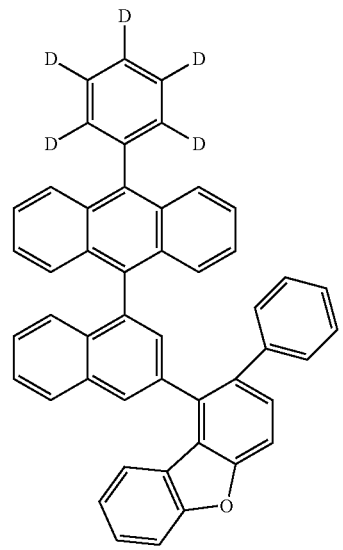
<Compound 316>
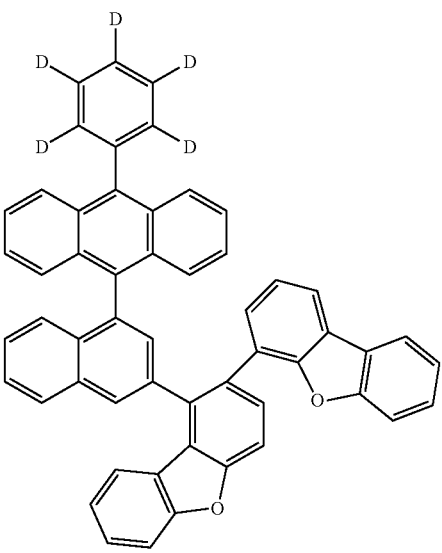

<Compound 317>
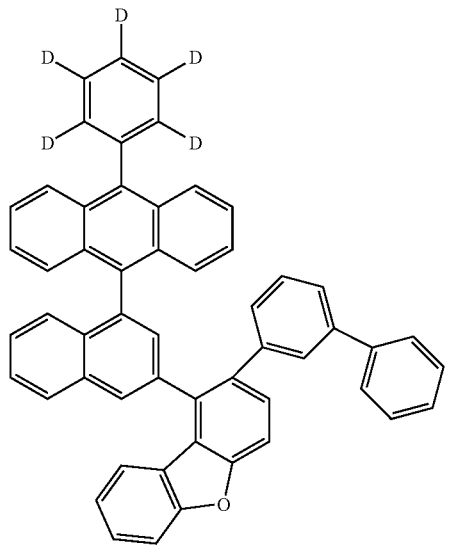
<Compound 318>
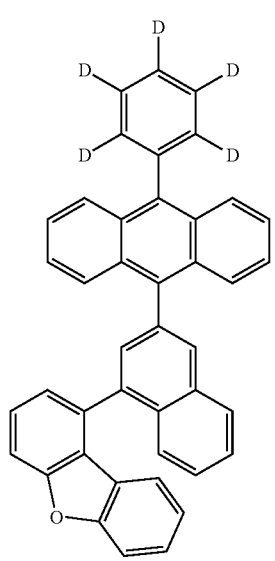
<Compound 319>
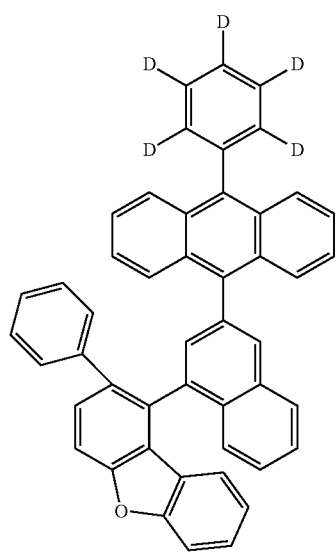
<Compound 320>
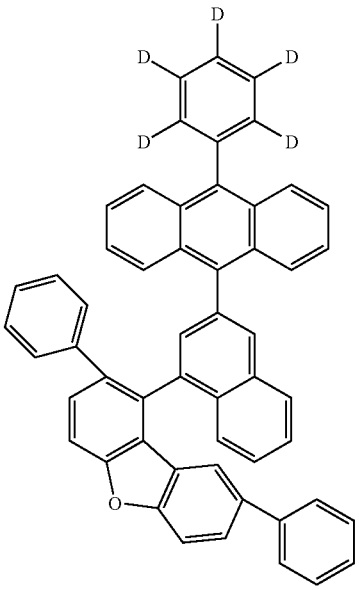
<Compound 321>
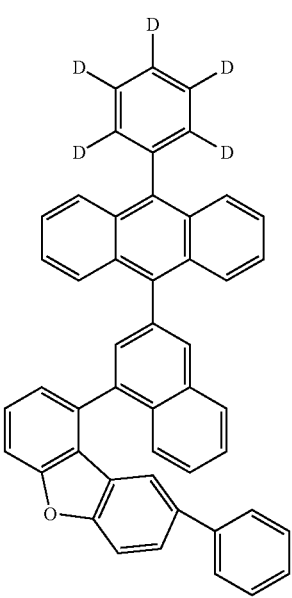

<Compound 322>
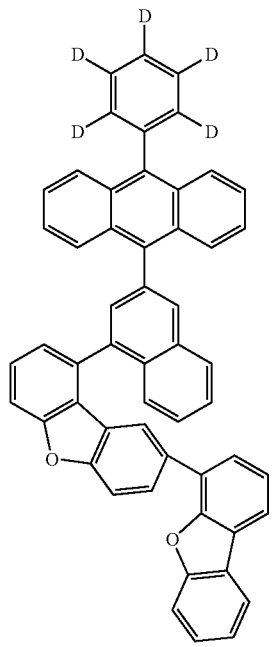
<Compound 323>
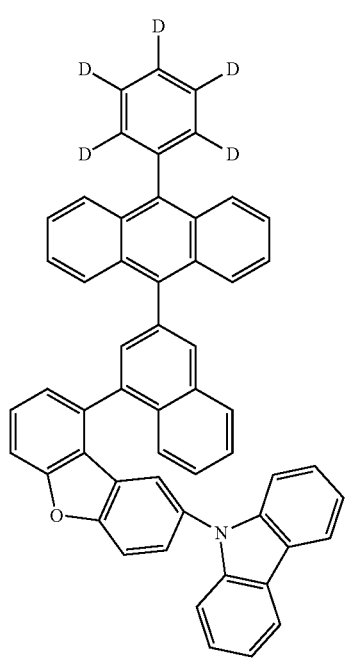
<Compound 324>
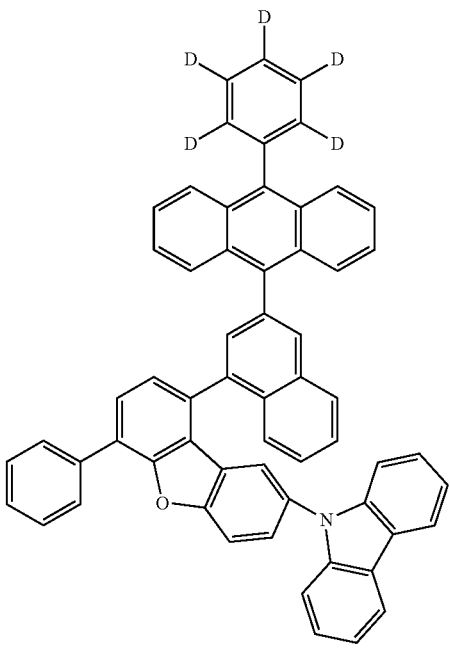
<Compound 325>
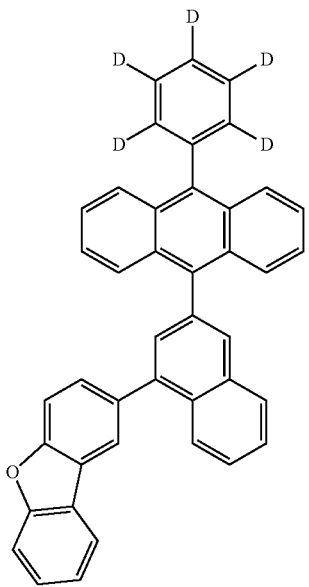

-continued
<Compound 326>
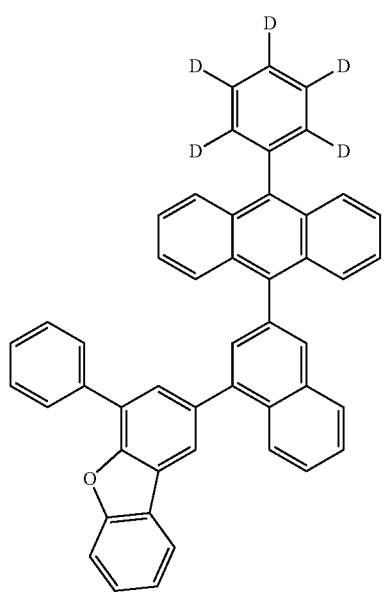
<Compound 328>
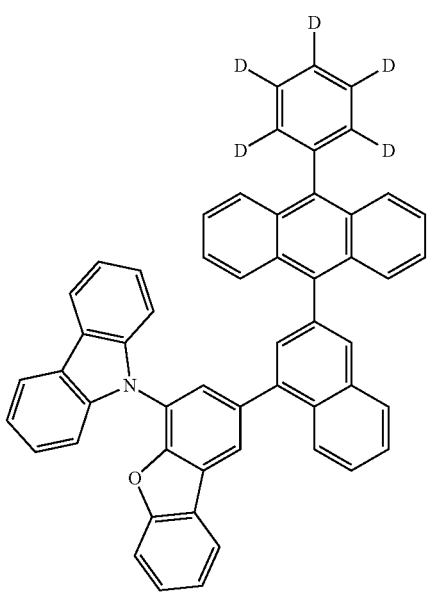
<Compound 327>
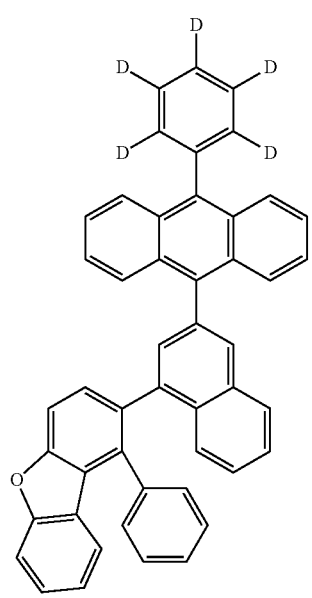
<Compound 329>
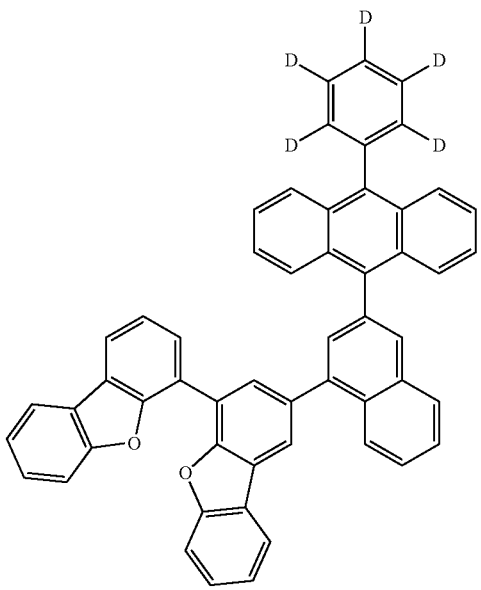

<Compound 330>
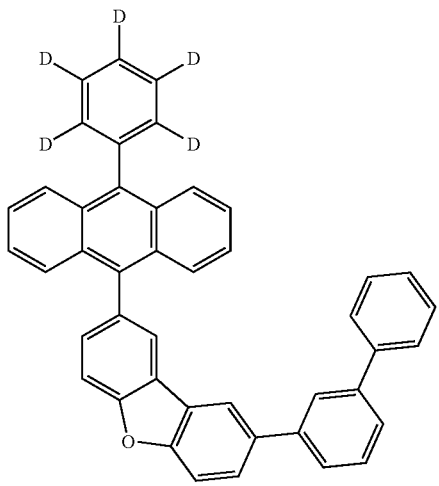
<Compound 331>
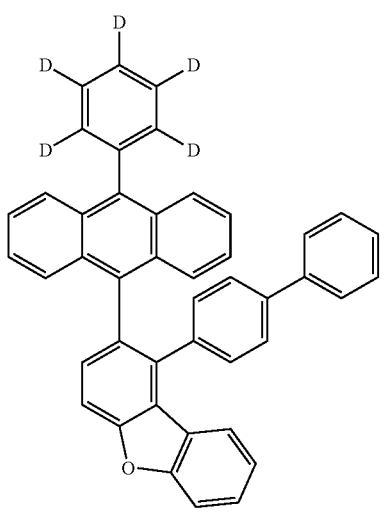
<Compound 332>
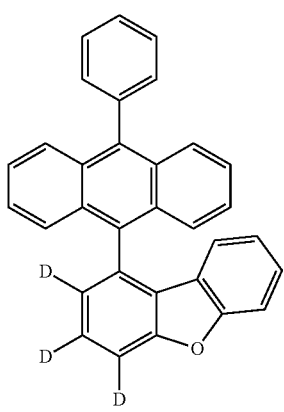
<Compound 333>
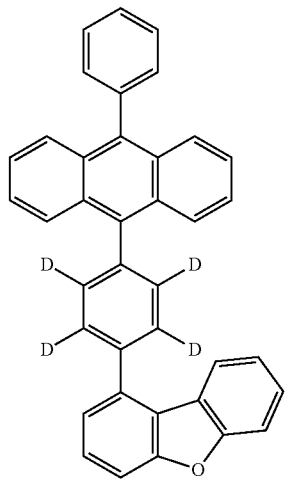
<Compound 334>
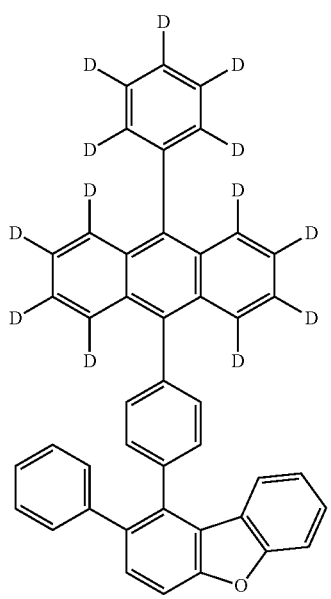
<Compound 335>
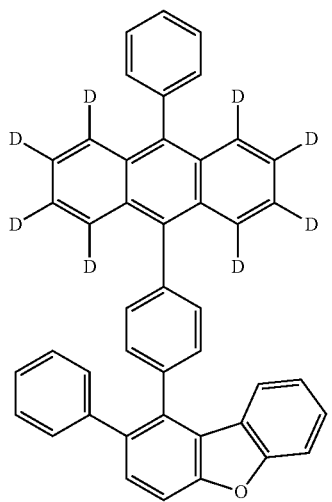

<Compound 336>
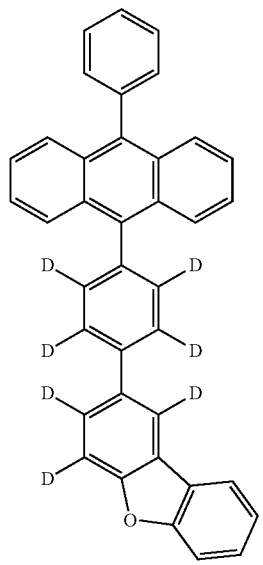
<Compound 337>
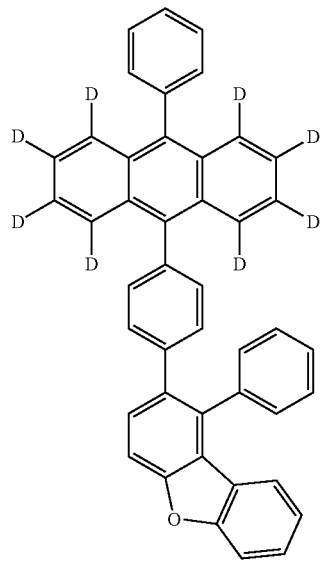
<Compound 338>
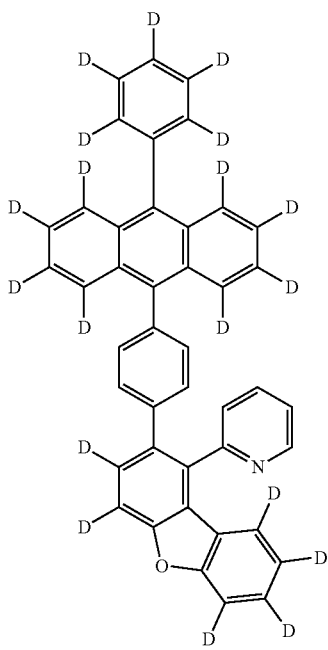
<Compound 339>
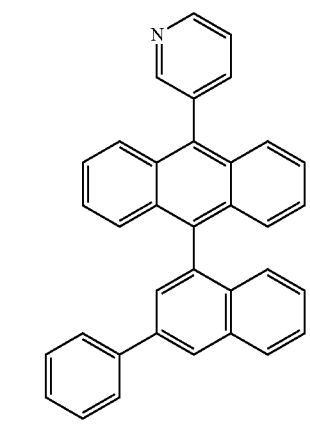
<Compound 340>
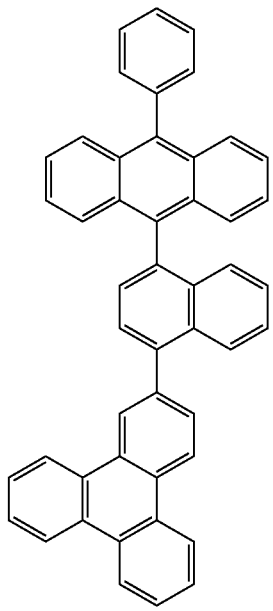

327
-continued
<Compound 341>
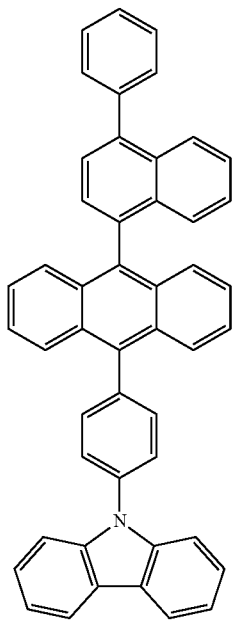
<Compound 342>
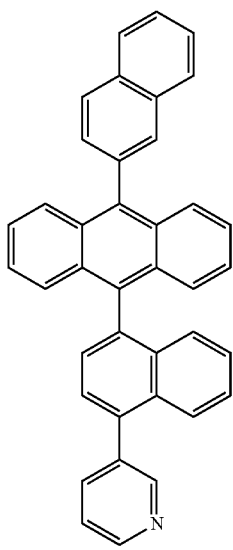
328
-continued
<Compound 343>
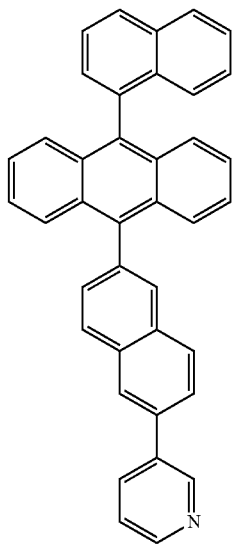
<Compound 344>
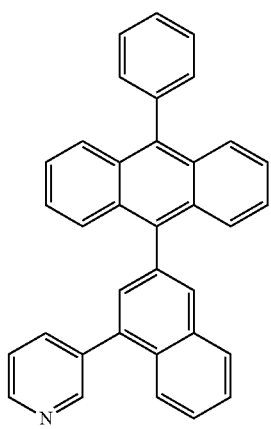
<Compound 345>
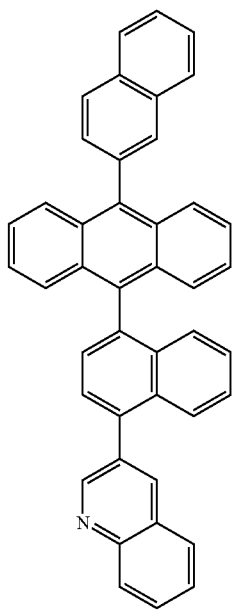

<Compound 346>
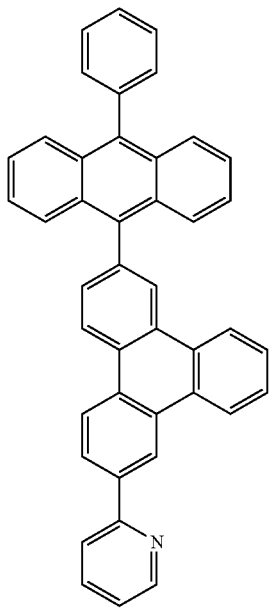
<Compound 348>
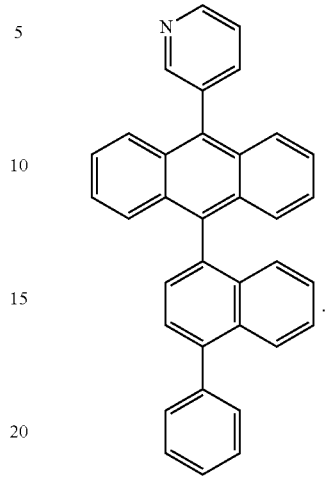
15. The organic light-emitting diode of claim 1, wherein the linkers $L_1$ to $L_{12}$ in Chemical Formulas A and B are each a single bond or any one selected from among the following Structural Formulas 22 to 30:
[Structural Formula 22]
[Structural Formula 23]
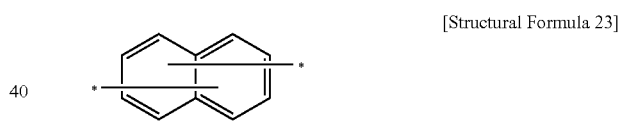
<Compound 347>
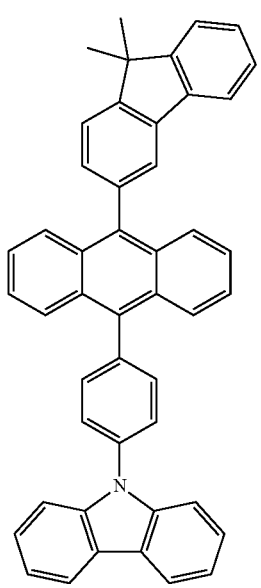
[Structural Formula 24]
[Structural Formula 25]
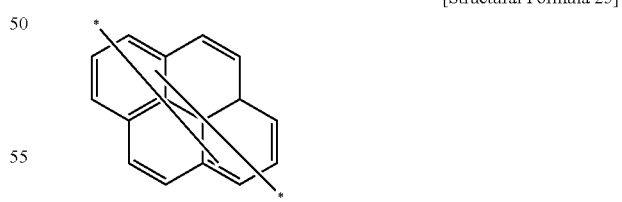
[Structural Formula 26]
[Structural Formula 27]
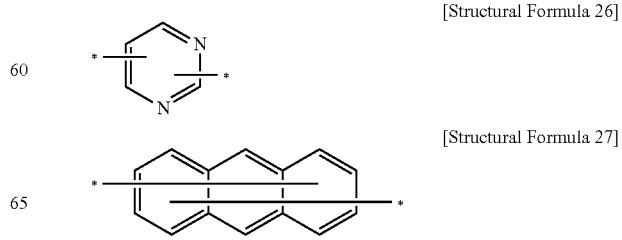

331
-continued

[Structural Formula 28]

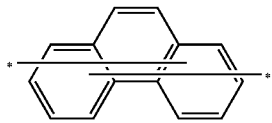

[Structural Formula 29]

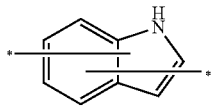

332
-continued

[Structural Formula 30]

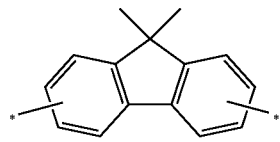

wherein each of the unsubstituted carbon atoms of the aromatic ring moiety is bound with a hydrogen atom or a deuterium atom.

16. The organic light-emitting diode of claim 1, wherein the amine compound is one selected from among the compounds represented by the following Chemical Formulas 1 to 239:

<Chemical Formula 1>

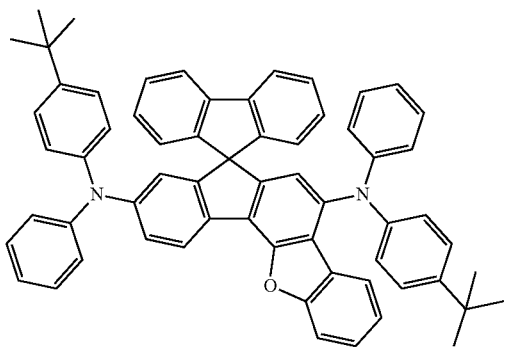

<Chemical Formula 2>

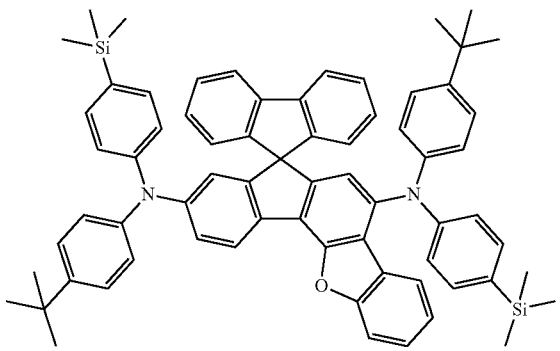

<Chemical Formula 3>

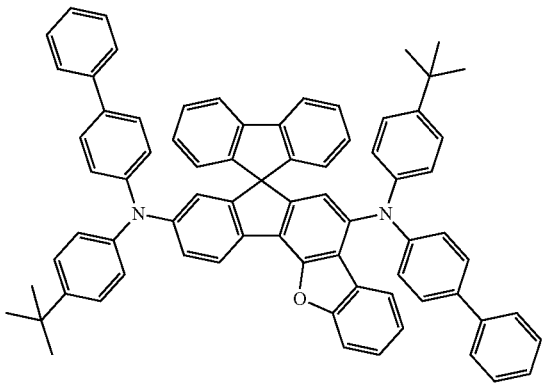

<Chemical Formula 4>

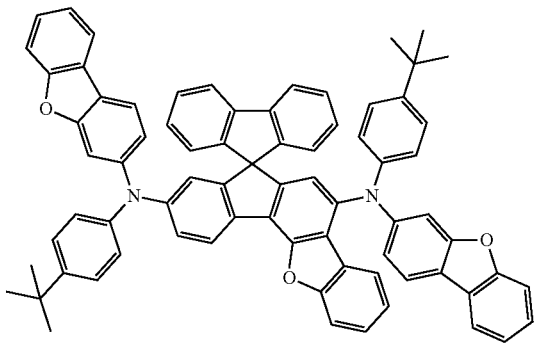

<Chemical Formula 5>

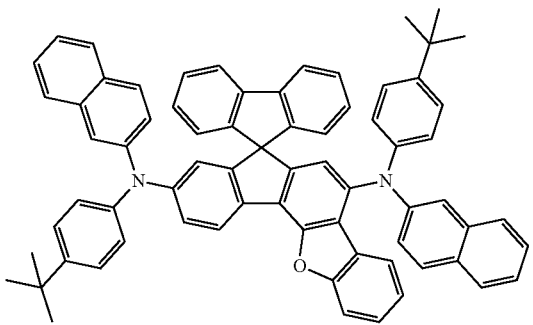

<Chemical Formula 6>

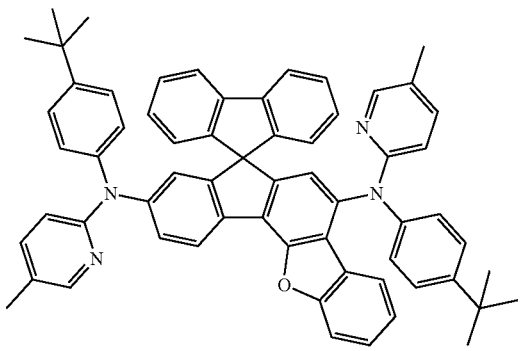

-continued
<Chemical Formula 7>
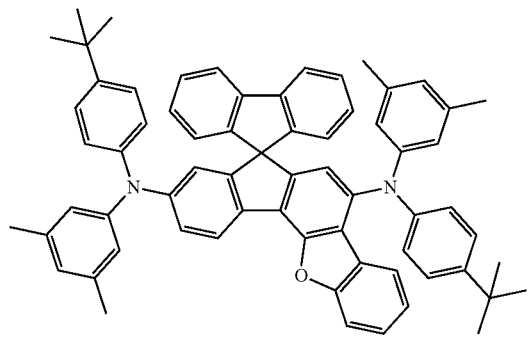
<Chemical Formula 8>
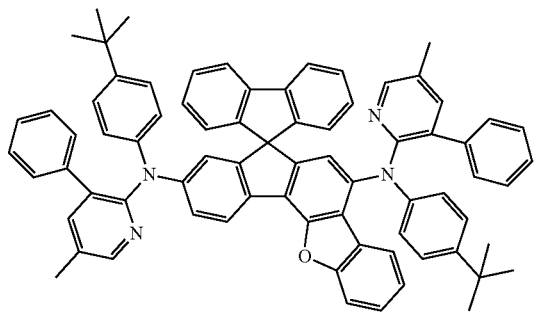
<Chemical Formula 9>
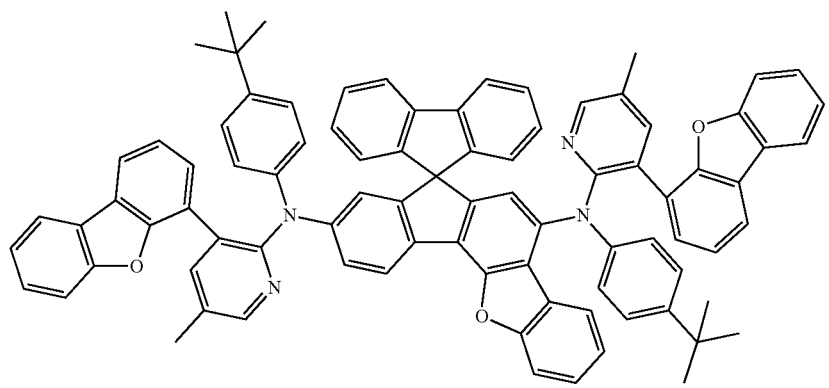
<Chemical Formula 10>
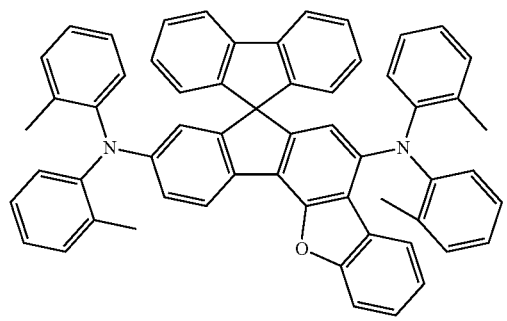
<Chemical Formula 11>
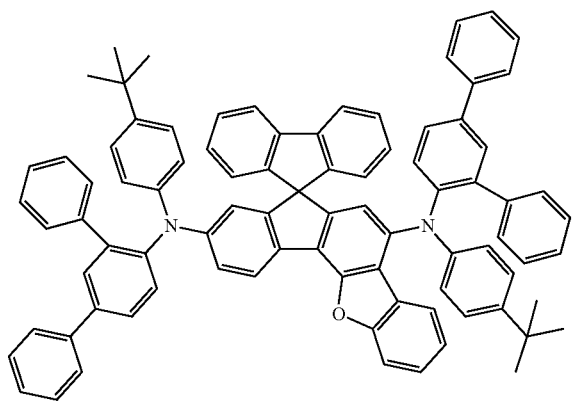
<Chemical Formula 12>
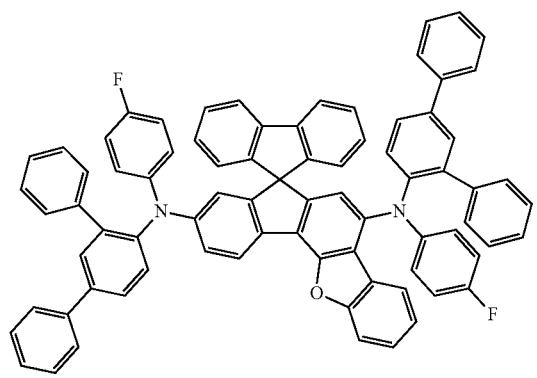
<Chemical Formula 13>
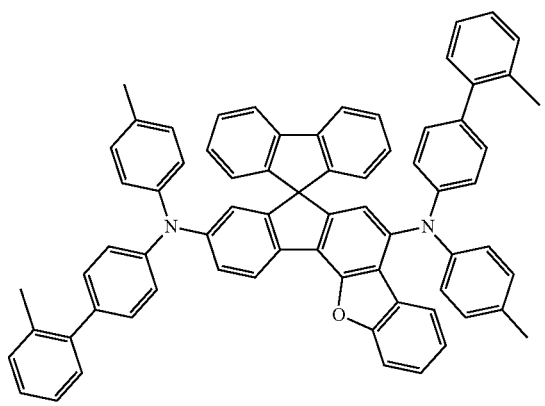

-continued
<Chemical Formula 14>
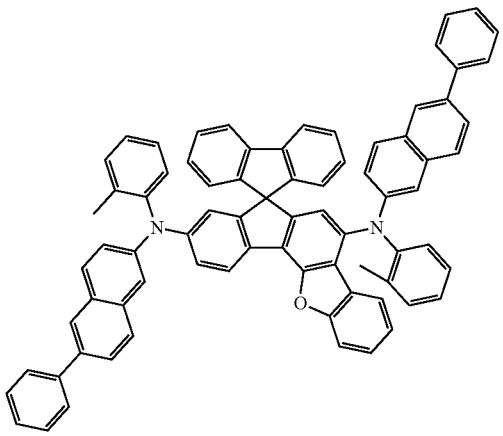
<Chemical Formula 15>
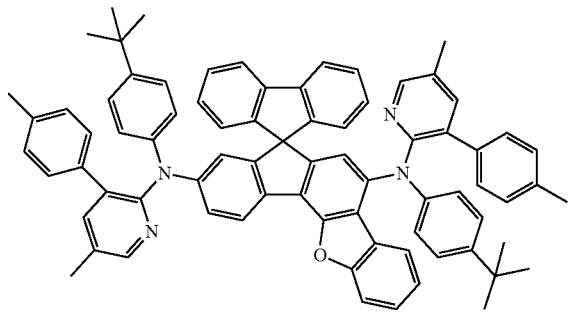
<Chemical Formula 16>
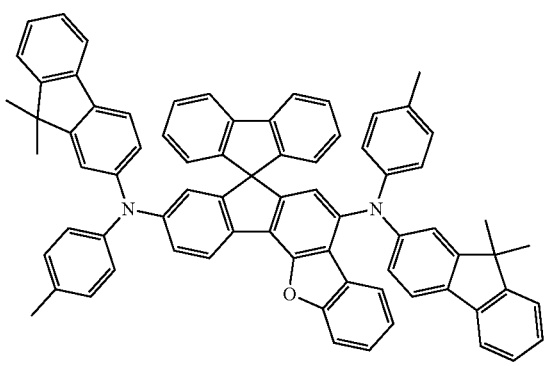
<Chemical Formula 17>
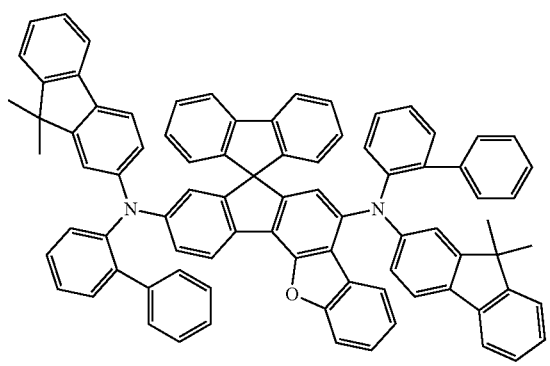
<Chemical Formula 18>
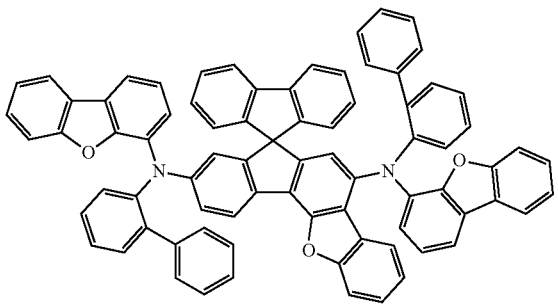
<Chemical Formula 19>
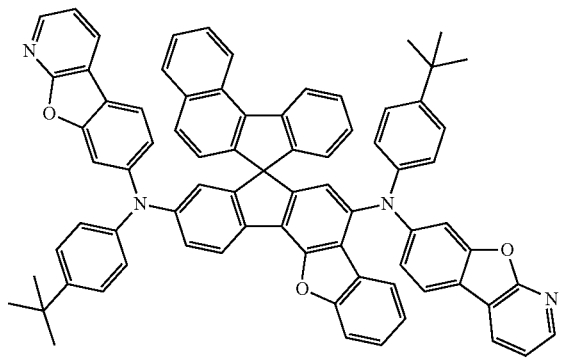
<Chemical Formula 20>
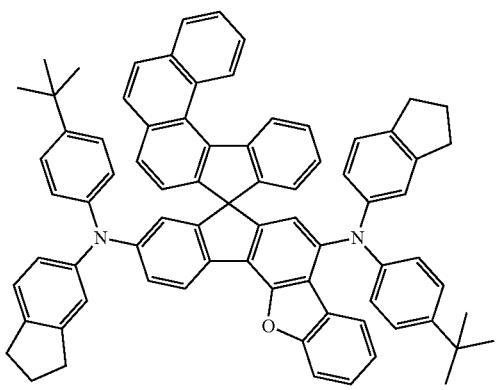
<Chemical Formula 21>
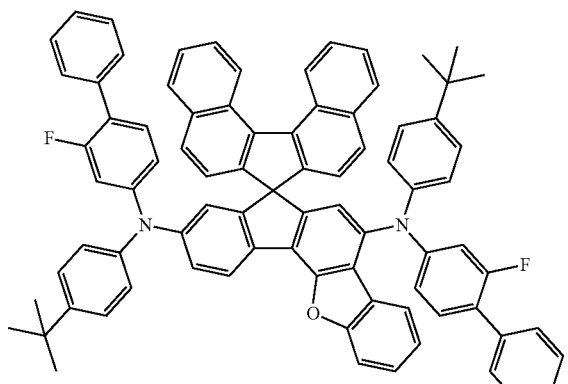

<Chemical Formula 22>
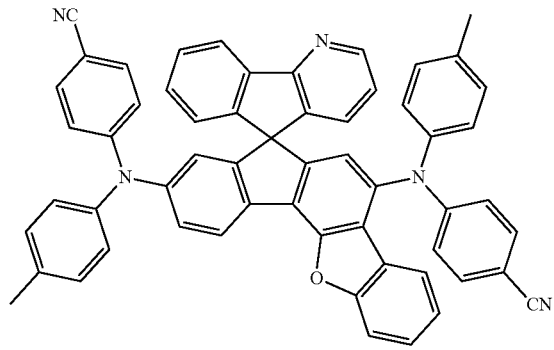
<Chemical Formula 23>
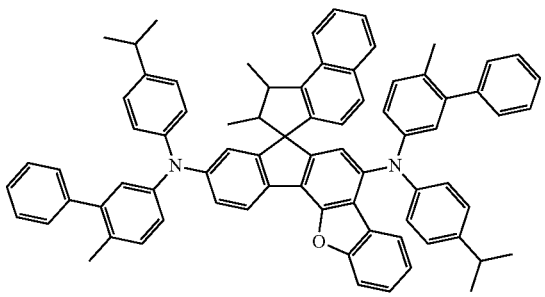
<Chemical Formula 24>
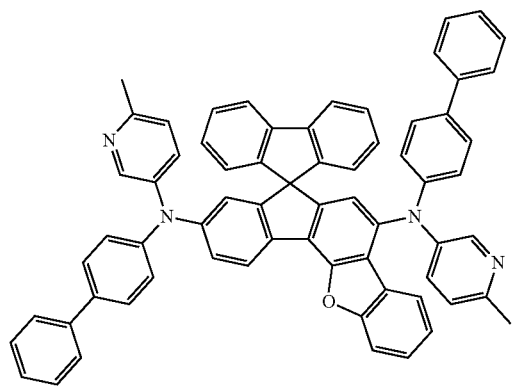
<Chemical Formula 25>
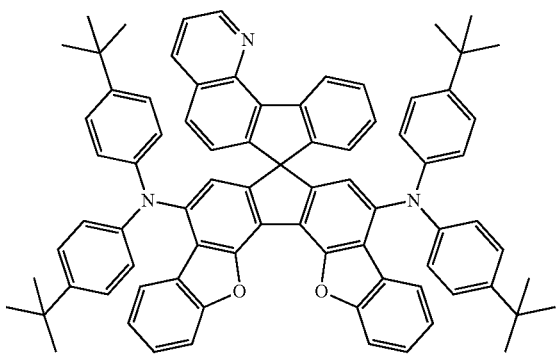
<Chemical Formula 26>
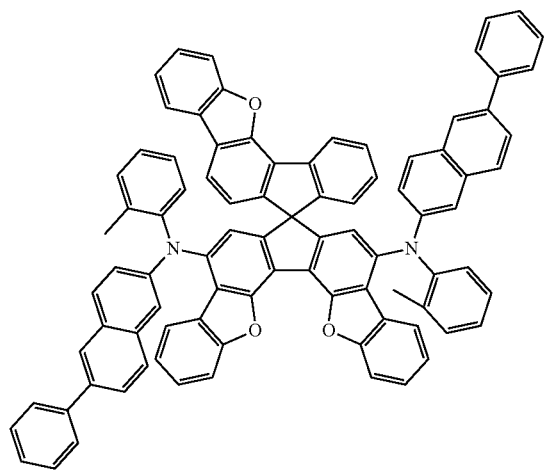
<Chemical Formula 27>
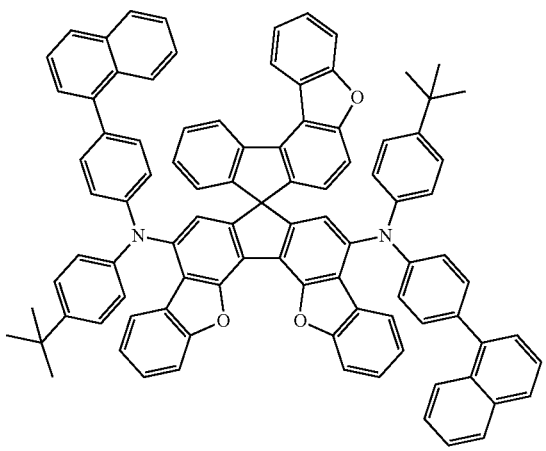

<Chemical Formula 28>
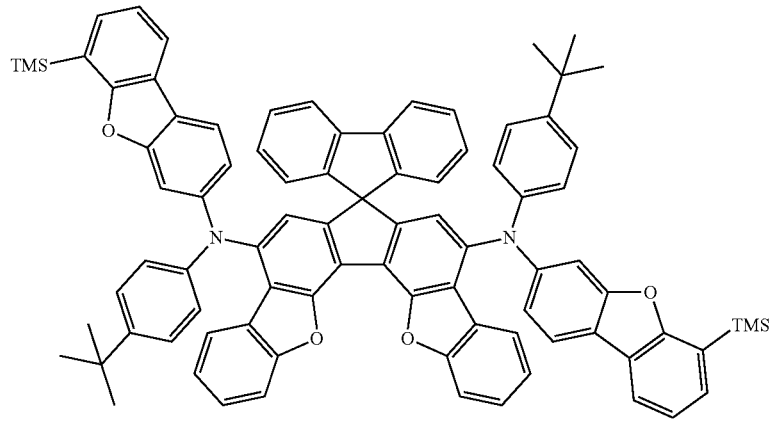
<Chemical Formula 29>
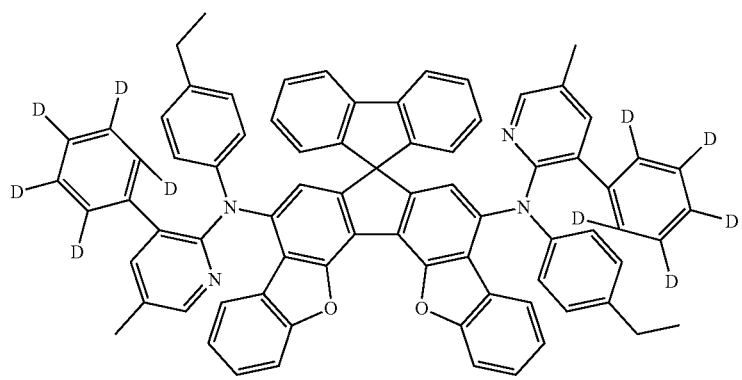
<Chemical Formula 30>
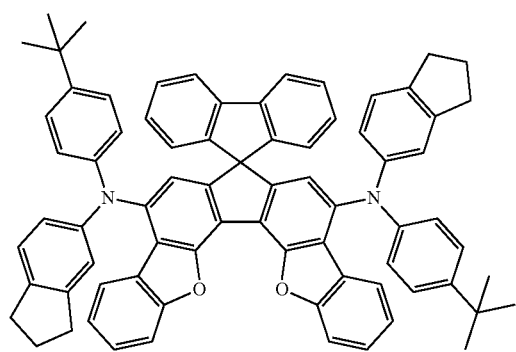
<Chemical Formula 31>
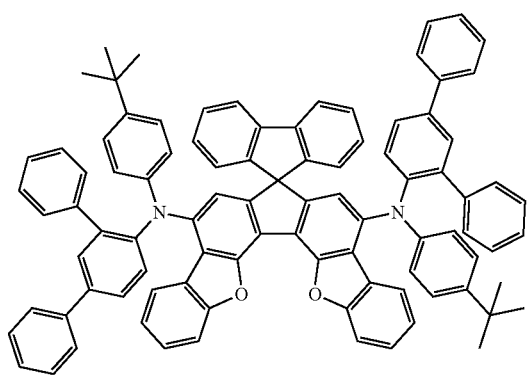
<Chemical Formula 32>
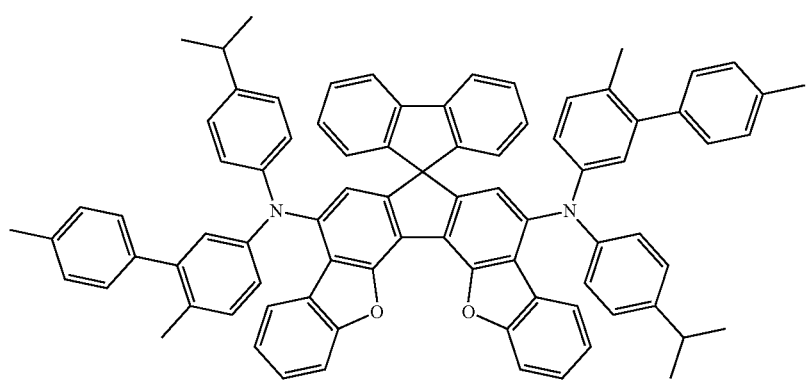

<Chemical Formula 33>
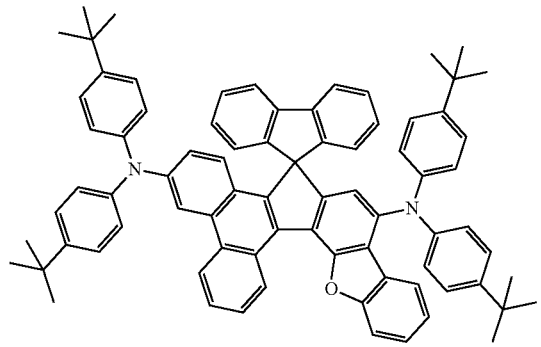
<Chemical Formula 34>
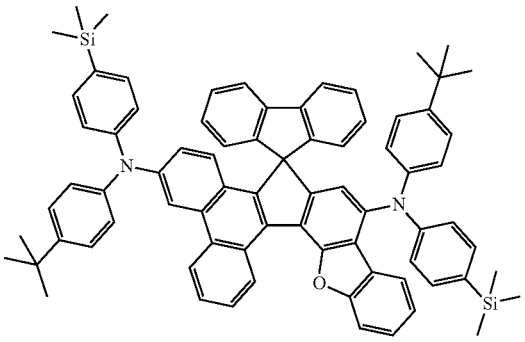
<Chemical Formula 35>
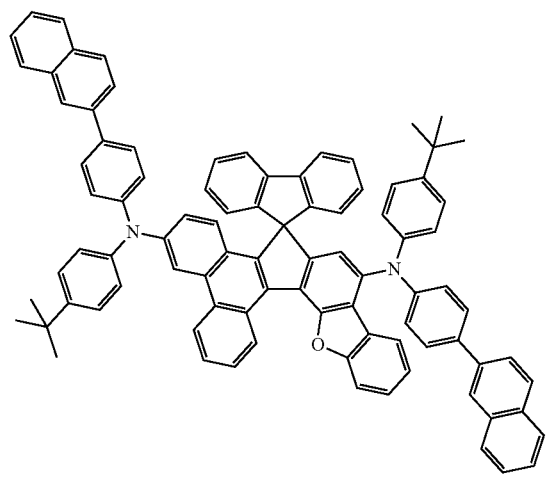
<Chemical Formula 36>
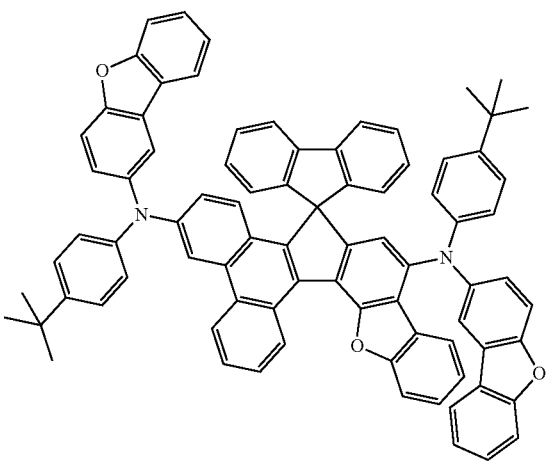
<Chemical Formula 37>
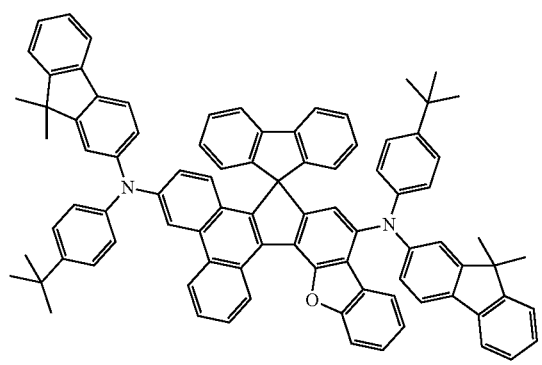
<Chemical Formula 38>
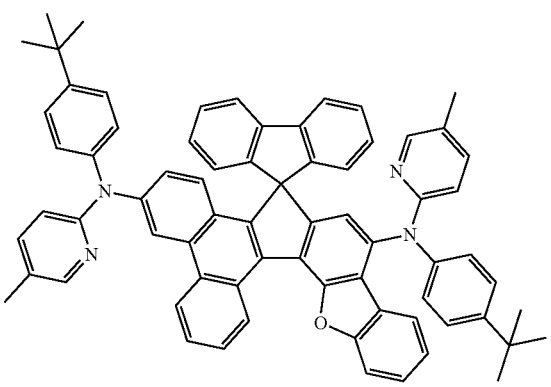

-continued
<Chemical Formula 39>
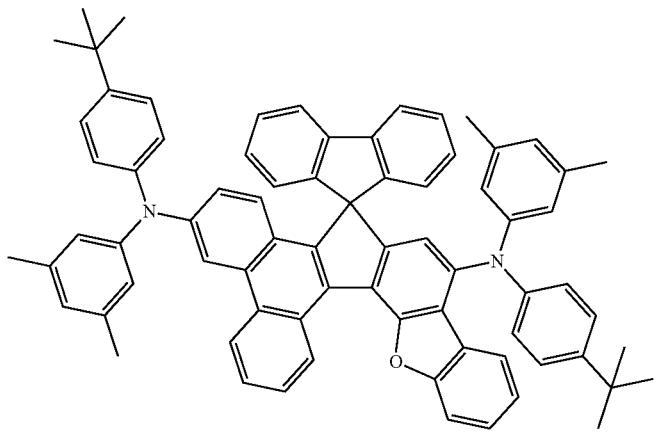
<Chemical Formula 40>
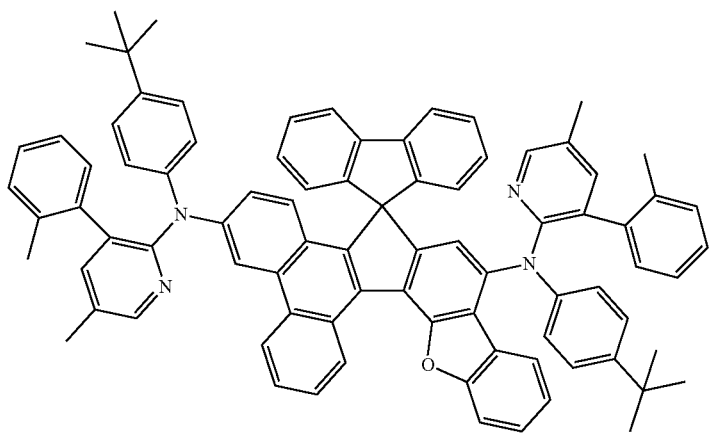
<Chemical Formula 41>
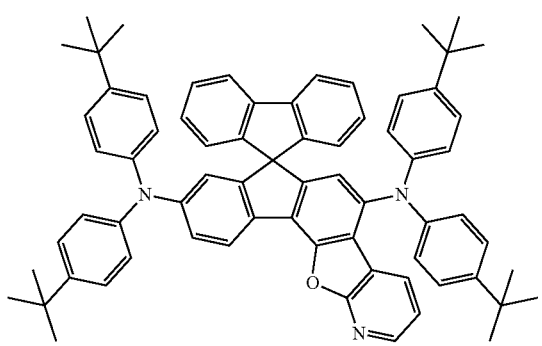
<Chemical Formula 42>
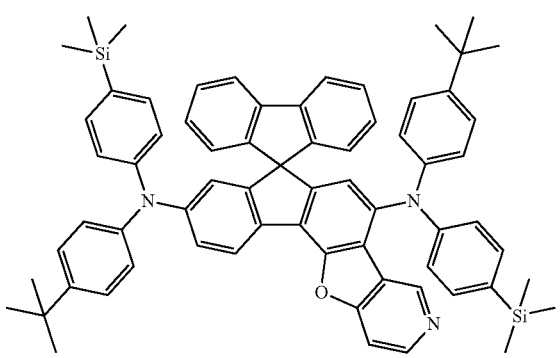
<Chemical Formula 43>
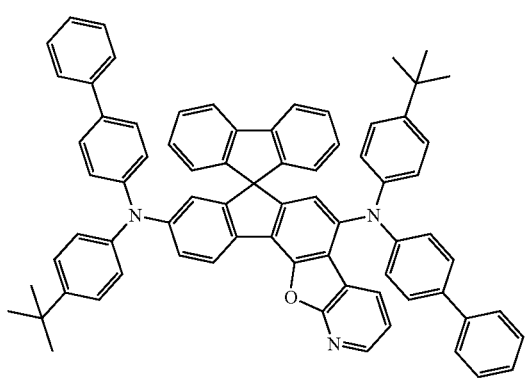
<Chemical Formula 44>
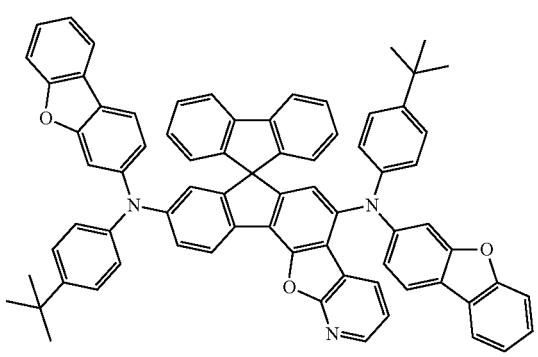

-continued
<Chemical Formula 45>
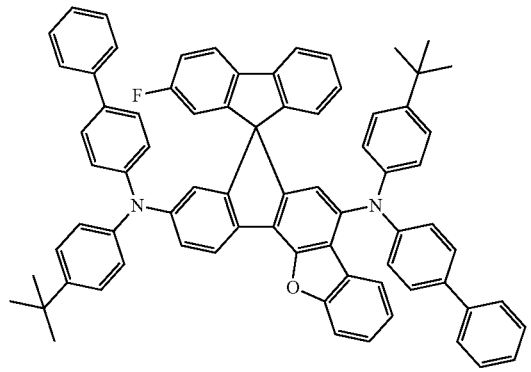
<Chemical Formula 46>
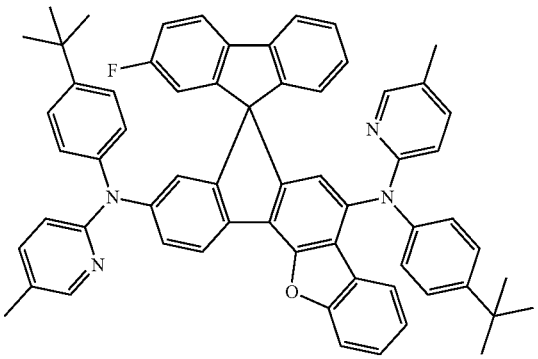
<Chemical Formula 47>
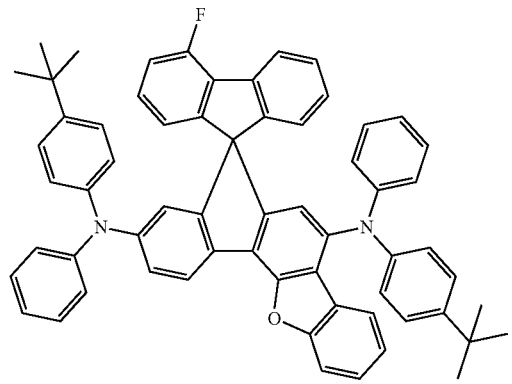
<Chemical Formula 48>
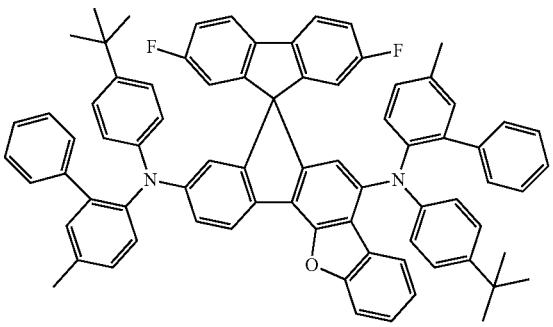
<Chemical Formula 49>
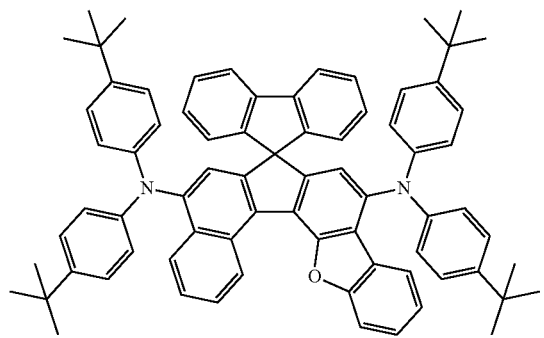
<Chemical Formula 50>
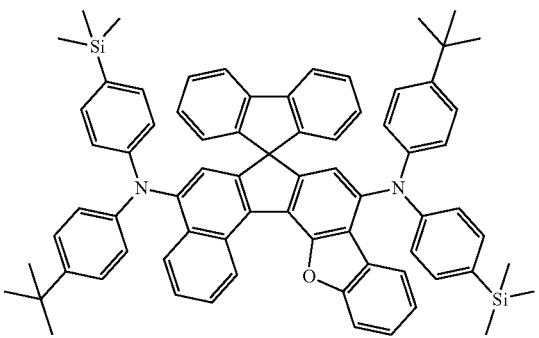
<Chemical Formula 51>
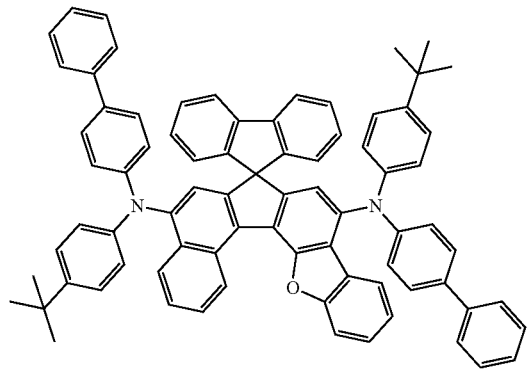
<Chemical Formula 52>
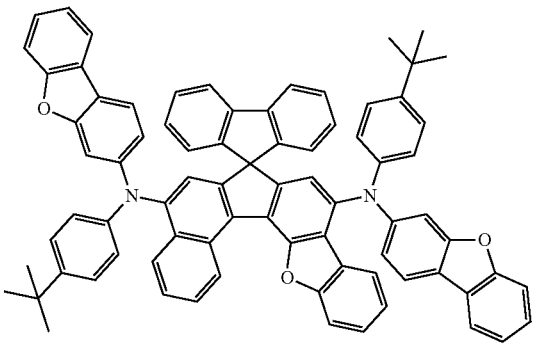

-continued
<Chemical Formula 53>
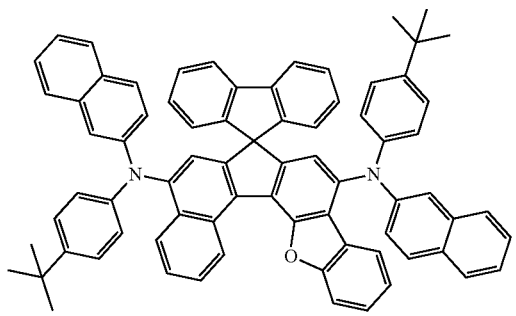
<Chemical Formula 54>
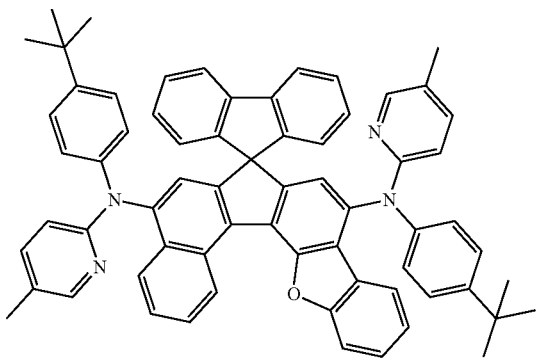
<Chemical Formula 55>
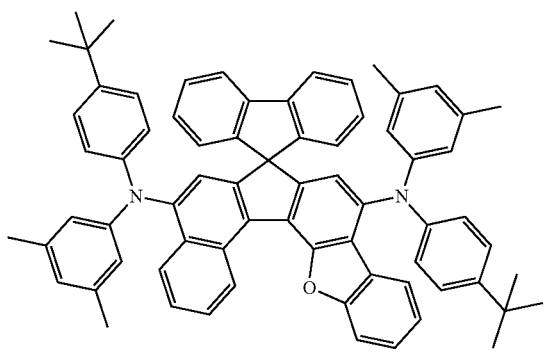
<Chemical Formula 56>
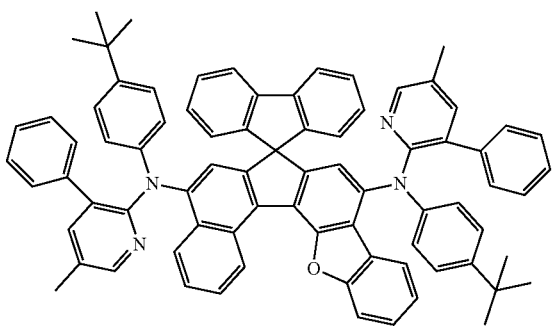
<Chemical Formula 57>
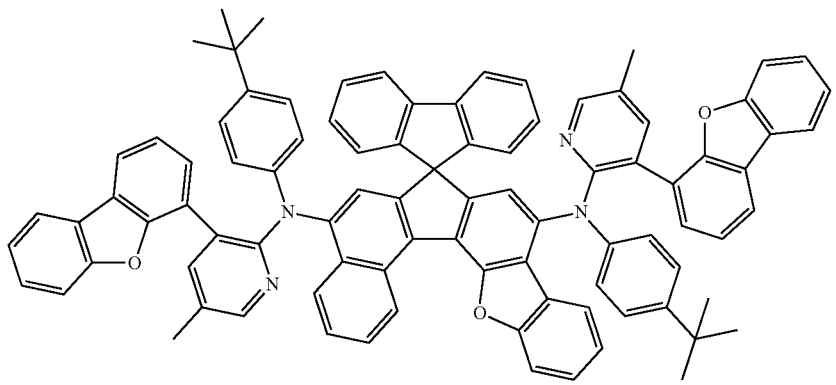
<Chemical Formula 58>
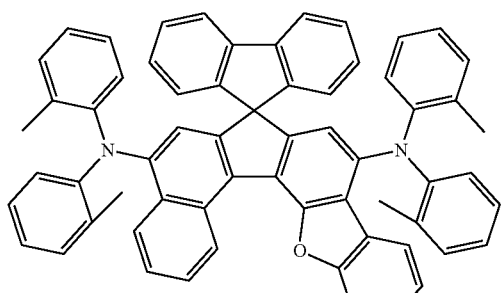
<Chemical Formula 59>
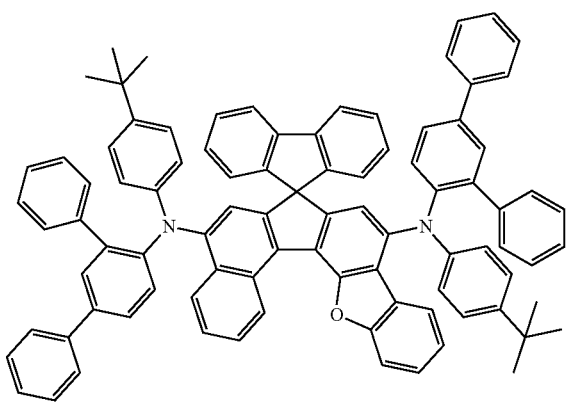

<Chemical Formula 60>
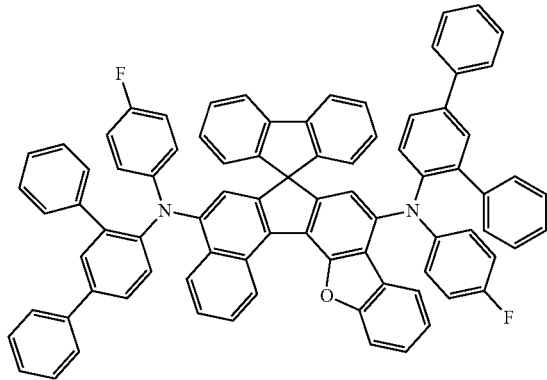
<Chemical Formula 61>
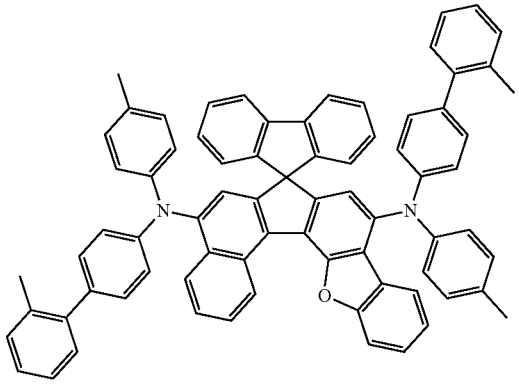
<Chemical Formula 62>
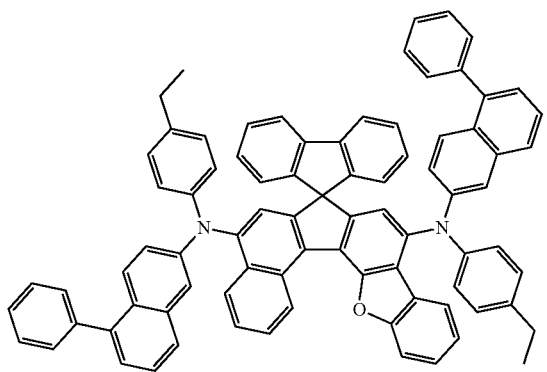
<Chemical Formula 63>
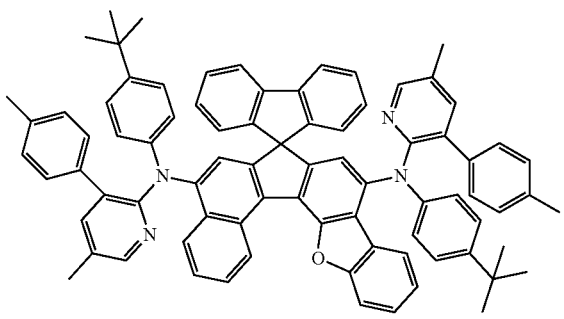
<Chemical Formula 64>
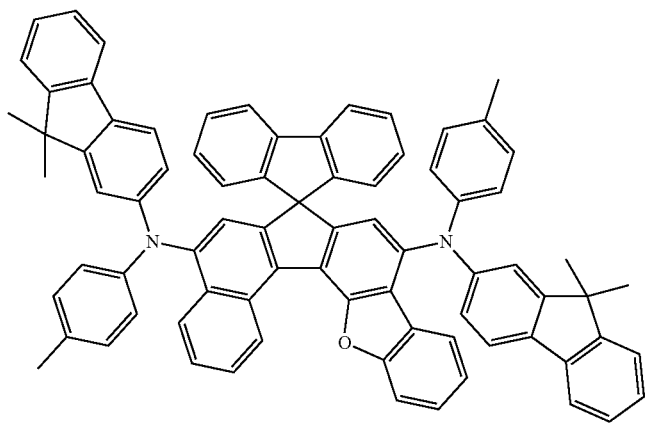

<Chemical Formula 65>
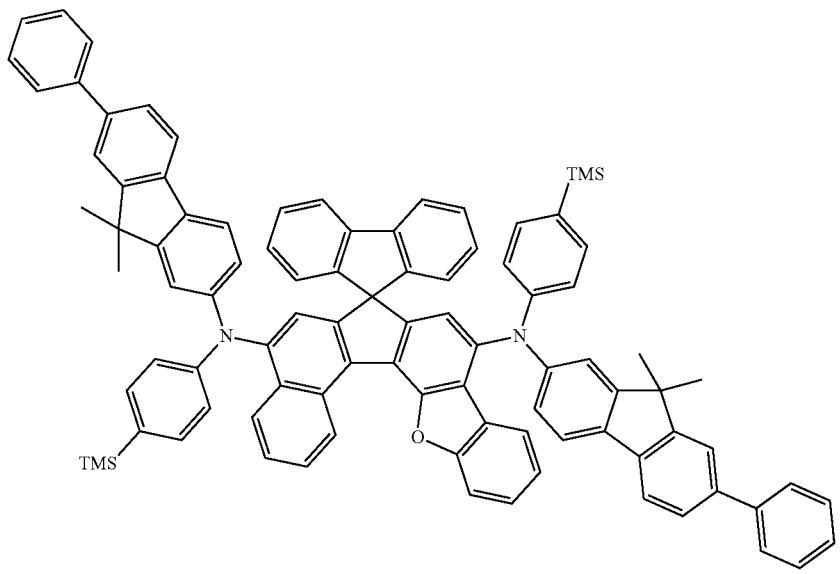
<Chemical Formula 66>
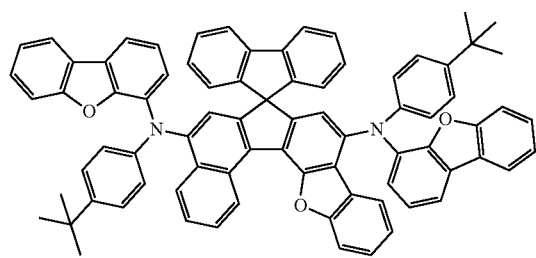
<Chemical Formula 67>
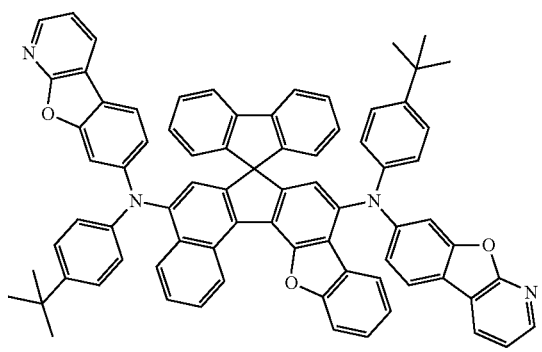
<Chemical Formula 68>
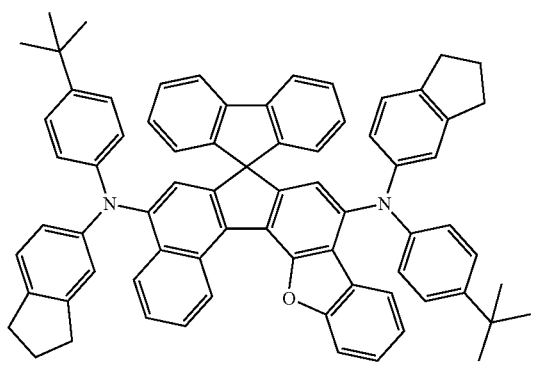
<Chemical Formula 69>
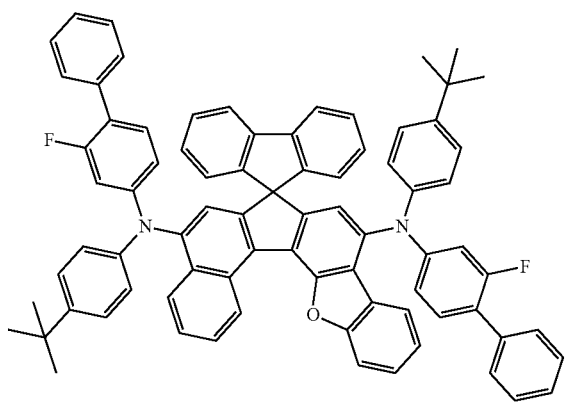

-continued
<Chemical Formula 70>
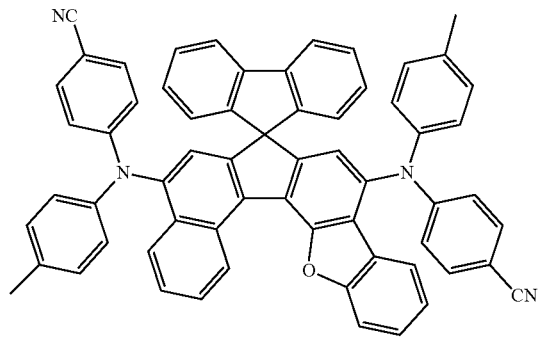
<Chemical Formula 71>
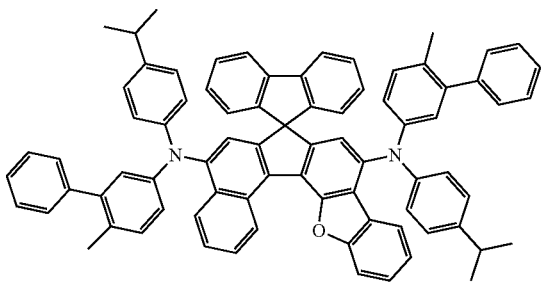
<Chemical Formula 72>
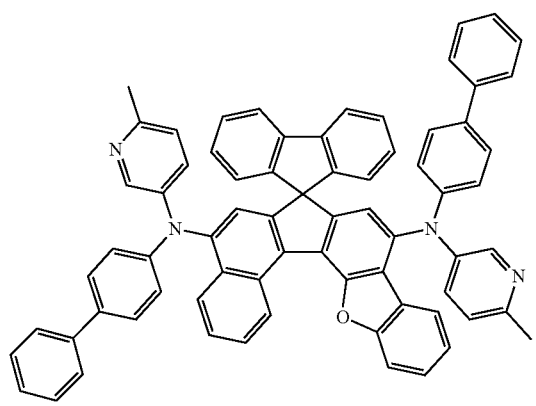
<Chemical Formula 73>
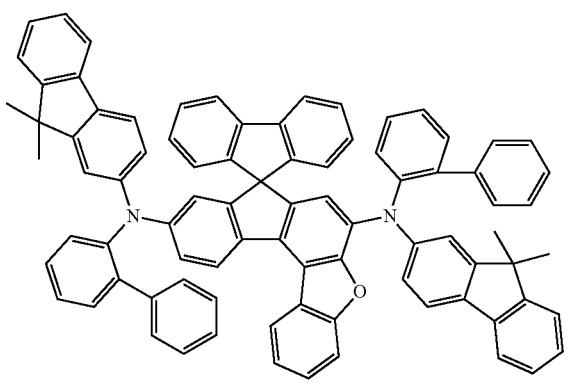
<Chemical Formula 74>
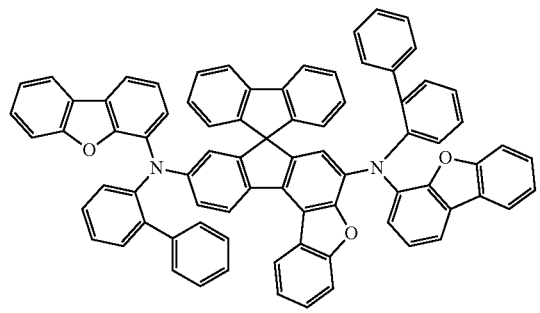
<Chemical Formula 75>
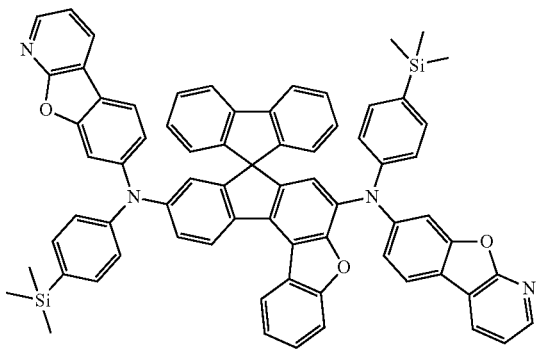
<Chemical Formula 76>
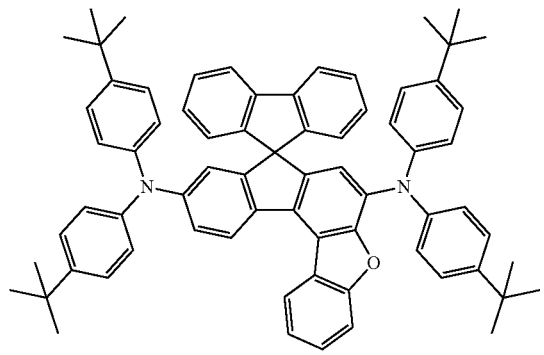
<Chemical Formula 77>
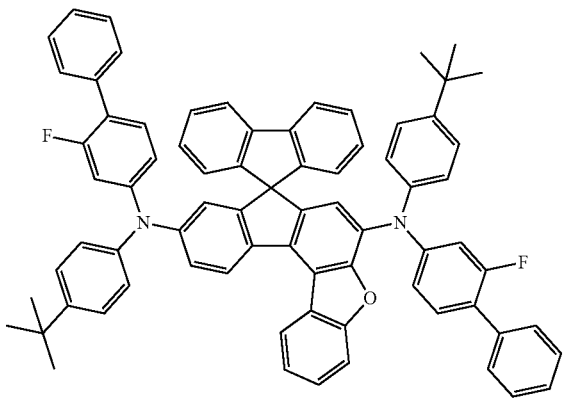

-continued
<Chemical Formula 78>
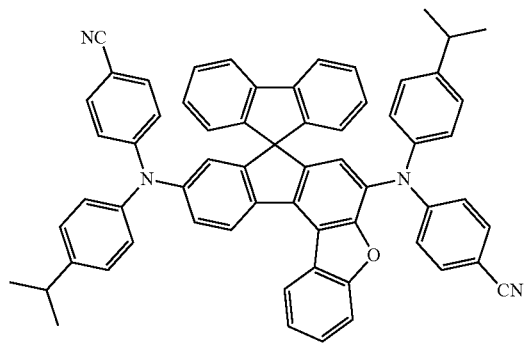
<Chemical Formula 79>
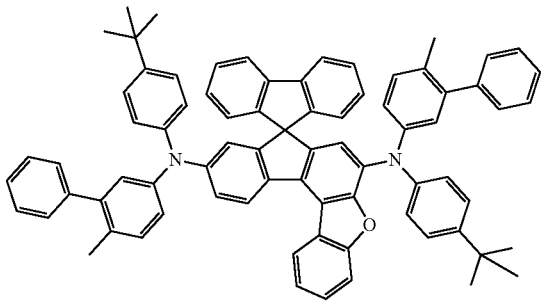
<Chemical Formula 80>
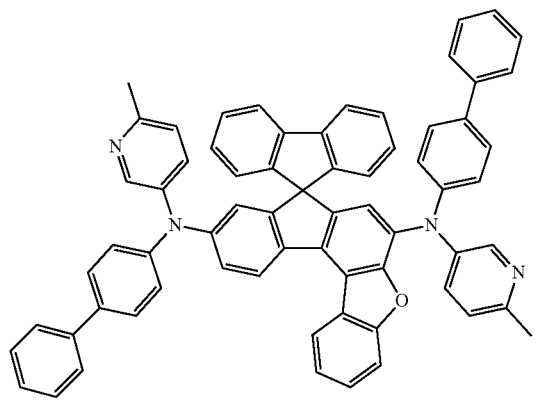
<Chemical Formula 81>
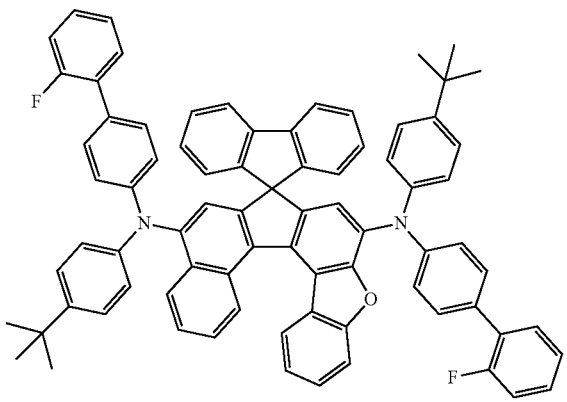
<Chemical Formula 82>
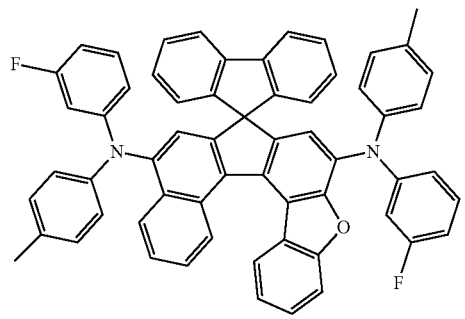
<Chemical Formula 83>
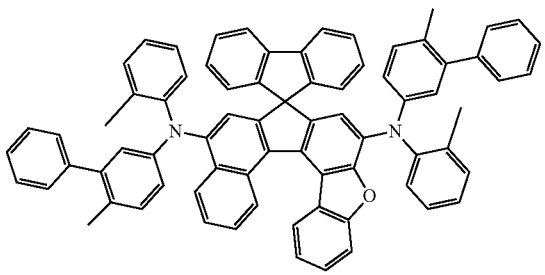
<Chemical Formula 84>
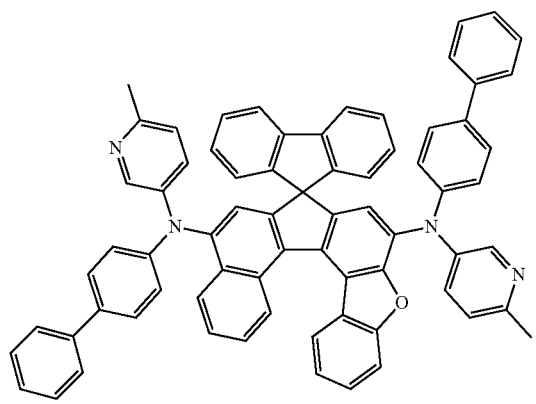
<Chemical Formula 85>
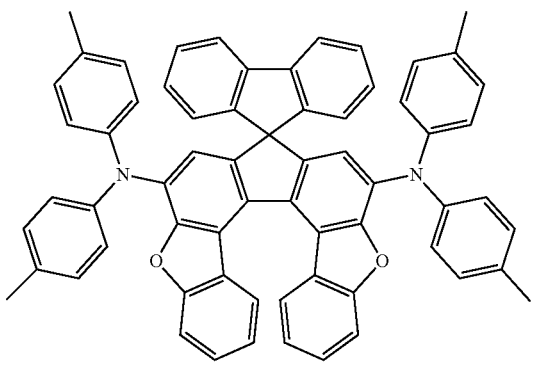

<Chemical Formula 86>
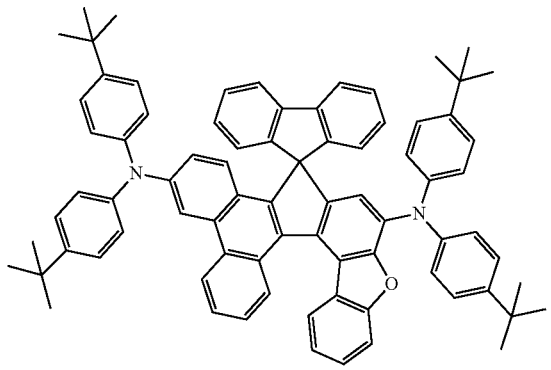
<Chemical Formula 87>
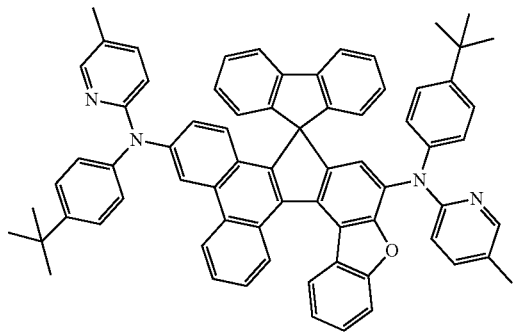
<Chemical Formula 88>
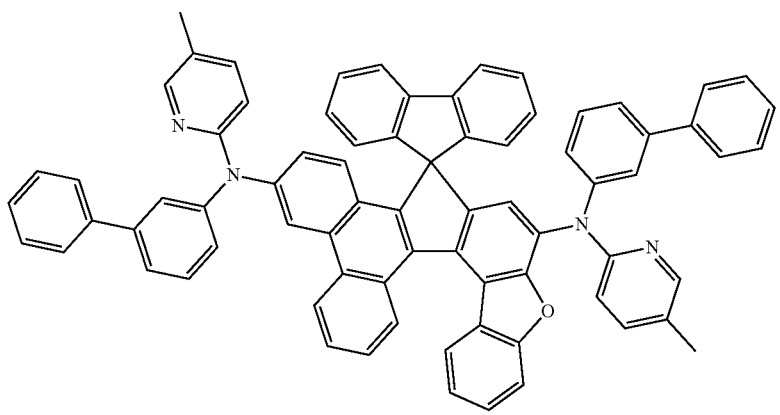
<Chemical Formula 89>
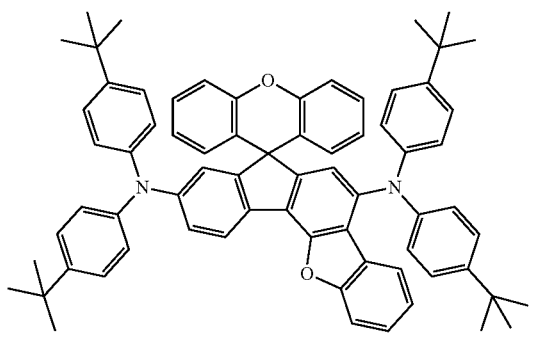
<Chemical Formula 90>
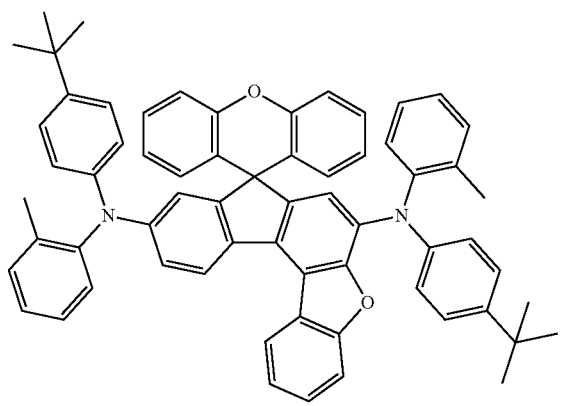
<Chemical Formula 91>
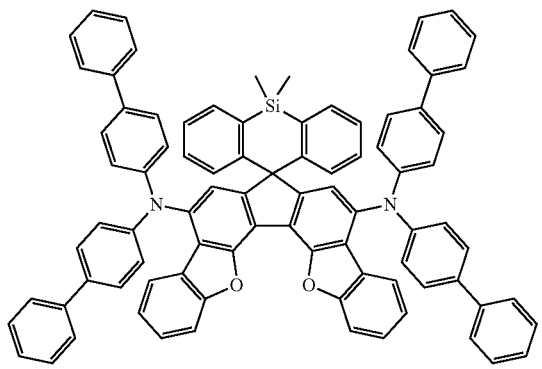
<Chemical Formula 92>
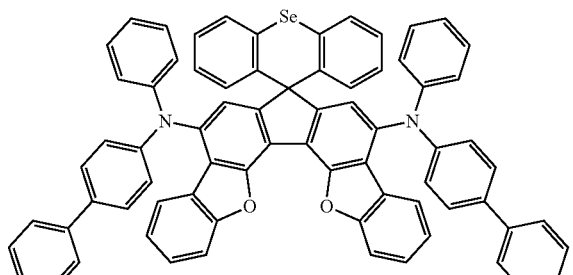

-continued
<Chemical Formula 93>
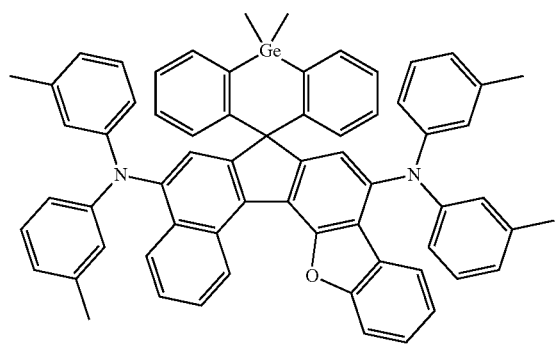
<Chemical Formula 94>
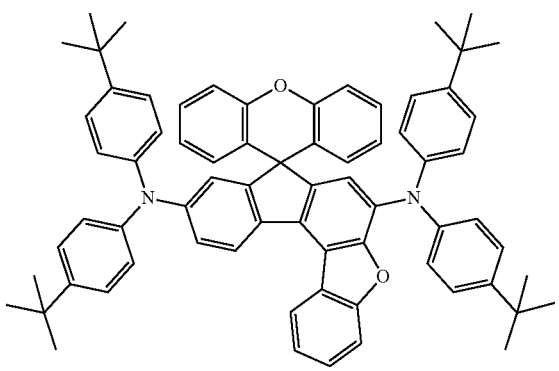
<Chemical Formula 95>
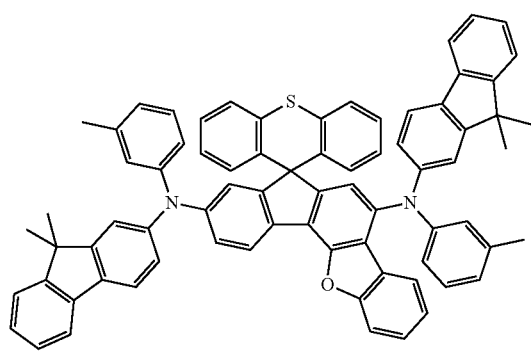
<Chemical Formula 96>
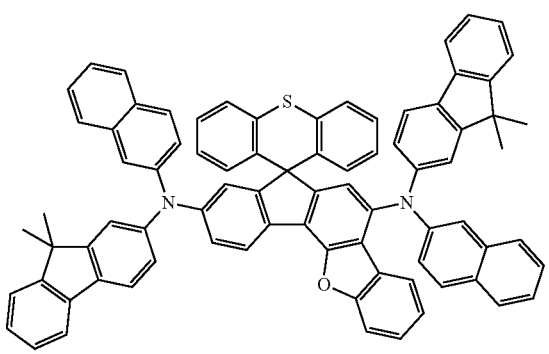
<Chemical Formula 97>
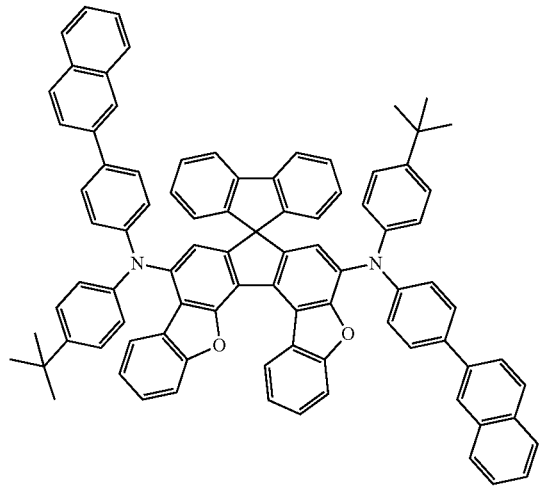
<Chemical Formula 98>
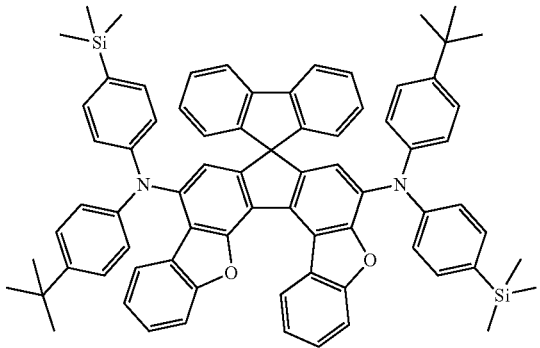
<Chemical Formula 99>
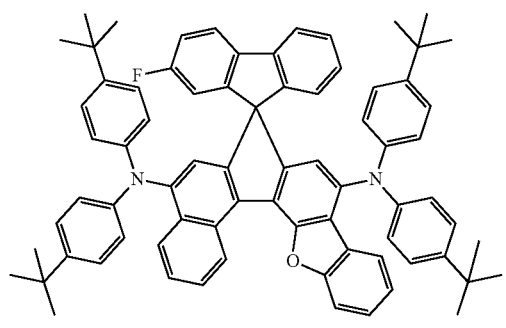
<Chemical Formula 100>
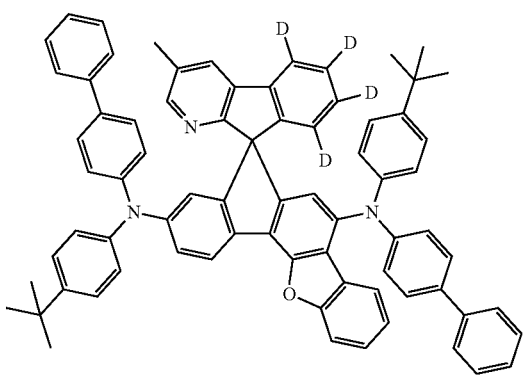

-continued
<Chemical Formula 101>
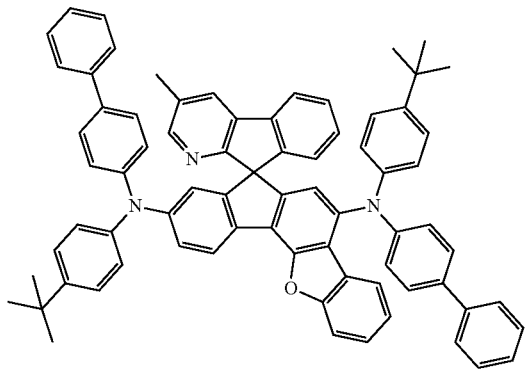
<Chemical Formula 102>
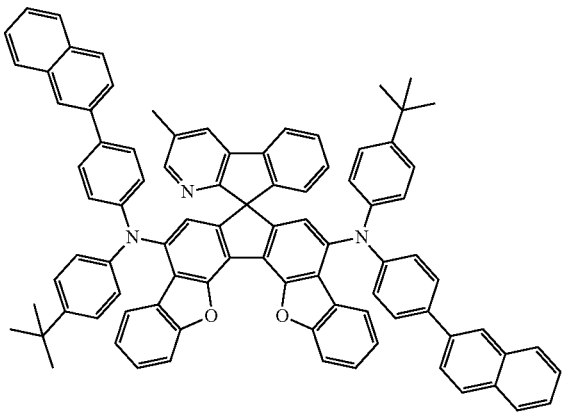
<Chemical Formula 103>
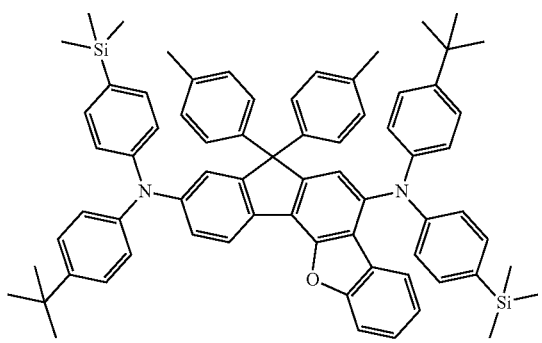
<Chemical Formula 104>
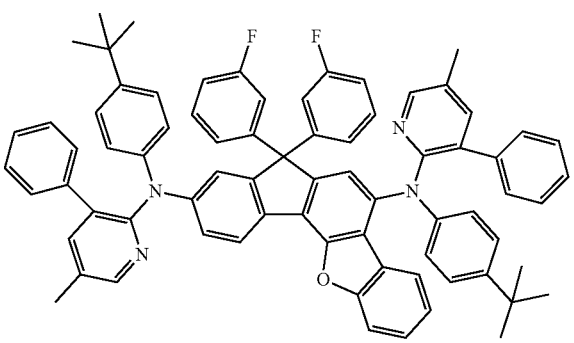
<Chemical Formula 105>
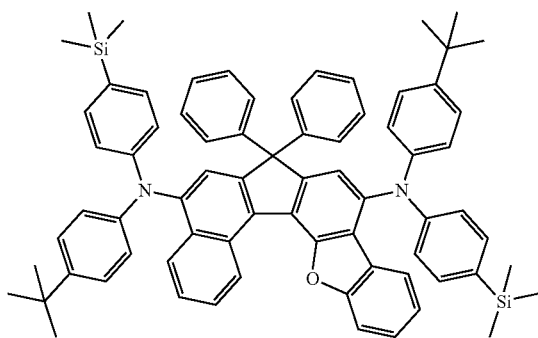
<Chemical Formula 106>
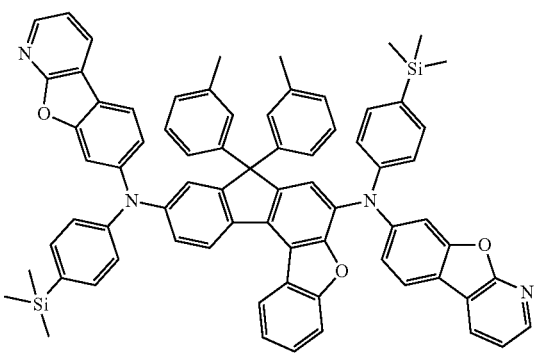
<Chemical Formula 107>
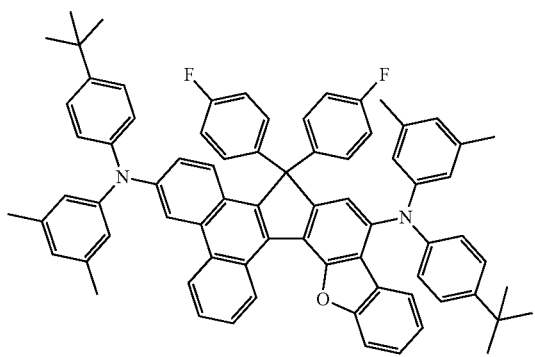
<Chemical Formula 108>
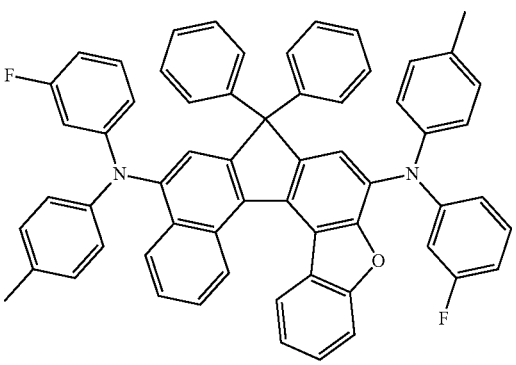

<Chemical Formula 109>
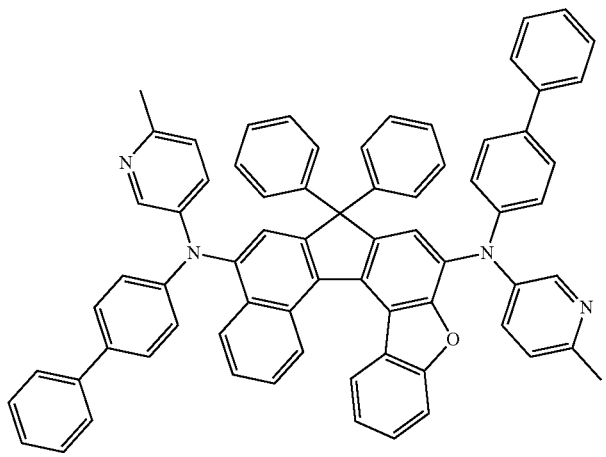
<Chemical Formula 110>
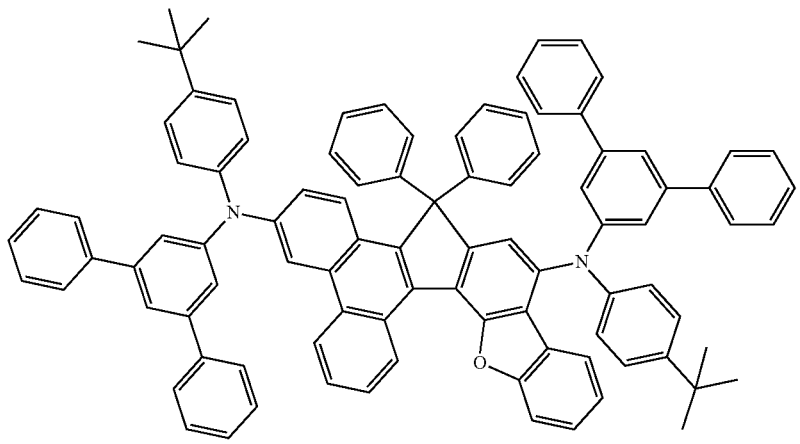
<Chemical Formula 111>
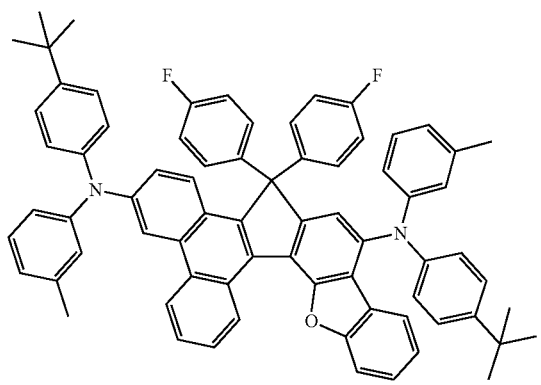
<Chemical Formula 112>
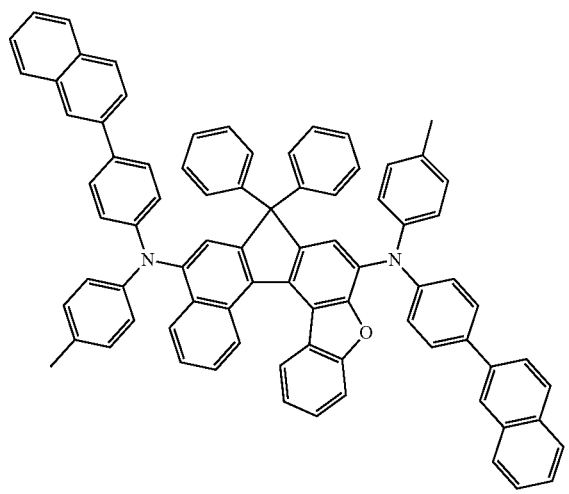

<Chemical Formula 113>
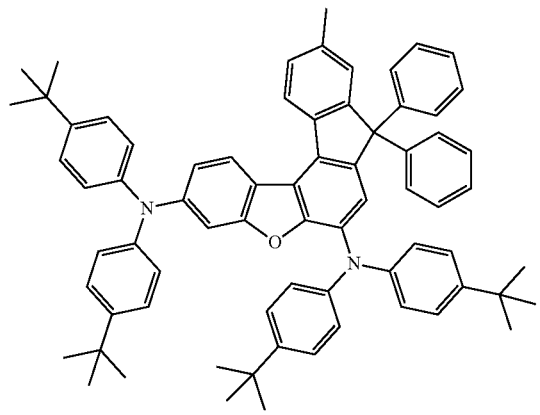
<Chemical Formula 114>
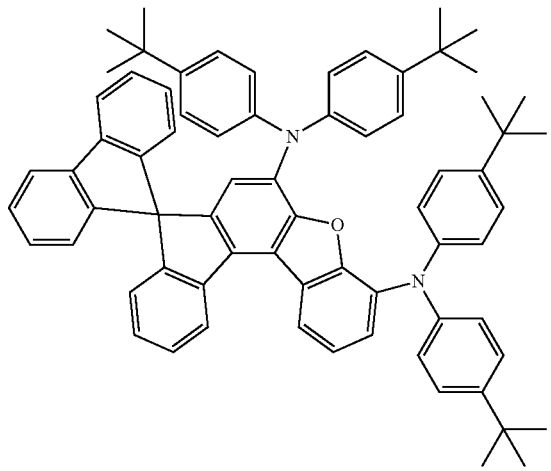
<Chemical Formula 115>
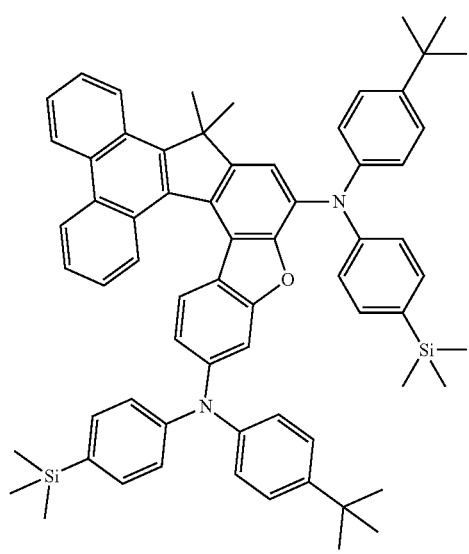
<Chemical Formula 116>
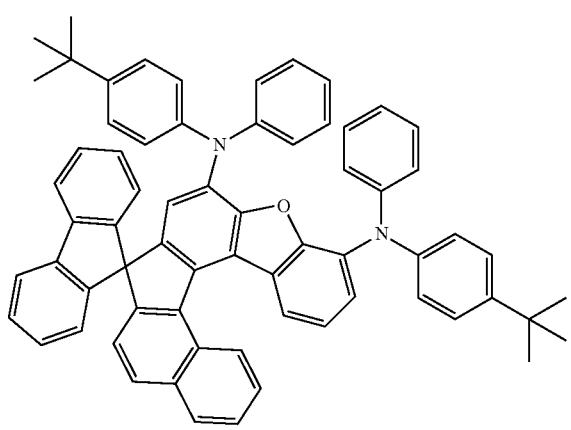
<Chemical Formula 117>
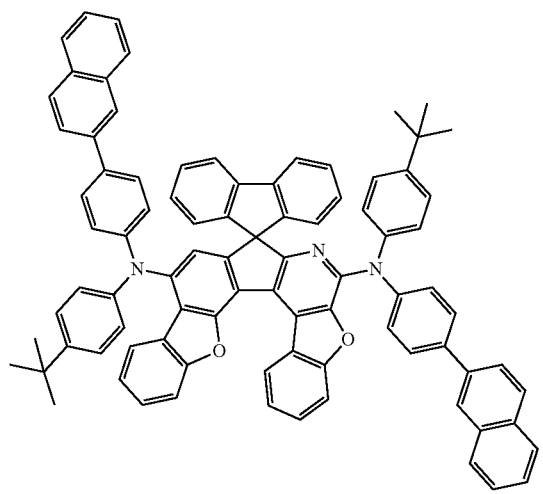
<Chemical Formula 118>
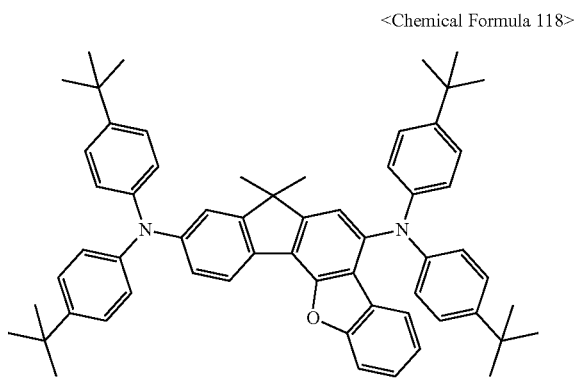

<Chemical Formula 119>
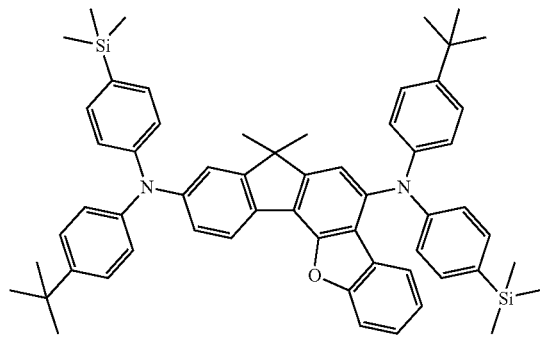
<Chemical Formula 120>
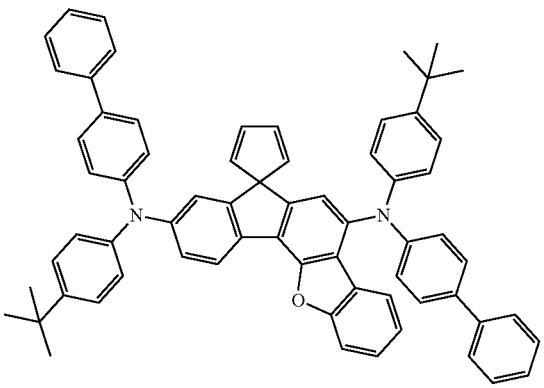
<Chemical Formula 121>
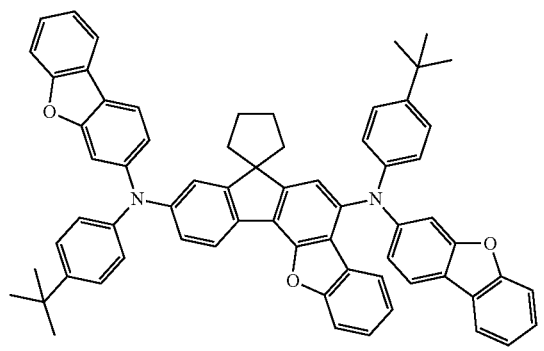
<Chemical Formula 122>
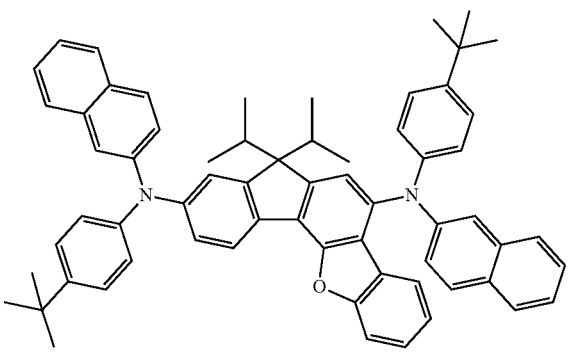
<Chemical Formula 123>
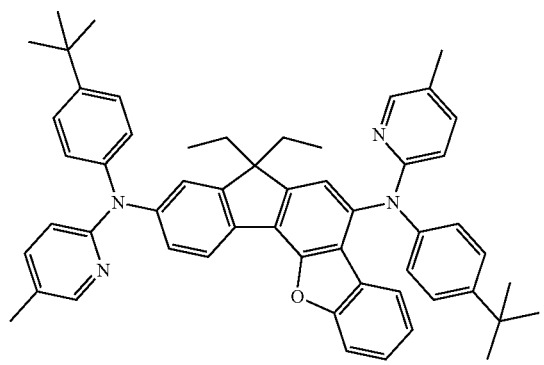
<Chemical Formula 124>
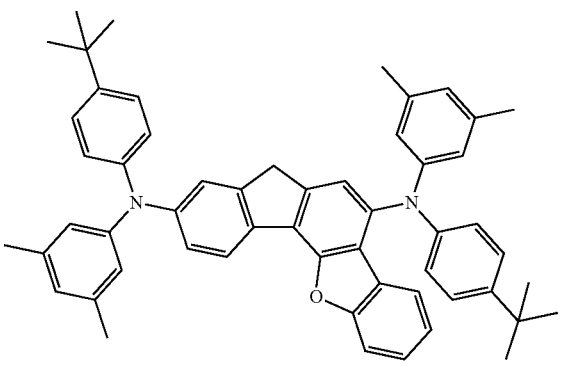
<Chemical Formula 125>
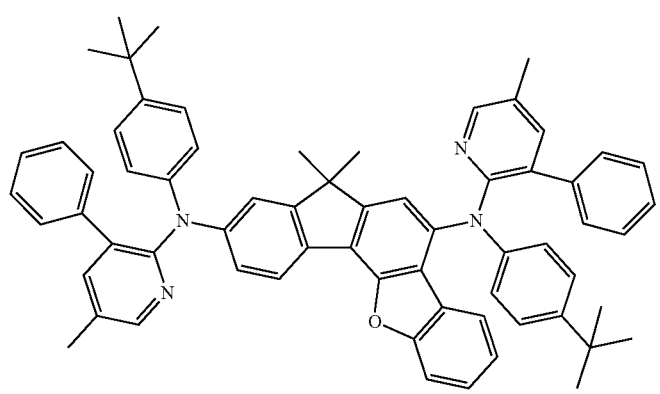

<Chemical Formula 126>
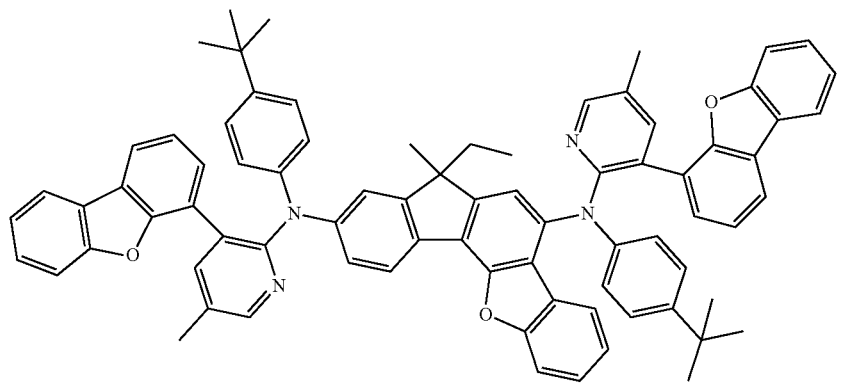
<Chemical Formula 127>
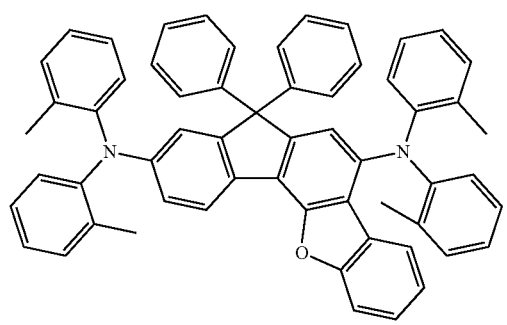
<Chemical Formula 128>
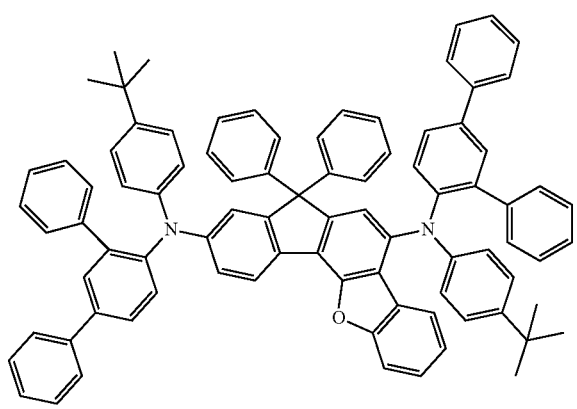
<Chemical Formula 129>
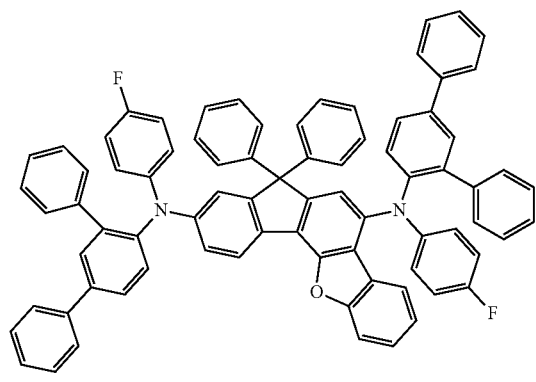
<Chemical Formula 130>
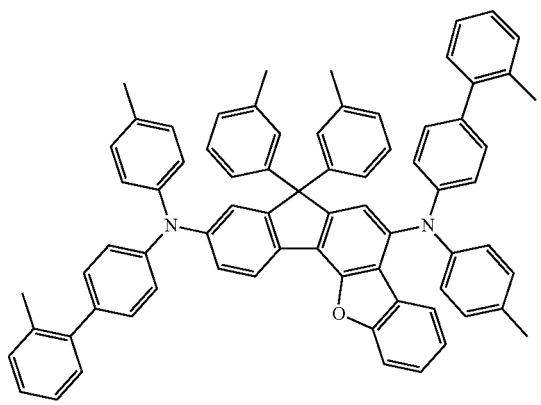

<Chemical Formula 131>
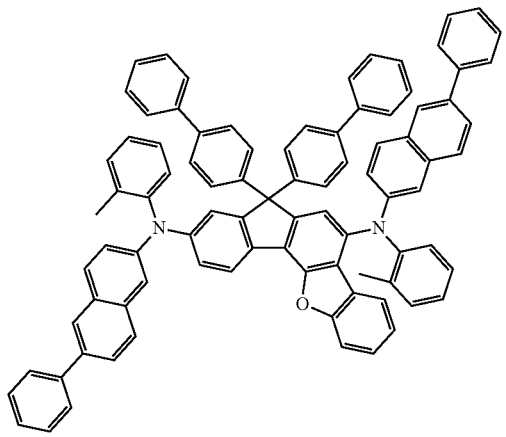
<Chemical Formula 132>
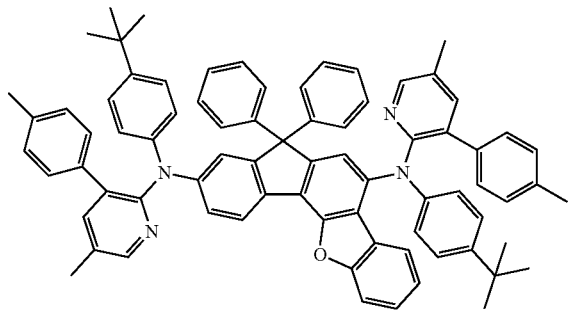
<Chemical Formula 133>
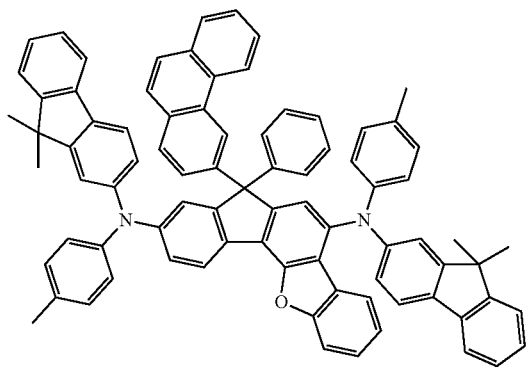
<Chemical Formula 134>
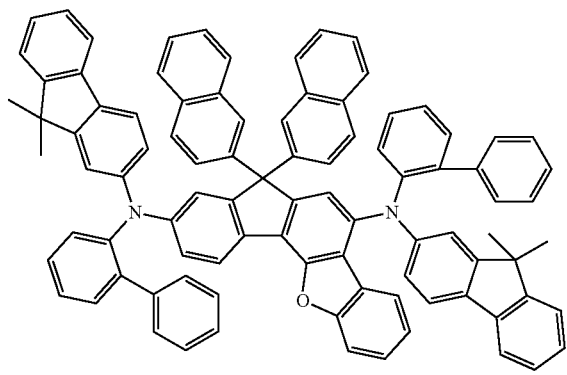
<Chemical Formula135>
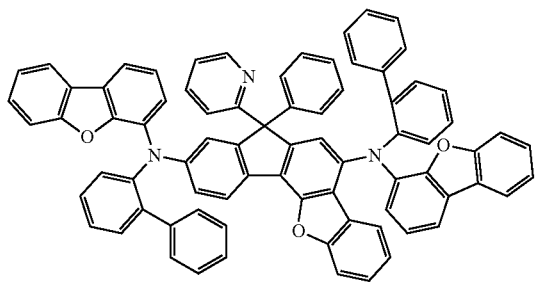
<Chemical Formula 136>
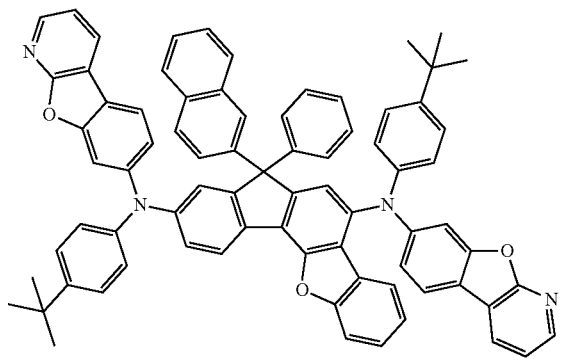
<Chemical Formula 137>
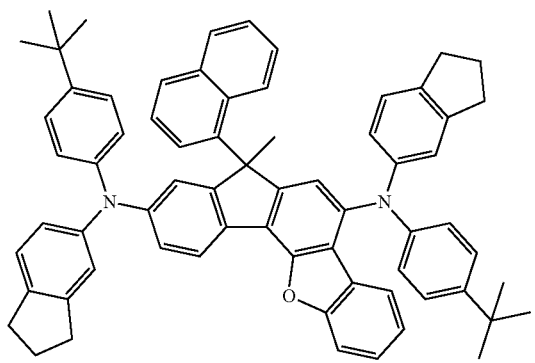
<Chemical Formula 138>
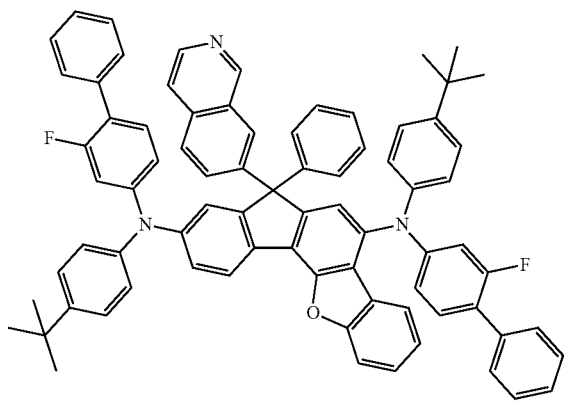

<Chemical Formula 139>
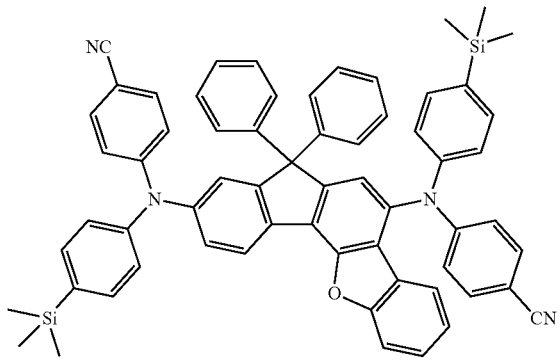
<Chemical Formula 140>
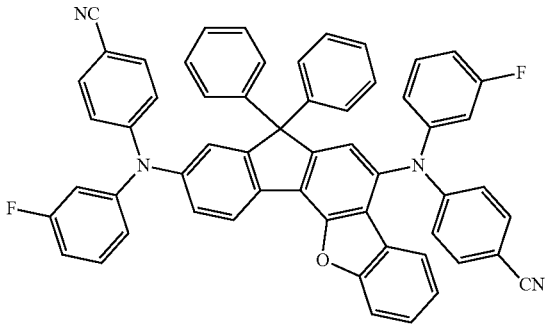
<Chemical Formula 141>
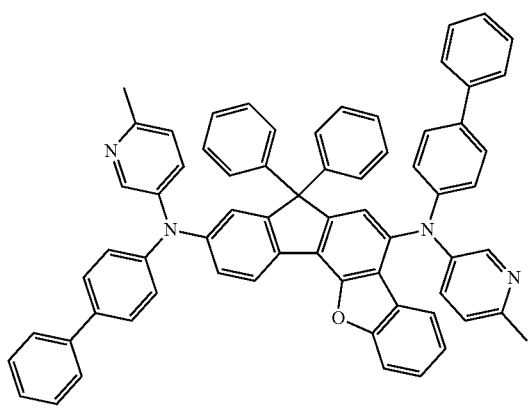
<Chemical Formula 142>
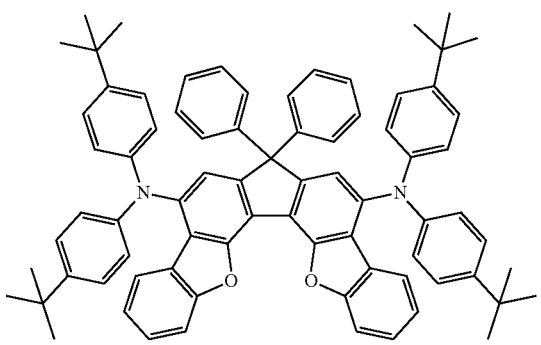
<Chemical Formula 143>
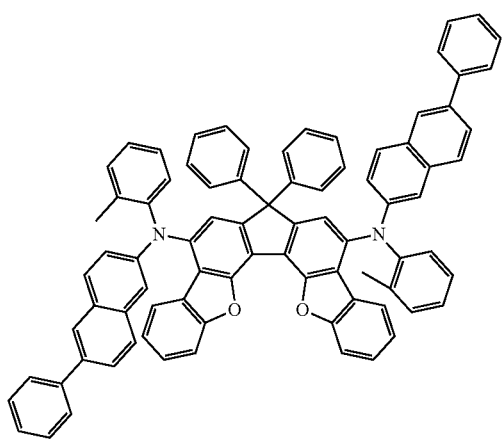
<Chemical Formula 144>
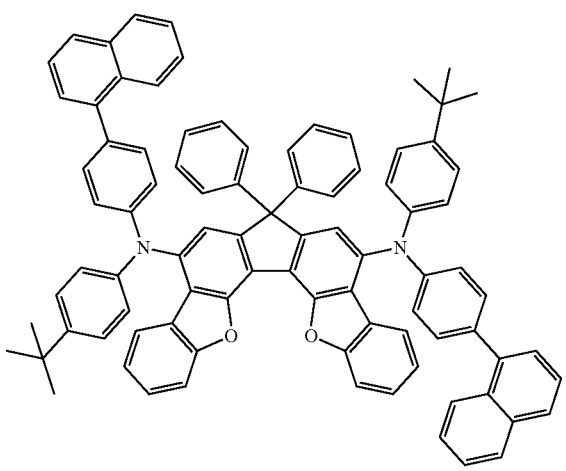

<Chemical Formula 145>
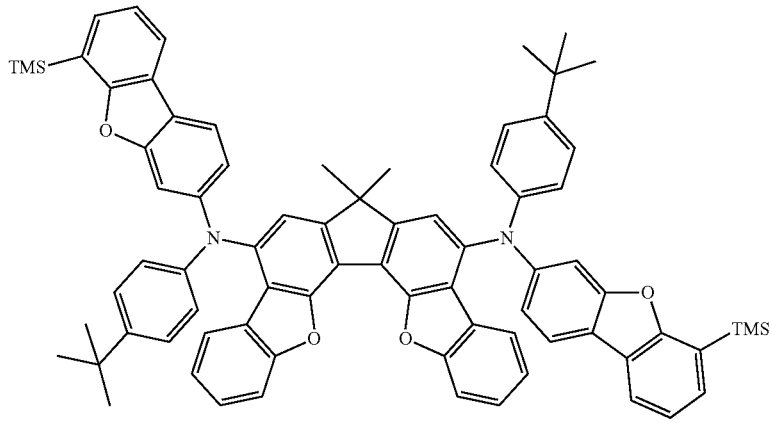
<Chemical Formula 146>
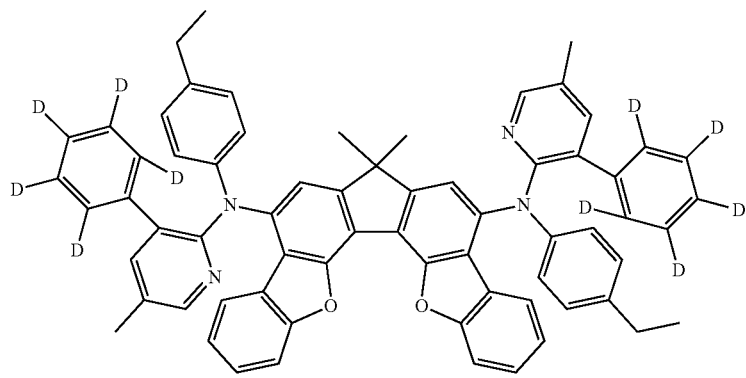
<Chemical Formula 147> <Chemical Formula 148>
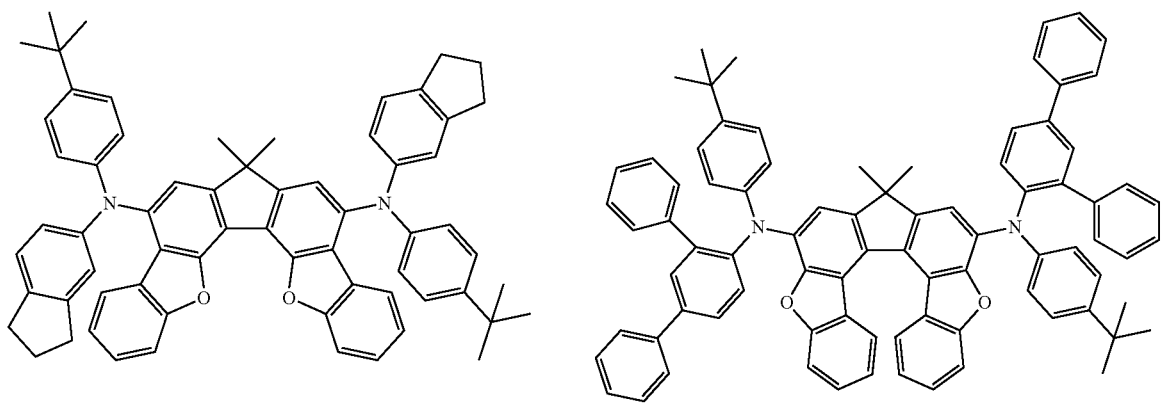
<Chemical Formula 149>
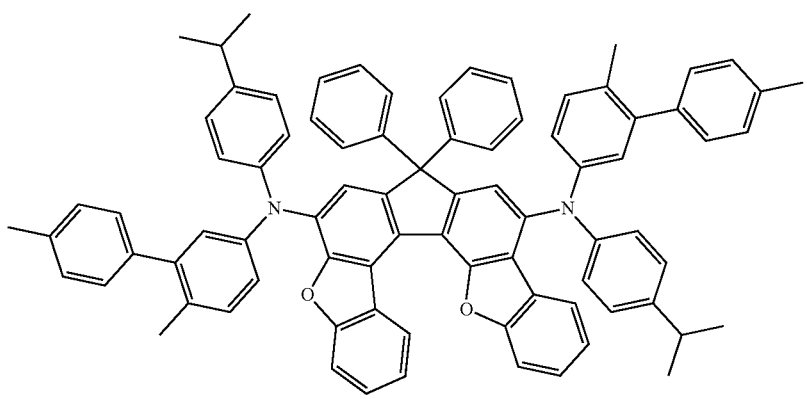

-continued
<Chemical Formula 150>
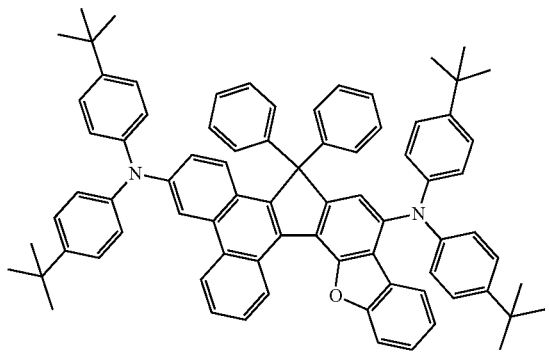
<Chemical Formula 151>
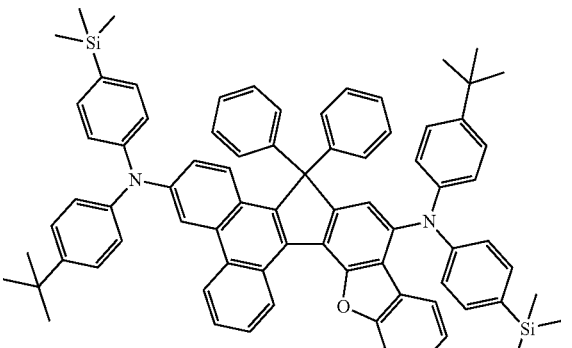
<Chemical Formula 152>
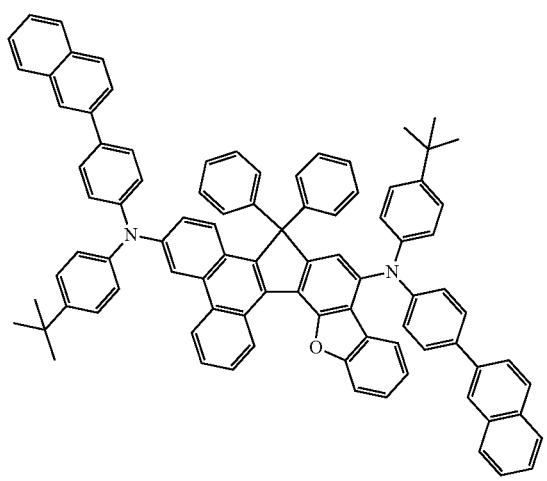
<Chemical Formula 153>
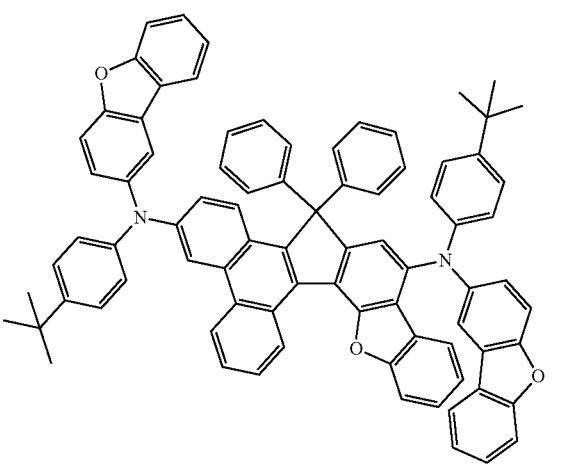
<Chemical Formula 154>
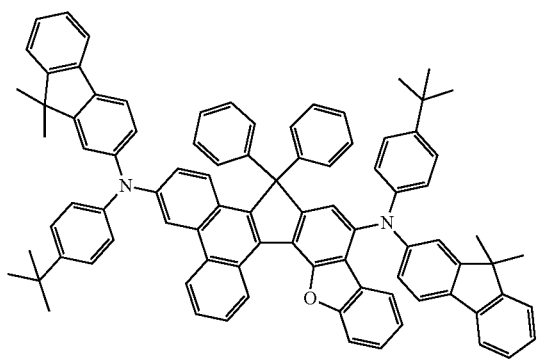
<Chemical Formula 155>
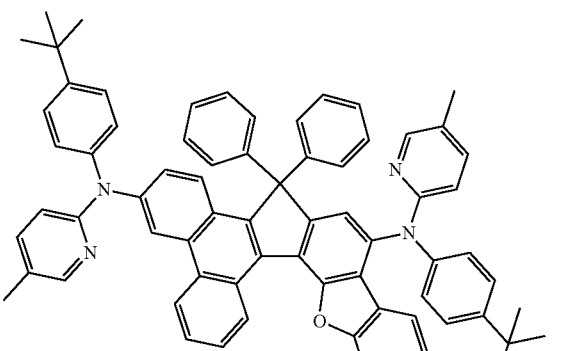
<Chemical Formula 156>
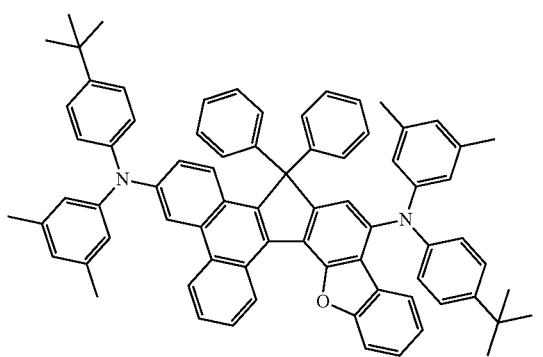
<Chemical Formula 157>
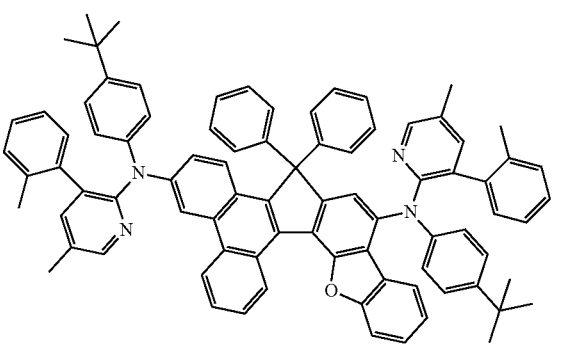

-continued
<Chemical Formula 158>
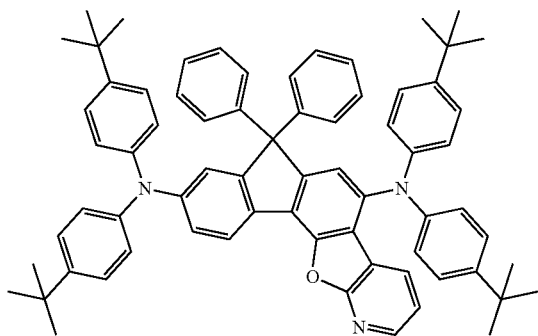
<Chemical Formula 159>
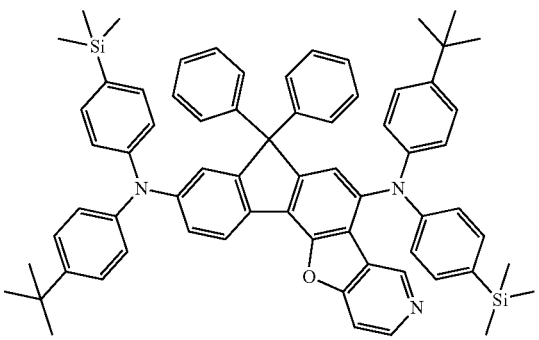
<Chemical Formula 160>
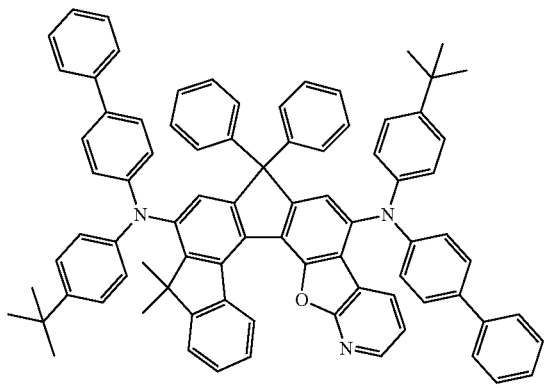
<Chemical Formula 161>
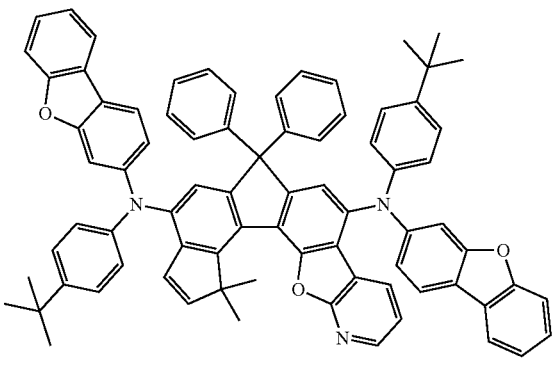
<Chemical Formula 162>
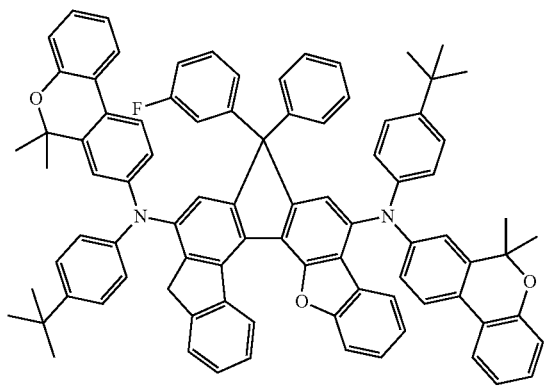
<Chemical Formula 163>
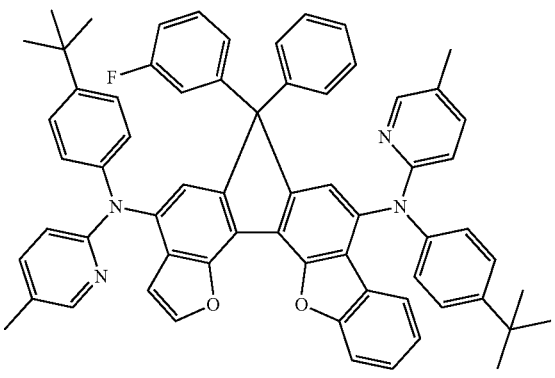
<Chemical Formula 164>
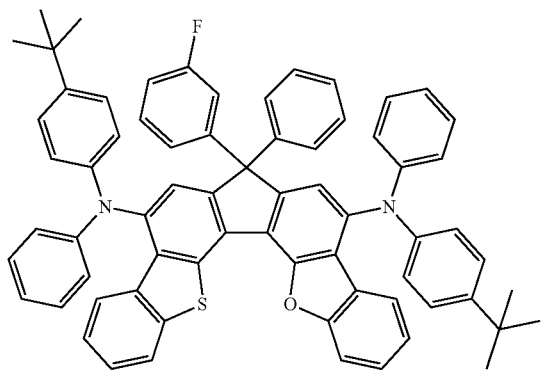
<Chemical Formula 165>
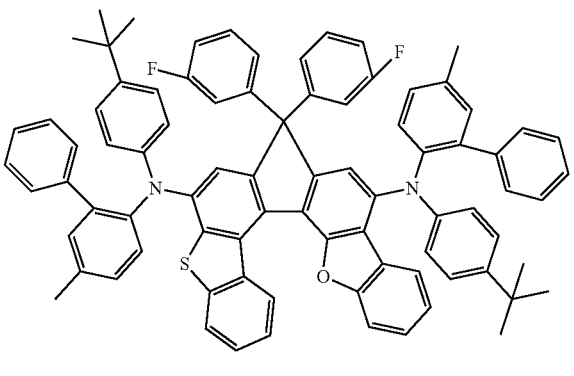

<Chemical Formula 166>
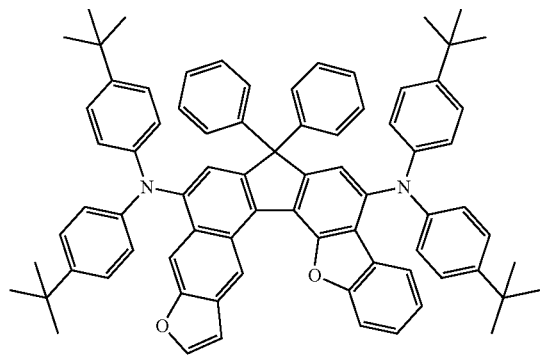
<Chemical Formula 167>
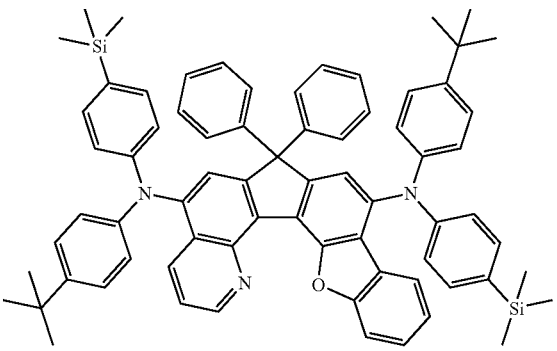
<Chemical Formula 168>
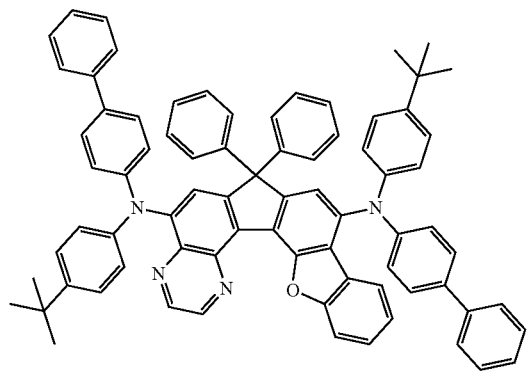
<Chemical Formula 169>
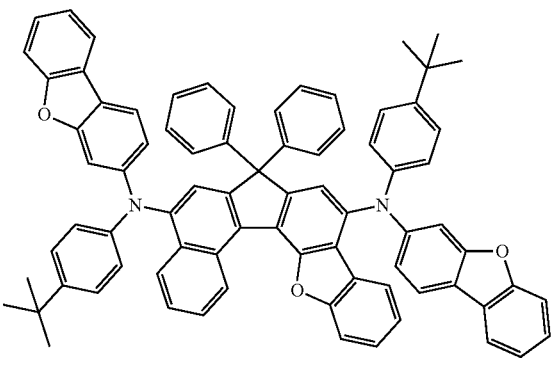
<Chemical Formula 170>
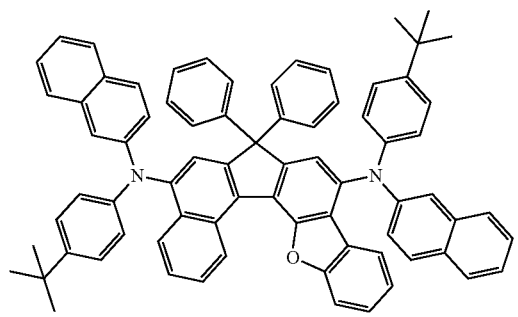
<Chemical Formula 171>
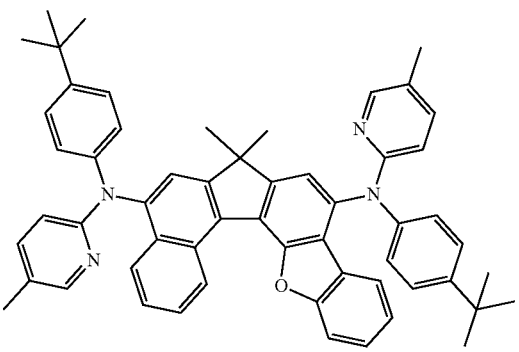
<Chemical Formula 172>
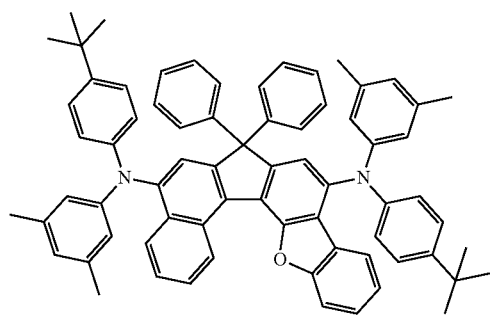
<Chemical Formula 173>
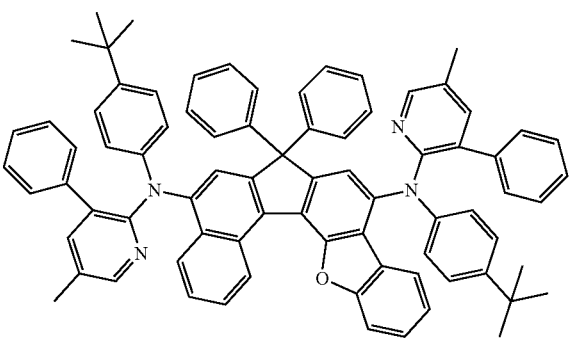

<Chemical Formula 174>
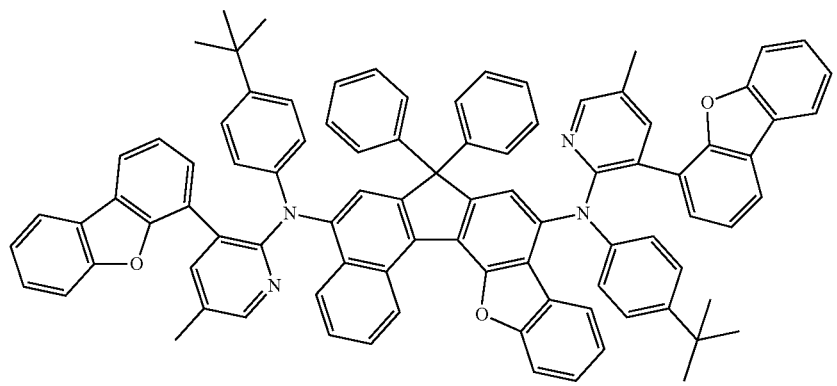
<Chemical Formula 175>
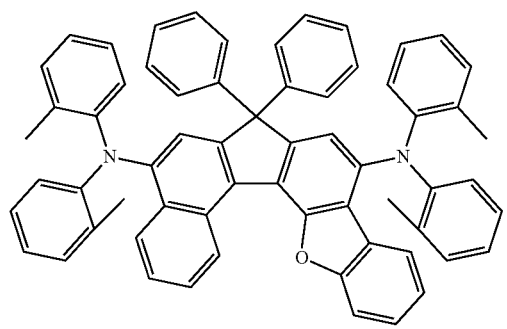
<Chemical Formula 176>
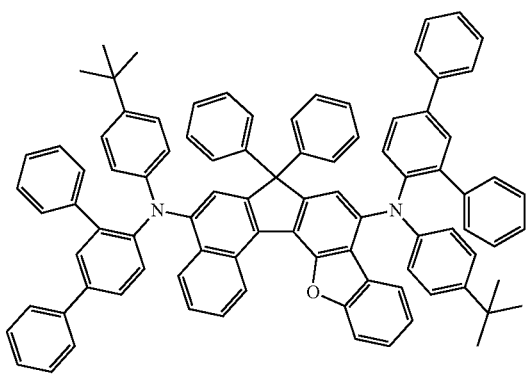
<Chemical Formula 177>
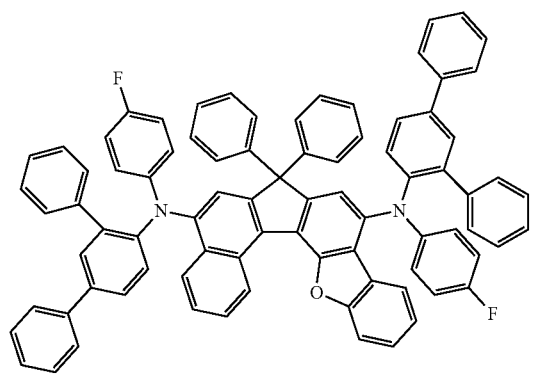
<Chemical Formula 178>
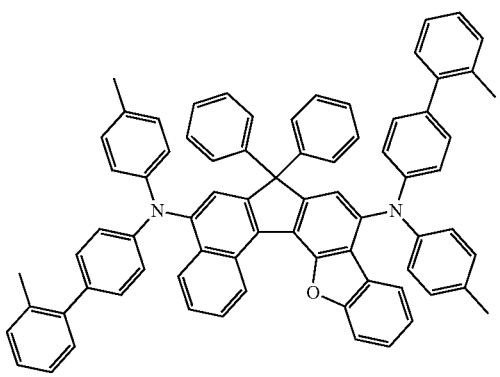
<Chemical Formula 179>
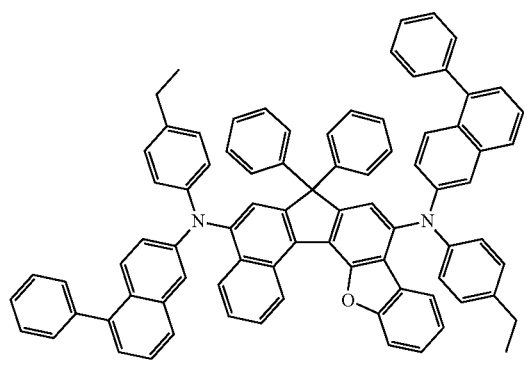
<Chemical Formula 180>
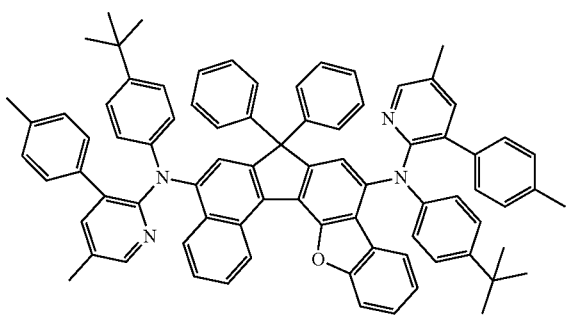

<Chemical Formula 181>
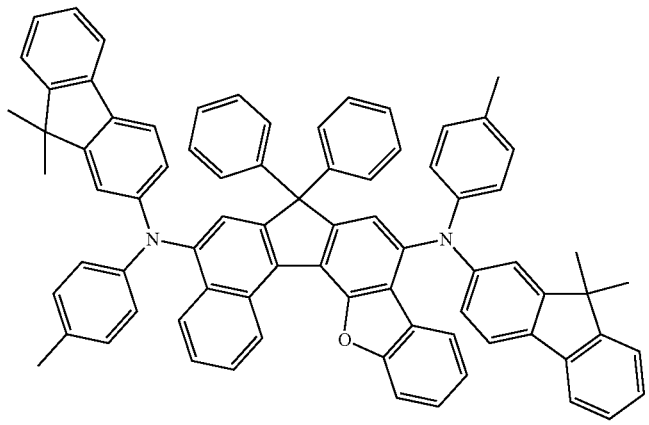
<Chemical Formula 182>
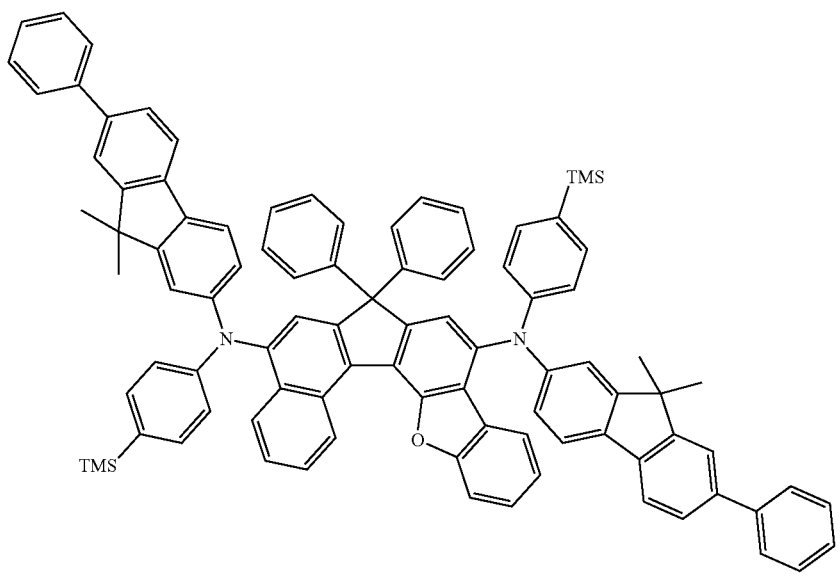
<Chemical Formula 183>
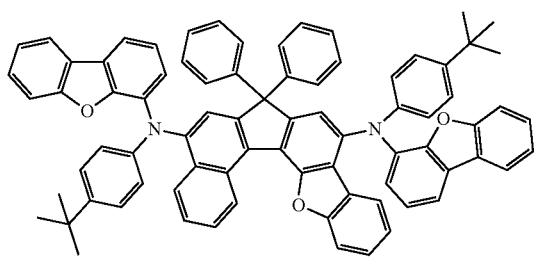
<Chemical Formula 184>
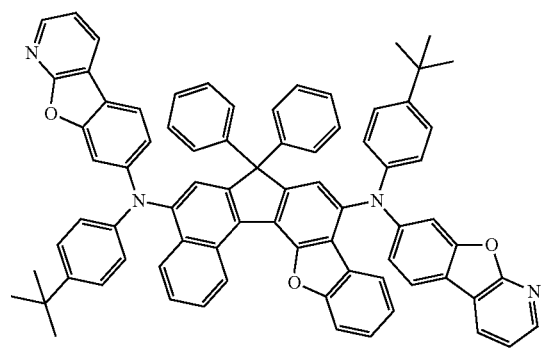

-continued
<Chemical Formula 185>
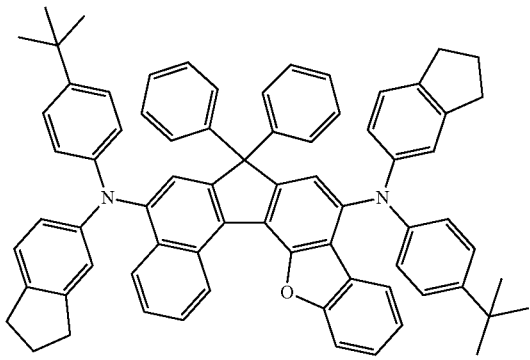
<Chemical Formula 186>
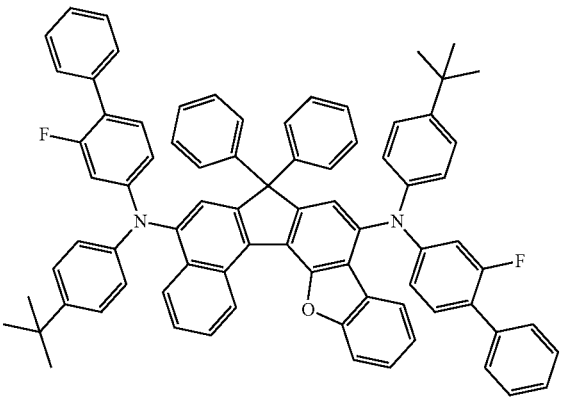
<Chemical Formula 187>
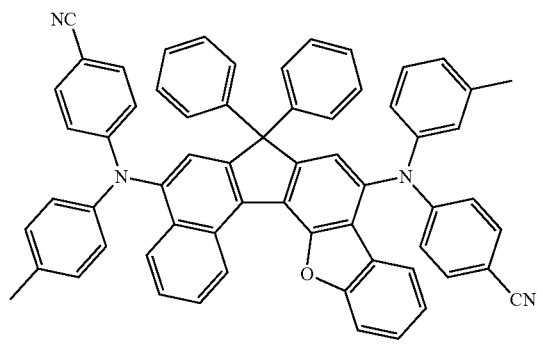
<Chemical Formula 188>
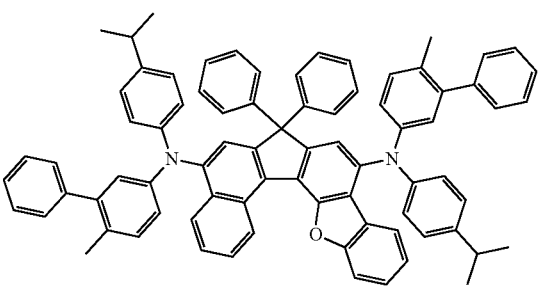
<Chemical Formula 189>
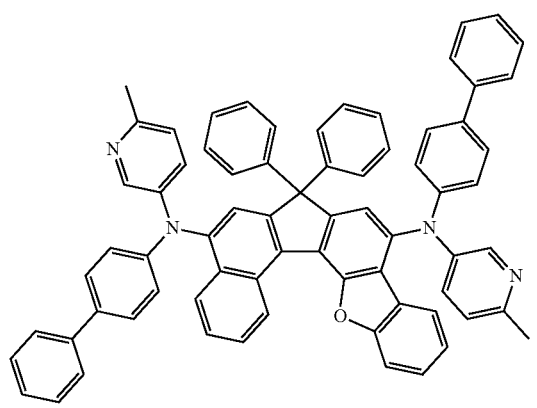
<Chemical Formula 190>
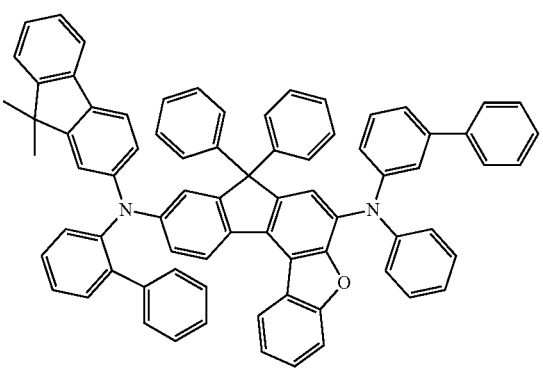
<Chemical Formula 191>
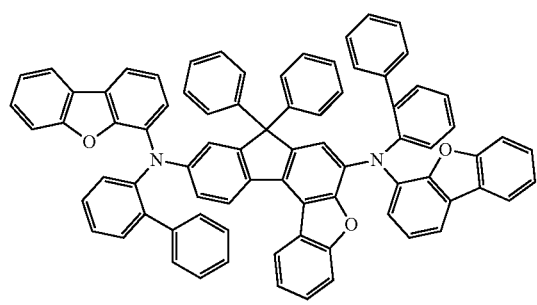
<Chemical Formula 192>
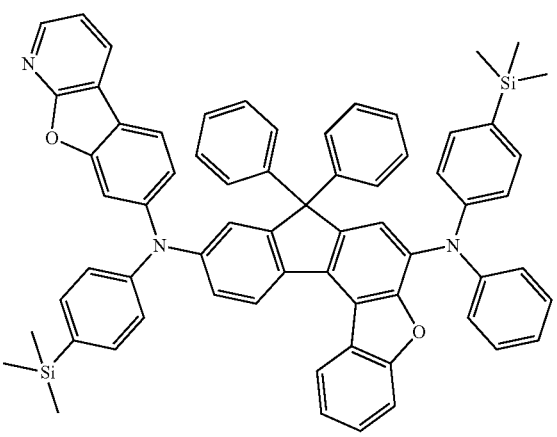

-continued
<Chemical Formula 193>
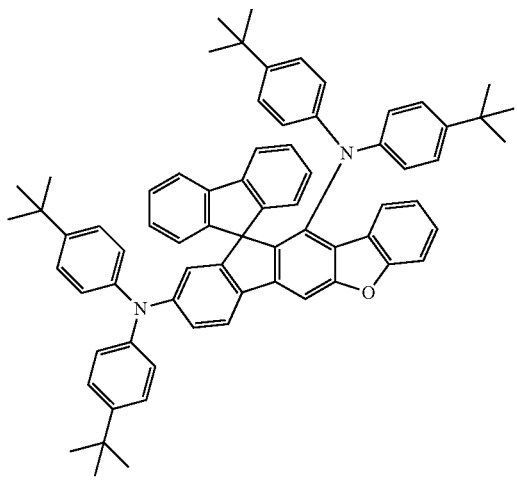
<Chemical Formula 194>
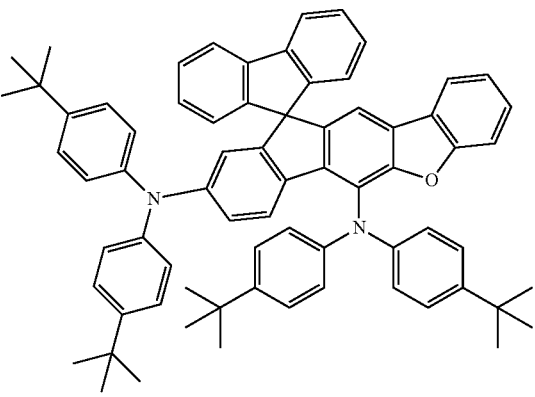
<Chemical Formula 195>
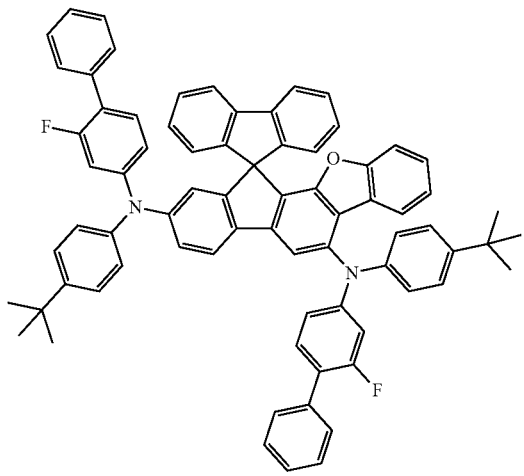
<Chemical Formula 196>
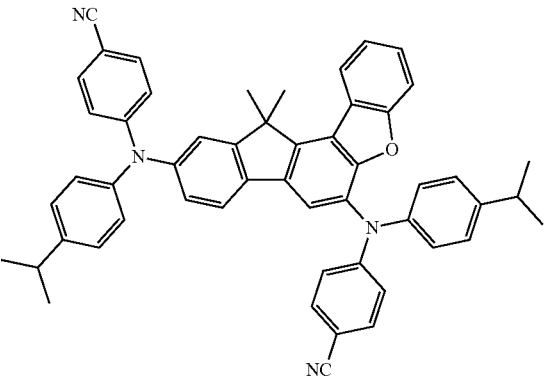
<Chemical Formula 197>
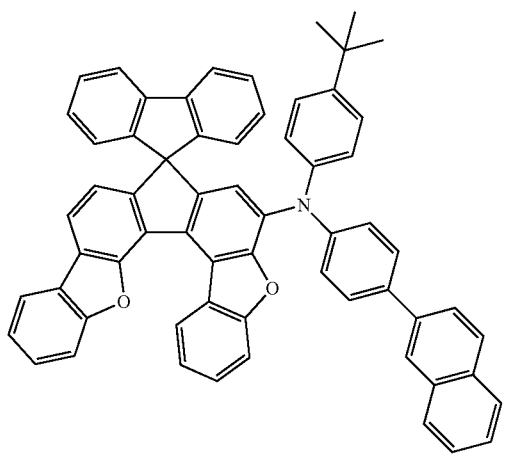
<Chemical Formula 198>
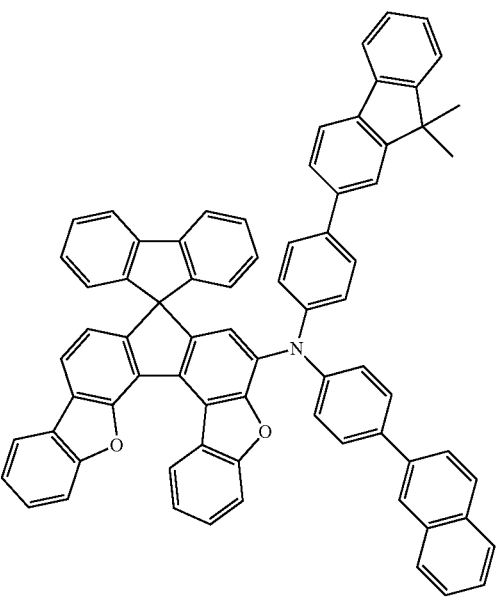

<Chemical Formula 199>
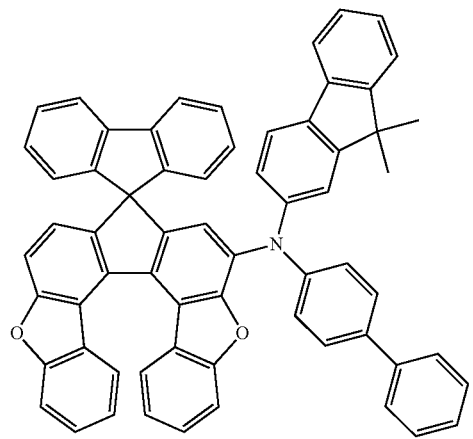
<Chemical Formula 200>
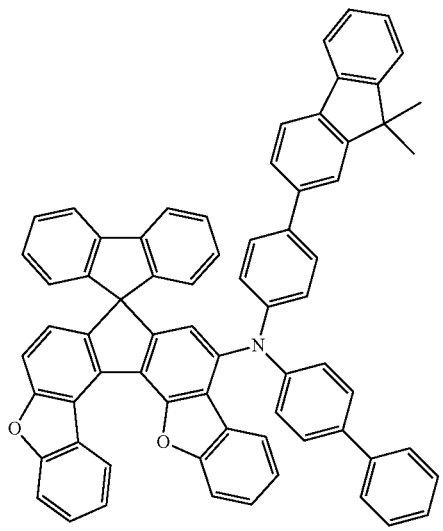
<Chemical Formula 201>
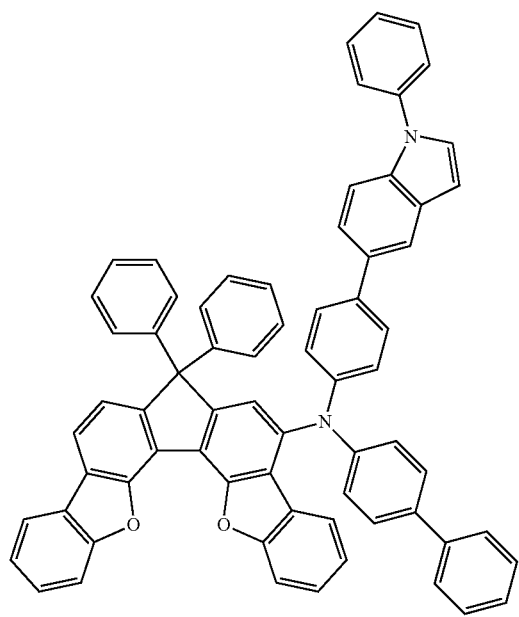
<Chemical Formula 202>
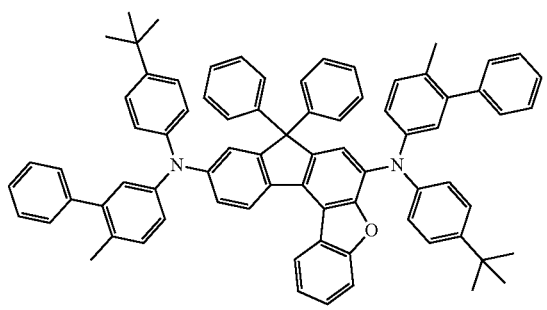

-continued
<Chemical Formula 203>
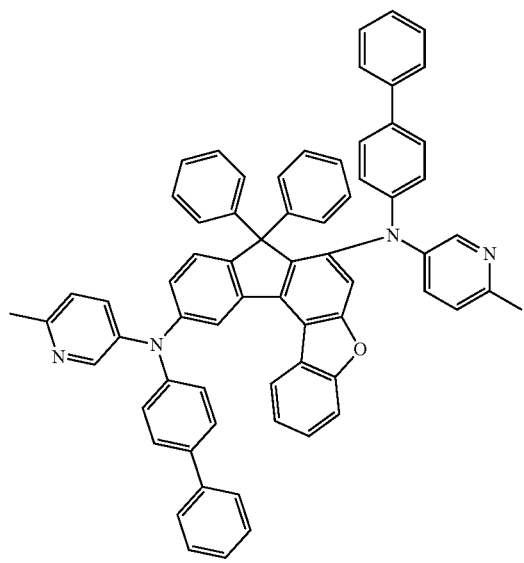
<Chemical Formula 204>
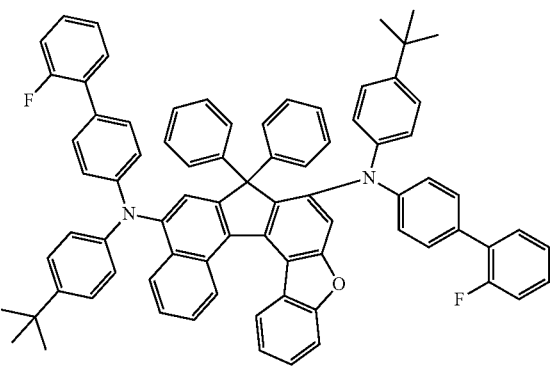
<Chemical Formula 205>
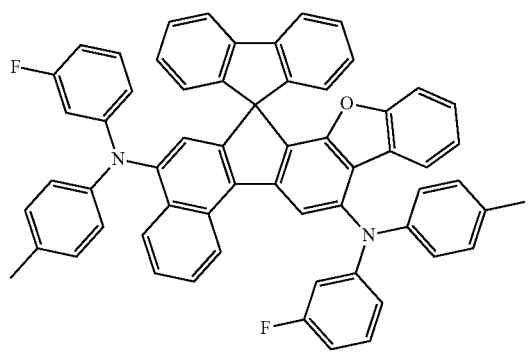
<Chemical Formula 206>
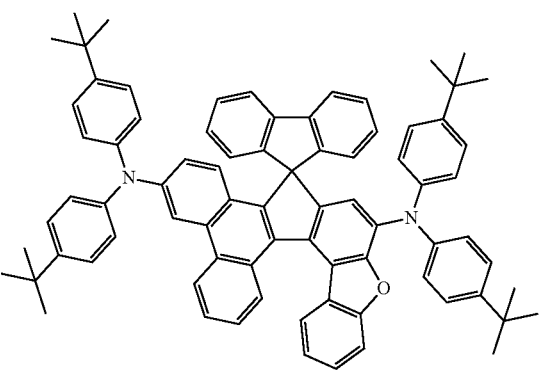
<Chemical Formula 207>
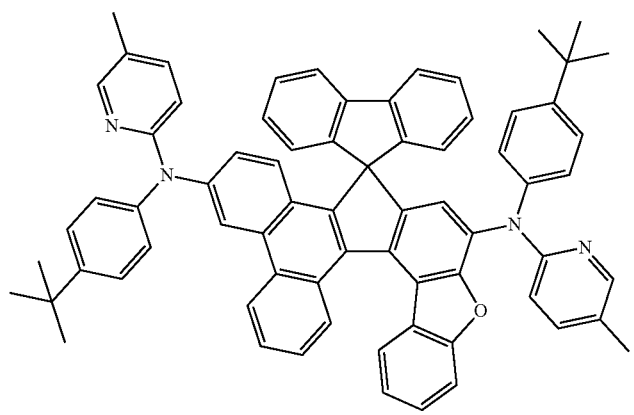

<Chemical Formula 208>
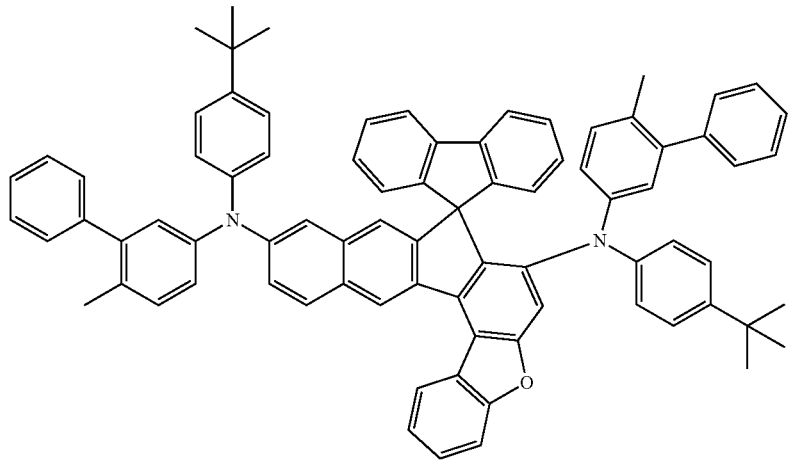
<Chemical Formula 209>
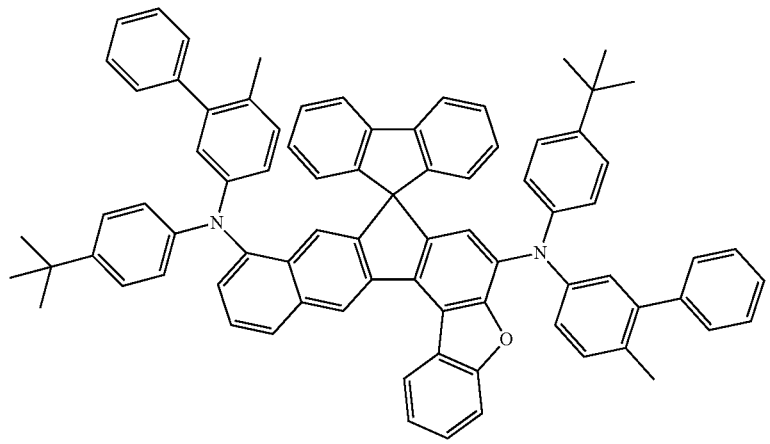
<Chemical Formula 210>
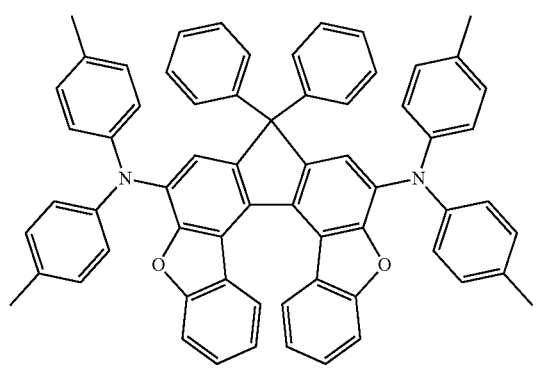
<Chemical Formula 211>
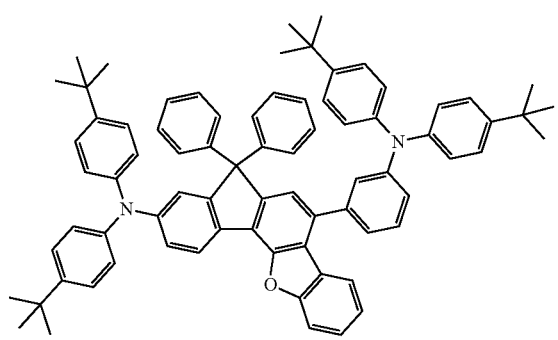

<Chemical Formula 212>
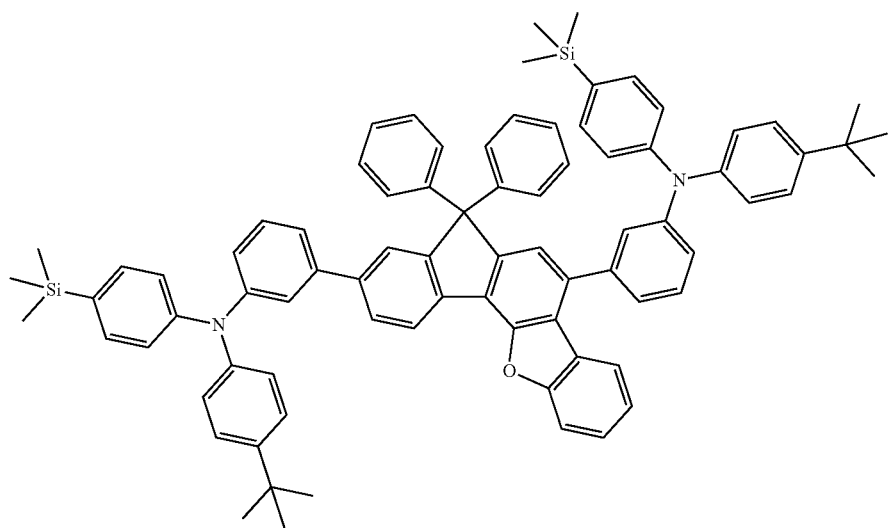
<Chemical Formula 213>
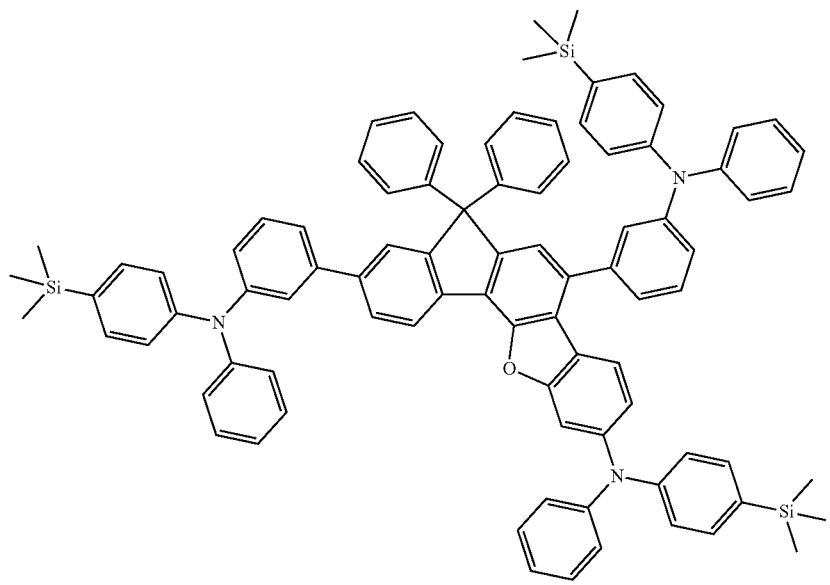
<Chemical Formula 214>
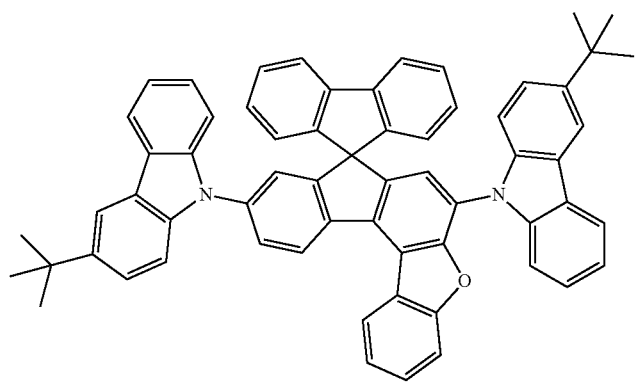

<Chemical Formula 215>
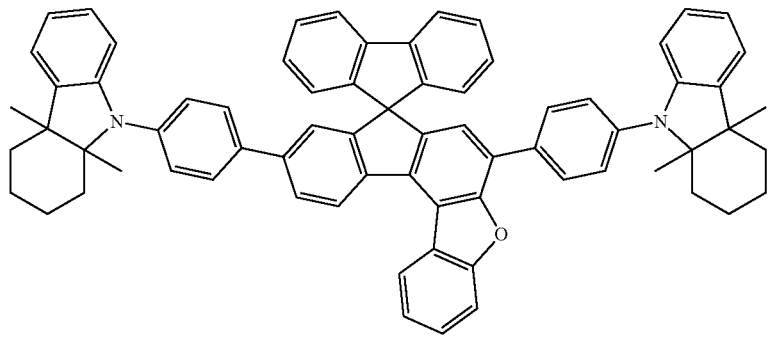
<Chemical Formula 216>
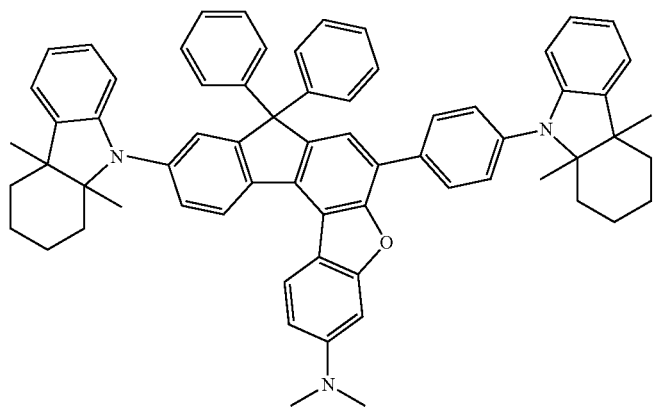
<Chemical Formula 217>
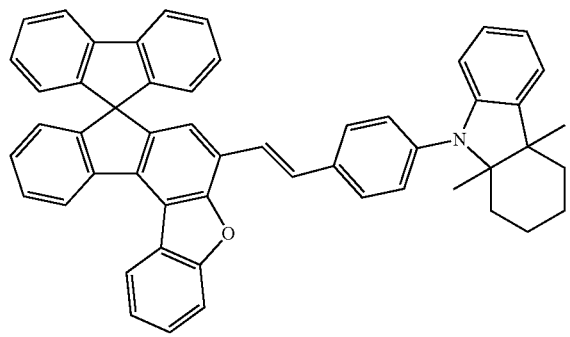
<Chemical Formula 218>
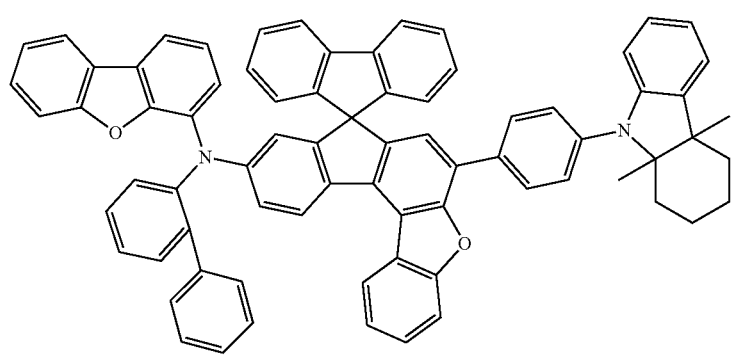

-continued
<Chemical Formula 219>
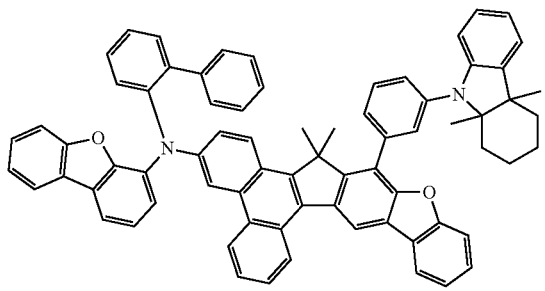
<Chemical Formula 220>
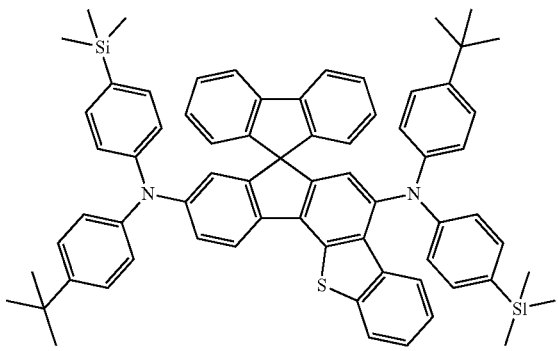
<Chemical Formual 221>
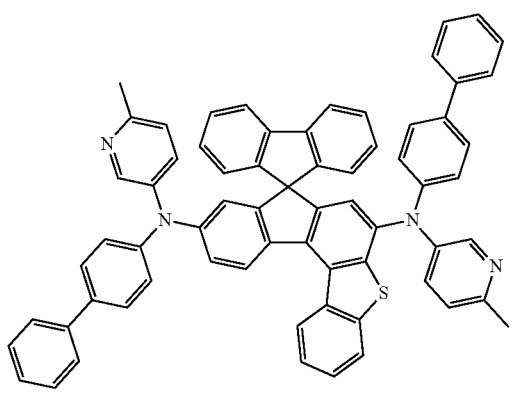
<Chemical Formula 222>
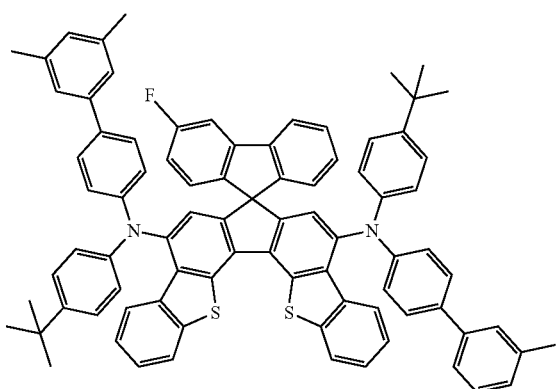
<Chemical Formula 223>
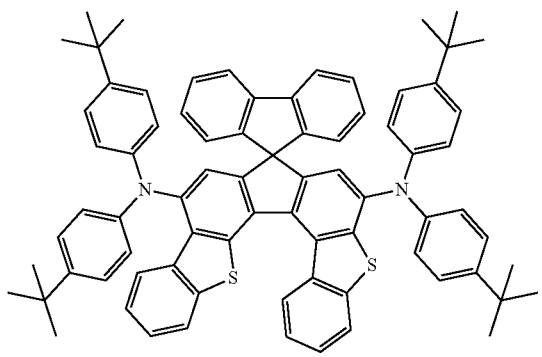
<Chemical Formula 224>
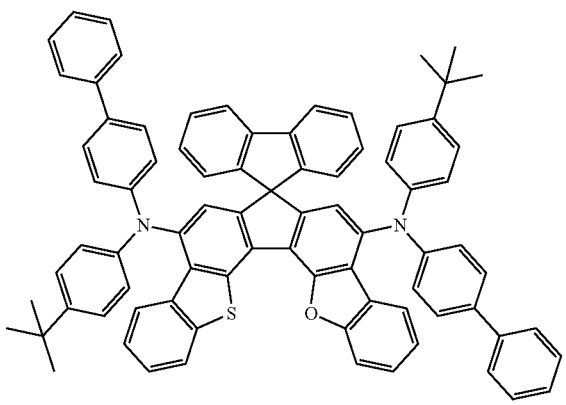
<Chemical Formuls 225>
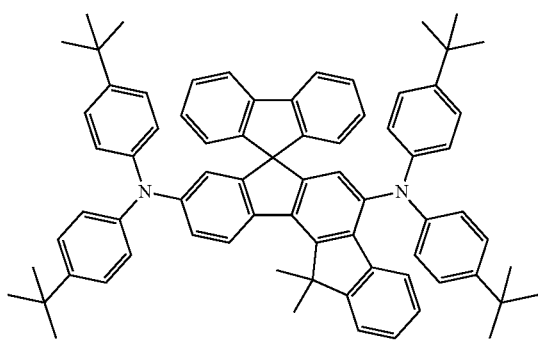
<Chemical Formuls 226>
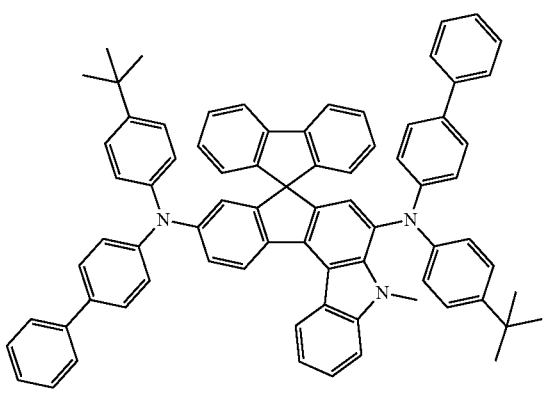

<Chemical Formuls 227>
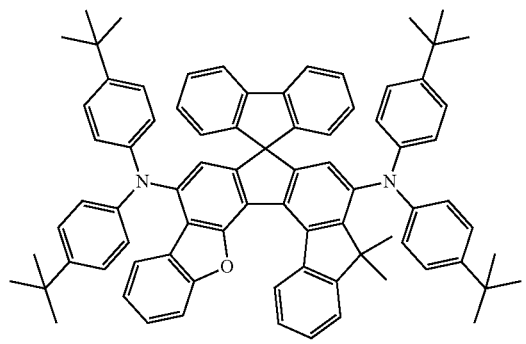
<Chemical Formuls 228>
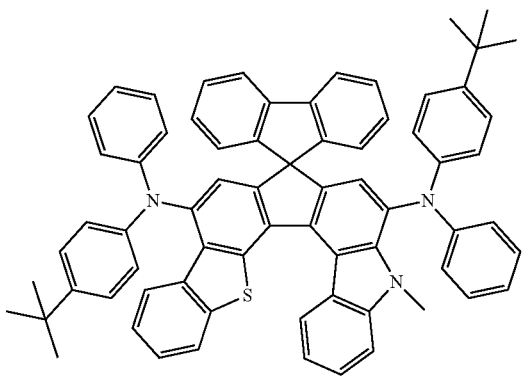
<Chemical Formuls 229>
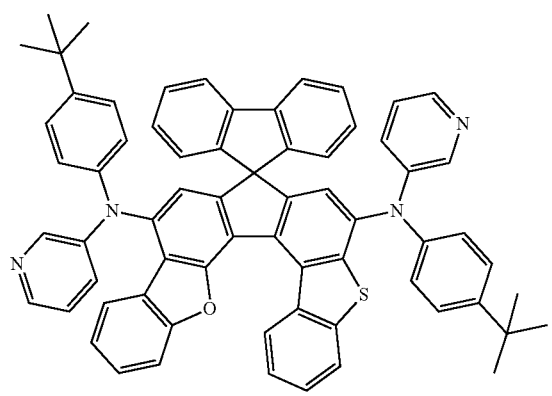
<Chemical Formuls 230>
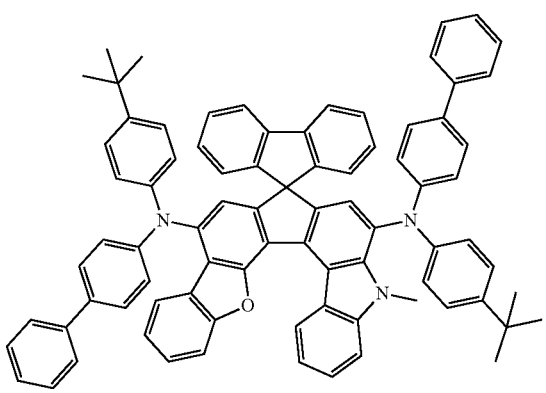
<Chemical Formuls 231>
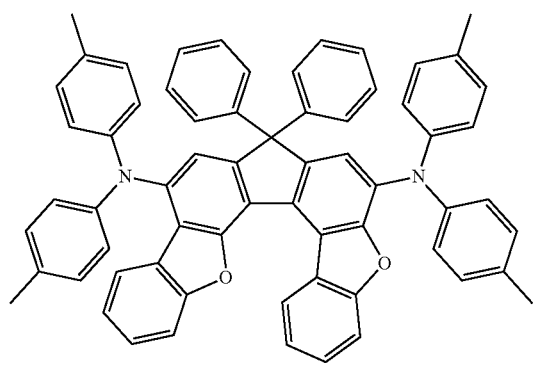
<Chemical Formula 232>
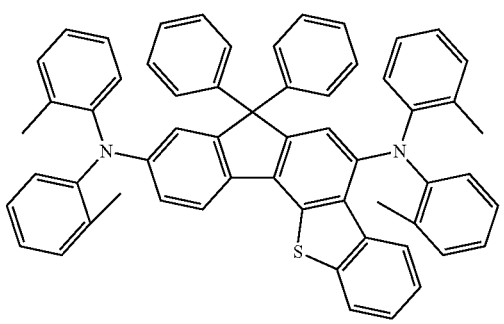
<Chemical Formula 233>
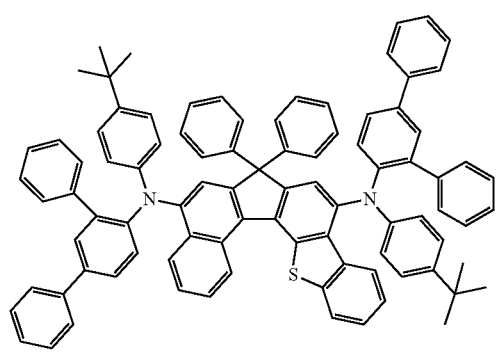
<Chemical Formula 234>
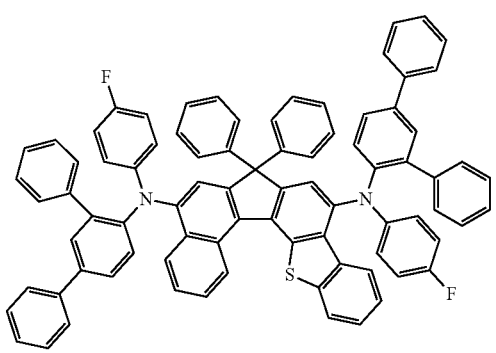

<Chemical Formula 235>

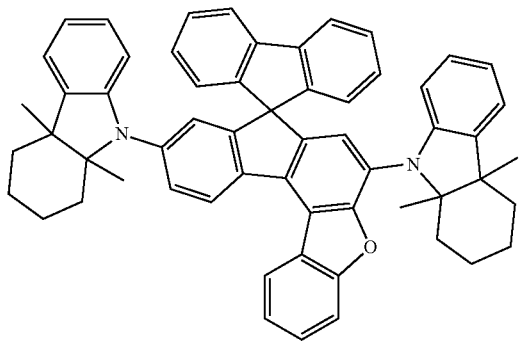

<Chemical Formula 236>

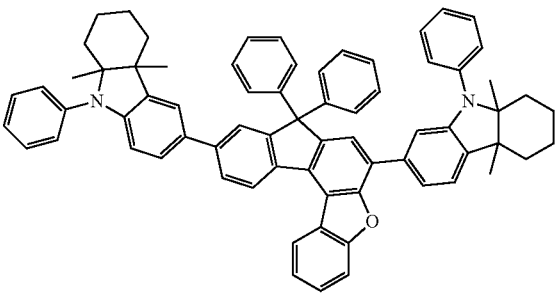

<Chemical Formula 237>

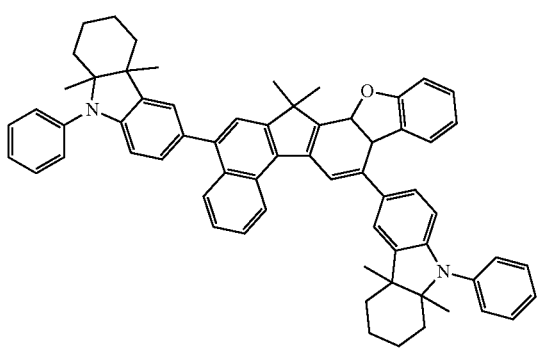

<Chemical Formula 238>

<Chemical Formula 239>

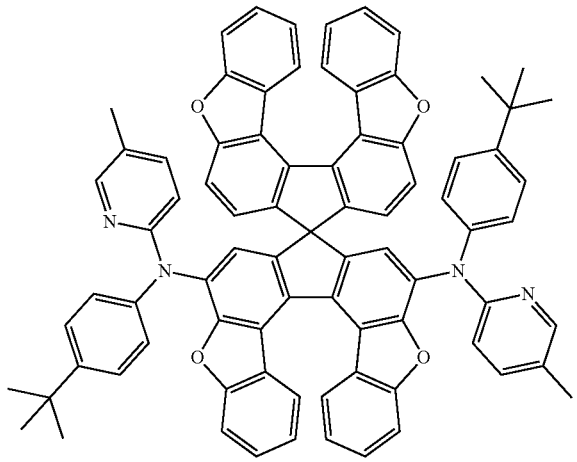

17. The organic light-emitting diode of claim 1, wherein the light-emitting layer includes a host and a dopant and the compound represented by Chemical Formula A or B is used as the dopant.

18. The organic light-emitting diode of claim 4, comprising a hole injection layer between the anode and the hole transport layer and an electron injection layer between the electron transport layer and the cathode.

19. The organic light-emitting diode of claim 1, wherein at least one of the layers is formed using a deposition process or a solution process.

20. The organic light-emitting diode of claim 1, wherein the organic light-emitting diode is used for a device selected from among a flat display device; a flexible display device; a monochrome or white flat illumination device; and a monochrome or white flexible illumination device.

* * * * *